(12) United States Patent
Smith et al.

(10) Patent No.: US 9,481,664 B2
(45) Date of Patent: *Nov. 1, 2016

(54) ANDROGEN RECEPTOR MODULATORS AND USES THEREOF

(71) Applicant: ARAGON PHARMACEUTICALS, INC., San Diego, CA (US)

(72) Inventors: Nicholas D. Smith, San Diego, CA (US); Celine Bonnefous, San Diego, CA (US); Jackaline D. Julien, Del Mar, CA (US)

(73) Assignee: Aragon Pharmaceuticals, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/656,031

(22) Filed: Mar. 12, 2015

(65) Prior Publication Data

US 2015/0182529 A1 Jul. 2, 2015

Related U.S. Application Data

(63) Continuation of application No. 13/579,009, filed as application No. PCT/US2011/025106 on Feb. 16, 2011, now Pat. No. 9,108,944.

(60) Provisional application No. 61/305,082, filed on Feb. 16, 2010, provisional application No. 61/329,023, filed on Apr. 28, 2010, provisional application No. 61/388,457, filed on Sep. 30, 2010.

(51) Int. Cl.
| | |
|---|---|
| *A61K 31/4439* | (2006.01) |
| *C07D 401/04* | (2006.01) |
| *C07D 487/04* | (2006.01) |
| *C07D 471/04* | (2006.01) |
| *C07D 401/14* | (2006.01) |
| *C07D 405/14* | (2006.01) |
| *A61K 31/444* | (2006.01) |
| *A61K 31/4545* | (2006.01) |
| *A61K 31/496* | (2006.01) |
| *A61K 31/497* | (2006.01) |
| *A61K 31/5025* | (2006.01) |
| *A61K 31/513* | (2006.01) |
| *A61K 45/06* | (2006.01) |

(52) U.S. Cl.
CPC ........... *C07D 401/04* (2013.01); *A61K 31/444* (2013.01); *A61K 31/4439* (2013.01); *A61K 31/4545* (2013.01); *A61K 31/496* (2013.01); *A61K 31/497* (2013.01); *A61K 31/5025* (2013.01); *A61K 31/513* (2013.01); *A61K 45/06* (2013.01); *C07D 401/14* (2013.01); *C07D 405/14* (2013.01); *C07D 471/04* (2013.01); *C07D 487/04* (2013.01)

(58) Field of Classification Search
CPC .......................... C07D 401/04; A61K 31/4439

USPC ............................................ 546/15; 514/278
See application file for complete search history.

(56) References Cited

U.S. PATENT DOCUMENTS

| | | |
|---|---|---|
| 3,823,240 A | 7/1974 | Sauli |
| 3,984,430 A | 10/1976 | Curran |
| 4,097,578 A | 6/1978 | Perronnet et al. |
| 4,229,447 A | 10/1980 | Porter |
| 4,234,736 A | 11/1980 | Bernauer et al. |
| 4,304,782 A | 12/1981 | Dumont et al. |
| 4,312,881 A | 1/1982 | Wootton |
| 4,399,216 A | 8/1983 | Axel et al. |
| 4,407,814 A | 10/1983 | Bernauer et al. |
| 4,427,438 A | 1/1984 | Nagano et al. |
| 4,473,393 A | 9/1984 | Nagpal |
| 4,482,739 A | 11/1984 | Bernauer et al. |
| 4,559,157 A | 12/1985 | Smith et al. |
| 4,596,795 A | 6/1986 | Pitha |
| 4,608,392 A | 8/1986 | Jacquet et al. |
| 4,749,403 A | 6/1988 | Liebl et al. |
| 4,755,386 A | 7/1988 | Hsiao et al. |
| 4,820,508 A | 4/1989 | Wortzman |
| 4,859,228 A | 8/1989 | Prisbylla |
| 4,873,256 A | 10/1989 | Coussediere et al. |
| 4,938,949 A | 7/1990 | Borch et al. |
| 4,944,791 A | 7/1990 | Schroder et al. |
| 4,992,478 A | 2/1991 | Geria |
| 5,010,182 A | 4/1991 | Brake et al. |
| 5,011,692 A | 4/1991 | Fujioka et al. |
| 5,017,381 A | 5/1991 | Maruyama et al. |

(Continued)

FOREIGN PATENT DOCUMENTS

| | | |
|---|---|---|
| AU | 217893 | 6/1958 |
| CN | 101032483 | 9/2007 |

(Continued)

OTHER PUBLICATIONS

LeRoith et al., The insulin-like growth factor system and cancer, Cancer Letters, 195, pp. 127-137 (2003).*

(Continued)

*Primary Examiner* — Patricia L Morris
(74) *Attorney, Agent, or Firm* — Baker & Hostetler LLP

(57) ABSTRACT

Described herein are compounds that are androgen receptor modulators. Also described are pharmaceutical compositions and medicaments that include the compounds described herein, as well as methods of using such androgen receptor modulators, alone and in combination with other compounds, for treating diseases or conditions that are mediated or dependent upon androgen receptors.

42 Claims, No Drawings

(56) References Cited

U.S. PATENT DOCUMENTS

| | | | |
|---|---|---|---|
| 5,033,252 | A | 7/1991 | Carter |
| 5,052,558 | A | 10/1991 | Carter |
| 5,069,711 | A | 12/1991 | Fischer et al. |
| 5,071,773 | A | 12/1991 | Evans et al. |
| 5,166,358 | A | 11/1992 | Seuron et al. |
| 5,229,135 | A | 7/1993 | Philippon et al. |
| 5,323,907 | A | 6/1994 | Kalvelage |
| 5,411,981 | A | 5/1995 | Gaillard-Kelly et al. |
| 5,434,176 | A | 7/1995 | Claussner et al. |
| 5,554,607 | A | 9/1996 | Elokdah et al. |
| 5,556,983 | A | 9/1996 | Claussner et al. |
| 5,589,497 | A | 12/1996 | Claussner et al. |
| 5,614,620 | A | 3/1997 | Liao et al. |
| 5,627,201 | A | 5/1997 | Gaillard-Kelly et al. |
| 5,646,172 | A | 7/1997 | Claussner et al. |
| 5,656,651 | A | 8/1997 | Sovak et al. |
| 5,705,654 | A | 1/1998 | Claussner et al. |
| 5,726,061 | A | 3/1998 | Robbins et al. |
| 5,739,136 | A | 4/1998 | Ellinwood, Jr. et al. |
| 5,750,553 | A | 5/1998 | Claussner et al. |
| 5,783,707 | A | 7/1998 | Elokdah et al. |
| RE35,956 | E | 11/1998 | Gaillard-Kelly et al. |
| 5,837,284 | A | 11/1998 | Mehta et al. |
| 5,840,329 | A | 11/1998 | Bai |
| 5,958,936 | A | 9/1999 | Claussner et al. |
| 5,968,875 | A | 10/1999 | Bis et al. |
| 5,985,868 | A | 11/1999 | Gray |
| 6,107,488 | A | 8/2000 | Bouchet et al. |
| 6,172,076 | B1 | 1/2001 | Embrey et al. |
| 6,235,910 | B1 | 5/2001 | Beller et al. |
| 6,242,611 | B1 | 6/2001 | Claussner et al. |
| 6,307,030 | B1 | 10/2001 | French et al. |
| 6,350,763 | B1 | 2/2002 | Kelly et al. |
| 6,472,415 | B1 | 10/2002 | Sovak et al. |
| 6,479,063 | B2 | 11/2002 | Weisman et al. |
| 6,489,163 | B1 | 12/2002 | Roy et al. |
| 6,506,607 | B1 | 1/2003 | Shyjan |
| 6,710,037 | B2 | 3/2004 | Wang et al. |
| 6,828,471 | B2 | 12/2004 | Sawyers et al. |
| 7,271,188 | B2 | 9/2007 | Tachibana et al. |
| 8,445,507 | B2 | 5/2013 | Jung et al. |
| 8,461,343 | B2 | 6/2013 | Ouerfelli et al. |
| 8,470,829 | B2 | 6/2013 | Tachibana et al. |
| 8,802,689 | B2 | 8/2014 | Jung et al. |
| 8,987,452 | B2 | 3/2015 | Ouerfelli et al. |
| 9,108,944 | B2 * | 8/2015 | Smith ............... C07D 401/04 |
| 2002/0133833 | A1 | 9/2002 | Sawyers et al. |
| 2003/0225138 | A1 | 12/2003 | Sircar et al. |
| 2004/0009969 | A1 | 1/2004 | Cleve et al. |
| 2004/0077605 | A1 | 4/2004 | Salvati et al. |
| 2004/0116417 | A1 | 6/2004 | Boubia et al. |
| 2005/0153968 | A1 | 7/2005 | Bi et al. |
| 2006/0025589 | A1 | 2/2006 | Binet et al. |
| 2006/0127092 | A1 | 6/2006 | Madden et al. |
| 2007/0249697 | A1 | 10/2007 | Tachibana et al. |
| 2011/0003839 | A1 | 1/2011 | Jung et al. |
| 2013/0045204 | A1 | 2/2013 | Andersen et al. |
| 2013/0072511 | A1 | 3/2013 | Jung et al. |
| 2013/0079241 | A1 | 3/2013 | Luo et al. |
| 2013/0225821 | A1 | 8/2013 | Ouerfelli et al. |
| 2013/0253035 | A1 | 9/2013 | McDonnell et al. |
| 2014/0088129 | A1 | 3/2014 | Chen |
| 2014/0199236 | A1 | 7/2014 | Chen et al. |
| 2014/0309262 | A1 | 10/2014 | Jung et al. |

FOREIGN PATENT DOCUMENTS

| | | |
|---|---|---|
| DE | 2102605 | 7/1971 |
| DE | 2614831 | 10/1977 |
| EP | 0017976 | 10/1980 |
| EP | 0002259 | 10/1984 |
| EP | 0144098 | 6/1985 |
| EP | 0331232 | 9/1989 |
| EP | 0362179 | 4/1990 |
| EP | 0494819 | 1/1992 |
| EP | 0572191 | 12/1993 |
| EP | 0578516 | 1/1994 |
| EP | 0580459 | 1/1994 |
| EP | 0770613 | 5/1997 |
| EP | 0721944 | 1/2001 |
| EP | 1632477 | 3/2006 |
| EP | 1790640 | 5/2007 |
| FR | 2693461 | 1/1994 |
| FR | 2715402 | 7/1995 |
| FR | 2845384 | 4/2004 |
| JP | 59210083 | 11/1984 |
| JP | 1009978 | 1/1989 |
| JP | 0219363 | 1/1990 |
| JP | 2006/510600 | 3/2006 |
| WO | WO 90/13646 | 11/1990 |
| WO | WO 97/00071 | 1/1997 |
| WO | WO 97/19064 | 5/1997 |
| WO | WO 97/19931 | 6/1997 |
| WO | WO 00/17163 | 3/2000 |
| WO | WO 00/26195 | 5/2000 |
| WO | WO 00/44731 | 8/2000 |
| WO | WO 01/07048 | 2/2001 |
| WO | WO 01/92253 | 12/2001 |
| WO | WO 01/94346 | 12/2001 |
| WO | WO 02/053155 | 7/2002 |
| WO | WO 02/081453 | 10/2002 |
| WO | WO 03/029245 | 4/2003 |
| WO | WO 03/032994 | 4/2003 |
| WO | WO 03/057220 | 7/2003 |
| WO | WO 03/093243 | 11/2003 |
| WO | WO 03/096980 | 11/2003 |
| WO | WO 2004/022572 | 3/2004 |
| WO | WO 2004/031160 | 4/2004 |
| WO | WO 2004/070050 | 8/2004 |
| WO | WO 2004/111031 | 12/2004 |
| WO | WO 2005/042488 | 5/2005 |
| WO | WO 2005/059109 | 6/2005 |
| WO | WO 2005/060661 | 7/2005 |
| WO | WO 2005/089752 | 9/2005 |
| WO | WO 2005/099693 | 10/2005 |
| WO | WO 2006/010642 | 2/2006 |
| WO | WO 2006/028226 | 3/2006 |
| WO | WO 2006/124118 | 11/2006 |
| WO | WO 2007/012661 | 2/2007 |
| WO | WO 2007/045877 | 4/2007 |
| WO | WO 2007/126765 | 11/2007 |
| WO | WO 2007/127010 | 11/2007 |
| WO | WO 2008/119015 | 10/2008 |
| WO | WO 2009/055053 | 4/2009 |
| WO | WO 2010/099238 | 9/2010 |
| WO | WO 2011/103202 A2 | 8/2011 |
| WO | WO 2011/106570 | 9/2011 |
| WO | WO 2012/158884 | 11/2012 |
| WO | WO 2013/079964 | 6/2013 |

OTHER PUBLICATIONS

Simone, Oncology:Introduction, Cecil Textbook of Medicine, ed Bennett et al. W.B.Saunders CO. 20th ed, vol. 1, 1996, pp. 1004-1010.*

Gura, Systems for identifying New Drugs Are Often Faulty, Cancer Models, Science, vol. 278, No. 5340, pp. 1041-1042, Nov. 1997.*

Johnson et al., Relationships between drug activity in NCI preclinical in vitro and in vivo models and early clinical trials, British Journal of Cancer (2001) 64(10): 1424-1431.*

Lodish et al., "Endocrine side, etc.," Endocrine-Related Cancer (2010) 17, R233-R244.*

Ouaissi et al., "Rationale for Possible, etc.," Journal of Biomedicine and Biotechnology, 2011, Article: ID 315939, 1-8.*

Golub et al, Science, vol. 286, Oct. 15, 1999, pp. 531-537.*

"ARN-509 Update: Phase I Study—Prostrate Cancer", HealingWell.com, 2014, 3 pages.

"Hormonal Treatments for Uterine Fibroids", Hormone Therapy for Fibroids, 2012, http://www.uterine-fibroids.org/Hormonal_Treatments.html, 2 pages.

"Prostate-Specific Antigen (PSA) Test", National Cancer Institute, 2012, 6 pages.

(56) References Cited

OTHER PUBLICATIONS

Auricchio et al., "VAL 201—An Inhibitor of Androgen Receptor-associated Src and a Potential Treatment of Castration-resistant Prostate Cancer", European Oncology & Haematology, 2012, vol. 8, No. 1, 32-35.
Ausubel et al., "Current Protocols in Molecular Biology", Wiley Interscience Publishers, 1995, 2, 18 pages.
Baek et al., "Exchange of N-CoR Corepressor and Tip60 Coactivator Complexes Links Gene Expression by NF-kappaB and Beta-Amyloid Precursor Protein", Cell, 2002, 110, 55-67.
Balk, "Androgen Receptor as a Target in Androgen-Independent Prostate Cancer", Urology, 2002, 60(3A), 132-138.
Batch et al., "Androgen Receptor Gene Mutations Identified by SSCP in Fourteen Subjects with Androgen Insensitivity Syndrome", Hum. Mol. Genet., 1992, 1(7), 497-503.
Bohl et al., "Structural Basis for Antagonism and Resistance of Bicalutamide in Prostate Cancer", Proc. Nat. Acad. Sci., 2005, 102(17), 6201-6206.
Brockschmidt et al., "The Two Most Common Alleles of the Coding GGN Repeat in the Androgen Receptor Gene Cause Differences in Protein Function", J. Mol. Endocrinol., 2007, 39, 1-8.
Bundgaard, "Design of Application of Prodrugs", Harwood Academic Publishers, 1991, Chapter 5, 113-191.
Burnstein et al., "Androgen Glucocorticoid Regulation of Androgen Receptor eDNA Expression", Molecular and Cellular Endocrinology, 1995, 115, 177-186.
Butler, "Mammalian Cell Biotechnology: A Practical Approach", 1991, 6 pages.
Cai et al., "c-Jun Has Multiple Enhancing Activities in the Novel Cross Talk Between the Androgen Receptor and ETS Variant Gene 1 in Prostate Cancer", Mol. Cancer Res., 2007, 5(7), 725-735.
Carver et al., "Reciprocal Feedback Regulation of P13K and Androgen Receptor Signaling in PTEN-Deficient Prostate Cancer", Cancer Cell., 2011, 19, 575-586.
Chang et al., "Molecular Cloning of Human and Rat Complementary DNA Encoding Androgen Receptors", Science, 1988, 240, 324-326.
Chen et al., "Molecular Determinants of Resistance to Antiandrogen Therapy", Nature Medicine, 2004, 10(1), 33-39.
Chobanian et al., "A Facile Microwave-Assisted Palladium-Catalyzed Cyanation of Aryl Chlorides", Tetrahed Lett., 2006, 47(19), 3303-3035.
Cinar et al. "Androgen Receptor Mediates the Reduced Tumor Growth, Enhanced Androgen Responsiveness, and Selected Target Gene Transactivation in Human Prostate Cancer Cell Line", Cancer Research, 2001, 61, 7310-7317.
Clegg et al., "ARN509: A Novel Antiandrogen for Prostate Cancer Treatment", Cancer Research, 2012, 72(6), 1494-1503.
Cook et al., "Development of GnRH Antagonists for Prostate Cancer: New Approaches to Treatment", The Oncologist, 2000, 5, 162-168.
Cousty-Berlin, et al., "Preliminary Pharmacokinetics and Metabolism of Novel Non-steroidal Antiandrogens in the Rat: Relation of their Systemic Activity to the Formation of a Common Metabolite", J. Steroid Biochem. Molecular Bio., 1994, 51(1/2), 47-55.
Craft et al., "A Mechanism for Hormone-Independent Prostate Cancer Through Modulation of Androgen Receptor Signaling by the HER-2/Neu Tyrosine Kinase", Nature Medicine, 1999, 5(3), 280-285.
Craft et al., "Evidence for Clonal Outgrowth of Androgen-Independent Prostate Cancer Cells from Androgen-Dependent Tumors Through a Two-Step Process", Cancer Res, 1999, 59,5030-5036.
Creaven et al., "Pharmacokinetics and Metabolism of Nilutamide", Supp. Urology, 1991, 37(2), 13-19.
Depalo et al., "GnRH agonist versus GnRH antagonist in in vitro fertilization and embryo transfer (IVF/ET)", Reproductive Biology and Endocrinology, 2012, 10, 26-33.
DePrimo et al. "Transcriptional Programs Activated by Exposure of Human Prostate Cancer Cells to Androgen", Genome Biology, 2002, 3(7), 1-12.
Dhal et al., "Synthesis of Thiohydantoins, Thiazolidones and their Derivatives from N1-(4'-aryl thiazole 2'-Yl) Thioureas", J. Indian Chem. Soc., 1973, 50(1), 680-684.
Edwards et al., "Androgen Receptor Gene Amplification and Protein Expression in Hormone Refractory Prostate Cancer", British Journal of Cancer, 2003, 89, 552-556.
Ellis et al., "Characterization of a Novel Androgen-Sensitive, Prostate-Specific Antigen-Producing Prostatic Carcinoma Xenograft: LuCaP 23", Clin Cancer Res, 1996, 2, 1039-1048.
Ellwood-Yen et al., "Myc-Driven Murine Prostate Cancer Shares Molecular Features with Human Prostate Tumors", Cancer Cell, 2003, 4(3), 223-238.
Elokdah et al., "Design, Synthesis, and Biological Evaluation of Thio-Containing Compounds with Serum HDL-Cholesterol-Elevating Properties", J. Med. Chem., 2004, 47(3), 681-695.
Feher et al., "BHB: A Simple Knowledge-Based Scoring Function to Improve the C95 Efficiency of Database Screening", J. Chem. Inf. Comput. Sci., 2003, 43(4), 1316-1327.
Feldman et al., "The Development of Androgen-Independent Prostate Cancer", Nature Reviews Cancer, 2001, 1, 34-45.
Foks et al., "Synthesis, Fungicidal and Antibacterial Activity of New Pyridazine Derivatives", Heterocycles, 2009, 78, 961-975.
Font de Mora et al., "AIB1 is a Conduit for Kinase-Mediated Growth Factor Signaling to the Estrogen Receptor", Mol. Cell. Biol., 2000, 20(14), 5041-5047.
Foury et al., "Control of the Proliferation of Prostate Cancer Cells by an Androgen and Two Antiandrogens. Cell Specific Sets of Responses", J. Steroid Biochem. Molec. Bioi., 1998, 66(4), 235-240.
Gelmann, "Molecular Biology of the Androgen Receptor", J. Clin. Oncol., 2002, 20, 3001-3015.
Gioeli et al., "Androgen Receptor Phosphorylation Regulation and Identification of the Phosphorylation Sites", J Biol Chem, 2002, 277(32), 29304-29314.
Glass et al., "The Coregulator Exchange on Transcriptional Functions of Nuclear Receptors", Genes Dev., 2000, 14, 121-141.
Goubet et al., "Conversion of a Thiohydantoin to the Corresponding Hydantoin via a Ring-Opening/Ring Closure Mechanism", Tetrahedon Letters, 1996, 37(43), 7727-7730.
Grad et al., "Multiple Androgen Response Elements and a Myc Consensus Site in the Androgen Receptor (AR) Coding Region are Involved in Androgen-Mediated Up-Regulation of AR Messenger RNA", Mol Endocrinol, 1999, 13, 1896-1911.
Graham et al., "A New Technique for the Assay of Infectivity of Human Adenovirus 5 DNA", Virology, 1973, 52, 456-467.
Gregory et al., "A Mechanism for Androgen Receptor-Mediated Prostate Cancer Recurrence After Androgen Deprivation Therapy", Cancer Res., 2001, 61, 4315-4319.
Gregory et al., "Androgen Receptor Stabilization in Recurrent Prostate Cancer is Associated with Hypersensitivity to Low Androgen", Cancer Res, 2001, 61, 2892-2898.
Hamilton-Reeves et al, "Isoflavone-Rich Soy Protein Isolate Suppresses Androgen Receptor Expression Without Altering Estrogen Receptor-Beta Expression or Serum Hormonal Profiles in Men at High Risk of Prostate Cancer", J. Nutr., 2007, 137, 1769-1775.
Heath et al., "A Phase I Dose-Escalation Study of Oral BR-DIM (Bioresponse 3.3 Diindolylmethane) in Castrate-Resistant, Non-Metastatic Prostate Cancer", American Journal of Translational Research, 2010, 2(4), 402-411.
Higuchi et al., "Pro-Drugs as Novel Delivery Systems", 1975, vol. 14 of the A.C.S. Symposium Series, 6 pages.
Holzbeierlein et al., "Gene Expression Analysis of Human Prostate Carcinoma During Hormonal Therapy Identifies Androgen-Responsive Genes and Mechanisms of Therapy Resistance", Am. J. Pathology, 2004, 164(1), 217-227.
Homma et al., "Differential Levels of Human Leukocyte Antigen-Class I, Multidrugresistance 1 and Androgen Receptor Expressions in Untreated Prostate Cancer Cells: The Robustness of Prostate Cancer", Oncol. Rep., 2007, 18, 343-346.
Horoszewicz et al., "LNCaP Model of Human Prostatic Carcinoma", Cancer Res., 1983, 43, 1809-1818.
Huang et al., "AR Possess an Intrinsic Hormone-Independent Transcriptional Activity", Mol Endocrinol., 2002, 16(5), 924-937.

(56) References Cited

OTHER PUBLICATIONS

Jones, "Proteinase Mutants of Saccharomyces Cerevisae", Genetics, 1977, 85, 23-33.
Kagabu, "Methyl, Trifluoromethyl, and Methoxycarbonyl—Introduction to the Fifth Position on the Pyridine Ring of Chloronicotinyl Insecticide Imidacloprid", Synth Comm. 2006, 36(9), 1235-1245.
Karp et al., Prostate Cancer Prevention: Investigational Approaches and Opportunities, Cancer Res., 1996, 56, 5547-5556.
Karvonen et al., "Interaction of Androgen Receptors with Androgen Response Element in Intact Cells", The Journal of Biological Chemistry, 1997, 272(25), 15973-15979.
Kato et al., "Activation of the Estrogen Receptor through Phosphorylation by Mitogenactivated Protein Kinase", Science, 1995, 270, 1491-1494.
Kawai et al., "Site-Specific Fluorescent Labeling Of RnA Molecules By Specific Transcription Using Unnatural Base Pairs", J. Am Chem. Soc., 2005, 127(49), 17286-17295.
Kemppainen et al., "Distinguishing Androgen Receptor Agonists and Antagonists: Distinct Mechanisms of Activation by Medroxyprogesterone Acetate and Dihydrotestosterone", Mol. Endocrinol., 1999, 13, 440-454.
Keown et al., "Methods for Introducing DNA Into Mammalian Cells", Methods in Enzymology, 1990, 185, 527-537.
Kingsman et al., "Replication in *Saccharomyces Cerevisiae* of Plasmid pBR313 Carrying DNA from the Yeast trpl REGION", Gene, 1979, 7, 141-152.
Kinoshita et al., "Methylation of the Androgen Receptor Minimal Promoter Silences Transcription in Human Prostate Cancer", Cancer Res, 2000, 60, 3623-3630.
Klein et al., "Progression of Metastatic Human Prostate Cancer to Androgen Independence in Immunodeficient SCID Mice", Nat Med, 1997, 3(4), 402-408.
Kliment, "Re: Salvage Therapy with Bicalutamide 150 mg in Nonmetastatic Castration-Resistant Prostate Cancer", European Urology, 2011, 59(6), 1066-1067.
Kousteni et al., "Nongenotropic, Sex-Nonspecific Signaling through the Estrogen or Androgen Receptors: Dissociation from Transcriptional Activity", Cell, 2001, 104, 719-730.
Kuethe et al., "Synthesis of Disubstituted Imidazo[4,5-b]pyridin-2-ones", J. Org. Chem., 2004, 29, 69(22), 7752-7754.
Laitinen et al., "Chromosomal Aberrations in Prostate Cancer Xenografts Detected by Comparative Genomic Hybridization", Genes Chromosomes Cancer, 2002, 35, 66-73.
Li et al., "Heterogeneous Expression and Functions of Androgen Receptor Co-Factors in Primary Prostate Cancer", Am J Pathol, 2002, 161(4), 1467-1474.
Linja et al., "Amplification and Overexpression of Androgen Receptor Gene in Hormone-Refractory Prostate Cancer", Cancer Research, 2001, 61, 3550-3555.
Lobaccaro et al., "Molecular Modeling and in Vitro Investigations of the Human Androgen Receptor DNA-Binding Domain: Application for the Study of Two Mutations", Mol. Cell. Endocrinol., 1996, 116, 137-147.
Lu et al., "Molecular Mechanisms of Androgen-Independent Growth of Human Prostate Cancer LNCaP-Al Cells", Endocrinol., 1999, 140(11), 5054-5059.
Manolagas et al., "Sex Steroids and Bone", Recent Prog Harm Res, 2002, 57, 385-409.
Mansour et al., "Disruption of the Proto-Oncogene int-2 in Mouse Embryo-Derived Stem Cells: A General Strategy for Targeting Mutations to Non-Selectable Genes", Nature, 1988, 336, 348-352.
Marhefka et al., "Homology Modeling Using Multiple Molecular Dynamics Simulations and Docking Studies of the Human Androgen Receptor Ligand Binding Domain Bound to Testosterone and Nonsteroidal Ligands", J. Med. Chem., 2001, 44(11), 1729-1740.
Masiello et al., "Bicalutamide Functions as an Androgen Receptor Antagonist by Assembly of a Transcriptionally Inactive Receptor", J Biol Chem, 2002, 277(29), 26321-26326.
Matias et al., "Local Inhibition of Sebaceous Gland Growth by Topically Applied RU 58841", NY Acad. Sci., 1995, 761, 56-65.
Matias et al., "Structural Basis for the Glucocorticoid Response in a Mutant Human Androgen Receptor (AR(ccr)) Derived from an Androgen-Independent Prostate Cancer", J Med Chem, 2002, 45, 1439-1446.
Matias et al., "Structural Evidence for Ligand Specificity in the Binding Domain of the Human Androgen Receptor: Implications for Pathogenic Gene Mutations", J Biol Chem, 2000, 275(34), 26164-26171.
McDonnell et al., "Expression of the Protooncogene bcl-2 in the Prostate and its Association with Emergence of Androgen-Independent Prostate Cancer", Cancer Res, 1992, 52, 6940-6944.
Migliaccio et al., "Steroid-Induced Androgen Receptor-Oestradiol Receptor beta-SRC Complex Triggers Prostate Cancer Cell Proliferation", Embo J, 2000, 19(20), 5406-5417.
Mulholland et al., "Cell Autonomous Role of PTEN in Regulating Castration-Resistant Prostate Cancer Growth", Cancer Cell., 2011, 19, 792-804.
Muller et al., "BCR First Exon Sequences Specifically Activate the BCRIABL Tyrosine Kinase Oncogene of Philadelphia ChromosomePositive Human Leukemias", Mol. & Cell, Biol., 1991, 11(4), 1785-1792.
Naik et al., "Synthesis, Spectroscopic and Thermal Studies of Bivalent Transition Metal Complexes with the Hydrazone Derived from 2-Benzimidazolyl Mercaptoaceto Hydrazile and o-Hydroxy Aromatic Aldehyde", Indian Journal of Chemistry, 2008, 1793-1797.
Nam et al., "Action of the Src Family Kinase Inhibitor, Dasatinib (BMS-354825), on Human Prostate Cancer Cells", Cancer Res., 2005, 65(20), 9185-9189.
Navone et al., "Model Systems of Prostate Cancer: Uses and Limitations", Cancer Metastasis, 1999, 17, 361-371.
NCBI, "Definition: Homo Sapiens Androgen", Nucleotide, 2007, 7 pages NM_000044<http://www.ncbi.nlm.nih.gov:80/entrez/viewer.fcgi?cmd=Retrieve&db=nucleotide&list_u ids=21322251 &dopt=Gen Ban k&term=sapiens+AR+androgen+receptor+prostate+cancer&qty=1>gi:21322251.
Norris et al. "Peptide Antagonists of the Human Estrogen Receptor", Science, 1999, 285, 744-746.
Ouk et al., "Development of Androgen Receptor Inhibitors For Hormone-Refractory Prostate Cancer", Prostate Cancer Foundation Meeting, Scottsdale, AZ, Sep. 29-Oct. 1, 2005, 1 page.
Perou et al., "Molecular Portraits of Human Breast Tumors", Nature, 2000, 406, 747-752.
Raffo et al., "Overexpression of bcl-2 Protects Prostate Cancer Cells from Apoptosis in Vitro and Confers Resistance to Androgen Depletion in Vivo", Cancer Research, 1995, 55, 4438-4445.
Rathkopf et al., "A First-In-Human. Open-Label. Phase 1/11 Safety. Pharmacokinetic and Proof-of-Concept Study of ARN-509 in Patients with Progressive Advanced Castration-Resistant Prostate Cancer (CRPC )", J. of Clin. Oncol.; ASCO Annual Meeting, 2011, 29(15), 2 pages.
Rathkopf et al., "A Phase I Study of the Androgen Signaling Inhibitor ARN-509 in Patients with Metastatic Castration-Resistant Prostate Cancer (mCRPC)", J. Clin. Oncol., 2012, 2 pages.
ReaganShaw et al, "Dose Translation from Animal to Human Studies Revisited", 2007, 22, 659-661.
Remington: Practice of The Science and Pharmacy, 19th Edition, Table of Contents, Gennaro (ed.), 1995, Mack Publishing Company, Easton, PA, 5 pages.
Rooseboom et al., "Enzyme-Catalyzed Activation of Anticancer Prodrugs", Pharmacological Reviews, 2004, 56, 53-102;.
Sack et al., "Crystallographic Structures of the Ligand-Binding Domains of the Androgen Receptor and its T877A Mutant Complexed with the Natural Agonist Dihydrotestosterone", Proc Natl Acad Sci, 2001, 98(9), 4904-4909.
Sambrook et al., "Molecular Cloning: A Laboratory Manual", $2^{nd}$ Edition, Table of Contents, Cold Spring Harbor Laboratory Press, Cold Spring Harbor, 1989, 30 pages.
Saunders et al., "Point Mutations Detected in the Androgen Receptor Gene of Three Men with Partial Androgen Insensitivity Syndrome", Clin. Endocrinol., 1992, 37, 214220.

(56) References Cited

OTHER PUBLICATIONS

Schellhammer et al., "Prostate Specific Antigen Decreases after Withdrawal of Antiandrogen Therapy with Bicalutamide or Flutamide in Patients Receiving Combined Androgen Blockade", J Urol, 1997, 157, 1731-1735.
Scher et al., "The Flutamide Withdrawal Syndrome: Its Impact on Clinical Trials in Hormone-Refractory Prostatic Cancer", J Clin Oncol 1993, 11, 1566-1572.
Sderholm et al., "Three-Dimensional Structure-Activity Relationships of Nonsteroidal Ligands in Complex with Androgen Receptor Ligand-Binding Domain," J. Med. Chem., 2005, 48(4), 917-925.
Shang et al., "Formation of the Androgen Receptor Transcription Complex", Mol Cell, 2002, 9, 601-610.
Shang et al., "Molecular Determinants for the Tissue Specificity of SERMs", Science, 2002, 295, 2465-2468.
Shi et al., "Functional Analysis of 44 Mutant Androgen Receptors from Human Prostate Cancer", Can Res, 2002, 62(5), 1496-1502.
Shiau et al., "The Structural Basis of Estrogen Receptor/Coactivator Recognition and the Antagonism of this Interaction by Tamoxifen", Cell, 1998, 95, 927-937.
Singh et al., "Androgen Receptor Antagonists (Antiandrogens): Structure-Activity Relationships", Current Medicinal Chemistry, 2000, 7, 211-247.
Smith et al., "ARN-509 in Men with High Risk Non-Metastatic Castration-Resistant Prostate Cancer", Annals of Oncology; Abstract Book of the 37th ESMO Congress, 2012, 23(9), No. Suppl. 9, 1 page.
Smith et al., "ARN-509 in Men with High Risk Non-Metastatic Castration-Resistant Prostate Cancer", European Journal of Cancer; European Cancer Congress, 2013, 49(2), 1 page.
Soto et al., "Control of Cell Proliferation: Evidence for Negative Control on C141 Estrogen-Sensitive T47D Human Breast Cancer Cells", Cancer Research, 1986, 46, 2271-2275.
Sperry et al., Androgen Binding Profiles of Two Distinct Nuclear Androgen Receptors in Atlantic Croaker (Micropogonias Undulates), Journal of Steroid Biochemistry & Molecular Biology, 2000, 73, 93-103.
Stinchcomb et al., "Isolation and Characterisation of a Yeast Chromosomal Replicator", 1979, 282, 39-43.
Su et al., "Polymorphisms of Androgen Receptor Gene in Childhood and Adolescent Males with First-Onset Major Depressive Disorder and Association with Related Symptomatology", Int. J. Neurosci., 2007, 117, 903-917.
Sweet et al., "A Unique Point Mutation in the Androgen Receptor Gene in a Family with Complete Androgen Insensitivity Syndrome", Fertil. Steril., 1992, 58(4), 703-707.
Szelei et al., "Androgen-Induced Inhibition of Proliferation in Human Breast Cancer MCF7 C138b Cells Transfected with Androgen Receptor", Endocrinology, 1997, 138(4), 1406-1412.
Takemoto et al., "Novel Pottasium Chanel Openers: Synthesis and Pharmacological Evaluation of New N-(substituted-3-pyridyl)-N'-alkylthioureas and Related Compounds", J Med. Chem., 1994, 37(1), 18-25.
Taplin et al. "Selection for Androgen Receptor Mutations in Prostate Cancers Treated with Androgen Antagonist", Cancer Res, 1999, 59, 2511-2555.
Taplin et al., "Androgen Receptor Mutations in Androgen-Independent Prostate Cancer: Cancer and Leukemia Group B Study 9663", J Clin Oncol, 2003, 21, 2673-2678.
Taplin et al., "Mutation of the Androgen-Receptor Gene in Metastatic Androgen Independent Prostate Cancer", N. Engl J Med, 1995, 332(21), 1393-1398.
Teutsch et al., "Non-steroidal Antiandrogens: Synthesis and Biological Profile of High-affinity Ligands for the Androgen Receptor", J. Steroid Biochem. Mol. Biol., 1994, 48,111-119.
Tran et al., "Development of a Second-Generation Antiandrogen for Treatment of Advanced Prostate Cancer", Science, 2009, 324(5928), 787-790.
Tremblay et al., "Ligand-Independent Recruitment of SRC-1 to Estrogen Receptor Beta through Phosphorylation of Activation Function AF-1", Mol Cell, 1999, 3, 513-519.
Tschumper et al., "Sequence of a Yeast DNA Fragment Containing a Chromosomal Replicator and the TRP1 Gene", Gene, 1980, 10, 157-166.
Urlaub et al., "Isolation of Chinese Hamster Cell Mutants Deficient in Dihydrofolate Reductase Activity", Proc. Natl. Acad. Sci. USA, 1980, 77(7), 4216-4220.
Van Dort et al., "Design, Synthesis, and Pharmacological Characterization of 4-[4,4-Dimethyl-3-(4-hydroxybutyl)-5-oxo-2-thioxo-1-imidazolidinyl]-2-iodobenzonitrile as a High-Affinity Nonsteroidal Androgen Receptor Ligand", J. Med. Chem., 2000, 43, 3344-3347.
Veldscholte et al., "A Mutation in the Ligand Binding Domain Of The Androgen Receptor of Human LNCaP Cells Affects Steroid Binding Characteristics and Response to Antiandrogens", Biochem Biophys Res Commun, 1990, 173, 534-540.
Visakorpi et al., "In Vivo Amplification of the Androgen Receptor Gene and Progression of Human Prostate Cancer", Nat Genetics, 1995, 9, 401-406.
Wainstein et al., "CWR22: Androgen-Dependent Xenograft Model Derived from a Primary Human Prostatic Carcinoma", Cancer Res, 1994, 54, 6049-6052.
Wallen et al., "Androgen Receptor Gene Mutations in Hormone-Refractory Prostate Cancer", J. Pathology, 1999, 189, 559-563.
Wang et al., "Overexpressed Androgen Receptor Linked to p21WAF1 Silencing May Be Responsible for Androgen Independence and Resistance to Apoptosis of a Prostate Cancer Cell Line", Cancer Research, 2001, 61(20), 7544-7551.
Wang et al., "Prostate-Specific Deletion of the Murine Pten Tumor Suppressor Gene Leads to Metastatic Prostate Cancer", Cancer Cell, 2003, 4, 209-221.
Wermuth et al., "Designing Prodrugs and Bioprecursors, I: Carrier Prodrugs", The Pharmacological Basis of Therapeutics, The Practice of Medicinal Chemistry, Goodman and Gilman, eds., Macmillan Publishing Co., New York, Chapter 31, 1996, 28 pages.
Wermuth, "Molecular Variations Based on Isosteric Replacements", The Practice of Medicinal Chemistry, 1996, 13, 203-237.
Wooster et al., "A Germline Mutation in the Androgen Receptor Gene in Two Brothers with Breast Cancer and Reifenstein Syndrome", Nat. Genet., 1992, 2, 132-134.
Zakikhani et al., "Metformin is an AMP Kinase-Dependent Growth Inhibitor for Breast Cancer Cells", Cancer Res, 2006, 66(21), 10269-10273.
Zarghami et al., "Steroid Hormone Regulation of Prostate-Specific Antigen Gene Expression in Breast Cancer", British Journal of Cancer, 1997, 75(4), 579-588.
Zhau et al., "Androgen-Repressed Phenotype in Human Prostate Cancer", Proc Natl Acad Sci USA, 1996, 93,15152-15157.
Zhou et al., "A Ligand-Dependent Bipartite Nuclear Targeting Signal in the Human Androgen Receptor, Requirement for the DNA-Binding Domain and Modulation by NH2-Terminal and Carboxyl-Terminal Sequences", J Bio Chem, 1994, 269(18), 13115-13123.
Zoppi et al., "Amino Acid Substitutions in the DNA-Binding Domain of the Human Androgen Receptor are a Frequent Cause of Receptor-Binding Positive Androgen Resistance", Mol. Endo., 1992, 6, 409-415.

* cited by examiner

ANDROGEN RECEPTOR MODULATORS AND USES THEREOF

RELATED APPLICATIONS

This application is a continuation of U.S. patent application Ser. No. 13/579,009, filed on Aug. 30, 2012, which is the National Stage Entry of International Application No. PCT/US2011/025106, filed on Feb. 16, 2011, which claims the benefit of priority to U.S. Provisional Patent Application No. 61/305,082, filed on Feb. 16, 2010; 61/329,023, filed on Apr. 28, 2010; and 61/388,457, filed on Sep. 30, 2010, all of which are incorporated by reference in their entirety

FIELD OF THE INVENTION

Described herein are compounds, including pharmaceutically acceptable salts, solvates, metabolites, prodrugs thereof, methods of making such compounds, pharmaceutical compositions comprising such compounds, and methods of using such compounds to treat, prevent or diagnose diseases or conditions that are androgen receptor dependent or androgen receptor mediated.

BACKGROUND OF THE INVENTION

The androgen receptor ("AR") is a ligand-activated transcriptional regulatory protein that mediates induction of a variety of biological effects through its interaction with endogenous androgens. Endogenous androgens include steroids such as testosterone and dihydrotestosterone. Testosterone is converted to dihydrotestosterone by the enzyme 5 alpha-reductase in many tissues.

The actions of androgens with androgen receptors have been implicated in a number of diseases or conditions, such as androgen dependent cancers, virilization in women, and acne, among others. Compounds that diminish the effects of androgens with androgen receptors and/or lower the concentrations of androgen receptors find use in the treatment of diseases or conditions in which androgen receptors play a role.

SUMMARY OF THE INVENTION

In one aspect, presented herein are compounds of Formula (I), (Ia), (II), (III), (IV), (V), (VI), (VII), (VIII), (VIIIa), (IX), (IXa) or (X) that diminish the effects of androgens with androgen receptors and/or lower the concentrations of androgen receptors, and therefore, are useful as agents for the treatment or prevention of diseases or conditions in which androgen receptors play a role, such as diseases or conditions in which androgen receptors participate, are involved in the etiology or pathology of the disease or condition, or contribute to at least one symptom of the disease or condition.

In one aspect, compounds of Formula (I), (Ia), (II), (III), (IV), (V), (VI), (VII), (VIII), (VIIIa), (IX), (IXa) and (X) are useful for the treatment of benign prostate hyperplasia, hirsutism, acne, adenomas and neoplasies of the prostate, benign or malignant tumor cells containing the androgen receptor, hyperpilosity, seborrhea, endometriosis, polycystic ovary syndrome, androgenic alopecia, hypogonadism, osteoporosis, suppression of spermatogenesis, libido, cachexia, anorexia, androgen supplementation for age related decreased testosterone levels, prostate cancer, breast cancer, endometrial cancer, uterine cancer, hot flashes, and Kennedy's disease muscle atrophy and weakness, skin atrophy, bone loss, anemia, arteriosclerosis, cardiovascular disease, loss of energy, loss of well-being, type 2 diabetes and abdominal fat accumulation. In some embodiments, a compound of Formula (I), (Ia), (II), (III), (IV), (V), (VI), (VII), (VIII), (VIIIa), (IX), (IXa) or (X) is used in the treatment of prostate cancer. In some embodiments, a compound of Formula (I), (Ia), (II), (III), (IV), (V), (VI), (VII), (VIII), (VIIIa), (IX), (IXa) or (X) are used in the treatment of hormone-sensitive prostate cancer. In some embodiments, a compound of Formula (I), (Ia), (II), (III), (IV), (V), (VI), (VII), (VIII), (VIIIa), (IX), (IXa) or (X) is used in the treatment of hormone refractory prostate cancer.

In one aspect, described herein are compounds of Formula (I), (Ia), (II), (III), (IV), (V), (VI), (VII), (VIII), (VIIIa), (IX), (IXa) and (X), pharmaceutically acceptable salts, solvates, metabolites and prodrugs thereof. In some embodiments, compounds of Formula (I), (Ia), (II), (III), (IV), (V), (VI), (VII), (VIII), (VIIIa), (IX), (IXa) and (X) are androgen receptor modulators. In some embodiments, the compound of Formula (I), (Ia), (II), (III), (IV), (V), (VI), (VII), (VIII), (VIIIa), (IX), (IXa) or (X) is an androgen receptor antagonist, an androgen receptor inverse agonist, an androgen receptor degrader, an androgen receptor trafficking modulator and/or an androgen receptor DNA-binding inhibitor. In some embodiments, the compound of Formula (I), (Ia), (II), (III), (IV), (V), (VI), (VII), (VIII), (VIIIa), (IX), (IXa) or (X) is an androgen receptor antagonist. In some embodiments, the compound of Formula (I), (II), (III), (IV), (V), (VI), (VII), (VIII), (IX) or (X) is an androgen receptor inverse agonist. In some embodiments, the compound of Formula (I), (Ia), (II), (III), (IV), (V), (VI), (VII), (VIII), (VIIIa), (IX), (IXa) or (X) is an androgen receptor degrader. In some embodiments, the compound of Formula (I), (Ia), (II), (III), (IV), (V), (VI), (VII), (VIII), (VIIIa), (IX), (IXa) or (X) is an androgen receptor trafficking modulator. In some embodiments, the compound of Formula (I), (Ia), (II), (III), (IV), (V), (VI), (VII), (VIII), (VIIIa), (IX), (IXa) or (X) is an androgen receptor DNA-binding inhibitor.

In one aspect, provided herein is a compound of Formula (I), or a pharmaceutically acceptable salt, solvate, N-oxide, metabolite or prodrug thereof:

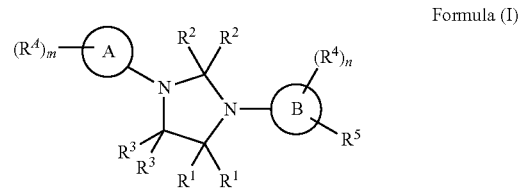

Formula (I)

wherein,
ring A is monocyclic heteroaryl, bicyclic heteroaryl, or naphthyl;
m is 0, 1, 2, 3 or 4;
each $R^4$ is independently selected from H, halogen, —CN, —$NO_2$, —OH, —$OR^9$, —$SR^9$, —S(=O)$R^{10}$, —S(=O)$_2R^{10}$, —N($R^{11}$)S(=O)$_2R^{10}$, —S(=O)$_2$N($R^9$)$_2$, —C(=O)$R^{10}$, —OC(=O)$R^{10}$, —$CO_2R^9$, —N($R^9$)$_2$, —C(=O)N($R^9$)$_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl or substituted or unsubstituted monocyclic heteroaryl;

each $R^1$ is independently selected from H, —OH, substituted or unsubstituted $C_1$-$C_6$alkyl, substituted or unsubstituted $C_1$-$C_6$alkoxy, and substituted or unsubstituted $C_1$-$C_6$fluoroalkyl;

or both $R^1$ are taken together with the carbon atom to which they are attached to form a substituted or unsubstituted $C_3$-$C_{10}$cycloalkyl or a substituted or unsubstituted $C_2$-$C_{10}$heterocycloalkyl;

each $R^2$ is H; or both $R^2$ are taken together with the carbon to which they are attached to form —C(=S)— or —C(=O)—;

each $R^3$ is H; or both $R^3$ are taken together with the carbon to which they are attached to form —C(=S)— or —C(=O)—; provided that each $R^2$ is not H if each $R^3$ is H;

ring B is phenyl, naphthyl, monocyclic heteroaryl, or bicyclic heteroaryl;

n is 0, 1, 2, 3 or 4;

each $R^4$ is independently selected from H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

$R^5$ is substituted or unsubstituted $C_2$-$C_{10}$alkyl, substituted or unsubstituted $C_2$-$C_{10}$fluoroalkyl, substituted or unsubstituted $C_2$-$C_{10}$alkoxy, substituted or unsubstituted $C_2$-$C_{10}$fluoroalkoxy, substituted or unsubstituted $C_2$-$C_{10}$heteroalkyl, substituted or unsubstituted $C_2$-$C_{10}$heterofluoroalkyl, or -L$^1$-L$^2$R$^6$;

L$^1$ is absent, —O—, —S—, —S(=O)—, —S(=O)$_2$—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)$_2$—, or —S(=O)$_2$NH—;

L$^2$ is substituted or unsubstituted $C_1$-$C_6$alkylene, substituted or unsubstituted $C_1$-$C_6$fluoroalkylene or substituted or unsubstituted $C_1$-$C_6$heteroalkylene;

R$^6$ is halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl;

each R$^9$ is independently selected from H, substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), and —$C_1$-$C_4$alkylene-(substituted or unsubstituted heteroaryl); or two R$^9$ groups attached to the same N atom are taken together with the N atom to which they are attached to form a substituted or unsubstituted $C_2$-$C_{10}$heterocycloalkyl;

R$^{10}$ is substituted or unsubstituted $C_1$-$C_6$alkyl, substituted or unsubstituted $C_1$-$C_6$heteroalkyl, substituted or unsubstituted $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted benzyl, a substituted or unsubstituted heteroaryl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), or —$C_1$-$C_4$alkylene-(substituted or unsubstituted heteroaryl);

R$^{11}$ is H or $C_1$-$C_4$alkyl.

For any and all of the embodiments, substituents are selected from among from a subset of the listed alternatives. For example, in some embodiments, both R$^1$ are taken together with the carbon atom to which they are attached to form a substituted or unsubstituted $C_3$-$C_{10}$cycloalkyl. In some embodiments, both R$^1$ are taken together with the carbon atom to which they are attached to form a substituted or unsubstituted cyclopropyl, cyclobutyl, cyclopentyl, or cyclohexyl. In some embodiments, each R$^1$ is independently selected from H, —OH, $C_1$-$C_6$alkyl, and $C_1$-$C_6$fluoroalkyl. In some embodiments, each R$^1$ is independently selected from H, —CH$_3$ and —CF$_3$.

In some embodiments, both R$^2$ are taken together with the carbon to which they are attached to form —C(=S)—; both R$^3$ are taken together with the carbon to which they are attached to form-C(=O)—.

In some embodiments, ring A is C-linked monocyclic heteroaryl, C-linked bicyclic heteroaryl, or naphthyl.

In some embodiments, both R$^1$ are taken together with the carbon atom to which they are attached to form a substituted or unsubstituted $C_3$-$C_{10}$cycloalkyl; both R$^2$ are taken together with the carbon to which they are attached to form —C(=S)—; both R$^3$ are taken together with the carbon to which they are attached to form-C(=O)—; ring A is N-containing monocyclic heteroaryl, or N-containing bicyclic heteroaryl; each R$^4$ is independently selected from H, halogen, —CN, —NO$_2$, —OH, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —C(=O)N(R$^9$)$_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, substituted or unsubstituted phenyl or substituted or unsubstituted monocyclic heteroaryl.

In some embodiments, both R$^1$ are taken together with the carbon atom to which they are attached to form a cyclopropyl, cyclobutyl, cyclopentyl, or cyclohexyl; ring A is N-containing monocyclic heteroaryl selected from pyridinyl, pyrimidinyl, pyridazinyl, pyrazinyl, triazinyl, pyrrolyl, thiazolyl, oxazolyl, isoxazolyl, oxadiazolyl, imidazolyl, pyrazolyl, isothiazolyl, triazolyl, and tetrazolyl.

In some embodiments, ring A is pyridinyl, pyrimidinyl, pyridazinyl, or pyrazinyl. In some embodiments, ring A is pyridinyl.

In some embodiments,

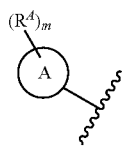

is

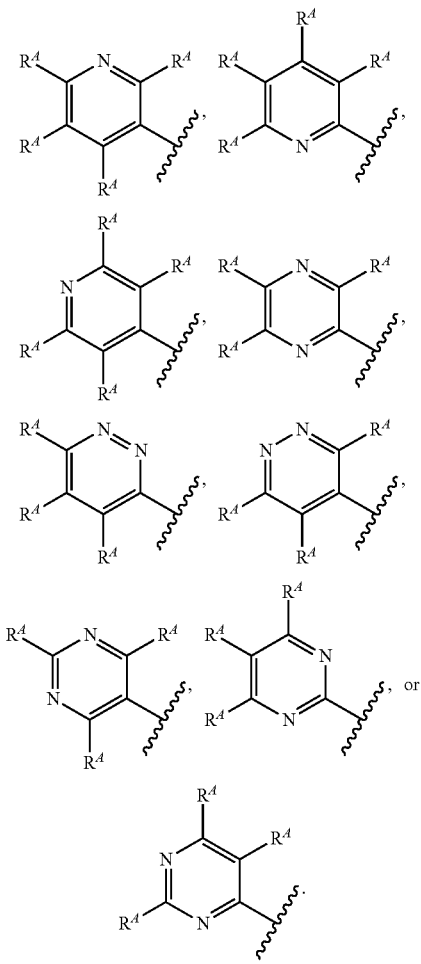

In some embodiments,

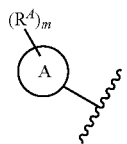

is

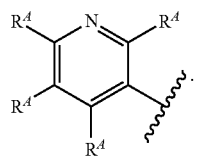

In some embodiments, ring A is pyridinyl; each $R^A$ is independently selected from H, halogen, —CN, —OH, —S(=O)$_2$R$^{10}$, —S(=O)$_2$N(R$^9$)$_2$, —C(=O)N(R$^9$)$_2$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, substituted or unsubstituted phenyl or substituted or unsubstituted monocyclic heteroaryl.

In some embodiments, both $R^1$ are taken together with the carbon atom to which they are attached to form a cyclopropyl, cyclobutyl, cyclopentyl, or cyclohexyl; ring A is N-containing bicyclic heteroaryl selected from quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, azaindolyl, pyrazolopyridinyl, thiazolopyrimidinyl, triazolopyridazinyl, thiazolopyridinyl, pyridothienyl, pyrimidiothienyl and pyrrolopyrimidinyl; each $R^A$ is independently selected from H, halogen, —CN, —OH, —S(=O)$_2$R$^{10}$, —S(=O)$_2$N(R$^9$)$_2$, —C(=O)N(R$^9$)$_2$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, substituted or unsubstituted phenyl or substituted or unsubstituted monocyclic heteroaryl.

In some embodiments, ring A is N-containing bicyclic heteroaryl selected from quinolinyl, isoquinolinyl, quinazolinyl, quinoxalinyl, pyridopyrimidinyl, pyrazolopyrimidinyl, triazolopyridazinyl, and pyrrolopyrimidinyl.

In some embodiments, ring A is [1,2,4]triazolo[4,3-b]pyridazinyl.

In some embodiments, ring B is phenyl or monocyclic heteroaryl; each $R^4$ is independently selected from H, halogen, —CN, —NO$_2$, —OH, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, and substituted or unsubstituted C$_1$-C$_6$heteroalkyl; $R^5$ is substituted or unsubstituted C$_2$-C$_{10}$alkyl, substituted or unsubstituted C$_2$-C$_{10}$fluoroalkyl, substituted or unsubstituted C$_2$-C$_{10}$alkoxy, substituted or unsubstituted C$_2$-C$_{10}$fluoroalkoxy, substituted or unsubstituted C$_2$-C$_{10}$heteroalkyl, substituted or unsubstituted C$_2$-C$_{10}$heterofluoroalkyl, or -L$^1$-L$^2$-R$^6$; L$^1$ is absent, —O—, —S—, —S(=O)—, —S(=O)$_2$—, —NH—, —C(=O)—, —C(=O)NH—, —NHC(=O)—, —NHS(=O)$_2$—, or —S(=O)$_2$NH—; L$^2$ is substituted or unsubstituted C$_1$-C$_6$alkylene, substituted or unsubstituted C$_1$-C$_6$fluoroalkylene or substituted or unsubstituted C$_1$-C$_6$heteroalkylene; $R^6$ is halogen, —CN, —NO$_2$, —OH, —OR$^9$, —SR$^9$, —S(=O)R$^{10}$, —S(=O)$_2$R$^{10}$, —S(=O)$_2$N(R$^9$)$_2$, —C(=O)R$^{10}$, —CO$_2$R$^9$, —N(R$^9$)$_2$, —C(=O)N(R$^9$)$_2$, substituted or unsubstituted C$_3$-C$_{10}$cycloalkyl, substituted or unsubstituted C$_2$-C$_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl.

In some embodiments, ring B is phenyl or monocyclic heteroaryl; each $R^4$ is independently selected from H, halogen, —CN, —NO$_2$, —OH, substituted or unsubstituted $C_1$-$C_4$alkyl, substituted or unsubstituted $C_1$-$C_4$fluoroalkyl, substituted or unsubstituted $C_1$-$C_4$fluoroalkoxy, and substituted or unsubstituted $C_1$-$C_4$alkoxy; $R^5$ is substituted or unsubstituted $C_2$-$C_{10}$alkyl, substituted or unsubstituted $C_2$-$C_{10}$fluoroalkyl, substituted or unsubstituted $C_2$-$C_{10}$alkoxy, substituted or unsubstituted $C_2$-$C_{10}$fluoroalkoxy, substituted or unsubstituted $C_2$-$C_{10}$heteroalkyl, substituted or unsubstituted $C_2$-$C_{10}$heterofluoroalkyl, or -$L^1$-$L^2$-$R^6$; $L^1$ is absent, —O—, or —C(=O)NH—; $L^2$ is substituted or unsubstituted $C_1$-$C_6$alkylene, substituted or unsubstituted $C_1$-$C_6$fluoroalkylene or substituted or unsubstituted $C_1$-$C_6$heteroalkylene; $R^6$ is —CN, —NO$_2$, —OH, —OR$^9$, —SR$^9$, —S(=O)R$^{10}$, —S(=O)$_2$R$^{10}$, —C(=O)R$^{10}$, —CO$_2$R$^9$, —C(=O)N(R$^9$)$_2$, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl.

In some embodiments, $L^2$ is substituted or unsubstituted $C_1$-$C_6$alkylene; $R^6$ is —CN, —OR$^9$, —SR$^9$, —S(=O)R$^{10}$, —S(=O)$_2$R$^{10}$, —C(=O)R$^{10}$, —C(=O)N(R$^9$)$_2$, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl.

In some embodiments, $R^6$ is substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl.

In some embodiments, $L^2$ is substituted or unsubstituted $C_1$-$C_6$alkylene; $R^6$ is —CN, —OR$^9$, —SR$^9$, —S(=O)R$^{10}$, —S(=O)$_2$R$^{10}$, —C(=O)R$^{10}$, or —C(=O)N(R$^9$)$_2$; each $R^9$ is independently selected from H, substituted or unsubstituted $C_1$-$C_6$alkyl, substituted or unsubstituted $C_1$-$C_6$fluoroalkyl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), and —$C_1$-$C_4$alkylene-(substituted or unsubstituted heteroaryl); or two $R^9$ groups attached to the same N atom are taken together with the N atom to which they are attached to form a substituted or unsubstituted $C_2$-$C_{10}$heterocycloalkyl; $R^{10}$ is substituted or unsubstituted $C_1$-$C_6$alkyl, substituted or unsubstituted $C_1$-$C_6$fluoroalkyl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), or —$C_1$-$C_4$alkylene-(substituted or unsubstituted heteroaryl).

In some embodiments, provided is a compound of Formula (Ia), or a pharmaceutically acceptable salt, or N-oxide thereof:

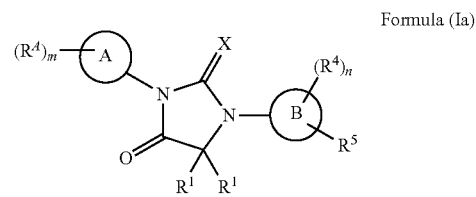

Formula (Ia)

wherein,
ring A is monocyclic heteroaryl, bicyclic heteroaryl, or naphthyl;
m is 1, 2, 3 or 4;
each $R^A$ is independently H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —N(R$^9$)$_2$, —C(=O)N(R$^9$)$_2$, $C_1$-$C_6$alkyl, $C_1$-$C_6$fluoroalkyl, $C_1$-$C_6$fluoroalkoxy, $C_1$-$C_6$alkoxy, or $C_1$-$C_6$heteroalkyl;
both $R^1$ are taken together with the carbon atom to which they are attached to form a substituted or unsubstituted $C_3$-$C_6$cycloalkyl or a substituted or unsubstituted $C_2$-$C_6$heterocycloalkyl;
or each $R^1$ is independently selected from H, —OH, $C_1$-$C_6$alkyl, $C_1$-$C_6$alkoxy, and $C_1$-$C_6$fluoroalkyl;
X is S or O;
ring B is phenyl, naphthyl, monocyclic heteroaryl, or bicyclic heteroaryl;
n is 0, 1, 2, 3 or 4;
each $R^4$ is independently selected from H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, $C_1$-$C_6$alkyl, $C_1$-$C_6$fluoroalkyl, $C_1$-$C_6$fluoroalkoxy, $C_1$-$C_6$alkoxy, and $C_1$-$C_6$heteroalkyl;
$R^5$ is -$L^1$-$L^2$-$R^6$ or -$L^1$-$R^7$;
$L^1$ is absent, —O—, —S—, —S(=O)—, —S(=O)$_2$—, —NH—, —C(=O)—, —C(=O)NH—, —NHC(=O)—, —NHC(=O)O—, —NHC(=O)NH—, —C(=O)O—, —OC(=O), —OC(=O)O—, —OC(=O)NH—, —NHS(=O)$_2$—, or —S(=O)$_2$NH—;
$L^2$ is $C_1$-$C_6$alkylene, $C_1$-$C_6$fluoroalkylene or $C_1$-$C_6$heteroalkylene;
$R^6$ is halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, $C_1$-$C_6$alkyl, $C_1$-$C_6$fluoroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl;
$R^7$ is substituted or unsubstituted monocyclic $C_2$-$C_6$heterocycloalkyl, or substituted or unsubstituted monocyclic heteroaryl;
each $R^9$ is independently selected from H, $C_1$-$C_6$alkyl, $C_1$-$C_6$heteroalkyl, $C_1$-$C_6$fluoroalkyl, substituted or unsubstituted $C_3$-$C_6$cycloalkyl, substituted or unsubstituted $C_2$-$C_{10}$heterocycloalkyl, substituted or unsubstituted phenyl, substituted or unsubstituted monocyclic heteroaryl, —$C_1$-$C_4$alkylene-(substituted or unsubstituted $C_3$-$C_6$cycloalkyl), —$C_1$-$C_4$alkylene-(substituted or unsubstituted monocyclic $C_2$-$C_6$heterocycloalkyl), —$C_1$-$C_4$alkylene-(substituted or unsubstituted phenyl), and —$C_1$-$C_4$alkylene-(substituted or unsubstituted monocyclic heteroaryl); or two $R^9$ groups attached to the same N atom are taken together with the N atom to which they are attached to form a substituted or unsubstituted monocyclic $C_2$-$C_6$heterocycloalkyl;

$R^{10}$ is $C_1$-$C_6$alkyl, $C_1$-$C_6$heteroalkyl, $C_1$-$C_6$fluoroalkyl, a substituted or unsubstituted $C_3$-$C_6$cycloalkyl, a substituted or unsubstituted monocyclic $C_2$-$C_6$heterocycloalkyl, a substituted or unsubstituted phenyl, a substituted or unsubstituted benzyl, a substituted or unsubstituted monocyclic heteroaryl, —$C_1$-$C_4$alkylene-(substituted or unsubstituted $C_3$-$C_6$cycloalkyl), —$C_1$-$C_4$alkylene-(substituted or unsubstituted monocyclic $C_2$-$C_6$heterocycloalkyl), —$C_1$-$C_4$alkylene-(substituted or unsubstituted phenyl), or —$C_1$-$C_4$alkylene-(substituted or unsubstituted monocyclic heteroaryl);

$R^{11}$ is H or $C_1$-$C_4$alkyl.

In some embodiments, both $R^1$ are taken together with the carbon atom to which they are attached to form a substituted or unsubstituted $C_3$-$C_6$cycloalkyl; X is S; ring A is N-containing monocyclic heteroaryl; each $R^4$ is independently selected from H, halogen, —CN, —$NO_2$, —OH, —S(=O)$_2R^{10}$, —N($R^{11}$)S(=O)$_2R^{10}$, —S(=O)$_2$N($R^9$)$_2$, —C(=O)$R^{10}$, —OC(=O)$R^{10}$, —$CO_2R^9$, —C(=O)N($R^9$)$_2$, $C_1$-$C_6$alkyl, $C_1$-$C_6$fluoroalkyl, $C_1$-$C_6$fluoroalkoxy, and $C_1$-$C_6$alkoxy; ring B is phenyl or monocyclic heteroaryl.

In some embodiments, both $R^1$ are taken together with the carbon atom to which they are attached to form a cyclopropyl, cyclobutyl, cyclopentyl, or cyclohexyl; ring A is pyridinyl, pyrimidinyl, pyridazinyl, or pyrazinyl.

In some embodiments, ring A is pyridinyl; each $R^4$ is independently selected from H, halogen, —CN, —OH, —S(=O)$_2R^{10}$, —S(=O)$_2$N($R^9$)$_2$, —C(=O)N($R^9$)$_2$, $C_1$-$C_6$alkyl, $C_1$-$C_6$fluoroalkyl, $C_1$-$C_6$fluoroalkoxy, and $C_1$-$C_6$alkoxy.

In some embodiments, ring B is phenyl; $R^5$ is -$L^1$-$L^2$-$R^6$; $L^1$ is absent, —O—, —S—, —S(=O)—, —S(=O)$_2$—, —NH—, —C(=O)—, —C(=O)NH—, —NHC(=O)—, —NHS(=O)$_2$—, or —S(=O)$_2$NH—; $L^2$ is $C_1$-$C_6$alkylene, $C_1$-$C_6$fluoroalkylene or $C_1$-$C_6$heteroalkylene; $R^6$ is halogen, —CN, —$NO_2$, —OH, —$OR^9$, —$SR^9$, —S(=O)$R^{10}$, —S(=O)$_2R^{10}$, —S(=O)$_2$N($R^9$)$_2$, —C(=O)$R^{10}$, —$CO_2R^9$, —N($R^9$)$_2$, —C(=O)N($R^9$)$_2$, substituted or unsubstituted $C_3$-$C_6$cycloalkyl, substituted or unsubstituted $C_2$-$C_6$heterocycloalkyl, substituted or unsubstituted monocyclic heteroaryl, or substituted or unsubstituted phenyl.

In some embodiments, ring B is phenyl; each $R^4$ is independently selected from H, halogen, —CN, —$NO_2$, —OH, $C_1$-$C_4$alkyl, $C_1$-$C_4$fluoroalkyl, $C_1$-$C_4$fluoroalkoxy, and $C_1$-$C_4$alkoxy; $R^5$ is -$L^1$-$L^2$-$R^6$; $L^1$ is absent, —O—, or —C(=O)NH—; $L^2$ is $C_1$-$C_6$alkylene, $C_1$-$C_6$fluoroalkylene or $C_1$-$C_6$heteroalkylene; $R^6$ is —CN, —$NO_2$, —OH, —$OR^9$, —$SR^9$, —S(=O)$R^{10}$, —S(=O)$_2R^{10}$, —C(=O)$R^{10}$, —$CO_2R^9$, —C(=O)N($R^9$)$_2$, substituted or unsubstituted $C_3$-$C_6$cycloalkyl, substituted or unsubstituted $C_2$-$C_6$heterocycloalkyl, substituted or unsubstituted monocyclic heteroaryl, or substituted or unsubstituted phenyl.

In some embodiments, $L^2$ is $C_1$-$C_6$alkylene; $R^6$ is —CN, —$OR^9$, —$SR^9$, —S(=O)$R^{10}$, —S(=O)$_2R^{10}$, —C(=O)$R^{10}$, —C(=O)N($R^9$)$_2$, substituted or unsubstituted $C_3$-$C_6$cycloalkyl, substituted or unsubstituted $C_2$-$C_6$heterocycloalkyl, substituted or unsubstituted monocyclic heteroaryl, or substituted or unsubstituted phenyl.

In some embodiments, $R^6$ is substituted or unsubstituted $C_3$-$C_6$cycloalkyl, substituted or unsubstituted $C_2$-$C_6$heterocycloalkyl, substituted or unsubstituted monocyclic heteroaryl, or substituted or unsubstituted phenyl.

In some embodiments, $L^2$ is $C_1$-$C_6$alkylene; $R^6$ is a substituted or unsubstituted $C_2$-$C_6$heterocycloalkyl.

In some embodiments, ring B is phenyl; each $R^4$ is independently selected from H, halogen, —CN, —$NO_2$, —OH, $C_1$-$C_4$alkyl, $C_1$-$C_4$fluoroalkyl, $C_1$-$C_4$fluoroalkoxy, and $C_1$-$C_4$alkoxy; $R^5$ is -$L^1$-$R^7$; $L^1$ is absent, —O—, —S—, —S(=O)—, —S(=O)$_2$—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)$_2$—, or —S(=O)$_2$NH—; $R^7$ is substituted or unsubstituted monocyclic $C_2$-$C_6$heterocycloalkyl, or substituted or unsubstituted monocyclic heteroaryl;

In some embodiments, $R^5$ is -$L^1$-$R^7$; $L^1$ is —O—, —S—, —S(=O)—, —S(=O)$_2$—, —NH—, —C(=O)—, —C(=O)NH—, or —S(=O)$_2$NH—; $R^7$ is substituted or unsubstituted monocyclic $C_2$-$C_6$heterocycloalkyl, or substituted or unsubstituted monocyclic heteroaryl.

In some embodiments, $R^5$ is -$L^1$-$R^7$; $L^1$ is absent, —O—, —S—, —S(=O)—, —S(=O)$_2$—, —NH—, —C(=O)—, —C(=O)NH—, or —S(=O)$_2$NH—; $R^7$ is substituted or unsubstituted monocyclic heteroaryl.

In some embodiments, the compound of Formula (I) or Formula (Ia) has the structure of Formula (II):

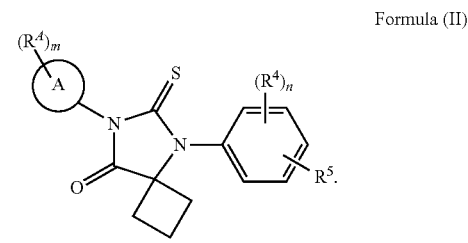

Formula (II)

In some embodiments, the compound of Formula (Ia) has the structure of Formula (II):

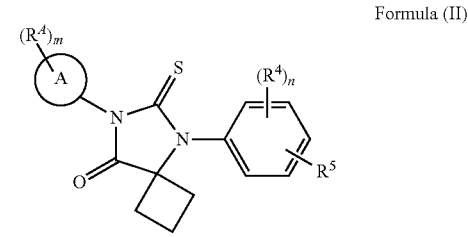

Formula (II)

wherein,

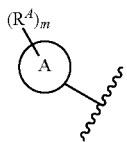

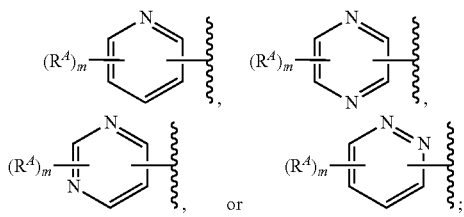

m is 2;
one $R^A$ is —CN, —NO$_2$, —S(=O)$_2$R$^{10}$, —S(=O)$_2$N(R$^9$)$_2$, —C(=O)R$^{10}$, —CO$_2$R$^9$, or —C(=O)N(R$^9$)$_2$; and the other $R^A$ is H, halogen, —OH, C$_1$-C$_6$alkyl, C$_1$-C$_6$fluoroalkyl, C$_1$-C$_6$fluoroalkoxy, or C$_1$-C$_6$alkoxy;
n is 0 or 1;
each $R^4$ is independently selected from H, halogen, —CN, —NO$_2$, —OH, C$_1$-C$_6$alkyl, C$_1$-C$_6$fluoroalkyl, C$_1$-C$_6$fluoroalkoxy, and C$_1$-C$_6$alkoxy;
$R^5$ is -L$^1$-L$^2$-R$^6$ or -L$^1$-R$^7$;
  L$^1$ is absent, —O—, or —C(=O)NH—;
  L$^2$ is C$_1$-C$_6$alkylene, C$_1$-C$_6$fluoroalkylene or C$_1$-C$_6$heteroalkylene;
  R$^6$ is —CN, —NO$_2$, —OH, —OR$^9$, —SR$^9$, —S(=O)R$^{10}$, —S(=O)$_2$R$^{10}$, —C(=O)R$^{10}$, —CO$_2$R$^9$, —N(R$^9$)$_2$, —C(=O)N(R$^9$)$_2$, substituted or unsubstituted C$_3$-C$_6$cycloalkyl, substituted or unsubstituted C$_2$-C$_6$heterocycloalkyl, substituted or unsubstituted monocyclic heteroaryl, or substituted or unsubstituted phenyl;
  R$^7$ is substituted or unsubstituted monocyclic C$_2$-C$_6$heterocycloalkyl, or substituted or unsubstituted monocyclic heteroaryl.
In some embodiments,

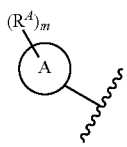

is

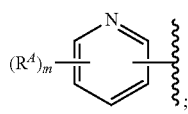

one $R^A$ is —CN and the other $R^A$ is H, halogen, —OH, C$_1$-C$_4$fluoroalkyl, C$_1$-C$_4$fluoroalkoxy, or C$_1$-C$_4$alkoxy; each $R^4$ is independently selected from H, halogen, —OH, C$_1$-C$_4$fluoroalkyl, C$_1$-C$_4$fluoroalkoxy, and C$_1$-C$_4$alkoxy; $R^5$ is -L$^1$-L$^2$-R$^6$ or -L$^1$-R$^7$; L$^1$ is absent, —O—, or —C(=O)NH—; L$^2$ is C$_1$-C$_6$alkylene, C$_1$-C$_6$fluoroalkylene or C$_1$-C$_6$heteroalkylene; R$^6$ is —CN, —NO$_2$, —OH, —OR$^9$, —SR$^9$, —S(=O)R$^{10}$, —S(=O)$_2$R$^{10}$, —C(=O)R$^{10}$, —CO$_2$R$^9$, —C(=O)N(R$^9$)$_2$, substituted or unsubstituted C$_3$-C$_6$cycloalkyl, substituted or unsubstituted C$_2$-C$_6$heterocycloalkyl, substituted or unsubstituted monocyclic heteroaryl, or substituted or unsubstituted phenyl; R$^7$ is substituted or unsubstituted monocyclic C$_2$-C$_6$heterocycloalkyl, or substituted or unsubstituted monocyclic heteroaryl.

In some embodiments, described herein is a compound of Formula (I), or a pharmaceutically acceptable salt, solvate, N-oxide, metabolite or prodrug thereof:

Formula (I)

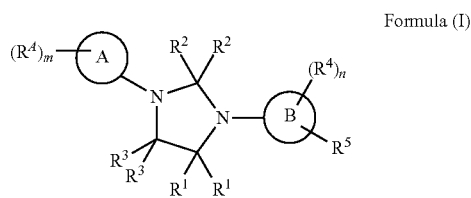

wherein,
ring A is bicyclic heteroaryl, or naphthyl;
m is 0, 1, 2, or 3;
each $R^A$ is independently selected from H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —N(R$^9$)$_2$, —C(=O)N(R$^9$)$_2$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted phenyl or substituted or unsubstituted monocyclic heteroaryl;
each $R^1$ is independently selected from H, —OH, substituted or unsubstituted C$_1$-C$_6$alkyl, substituted or unsubstituted C$_1$-C$_6$alkoxy, and substituted or unsubstituted C$_1$-C$_6$fluoroalkyl;
or both $R^1$ are taken together with the carbon atom to which they are attached to form a substituted or unsubstituted C$_3$-C$_{10}$cycloalkyl or a substituted or unsubstituted C$_2$-C$_{10}$heterocycloalkyl;
each $R^2$ is H; or both $R^2$ are taken together with the carbon to which they are attached to form —C(=S)— or —C(=O)—;
each $R^3$ is H; or both $R^3$ are taken together with the carbon to which they are attached to form —C(=S)— or —C(=O)—; provided that each $R^2$ is not H if each $R^3$ is H;
ring B is phenyl, naphthyl, monocyclic heteroaryl, or bicyclic heteroaryl;
n is 0, 1, or 2;
each $R^4$ is independently selected from H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

$R^5$ is H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted $C_1$-$C_{10}$alkyl, substituted or unsubstituted $C_1$-$C_{10}$fluoroalkyl, substituted or unsubstituted $C_1$-$C_{10}$fluoroalkoxy, $C_1$-$C_{10}$alkoxy, substituted or unsubstituted $C_1$-$C_{10}$heteroalkyl, or -L$^1$-L$^2$-R$^6$;

$L^1$ is absent, —O—, —S—, —S(=O)—, —S(=O)$_2$—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)$_2$—, or —S(=O)$_2$NH—;

$L^2$ is substituted or unsubstituted $C_1$-$C_6$alkylene, substituted or unsubstituted $C_1$-$C_6$fluoroalkylene or substituted or unsubstituted $C_1$-$C_6$heteroalkylene;

$R^6$ is halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl;

each $R^9$ is independently selected from H, substituted or unsubstituted $C_1$-$C_6$alkyl, substituted or unsubstituted $C_1$-$C_6$heteroalkyl, substituted or unsubstituted $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —C$_1$-C$_4$alkylene-(substituted or unsubstituted $C_3$-$C_{10}$cycloalkyl), —C$_1$-C$_4$alkylene-(substituted or unsubstituted $C_2$-$C_{10}$heterocycloalkyl), —C$_1$-C$_4$alkylene-(substituted or unsubstituted aryl), and —C$_1$-C$_4$alkylene-(substituted or unsubstituted heteroaryl); or two $R^9$ groups attached to the same N atom are taken together with the N atom to which they are attached to form a substituted or unsubstituted $C_2$-$C_{10}$heterocycloalkyl;

$R^{10}$ is substituted or unsubstituted $C_1$-$C_6$alkyl, substituted or unsubstituted $C_1$-$C_6$heteroalkyl, substituted or unsubstituted $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —C$_1$-C$_4$alkylene-(substituted or unsubstituted $C_3$-$C_{10}$cycloalkyl), —C$_1$-C$_4$alkylene-(substituted or unsubstituted $C_2$-$C_{10}$heterocycloalkyl), —C$_1$-C$_4$alkylene-(substituted or unsubstituted aryl), or —C$_1$-C$_4$alkylene-(substituted or unsubstituted heteroaryl);

$R^{11}$ is H or $C_1$-$C_4$alkyl.

In some embodiments, ring A is selected from quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, azaindolyl, pyrazolopyridinyl, thiazolopyrimidinyl, triazolopyridazinyl, thiazolopyridinyl, pyridothienyl, pyrimidiothienyl, pyrrolopyrimidinyl and naphthyl.

In some embodiments, ring A is selected from quinolinyl, isoquinolinyl, quinazolinyl, quinoxalinyl, pyridopyrimidinyl, pyrazolopyrimidinyl, triazolopyridazinyl, pyrrolopyrimidinyl, and napthyl.

In some embodiments, ring A is [1,2,4]triazolo[4,3-b]pyridazinyl.

In some embodiments, described herein is a compound of Formula (I), or a pharmaceutically acceptable salt, solvate, N-oxide, metabolite or prodrug thereof:

wherein,

Formula (I)

ring A is a 5-membered heteroaryl;

m is 0, 1, 2, or 3;

each $R^4$ is independently selected from H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —N(R$^9$)$_2$, —C(=O)N(R$^9$)$_2$, substituted or unsubstituted $C_1$-$C_4$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl or substituted or unsubstituted monocyclic heteroaryl;

each $R^1$ is independently selected from H, —OH, substituted or unsubstituted $C_1$-$C_6$alkyl, substituted or unsubstituted $C_1$-$C_6$alkoxy, and substituted or unsubstituted $C_1$-$C_6$fluoroalkyl;

or both $R^1$ are taken together with the carbon atom to which they are attached to form a substituted or unsubstituted $C_3$-$C_{10}$cycloalkyl or a substituted or unsubstituted $C_2$-$C_{10}$heterocycloalkyl;

each $R^2$ is H; or both $R^2$ are taken together with the carbon to which they are attached to form —C(=S)— or —C(=O)—;

each $R^3$ is H; or both $R^3$ are taken together with the carbon to which they are attached to form —C(=S)— or —C(=O)—; provided that each $R^2$ is not H if each $R^3$ is H;

ring B is phenyl, naphthyl, monocyclic heteroaryl, or bicyclic heteroaryl;

n is 0, 1, or 2;

each $R^4$ is independently selected from H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, and substituted or unsubstituted C$_1$-C$_6$heteroalkyl;

$R^5$ is H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted C$_1$-C$_{10}$alkyl, substituted or unsubstituted C$_1$-C$_{10}$fluoroalkyl, substituted or unsubstituted C$_1$-C$_{10}$fluoroalkoxy, substituted or unsubstituted C$_1$-C$_{10}$alkoxy, substituted or unsubstituted C$_1$-C$_{10}$heteroalkyl, or -L$^1$-L$^2$-R$^6$;

L$^1$ is absent, —O—, —S—, —S(=O)—, —S(=O)$_2$—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)$_2$—, or —S(=O)$_2$NH—;

L$^2$ is substituted or unsubstituted C$_1$-C$_6$alkylene, substituted or unsubstituted C$_1$-C$_6$fluoroalkylene or substituted or unsubstituted C$_1$-C$_6$heteroalkylene;

$R^6$ is halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted C$_1$-C$_6$alkyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl;

each $R^9$ is independently selected from H, substituted or unsubstituted C$_1$-C$_6$alkyl, substituted or unsubstituted C$_1$-C$_6$heteroalkyl, substituted or unsubstituted C$_1$-C$_6$fluoroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_4$alkylene-(substituted or unsubstituted C$_3$-C$_{10}$cycloalkyl), —C$_1$-C$_4$alkylene-(substituted or unsubstituted C$_2$-C$_{10}$heterocycloalkyl), —C$_1$-C$_4$alkylene-(substituted or unsubstituted aryl), and —C$_1$-C$_4$alkylene-(substituted or unsubstituted heteroaryl); or two $R^9$ groups attached to the same N atom are taken together with the N atom to which they are attached to form a substituted or unsubstituted C$_2$-C$_{10}$heterocycloalkyl;

$R^{10}$ is substituted or unsubstituted C$_1$-C$_6$alkyl, substituted or unsubstituted C$_1$-C$_6$heteroalkyl, substituted or unsubstituted C$_1$-C$_6$fluoroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_4$alkylene-(substituted or unsubstituted C$_3$-C$_{10}$cycloalkyl), —C$_1$-C$_4$alkylene-(substituted or unsubstituted C$_2$-C$_{10}$heterocycloalkyl), —C$_1$-C$_4$alkylene-(substituted or unsubstituted aryl), or —C$_1$-C$_4$alkylene-(substituted or unsubstituted heteroaryl);

$R^{11}$ is H or C$_1$-C$_4$alkyl.

In some embodiments, ring A is selected from pyrrolyl, thiazolyl, oxazolyl, isoxazolyl, oxadiazolyl, imidazolyl, pyrazolyl, isothiazolyl, triazolyl, and tetrazolyl.

In some embodiments,

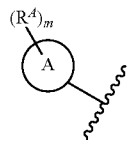

is selected from:

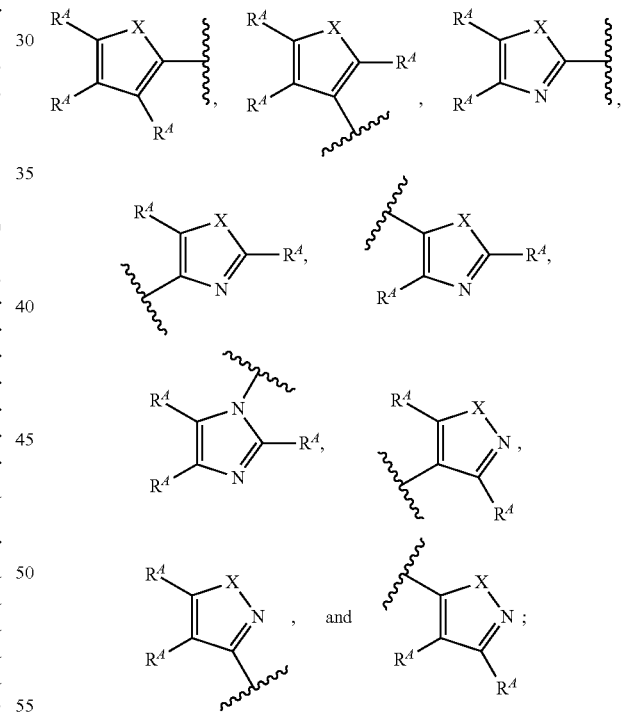

where X is O, S, or NR$^A$. In some embodiments, X is O. In some embodiments, X is S. In some embodiments, X is NR$^A$.

In some embodiments, both $R^1$ are taken together with the carbon atom to which they are attached to form a C$_3$-C$_{10}$cycloalkyl; both $R^2$ are taken together with the carbon to which they are attached to form —C(=S)—; both $R^3$ are taken together with the carbon to which they are attached to form -C(=O)—.

In some embodiments, the compound described herein has the structure of Formula (III):

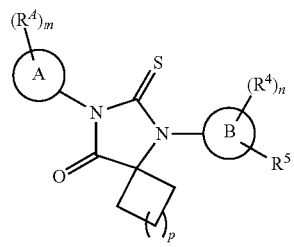

Formula (III)

wherein,
p is 0, 1, 2, or 3.

In some embodiments, each $R^A$ is independently selected from H, halogen, —CN, —NO$_2$, —OH, —S(=O)$_2$R$^{10}$, —S(=O)$_2$N(R$^9$)$_2$, —C(=O)R$^{10}$, —CO$_2$R$^9$, —C(=O)N(R$^9$)$_2$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, substituted or unsubstituted phenyl or substituted or unsubstituted monocyclic heteroaryl.

In some embodiments, each $R^4$ is independently selected from H, halogen, —CN, —NO$_2$, —OH, substituted or unsubstituted C$_1$-C$_6$alkyl, substituted or unsubstituted C$_1$-C$_6$fluoroalkyl, substituted or unsubstituted C$_1$-C$_6$fluoroalkoxy, and substituted or unsubstituted C$_1$-C$_6$alkoxy; R$^5$ is substituted or unsubstituted C$_2$-C$_{10}$alkyl, substituted or unsubstituted C$_2$-C$_{10}$fluoroalkyl, substituted or unsubstituted C$_2$-C$_{10}$alkoxy, substituted or unsubstituted C$_2$-C$_{10}$fluoroalkoxy, substituted or unsubstituted C$_2$-C$_{10}$heteroalkyl, substituted or unsubstituted C$_2$-C$_{10}$heterofluoroalkyl, or -L$^1$-L$^2$-R$^6$; L$^1$ is absent, —O—, —S—, —S(=O)—, —S(=O)$_2$—, —NH—, —C(=O)—, —C(=O)NH—, —NHC(=O)—, —NHS(=O)$_2$—, or —S(=O)$_2$NH—; L$^2$ is substituted or unsubstituted C$_1$-C$_6$alkylene, substituted or unsubstituted C$_1$-C$_6$fluoroalkylene or substituted or unsubstituted C$_1$-C$_6$heteroalkylene; R$^6$ is halogen, —CN, —NO$_2$, —OH, —OR$^9$, —SR$^9$, —S(=O)R$^{10}$, —S(=O)$_2$R$^{10}$, —S(=O)$_2$N(R$^9$)$_2$, —C(=O)R$^{10}$, —CO$_2$R$^9$, —N(R$^9$)$_2$, —C(=O)N(R$^9$)$_2$, substituted or unsubstituted C$_3$-C$_{10}$cycloalkyl, substituted or unsubstituted C$_2$-C$_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl.

In some embodiments, each $R^4$ is independently selected from H, halogen, —CN, —NO$_2$, —OH, substituted or unsubstituted C$_1$-C$_6$alkyl, substituted or unsubstituted C$_1$-C$_6$fluoroalkyl, substituted or unsubstituted C$_1$-C$_6$fluoroalkoxy, and substituted or unsubstituted C$_1$-C$_6$alkoxy; R$^5$ is H, halogen, —CN, —NO$_2$, —OH, —OR$^9$, —SR$^9$, —S(=O)R$^{10}$, —S(=O)$_2$R$^{10}$, —S(=O)$_2$N(R$^9$)$_2$, —C(=O)R$^{10}$, —CO$_2$R$^9$, —C(=O)N(R$^9$)$_2$, —NR$^{11}$C(=O)R$^{10}$, —NR$^{11}$C(=O)OR$^{10}$, substituted or unsubstituted C$_1$-C$_{10}$alkyl, substituted or unsubstituted C$_1$-C$_{10}$fluoroalkyl, substituted or unsubstituted C$_1$-C$_{10}$fluoroalkoxy, substituted or unsubstituted C$_1$-C$_{10}$alkoxy, substituted or unsubstituted C$_1$-C$_{10}$heteroalkyl, or -L$^1$-L$^2$-R$^6$; L$^1$ is absent, —O—, or —C(=O)NH—; L$^2$ is C$_1$-C$_6$alkylene, C$_1$-C$_6$fluoroalkylene or C$_1$-C$_6$heteroalkylene; R$^6$ is —CN, —NO$_2$, —OH, —OR$^9$, —SR$^9$, —S(=O)R$^{10}$, —S(=O)$_2$R$^{10}$, —C(=O)R$^{10}$, —CO$_2$R$^9$, —C(=O)N(R$^9$)$_2$, substituted or unsubstituted C$_3$-C$_{10}$cycloalkyl, substituted or unsubstituted C$_2$-C$_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl.

In some embodiments, described herein is a compound of Formula (IV), or a pharmaceutically acceptable salt, solvate, N-oxide, metabolite or prodrug thereof:

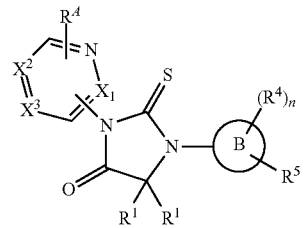

Formula (IV)

wherein,
each R$^1$ is independently selected from H, —OH, substituted or unsubstituted C$_1$-C$_6$alkyl, substituted or unsubstituted C$_1$-C$_6$alkoxy, and substituted or unsubstituted C$_1$-C$_6$fluoroalkyl;
or both R$^1$ are taken together with the carbon atom to which they are attached to form a substituted or unsubstituted C$_3$-C$_{10}$cycloalkyl or a substituted or unsubstituted C$_2$-C$_{10}$heterocycloalkyl;
X$^1$ is CR$^A$ or N;
X$^2$ is CR$^A$ or N;
X$^3$ is CR$^A$ or N; provided that at least two of X$^1$, X$^2$, and X$^3$ is CR$^A$;
each R$^A$ is independently selected from H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —N(R$^9$)$_2$, —C(=O)N(R$^9$)$_2$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted phenyl or substituted or unsubstituted monocyclic heteroaryl;
ring B is phenyl, naphthyl, monocyclic heteroaryl, or bicyclic heteroaryl;
n is 0, 1, or 2;
R$^4$ is H, halogen, —CN, —NO$_2$, —OH, —OR$^9$, —SR$^9$, —S(=O)R$^{10}$, —S(=O)$_2$R$^{10}$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, or substituted or unsubstituted C$_1$-C$_6$heteroalkyl;
R$^5$ is halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted C$_2$-C$_{10}$alkyl, substituted or unsubstituted C$_2$-C$_{10}$fluoroalkyl, substituted or unsubstituted C$_1$-C$_{10}$fluoroalkoxy, substituted or unsubstituted C₁-C₁₀alkoxy, substituted or unsubstituted C₁-C₁₀heteroalkyl, substituted or unsubstituted C₃-C₁₀cycloalkyl, substituted or unsubstituted C₂-C₁₀heterocycloalkyl, substituted or unsubstituted phenyl, substituted or unsubstituted monocyclic heteroaryl, or -L¹-L²-R⁶;

L¹ is absent, —O—, —S—, —S(O)—, —S(O)₂—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)₂—, or —S(=O)₂NH—;

L² is substituted or unsubstituted C₁-C₆alkylene, substituted or unsubstituted C₁-C₆fluoroalkylene or substituted or unsubstituted C₁-C₆heteroalkylene;

R⁶ is —CN, —NO₂, —OH, —OR⁹, —SR⁹, —S(=O)R¹⁰, —S(=O)₂R¹⁰, —N(R¹¹)S(=O)₂R¹⁰, —S(=O)₂N(R⁹)₂, —C(=O)R¹⁰, —OC(=O)R¹⁰, —CO₂R⁹, —OCO₂R¹⁰, —N(R⁹)₂, —C(=O)N(R⁹)₂, —OC(=O)N(R⁹)₂, —NR¹¹C(=O)N(R⁹)₂, —NR¹¹C(=O)R¹⁰, —NR¹¹C(=O)OR¹⁰, substituted or unsubstituted C₃-C₁₀cycloalkyl, substituted or unsubstituted C₂-C₁₀heterocycloalkyl, substituted or unsubstituted monocyclic heteroaryl, substituted or unsubstituted bicyclic heteroaryl, or substituted or unsubstituted aryl;

each R⁹ is independently selected from H, substituted or unsubstituted C₁-C₆alkyl, substituted or unsubstituted C₁-C₆heteroalkyl, substituted or unsubstituted C₁-C₆fluoroalkyl, a substituted or unsubstituted C₃-C₁₀cycloalkyl, a substituted or unsubstituted C₂-C₁₀heterocycloalkyl, a substituted or unsubstituted aryl, a substituted or unsubstituted benzyl, a substituted or unsubstituted heteroaryl, —C₁-C₄alkylene-(substituted or unsubstituted C₃-C₁₀cycloalkyl), —C₁-C₄alkylene-(substituted or unsubstituted C₂-C₁₀heterocycloalkyl), —C₁-C₄alkylene-(substituted or unsubstituted aryl), and —C₁-C₄alkylene-(substituted or unsubstituted heteroaryl); or two R⁹ groups attached to the same N atom are taken together with the N atom to which they are attached to form a substituted or unsubstituted C₂-C₁₀heterocycloalkyl;

R¹⁰ is substituted or unsubstituted C₁-C₆alkyl, substituted or unsubstituted C₁-C₆heteroalkyl, substituted or unsubstituted C₁-C₆fluoroalkyl, a substituted or unsubstituted C₃-C₁₀cycloalkyl, a substituted or unsubstituted C₂-C₁₀heterocycloalkyl, a substituted or unsubstituted aryl, a substituted or unsubstituted benzyl, a substituted or unsubstituted heteroaryl, —C₁-C₄alkylene-(substituted or unsubstituted C₃-C₁₀cycloalkyl), —C₁-C₄alkylene-(substituted or unsubstituted C₂-C₁₀heterocycloalkyl), —C₁-C₄alkylene-(substituted or unsubstituted aryl), or —C₁-C₄alkylene-(substituted or unsubstituted heteroaryl);

R¹¹ is H or C₁-C₄alkyl.

In some embodiments,

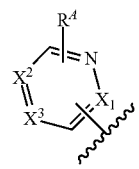

is

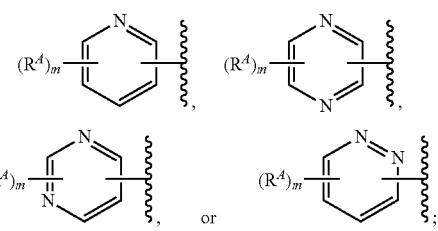

m is 0, 1, 2, 3, or 4.

In some embodiments,

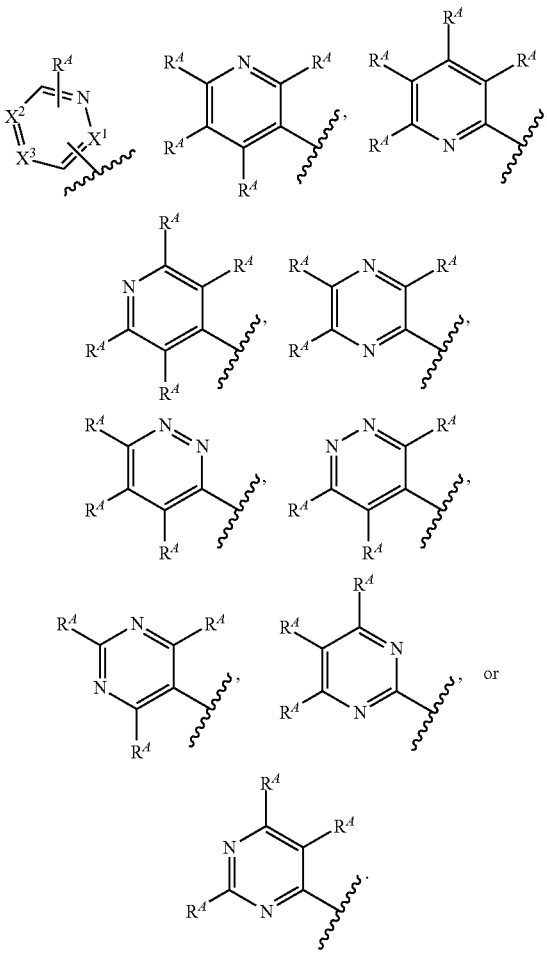

In some embodiments, the compound of Formula (IV) has the structure of Formula (V):

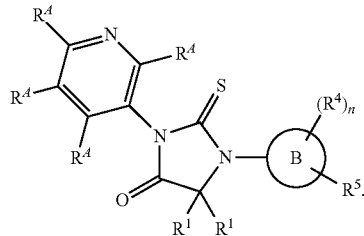

Formula (V)

In some embodiments, ring B is phenyl; $R^4$ is H, halogen, —CN, —OH, substituted or unsubstituted $C_1$-$C_6$alkyl, substituted or unsubstituted $C_1$-$C_6$fluoroalkyl, substituted or unsubstituted $C_1$-$C_6$fluoroalkoxy, or substituted or unsubstituted $C_1$-$C_6$alkoxy; $R^5$ is halogen, —CN, —NO$_2$, —OH, —OR$^9$, —SR$^9$, —S(=O)R$^{10}$, —S(=O)$_2$R$^{10}$, —S(=O)$_2$N(R$^9$)$_2$, —C(=O)R$^{10}$, —CO$_2$R$^9$, —N(R$^9$)$_2$, substituted or unsubstituted $C_2$-$C_{10}$alkyl, substituted or unsubstituted $C_2$-$C_{10}$fluoroalkyl, substituted or unsubstituted $C_1$-$C_{10}$fluoroalkoxy, substituted or unsubstituted $C_1$-$C_{10}$alkoxy, substituted or unsubstituted $C_1$-$C_{10}$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, or -L$^1$-L$^2$-R$^6$; L$^1$ is absent, —O—, —S—, —S(O)—, —S(O)$_2$—, —NH—, —C(=O)—, —C(=O)NH—, or —S(=O)$_2$NH—; L$^2$ is substituted or unsubstituted $C_1$-$C_6$alkylene, substituted or unsubstituted $C_1$-$C_6$fluoroalkylene or substituted or unsubstituted $C_1$-$C_6$heteroalkylene; R$^6$ is —CN, —NO$_2$, —OH, —OR$^9$, —SR$^9$, —S(=O)R$^{10}$, —S(=O)$_2$R$^{10}$, —S(=O)$_2$N(R$^9$)$_2$, —CO$_2$R$^9$, —C(=O)N(R$^9$)$_2$, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, or substituted or unsubstituted aryl.

In some embodiments, each R$^A$ is independently selected from H, halogen, —CN, —NO$_2$, —OH, —S(=O)$_2$R$^{10}$, —S(=O)$_2$N(R$^9$)$_2$, —C(=O)R$^{10}$, —CO$_2$R$^9$, —C(=O)N(R$^9$)$_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, or substituted or unsubstituted $C_1$-$C_6$alkoxy.

In some embodiments, the compound of Formula (I), (Ia), (II), (IV) or (V) has the structure of Formula (VI):

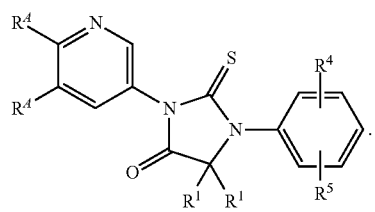

Formula (VI)

In some embodiments, the compound of Formula (I), (Ia), (II), (IV) or (V) has the structure of Formula (VI):

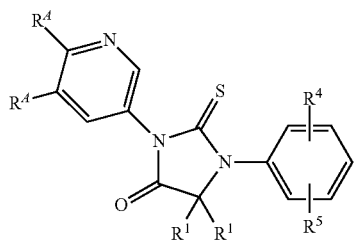

Formula (VI)

wherein,
one R$^A$ is —CN, —NO$_2$, —S(=O)$_2$R$^{10}$, —S(=O)$_2$N(R$^9$)$_2$, —C(=O)R$^{10}$, —CO$_2$R$^9$, or —C(=O)N(R$^9$)$_2$; and the other R$^A$ is H, halogen, —OH, $C_1$-$C_6$alkyl, $C_1$-$C_6$fluoroalkyl, $C_1$-$C_6$fluoroalkoxy, or $C_1$-$C_6$alkoxy; both R$^1$ are taken together with the carbon atom to which they are attached to form a $C_3$-$C_6$cycloalkyl;
or each R$^1$ is independently $C_1$-$C_4$alkyl;
R$^4$ is H, halogen, —OH, $C_1$-$C_4$alkyl, $C_1$-$C_4$fluoroalkyl, $C_1$-$C_4$fluoroalkoxy, or $C_1$-$C_4$alkoxy.

In some embodiments, R$^5$ is -L$^1$-L$^2$-R$^6$ or -L$^1$-R$^7$; L$^1$ is absent, —O—, or —C(=O)NH—; L$^2$ is $C_1$-$C_6$alkylene, $C_1$-$C_6$fluoroalkylene or $C_1$-$C_6$heteroalkylene; R$^6$ is —CN, —NO$_2$, —OH, —OR$^9$, —SR$^9$, —S(=O)R$^1$, —S(=O)$_2$R$^{10}$, —C(=O)R$^{10}$, —CO$_2$R$^9$, —C(=O)N(R$^9$)$_2$, substituted or unsubstituted $C_3$-$C_6$cycloalkyl, substituted or unsubstituted $C_2$-$C_6$heterocycloalkyl, substituted or unsubstituted monocyclic heteroaryl, or substituted or unsubstituted phenyl; R$^7$ is substituted or unsubstituted monocyclic $C_2$-$C_6$heterocycloalkyl, or substituted or unsubstituted monocyclic heteroaryl.

In some embodiments, one R$^A$ is —CN, —NO$_2$, —S(=O)$_2$R$^{10}$, —S(=O)$_2$N(R$^9$)$_2$, —C(=O)R$^{10}$, —CO$_2$R$^9$, —C(=O)N(R$^9$)$_2$, substituted or unsubstituted phenyl or substituted or unsubstituted monocyclic heteroaryl; and the other R$^A$ is H, halogen, —OH, substituted or unsubstituted $C_1$-$C_6$alkyl, substituted or unsubstituted $C_1$-$C_6$fluoroalkyl, substituted or unsubstituted $C_1$-$C_6$fluoroalkoxy, or substituted or unsubstituted $C_1$-$C_6$alkoxy; R$^4$ is H, halogen, —CN, —OH, substituted or unsubstituted $C_1$-$C_6$alkyl, substituted or unsubstituted $C_1$-$C_6$fluoroalkyl, substituted or unsubstituted $C_1$-$C_6$fluoroalkoxy, or substituted or unsubstituted $C_1$-$C_6$alkoxy; R$^5$ is halogen, —CN, —NO$_2$, —OH, —OR$^9$, —S(=O)$_2$R$^{10}$, —S(=O)$_2$N(R$^9$)$_2$, —C(=O)R$^{10}$, —CO$_2$R$^9$, substituted or unsubstituted $C_2$-$C_{10}$alkyl, substituted or unsubstituted $C_2$-$C_{10}$fluoroalkyl, substituted or unsubstituted $C_1$-$C_{10}$fluoroalkoxy, substituted or unsubstituted $C_1$-$C_{10}$alkoxy, substituted or unsubstituted $C_1$-$C_{10}$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, or -L$^1$-L$^2$-R$^6$; L$^1$ is absent, —O—, or —C(=O)NH—; L$^2$ is substituted or unsubstituted $C_1$-$C_6$alkylene, substituted or unsubstituted $C_1$-$C_6$fluoroalkylene or substituted or unsubstituted $C_1$-$C_6$heteroalkylene; R$^6$ is —CN, —NO$_2$, —OH, —OR$^9$, —SR$^9$, —S(=O)R$^{10}$, —S(=O)$_2$R$^{10}$, —S(=O)$_2$N(R$^9$)$_2$, —CO$_2$R$^9$, —C(=O)N(R$^9$)$_2$, substituted or unsubstituted monocyclic heteroaryl, or substituted or unsubstituted phenyl.

In some embodiments, described herein is a compound of Formula (VII), or a pharmaceutically acceptable salt, solvate, N-oxide, metabolite or prodrug thereof:

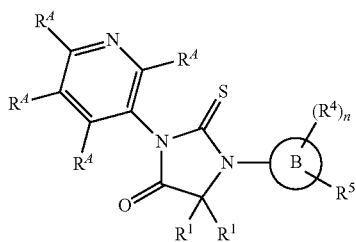

Formula (VII)

wherein,
each $R^1$ is independently selected from H, —OH, substituted or unsubstituted $C_1$-$C_6$alkyl, substituted or unsubstituted $C_1$-$C_6$alkoxy, and substituted or unsubstituted $C_1$-$C_6$fluoroalkyl;
or both $R^1$ are taken together with the carbon atom to which they are attached to form a substituted or unsubstituted $C_3$-$C_{10}$cycloalkyl or a substituted or unsubstituted $C_2$-$C_{10}$heterocycloalkyl;
each $R^A$ is independently selected from H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —N(R$^9$)$_2$, —C(=O)N(R$^9$)$_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, substituted or unsubstituted $C_1$-$C_6$heteroalkyl, substituted or unsubstituted cycloalkyl, substituted or unsubstituted heterocycloalkyl, substituted or unsubstituted phenyl or substituted or unsubstituted monocyclic heteroaryl;
ring B is 5-membered heteroaryl, bicyclic heteroaryl or naphthyl;
n is 0, 1, or 2;
$R^4$ is H, halogen, —CN, —NO$_2$, —OH, substituted or unsubstituted $C_1$-$C_6$alkyl, substituted or unsubstituted $C_1$-$C_6$fluoroalkyl, substituted or unsubstituted $C_1$-$C_6$fluoroalkoxy, or substituted or unsubstituted $C_1$-$C_6$alkoxy;
$R^5$ is H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted $C_2$-$C_{10}$alkyl, substituted or unsubstituted $C_2$-$C_{10}$fluoroalkyl, substituted or unsubstituted $C_1$-$C_{10}$fluoroalkoxy, substituted or unsubstituted $C_1$-$C_{10}$alkoxy, substituted or unsubstituted $C_1$-$C_{10}$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, or -L$^1$-L$^2$-R$^6$;
L$^1$ is absent, —O—, —S—, —S(O)—, —S(O)$_2$—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)$_2$—, or —S(=O)$_2$NH—;
L$^2$ is substituted or unsubstituted $C_1$-$C_6$alkylene, substituted or unsubstituted $C_1$-$C_6$fluoroalkylene or substituted or unsubstituted $C_1$-$C_6$heteroalkylene;

$R^6$ is halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NRC(=O)N(R$^9$)$_2$, —NR$^{11}$C(=O)R$^{10}$, —NR$^{11}$C(=O)OR$^{10}$, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, or substituted or unsubstituted aryl;
each $R^9$ is independently selected from H, substituted or unsubstituted $C_1$-$C_6$alkyl, substituted or unsubstituted $C_1$-$C_6$heteroalkyl, substituted or unsubstituted $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted benzyl, a substituted or unsubstituted heteroaryl, —C$_1$-C$_4$alkylene-(substituted or unsubstituted $C_3$-$C_{10}$cycloalkyl), —C$_1$-C$_4$alkylene-(substituted or unsubstituted $C_2$-$C_{10}$heterocycloalkyl), —C$_1$-C$_4$alkylene-(substituted or unsubstituted aryl), and —C$_1$-C$_4$alkylene-(substituted or unsubstituted heteroaryl); or
two $R^9$ groups attached to the same N atom are taken together with the N atom to which they are attached to form a substituted or unsubstituted $C_2$-$C_{10}$heterocycloalkyl;
$R^{10}$ is substituted or unsubstituted $C_1$-$C_6$alkyl, substituted or unsubstituted $C_1$-$C_6$heteroalkyl, substituted or unsubstituted $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted benzyl, a substituted or unsubstituted heteroaryl, —C$_1$-C$_4$alkylene-(substituted or unsubstituted $C_3$-$C_{10}$cycloalkyl), —C$_1$-C$_4$alkylene-(substituted or unsubstituted $C_2$-$C_{10}$heterocycloalkyl), —C$_1$-C$_4$alkylene-(substituted or unsubstituted aryl), or —C$_1$-C$_4$alkylene-(substituted or unsubstituted heteroaryl);
$R^{11}$ is H or $C_1$-$C_4$alkyl.

In some embodiments, described herein is a compound of Formula (VIII), or a pharmaceutically acceptable salt, solvate, N-oxide, metabolite or prodrug thereof:

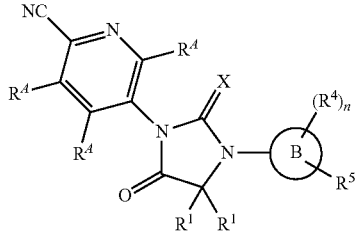

Formula (VIII)

wherein,
each $R^1$ is independently selected from H, —OH, substituted or unsubstituted $C_1$-$C_6$alkyl, substituted or unsubstituted $C_1$-$C_6$alkoxy, and substituted or unsubstituted $C_1$-$C_6$fluoroalkyl;
or both $R^1$ are taken together with the carbon atom to which they are attached to form a substituted or unsubstituted $C_3$-$C_6$cycloalkyl or a substituted or unsubstituted $C_2$-$C_6$heterocycloalkyl;

X is O or S;

each $R^A$ is independently selected from H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —N(R$^9$)$_2$, —C(=O)N(R$^9$)$_2$, C$_1$-C$_6$alkyl, C$_1$-C$_6$alkoxy, C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted phenyl or substituted or unsubstituted monocyclic heteroaryl;

ring B is phenyl, naphthyl, monocyclic heteroaryl, or bicyclic heteroaryl;

n is 0, 1, or 2;

$R^4$ is H, halogen, —CN, —NO$_2$, —OH, —OR$^9$, —SR$^9$, —S(=O)R$^{10}$, —S(=O)$_2$R$^{10}$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, or substituted or unsubstituted C$_1$-C$_6$heteroalkyl;

$R^5$ is halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OC$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted C$_1$-C$_{10}$alkyl, substituted or unsubstituted C$_1$-C$_{10}$fluoroalkyl, substituted or unsubstituted C$_1$-C$_{10}$fluoroalkoxy, substituted or unsubstituted C$_1$-C$_{10}$alkoxy, substituted or unsubstituted C$_1$-C$_{10}$heteroalkyl, substituted or unsubstituted C$_3$-C$_{10}$cycloalkyl, substituted or unsubstituted C$_2$-C$_{10}$heterocycloalkyl, substituted or unsubstituted phenyl, substituted or unsubstituted monocyclic heteroaryl, or -L$^1$-L$^2$-R$^6$;

L$^1$ is absent, —O—, —S—, —S(O)—, —S(O)$_2$—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)$_2$—, or —S(=O)$_2$NH—;

L$^2$ is substituted or unsubstituted C$_1$-C$_6$alkylene, substituted or unsubstituted C$_1$-C$_6$fluoroalkylene or substituted or unsubstituted C$_1$-C$_6$heteroalkylene;

R$^6$ is —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted C$_3$-C$_{10}$cycloalkyl, substituted or unsubstituted C$_2$-C$_{10}$heterocycloalkyl, substituted or unsubstituted monocyclic heteroaryl, substituted or unsubstituted bicyclic heteroaryl, or substituted or unsubstituted aryl;

each R$^9$ is independently selected from H, substituted or unsubstituted C$_1$-C$_6$alkyl, substituted or unsubstituted C$_1$-C$_6$heteroalkyl, substituted or unsubstituted C$_1$-C$_6$fluoroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted benzyl, a substituted or unsubstituted heteroaryl, —C$_1$-C$_4$alkylene-(substituted or unsubstituted C$_3$-C$_{10}$cycloalkyl), —C$_1$-C$_4$alkylene-(substituted or unsubstituted C$_2$-C$_{10}$heterocycloalkyl), —C$_1$-C$_4$alkylene-(substituted or unsubstituted aryl), and —C$_1$-C$_4$alkylene-(substituted or unsubstituted heteroaryl); or two R$^9$ groups attached to the same N atom are taken together with the N atom to which they are attached to form a substituted or unsubstituted C$_2$-C$_{10}$heterocycloalkyl;

R$^{10}$ is substituted or unsubstituted C$_1$-C$_6$alkyl, substituted or unsubstituted C$_1$-C$_6$heteroalkyl, substituted or unsubstituted C$_1$-C$_6$fluoroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted benzyl, a substituted or unsubstituted heteroaryl, —C$_1$-C$_4$alkylene-(substituted or unsubstituted C$_3$-C$_{10}$cycloalkyl), —C$_1$-C$_4$alkylene-(substituted or unsubstituted C$_2$-C$_{10}$heterocycloalkyl), —C$_1$-C$_4$alkylene-(substituted or unsubstituted aryl), or —C$_1$-C$_4$alkylene-(substituted or unsubstituted heteroaryl);

R$^{11}$ is H or C$_1$-C$_4$alkyl.

In some embodiments, X is S; ring B is phenyl; $R^4$ is H, halogen, —CN, —OH, C$_1$-C$_6$alkyl, C$_1$-C$_6$fluoroalkyl, C$_1$-C$_6$fluoroalkoxy, or C$_1$-C$_6$alkoxy; $R^5$ is halogen, —CN, —NO$_2$, —OH, —OR$^9$, —SR$^9$, —S(=O)R$^{10}$, —S(=O)$_2$R$^{10}$, —S(=O)$_2$N(R$^9$)$_2$, —C(=O)R$^{10}$, —CO$_2$R$^9$, —N(R$^9$)$_2$, —C(=O)N(R$^9$)$_2$, substituted or unsubstituted C$_1$-C$_{10}$alkyl, substituted or unsubstituted C$_1$-C$_{10}$fluoroalkyl, substituted or unsubstituted C$_1$-C$_{10}$fluoroalkoxy, substituted or unsubstituted C$_1$-C$_{10}$alkoxy, substituted or unsubstituted C$_1$-C$_{10}$heteroalkyl, substituted or unsubstituted C$_3$-C$_{10}$cycloalkyl, substituted or unsubstituted C$_2$-C$_{10}$heterocycloalkyl, substituted or unsubstituted phenyl, substituted or unsubstituted monocyclic heteroaryl, or -L$^1$-L$^2$-R$^6$; L$^1$ is absent, —O—, —S—, —S(O)—, —S(O)$_2$—, —NH—, —C(=O)—, —C(=O)NH—, or —S(=O)$_2$NH—; L$^2$ is substituted or unsubstituted C$_1$-C$_6$alkylene, substituted or unsubstituted C$_1$-C$_6$fluoroalkylene or substituted or unsubstituted C$_1$-C$_6$heteroalkylene; R$^6$ is —CN, —NO$_2$, —OH, —OR$^9$, —SR$^9$, —S(=O)R$^{10}$, —S(=O)$_2$R$^{10}$, —S(=O)$_2$N(R$^9$)$_2$, —CO$_2$R$^9$, —C(=O)N(R$^9$)$_2$, substituted or unsubstituted C$_3$-C$_{10}$cycloalkyl, substituted or unsubstituted C$_2$-C$_{10}$heterocycloalkyl, substituted or unsubstituted monocyclic heteroaryl, substituted or unsubstituted bicyclic heteroaryl, or substituted or unsubstituted aryl.

In some embodiments, each $R^A$ is independently selected from H, halogen, —CN, —NO$_2$, —OH, —S(=O)$_2$R$^{10}$, —S(=O)$_2$N(R$^9$)$_2$, —C(=O)R$^{10}$, —CO$_2$R$^9$, —C(=O)N(R$^9$)$_2$, C$_1$-C$_6$alkyl, and C$_1$-C$_6$alkoxy.

In some embodiments, described herein is a compound of Formula (VIIIa), or a pharmaceutically acceptable salt, or N-oxide thereof:

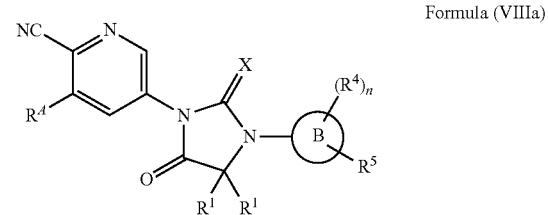

Formula (VIIIa)

wherein, both $R^1$ are taken together with the carbon atom to which they are attached to form a substituted or unsubstituted $C_3$-$C_6$cycloalkyl or a substituted or unsubstituted $C_2$-$C_6$heterocycloalkyl;

or each $R^1$ is independently H, —OH, $C_1$-$C_6$alkyl, $C_1$-$C_6$alkoxy, or $C_1$-$C_6$fluoroalkyl;

X is O or S;

$R^4$ is $C_1$-$C_6$alkyl;

ring B is phenyl, naphthyl, monocyclic heteroaryl, or bicyclic heteroaryl;

n is 0, 1, or 2;

$R^4$ is H, halogen, —CN, —NO$_2$, —OH, —OR$^9$, —SR$^9$, —S(=O)R$^{10}$, —S(=O)$_2$R$^{10}$, $C_1$-$C_6$alkyl, $C_1$-$C_6$fluoroalkyl, $C_1$-$C_6$fluoroalkoxy, $C_1$-$C_6$alkoxy, or $C_1$-$C_6$heteroalkyl;

$R^5$ is halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, $C_1$-$C_{10}$alkyl, $C_1$-$C_{10}$fluoroalkyl, $C_1$-$C_{10}$fluoroalkoxy, $C_1$-$C_{10}$alkoxy, $C_1$-$C_{10}$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, or -L$^1$-L$^2$-R$^6$;

$L^1$ is absent, —O—, —S—, —S(O)—, —S(O)$_2$—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)$_2$—, or —S(=O)$_2$NH—;

$L^2$ is $C_1$-$C_6$alkylene, $C_1$-$C_6$fluoroalkylene or $C_1$-$C_6$heteroalkylene;

$R^6$ is —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, or substituted or unsubstituted aryl;

each $R^9$ is independently selected from H, $C_1$-$C_6$alkyl, $C_1$-$C_6$heteroalkyl, $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted benzyl, a substituted or unsubstituted heteroaryl, —C$_1$-C$_4$alkylene-(substituted or unsubstituted $C_3$-$C_{10}$cycloalkyl), —C$_1$-C$_4$alkylene-(substituted or unsubstituted $C_2$-$C_{10}$heterocycloalkyl), —C$_1$-C$_4$alkylene-(substituted or unsubstituted aryl), and —C$_1$-C$_4$alkylene-(substituted or unsubstituted heteroaryl); or two $R^9$ groups attached to the same N atom are taken together with the N atom to which they are attached to form a substituted or unsubstituted $C_2$-$C_{10}$heterocycloalkyl;

$R^{10}$ is $C_1$-$C_6$alkyl, $C_1$-$C_6$heteroalkyl, $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted benzyl, a substituted or unsubstituted heteroaryl, —C$_1$-C$_4$alkylene-(substituted or unsubstituted $C_3$-$C_{10}$cycloalkyl), —C$_1$-C$_4$alkylene-(substituted or unsubstituted $C_2$-$C_{10}$heterocycloalkyl), —C$_1$-C$_4$alkylene-(substituted or unsubstituted aryl), or —C$_1$-C$_4$alkylene-(substituted or unsubstituted heteroaryl);

$R^{11}$ is H or $C_1$-$C_4$alkyl.

In some embodiments, X is S; ring B is phenyl; $R^4$ is H, halogen, —CN, —OH, $C_1$-$C_6$alkyl, $C_1$-$C_6$fluoroalkyl, $C_1$-$C_6$fluoroalkoxy, or $C_1$-$C_6$alkoxy; $R^5$ is halogen, —CN, —NO$_2$, —OH, —OR$^9$, —SR$^9$, —S(=O)R$^{10}$, —S(=O)$_2$R$^{10}$, —S(=O)$_2$N(R$^9$)$_2$, —C(=O)R$^{10}$, —CO$_2$R$^9$, —N(R$^9$)$_2$, —C(=O)N(R$^9$)$_2$, $C_1$-$C_{10}$alkyl, $C_1$-$C_{10}$fluoroalkyl, $C_1$-$C_{10}$fluoroalkoxy, $C_1$-$C_{10}$alkoxy, $C_1$-$C_{10}$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, or -L$^1$-L$^2$-R$^6$; $L^1$ is absent, —O—, —S—, —S(O)—, —S(O)$_2$—, —NH—, —C(=O)—, —C(=O)NH—, or —S(=O)$_2$NH—; $L^2$ is $C_1$-$C_6$alkylene, $C_1$-$C_6$fluoroalkylene or $C_1$-$C_6$heteroalkylene; $R^6$ is —CN, —NO$_2$, —OH, —OR$^9$, —SR$^9$, —S(=O)R$^{10}$, —S(=O)$_2$R$^{10}$, —S(=O)$_2$N(R$^9$)$_2$, —CO$_2$R$^9$, —C(=O)N(R$^9$)$_2$, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, or substituted or unsubstituted aryl.

In some embodiments, $R^4$ is $C_1$-$C_6$alkyl; both $R^1$ are taken together with the carbon atom to which they are attached to form a $C_3$-$C_6$cycloalkyl; or each $R^1$ is independently $C_1$-$C_4$alkyl.

In some embodiments, the compound of Formula (VIII) has the structure of Formula (IX):

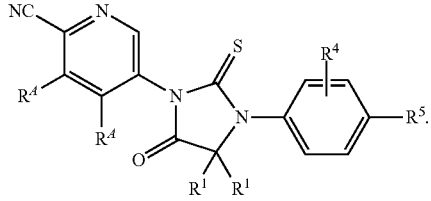

Formula (IX)

In some embodiments, each $R^4$ is independently selected from H, halogen, —OH, $C_1$-$C_6$alkyl, and $C_1$-$C_6$alkoxy.

In some embodiments, the compound of Formula (VIII) or Formula (VIIIa) has the structure of Formula (IXa):

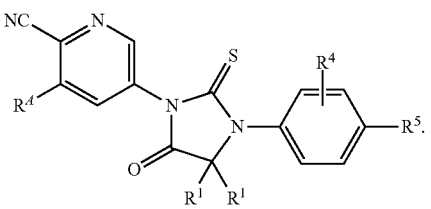

Formula (IXa)

In some embodiments, each $R^9$ is independently selected from H, $C_1$-$C_6$alkyl, $C_1$-$C_6$heteroalkyl, $C_1$-$C_6$fluoroalkyl, a substituted or unsubstituted $C_3$-$C_6$cycloalkyl, a substituted or unsubstituted $C_2$-$C_6$heterocycloalkyl, a substituted or unsubstituted phenyl, a substituted or unsubstituted benzyl, and a substituted or unsubstituted monocyclic heteroaryl; or two $R^9$ groups attached to the same N atom are taken together with the N atom to which they are attached to form a substituted or unsubstituted $C_2$-$C_6$heterocycloalkyl; $R^{10}$ is $C_1$-$C_6$alkyl, $C_1$-$C_6$heteroalkyl, $C_1$-$C_6$fluoroalkyl, a substituted or unsubstituted $C_3$-$C_6$cycloalkyl, a substituted or unsubstituted $C_2$-$C_6$heterocycloalkyl, a substituted or unsubstituted phenyl, or a substituted or unsubstituted monocyclic heteroaryl.

In some embodiments, $R^5$ is halogen, —CN, —OH, —$OR^9$, —$SR^9$, —S(=O)$R^{10}$, —S(=O)$_2R^{10}$, —S(=O)$_2$N($R^9$)$_2$, —C(=O)$R^{10}$, —CO$_2R^9$, —N($R^9$)$_2$, —C(=O)NH($R^9$), $C_1$-$C_{10}$alkyl, $C_1$-$C_{10}$fluoroalkyl, $C_1$-$C_{10}$fluoroalkoxy, $C_1$-$C_{10}$alkoxy, $C_1$-$C_{10}$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, or -$L^1$-$L^2$-$R^6$; $L^1$ is absent, —O—, —S—, —S(O)—, —S(O)$_2$—, —NH—, —C(=O)—, —C(=O)NH—, or —S(=O)$_2$NH—; $L^2$ is $C_1$-$C_6$alkylene; $R^6$ is —CN, —OH, —$OR^9$, —$SR^9$, —S(=O)$R^{10}$, —S(=O)$_2R^{10}$, —S(=O)$_2$N($R^9$)$_2$, —CO$_2R^9$, —C(=O)N($R^9$)$_2$, substituted or unsubstituted $C_3$-$C_6$cycloalkyl, substituted or unsubstituted $C_2$-$C_6$heterocycloalkyl, substituted or unsubstituted monocyclic heteroaryl, or substituted or unsubstituted phenyl.

In some embodiments, $R^4$ is —$CH_3$; both $R^1$ are taken together with the carbon atom to which they are attached to form a cyclopropyl, cyclobutyl, cyclopentyl, or cyclohexyl; or each $R^1$ is —$CH_3$; $R^5$ is halogen, —CN, —OH, —$OR^9$, —$SR^9$, —S(=O)$R^{10}$, —S(=O)$_2R^{10}$, —S(=O)$_2$N($R^9$)$_2$, —C(=O)$R^{10}$, —CO$_2R^9$, —N($R^9$)$_2$, —C(=O)NH($R^9$), $C_1$-$C_{10}$alkyl, $C_1$-$C_{10}$fluoroalkyl, $C_1$-$C_{10}$fluoroalkoxy, $C_1$-$C_{10}$alkoxy, $C_1$-$C_{10}$heteroalkyl, substituted or unsubstituted $C_3$-$C_6$cycloalkyl, substituted or unsubstituted $C_2$-$C_6$heterocycloalkyl, substituted or unsubstituted phenyl, substituted or unsubstituted monocyclic heteroaryl, or -$L^1$-$L^2$-$R^6$; $L^1$ is absent, —O—, —S—, —S(O)—, —S(O)$_2$—, —NH—, —C(=O)—, —C(=O)NH—, or —S(=O)$_2$NH—; $L^2$ is $C_1$-$C_6$alkylene; $R^6$ is substituted or unsubstituted $C_2$-$C_6$heterocycloalkyl, or unsubstituted monocyclic heteroaryl, or substituted or unsubstituted phenyl.

In some embodiments, described herein is a compound of Formula (X), or a pharmaceutically acceptable salt, solvate, N-oxide, metabolite or prodrug thereof:

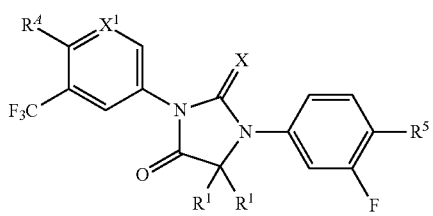

Formula (X)

wherein,
each $R^1$ is independently selected from H and —$CH_3$;
or both $R^1$ are taken together with the carbon atom to which they are attached to form a cyclobutyl;
X is O or S;
$X^1$ is CH or N;
$R^4$ is —CN or —C(=O)$NH_2$;
$R^5$ is —$CO_2H$, or —C(=O)$NH_2$.

In some embodiments, described herein is a compound of Formula (X), or a pharmaceutically acceptable salt, solvate, N-oxide, metabolite or prodrug thereof:

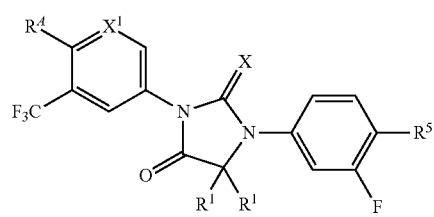

Formula (X)

wherein,
each $R^1$ is independently selected from H and —$CH_3$;
or both $R^1$ are taken together with the carbon atom to which they are attached to form a cyclobutyl;
X is O;
$X^1$ is CH or N;
$R^4$ is —CN or —C(=O)$NH_2$;
$R^5$ is —$CO_2H$, —C(=O)$NH_2$ or —C(=O)NH($CH_3$).

In some embodiments, described herein is a compound of Formula (X), or a pharmaceutically acceptable salt, solvate, N-oxide, metabolite or prodrug thereof:

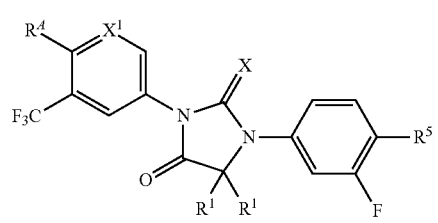

Formula (X)

wherein,
each $R^1$ is independently selected from H and —$CH_3$;
or both $R^1$ are taken together with the carbon atom to which they are attached to form a cyclobutyl;
X is O or S;
$X^1$ is CH or N;
$R^4$ is —C(=O)$NH_2$;
$R^5$ is —$CO_2H$, —C(=O)$NH_2$ or —C(=O)NH($CH_3$).

Throughout the specification, groups and substituents thereof can be chosen by one skilled in the field to provide stable moieties and compounds.

Compounds disclosed herein are selective androgen receptor modulators. In some embodiments, compounds disclosed herein have high specificity for the androgen receptor and have desirable, tissue-selective pharmacological activities. Desirable, tissue-selective pharmacological activities include, but are not limited to, AR antagonist activity in prostate cells and no AR antagonist activity in non-prostate cells. In some embodiments, compounds disclosed herein are antiandrogens that display negligible or no AR agonist activity.

In some embodiments, presented herein are compounds selected from active metabolites, tautomers, pharmaceutically acceptable solvates, pharmaceutically acceptable salts or prodrugs of a compound of Formula (I), (Ia), (II), (III), (IV), (V), (VI), (VII), (VIII), (VIIIa), (IX), (IXa) or (X).

In some embodiments, provided is a pharmaceutical composition comprising a therapeutically effective amount of a compound of Formula (I), (Ia), (II), (III), (IV), (V), (VI), (VII), (VIII), (VIIIa), (IX), (IXa) or (X). In some embodiments, the pharmaceutical composition also contains at least one pharmaceutically acceptable inactive ingredient. In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a colloid, a dispersion, a suspension, a solution, an emulsion, an ointment, or a lotion.

In some embodiments, the pharmaceutical composition further comprises one or more additional therapeutically active agents selected from: corticosteroids, anti-emetic agents, analgesics, anti-cancer agents, anti-inflammatories, kinase inhibitors, HSP90 inhibitors, histone deacetylase (HDAC) inhibitors.

In some embodiments, provided is a method comprising administering a compound of Formula (I), (Ia), (II), (III), (IV), (V), (VI), (VII), (VIII), (VIIIa), (IX), (IXa) or (X) to a human with a diseases or condition that is androgen receptor meditated or androgen receptor dependent. In some embodiments, the human is already being administered one or more additional therapeutically active agents other than a compound of Formula (I), (Ia), (II), (III), (IV), (V), (VI), (VII), (VIII), (VIIIa), (IX), (IXa) or (X). In some embodiments, the method further comprises administering one or more additional therapeutically active agents other than a compound of Formula (I), (Ia), (II), (III), (IV), (V), (VI), (VII), (VIII), (VIIIa), (IX), (IXa) or (X).

In some embodiments, the one or more additional therapeutically active agents other than a compound of Formula (I), (Ia), (II), (III), (IV), (V), (VI), (VII), (VIII), (VIIIa), (IX), (IXa) or (X) are selected from: corticosteroids, anti-emetic agents, analgesics, anti-cancer agents, anti-inflammatories, kinase inhibitors, HSP90 inhibitors, histone deacetylase (HDAC) inhibitors.

In some embodiments, described herein is a method of treating an androgen receptor dependent or androgen receptor mediated disease or condition in mammal comprising administering to the mammal a therapeutically effective amount of a compound of Formula (I), (Ia), (II), (III), (IV), (V), (VI), (VII), (VIII), (VIIIa), (IX), (IXa) or (X), or a pharmaceutically acceptable salt thereof or N-oxide thereof. In some embodiments, the androgen receptor dependent or androgen receptor mediated disease or condition is benign prostate hyperplasia, hirsutism, acne, adenomas and neoplasies of the prostate, benign or malignant tumor cells containing the androgen receptor, hyperpilosity, seborrhea, endometriosis, polycystic ovary syndrome, androgenic alopecia, hypogonadism, osteoporosis, suppression of spermatogenesis, libido, cachexia, anorexia, androgen supplementation for age related decreased testosterone levels, prostate cancer, breast cancer, endometrial cancer, uterine cancer, hot flashes, and Kennedy's disease muscle atrophy and weakness, skin atrophy, bone loss, anemia, arteriosclerosis, cardiovascular disease, loss of energy, loss of well-being, type 2 diabetes or abdominal fat accumulation.

In some embodiments, described herein is a method of treating cancer in a mammal comprising administering to the mammal a therapeutically effective amount of a compound of Formula (I), (Ia), (II), (III), (IV), (V), (VI), (VII), (VIII), (VIIIa), (IX), (IXa) or (X), or a pharmaceutically acceptable salt thereof or N-oxide thereof. In some embodiments, the cancer is a hormone dependent cancer. In some embodiments, the hormone dependent cancer is an androgen receptor dependent cancer. In some embodiments, the cancer is prostate cancer. In some embodiments, the cancer is hormone refractory prostate cancer. In some embodiments, the method of treating cancer further comprises administering to the mammal at least one additional anti-cancer agent.

In some embodiments, described herein is a method of treating cancer in a mammal comprising administering to the mammal a therapeutically effective amount of a compound, wherein the compound is: an androgen receptor inverse agonist; androgen receptor antagonist; androgen receptor degrader; androgen receptor trafficking modulator; androgen receptor degrader; androgen receptor DNA-binding inhibitor; or combinations thereof. In some embodiments, the cancer is prostate cancer. In some embodiments, the cancer is hormone refractory prostate cancer. In some embodiments, the compound is a compound of Formula (I), (Ia), (II), (III), (IV), (V), (VI), (VII), (VIII), (VIIIa), (IX), (IXa) or (X), or a pharmaceutically acceptable salt thereof or N-oxide thereof.

Pharmaceutical formulations described herein are administrable to a subject in a variety of ways by multiple administration routes, including but not limited to, oral, parenteral (e.g., intravenous, subcutaneous, intramuscular), buccal, topical or transdermal administration routes. The pharmaceutical formulations described herein include, but are not limited to, aqueous liquid dispersions, self-emulsifying dispersions, solid solutions, liposomal dispersions, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds of Formula (I), (Ia), (II), (III), (IV), (V), (VI), (VII), (VIII), (VIIIa), (IX), (IXa) and (X) are administered orally.

In some embodiments, the compounds of Formula (I), (Ia), (II), (III), (IV), (V), (VI), (VII), (VIII), (VIIIa), (IX), (IXa) and (X) are administered topically. In such embodiments, the compound of Formula (I), (Ia), (II), (III), (IV), (V), (VI), (VII), (VIII), (VIIIa), (IX), (IXa) or (X) is formulated into a variety of topically administrable compositions, such as solutions, suspensions, lotions, gels, pastes, shampoos, scrubs, rubs, smears, medicated sticks, medicated bandages, balms, creams or ointments. Such pharmaceutical compounds can contain solubilizers, stabilizers, tonicity enhancing agents, buffers and preservatives. In one aspect, the compounds of Formula (I), (Ia), (II), (III), (IV), (V), (VI), (VII), (VIII), (VIIIa), (IX), (IXa) and (X) are administered topically to the skin.

In another aspect is the use of a compound of Formula (I), (Ia), (II), (III), (IV), (V), (VI), (VII), (VIII), (VIIIa), (IX), (IXa) or (X) in the manufacture of a medicament for treating a disease, disorder or conditions in which the activity of androgen receptors contributes to the pathology and/or symptoms of the disease or condition. In one aspect, the disease or condition is any of the diseases or conditions specified herein.

In any of the aforementioned aspects are further embodiments in which: (a) the effective amount of the compound of Formula (I), (II), (III), (IV), (V), (VI), (VII), (VIII), (IX) or (X) is systemically administered to the mammal; and/or (b) the effective amount of the compound is administered orally to the mammal; and/or (c) the effective amount of the compound is intravenously administered to the mammal; and/or (d) the effective amount of the compound is administered by injection to the mammal; and/or (e) the effective amount of the compound is administered topically to the mammal; and/or (f) the effective amount is administered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Also provided is a method of reducing AR activation in a mammal comprising administering to the mammal at least one compound having the structure of Formula (I), (Ia), (II), (III), (IV), (V), (VI), (VII), (VIII), (VIIIa), (IX), (IXa) or (X). In some embodiments, the method comprises reducing AR activation in prostate cells in the mammal. In some embodiments, the method comprises reducing AR activation in prostate cells in the mammal and not in non-prostate cells. In some embodiments, the method of reducing AR activation comprises reducing the binding of androgens to the androgen receptor. In some embodiments, the method of reducing AR activation comprises reducing AR concentrations.

In some cases disclosed herein is the use of a compound of Formula (I), (Ia), (II), (III), (IV), (V), (VI), (VII), (VIII), (VIIIa), (IX), (IXa) or (X) in the manufacture of a medicament for the treatment of diseases or conditions that are androgen receptor dependent or androgen receptor mediated. In some embodiments, the disease or condition is prostrate cancer. In some embodiments, the androgen receptor dependent or androgen receptor mediated disease or condition is described herein.

In some cases disclosed herein is the use of a compound of Formula (I), (Ia), (II), (III), (IV), (V), (VI), (VII), (VIII), (VIIIa), (IX), (IXa) or (X) in the treatment or prevention of diseases or conditions that are androgen receptor dependent or androgen receptor mediated. In some embodiments, the androgen receptor dependent or androgen receptor mediated disease or condition is described herein.

In any of the embodiments disclosed herein, the mammal is a human.

In some embodiments, compounds provided herein are administered to a human.

In some embodiments, compounds provided herein are orally administered.

In some embodiments, compounds provided herein are used to diminish, reduce, or eliminate the activity of androgen receptors.

Articles of manufacture, which include packaging material, a compound of Formula (I), (Ia), (II), (III), (IV), (V), (VI), (VII), (VIII), (VIIIa), (IX), (IXa) or (X) within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for reducing, diminishing or eliminating the effects of androgen receptors, or for the treatment, prevention or amelioration of one or more symptoms of a disease or condition that would benefit from a reduction or elimination of androgen receptor activity, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

DETAILED DESCRIPTION OF THE INVENTION

Androgen receptor (AR) is a member of the steroid and nuclear receptor superfamily. Among this large family of proteins, only five vertebrate steroid receptors are known and include the androgen receptor, estrogen receptor, progesterone receptor, glucocorticoid receptor, and mineralocorticoid receptor. AR is a soluble protein that functions as an intracellular transcriptional factor. AR function is regulated by the binding of androgens, which initiates sequential conformational changes of the receptor that affect receptor-protein interactions and receptor-DNA interactions.

AR is mainly expressed in androgen target tissues, such as the prostate, skeletal muscle, liver, and central nervous system (CNS), with the highest expression level observed in the prostate, adrenal gland, and epididymis. AR can be activated by the binding of endogenous androgens, including testosterone and 5α-dihydrotestosterone (5α-DHT).

The androgen receptor (AR), located on Xq11-12, is a 110 kD nuclear receptor that, upon activation by androgens, mediates transcription of target genes that modulate growth and differentiation of prostate epithelial cells. Similar to the other steroid receptors, unbound AR is mainly located in the cytoplasm and associated with a complex of heat shock proteins (HSPs) through interactions with the ligand-binding domain. Upon agonist binding, AR goes through a series of conformational changes: the heat shock proteins dissociate from AR, and the transformed AR undergoes dimerization, phosphorylation, and translocation to the nucleus, which is mediated by the nuclear localization signal. Translocated receptor then binds to the androgen response element (ARE), which is characterized by the six-nucleotide half-site consensus sequence 5'-TGTTCT-3' spaced by three random nucleotides and is located in the promoter or enhancer region of AR gene targets. Recruitment of other transcription co-regulators (including co-activators and co-repressors) and transcriptional machinery further ensures the transactivation of AR-regulated gene expression. All of these processes are initiated by the ligand-induced conformational changes in the ligand-binding domain.

AR signaling is crucial for the development and maintenance of male reproductive organs including the prostate gland, as genetic males harboring loss of function AR mutations and mice engineered with AR defects do not develop prostates or prostate cancer. This dependence of prostate cells on AR signaling continues even upon neoplastic transformation. Androgen depletion (now using GnRH agonists) continues to be the mainstay of prostate cancer treatment. However androgen depletion is usually effective for a limited duration and prostate cancer evolves to regain the ability to grow despite low levels of circulating androgens. Treatment options for castration resistant prostate cancer (CRPC) are an unmet need with docetaxel being the only agent that has been shown to prolong survival. Interestingly, while a small minority of CRPC does bypass the requirement for AR signaling, the vast majority of CRPC, though frequently termed "androgen independent prostate cancer" or "hormone refractory prostate cancer," retains its lineage dependence on AR signaling.

Prostate cancer is the second most common cause of cancer death in men in the US, and approximately one in every six American men will be diagnosed with the disease during his lifetime. Treatment aimed at eradicating the tumor is unsuccessful in 30% of men, who develop recurrent disease that is usually manifest first as a rise in plasma prostate-specific antigen (PSA) followed by spread to distant sites. Given that prostate cancer cells depend on androgen receptor (AR) for their proliferation and survival, these men are treated with agents that block production of testosterone (e.g. GnRH agonists), alone or in combination with anti-androgens (e.g. bicalutamide), which antagonize the effect of any residual testosterone. The approach is effective as evidenced by a drop in PSA and regression of visible tumor (if present); however, this is followed by regrowth as a "castration resistant" prostate cancer (CRPC) to which most patients eventually succumb. Recent studies on the molecular basis of CRPC have demonstrated that CRPC continues to depend on AR signaling and that a key mechanism of acquired resistance is an elevated level of AR protein (*Nat. Med*, 2004, 10, 33-39). AR targeting agents with activity in hormone sensitive and castration resistant prostate cancer have great promise in treating this lethal disease.

Anti-androgens are useful for the treatment of prostate cancer during its early stages. However, prostate cancer often advances to a hormone-refractory state in which the disease progresses in the presence of continued androgen ablation or anti-androgen therapy. Instances of antiandrogen withdrawal syndrome have also been reported after prolonged treatment with anti-androgens. Antiandrogen withdrawal syndrome is commonly observed clinically and is defined in terms of the tumor regression or symptomatic relief observed upon cessation of antiandrogen therapy. AR mutations that result in receptor promiscuity and the ability of these anti-androgens to exhibit agonist activity might at least partially account for this phenomenon. For example, hydroxyflutamide and bicalutamide act as AR agonists in T877A and W741L/W741C AR mutants, respectively.

In the setting of prostate cancer cells that were rendered "castration resistant" via overexpression of AR, it has been demonstrated that certain anti-androgen compounds, such as bicalutamide, have no antagonist activity, but instead have modest agonist activity (Science, 2009 May 8; 324(5928): 787-90). This agonist activity helps to explain a clinical observation, called the anti-androgen withdrawal syndrome, whereby about 30% of men who progress on AR antagonists experience a decrease in serum PSA when therapy is discontinued (*J Clin Oncol*, 1993. 11(8): p. 1566-72).

Given the central role of AR in prostate cancer development and progression, compounds disclosed herein are useful in the treatment of prostate cancer, either alone or in combination with other agent agents that can modulate other critical pathways in prostate cancer, including but not limited to those that target IGF1R, the PI3K/AKT/mTOR axis, HSP90, or histone deacetylases.

AR-related diseases or conditions include, but are not limited to, benign prostate hyperplasia, hirsutism, acne, adenomas and neoplasies of the prostate, benign or malignant tumor cells containing the androgen receptor, hyperpilosity, seborrhea, endometriosis, polycystic ovary syndrome, androgenic alopecia, hypogonadism, osteoporosis, suppression of spermatogenesis, libido, cachexia, anorexia, androgen supplementation for age related decreased testosterone levels, prostate cancer, breast cancer, endometrial cancer, uterine cancer, hot flashes, and Kennedy's disease muscle atrophy and weakness, skin atrophy, bone loss, anemia, arteriosclerosis, cardiovascular disease, loss of energy, loss of well-being, type 2 diabetes and abdominal fat accumulation.

In some embodiments, compounds disclosed herein inhibit AR nuclear translocation, DNA binding to androgen response elements, and coactivator recruitment. In some embodiments, compounds disclosed herein exhibit no agonist activity in AR-overexpressing prostate cancer cells.

In some embodiments, compounds disclosed herein are used to treat prostrate cancer in a mammal, wherein the mammal is chemotherapy-naïve.

In some embodiments, compounds disclosed herein are used to treat prostrate cancer in a mammal, wherein the mammal is being treated for prostrate cancer with at least one anti-cancer agent. In one embodiment, the prostrate cancer is hormone refractory prostate cancer. In one embodiment, the prostate cancer is bicalutamide-resistant prostate cancer.

Compounds

Compounds of Formula (I), (Ia), (II), (III), (IV), (V), (VI), (VII), (VIII), (VIIIa), (IX), (IXa) and (X), including pharmaceutically acceptable salts, prodrugs, and pharmaceutically acceptable solvates thereof, are androgen receptor modulators, such as, for example, AR inverse agonists, AR antagonists, AR degraders, AR trafficking modulators and/or AR DNA-binding inhibitors, and are useful in the treatment of androgen receptor-dependent or androgen receptor-mediated conditions or diseases of diseases or conditions.

In one aspect, provided herein is a compound of Formula (I), or a pharmaceutically acceptable salt, solvate, N-oxide, metabolite or prodrug thereof:

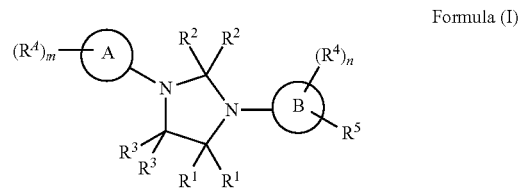

Formula (I)

wherein, ring A is monocyclic heteroaryl, bicyclic heteroaryl, or naphthyl;

m is 0, 1, 2, 3 or 4;

each $R^4$ is independently selected from H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —N(R$^9$)$_2$, —C(=O)N(R$^9$)$_2$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, substituted or unsubstituted C$_1$-C$_6$heteroalkyl, substituted or unsubstituted $C_3$-$C_{10}$cycloalkyl, substituted or unsubstituted $C_2$-$C_{10}$heterocycloalkyl, substituted or unsubstituted phenyl or substituted or unsubstituted monocyclic heteroaryl;

each $R^1$ is independently selected from H, —OH, substituted or unsubstituted $C_1$-$C_6$alkyl, substituted or unsubstituted $C_1$-$C_6$alkoxy, and substituted or unsubstituted $C_1$-$C_6$fluoroalkyl;

or both $R^1$ are taken together with the carbon atom to which they are attached to form a substituted or unsubstituted $C_3$-$C_{10}$cycloalkyl or a substituted or unsubstituted $C_2$-$C_{10}$heterocycloalkyl;

each $R^2$ is H; or both $R^2$ are taken together with the carbon to which they are attached to form —C(=S)— or —C(=O)—;

each $R^3$ is H; or both $R^3$ are taken together with the carbon to which they are attached to form —C(=S)— or —C(=O)—; provided that each $R^2$ is not H if each $R^3$ is H;

ring B is phenyl, naphthyl, monocyclic heteroaryl, or bicyclic heteroaryl;

n is 0, 1, 2, 3 or 4;

each $R^4$ is independently selected from H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

$R^5$ is substituted or unsubstituted $C_2$-$C_{10}$alkyl, substituted or unsubstituted $C_2$-$C_{10}$fluoroalkyl, substituted or unsubstituted $C_2$-$C_{10}$alkoxy, substituted or unsubstituted $C_2$-$C_{10}$fluoroalkoxy, substituted or unsubstituted $C_2$-$C_{10}$heteroalkyl, substituted or unsubstituted $C_2$-$C_{10}$heterofluoroalkyl, or -L$^1$-L$^2$-R$^6$;

L$^1$ is absent, —O—, —S—, —S(=O)—, —S(=O)$_2$—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)$_2$—, or —S(=O)$_2$NH—;

L$^2$ is substituted or unsubstituted $C_1$-$C_6$alkylene, substituted or unsubstituted $C_1$-$C_6$fluoroalkylene or substituted or unsubstituted $C_1$-$C_6$heteroalkylene;

$R^6$ is halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl;

each $R^9$ is independently selected from H, substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl, —C$_1$-C$_4$alkylene-(substituted or unsubstituted $C_3$-$C_{10}$cycloalkyl), —C$_1$-C$_4$alkylene-(substituted or unsubstituted $C_2$-$C_{10}$heterocycloalkyl), —C$_1$-C$_4$alkylene-(substituted or unsubstituted aryl), and —C$_1$-C$_4$alkylene-(substituted or unsubstituted heteroaryl); or two $R^9$ groups attached to the same N atom are taken together with the N atom to which they are attached to form a substituted or unsubstituted $C_2$-$C_{10}$heterocycloalkyl;

$R^{10}$ is substituted or unsubstituted $C_1$-$C_6$alkyl, substituted or unsubstituted $C_1$-$C_6$heteroalkyl, substituted or unsubstituted $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted benzyl, a substituted or unsubstituted heteroaryl, —C$_1$-C$_4$alkylene-(substituted or unsubstituted $C_3$-$C_{10}$cycloalkyl), —C$_1$-C$_4$alkylene-(substituted or unsubstituted $C_2$-$C_{10}$heterocycloalkyl), —C$_1$-C$_4$alkylene-(substituted or unsubstituted aryl), or —C$_1$-C$_4$alkylene-(substituted or unsubstituted heteroaryl);

$R^{11}$ is H or $C_1$-$C_4$alkyl.

For any and all of the embodiments, substituents are selected from among from a subset of the listed alternatives. For example, in some embodiments, both $R^1$ are taken together with the carbon atom to which they are attached to form a substituted or unsubstituted $C_3$-$C_{10}$cycloalkyl. In some embodiments, both $R^1$ are taken together with the carbon atom to which they are attached to form a $C_3$-$C_6$cycloalkyl. In some embodiments, both $R^1$ are taken together with the carbon atom to which they are attached to form a substituted or unsubstituted cyclopropyl, cyclobutyl, cyclopentyl, or cyclcohexyl. In some embodiments, both $R^1$ are taken together with the carbon atom to which they are attached to form a cyclopropyl. In some embodiments, both $R^1$ are taken together with the carbon atom to which they are attached to form a cyclobutyl. In some embodiments, both $R^1$ are taken together with the carbon atom to which they are attached to form a cyclopentyl. In some embodiments, both $R^1$ are taken together with the carbon atom to which they are attached to form a cyclohexyl. In some embodiments, each $R^1$ is independently selected from H, —OH, $C_1$-$C_6$alkyl, and $C_1$-$C_6$fluoroalkyl. In some embodiments, each $R^1$ is independently selected from H, —CH$_3$ and —CF$_3$. In some embodiments, each $R^1$ is —CH$_3$. In some embodiments, both $R^1$ are taken together with the carbon atom to which they are attached to form a cyclobutyl or each $R^1$ is —CH$_3$.

In some embodiments, both $R^2$ are taken together with the carbon to which they are attached to form —C(=S)— or —C(=O)—; both $R^3$ are taken together with the carbon to which they are attached to form-C(=O)—. In some embodiments, both $R^2$ are taken together with the carbon to which they are attached to form —C(=S)—; both $R^3$ are taken together with the carbon to which they are attached to form-C(=O)—.

In some embodiments, ring A is C-linked monocyclic heteroaryl, C-linked bicyclic heteroaryl, or naphthyl. In some embodiments, ring A is C-linked monocyclic heteroaryl. In some embodiments, ring A is C-linked monocyclic 5-membered or 6-membered heteroaryl. In some embodiments, ring A is C-linked monocyclic 6-membered heteroaryl. In some embodiments, ring A is an N-containing heteroaryl.

In some embodiments, both $R^1$ are taken together with the carbon atom to which they are attached to form a substituted or unsubstituted $C_3$-$C_{10}$cycloalkyl; both $R^2$ are taken together with the carbon to which they are attached to form —C(=S)—; both $R^3$ are taken together with the carbon to which they are attached to form-C(=O)—; ring A is N-containing monocyclic heteroaryl, or N-containing bicyclic heteroaryl; each $R^4$ is independently selected from H, halogen, —CN, —NO$_2$, —OH, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —C(=O)N(R$^9$)$_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, substituted or unsubstituted phenyl or substituted or unsubstituted monocyclic heteroaryl.

In some embodiments, both $R^1$ are taken together with the carbon atom to which they are attached to form a cyclopropyl, cyclobutyl, cyclopentyl, or cyclohexyl; ring A is N-containing monocyclic heteroaryl selected from pyridinyl, pyrimidinyl, pyridazinyl, pyrazinyl, triazinyl, pyrrolyl, thiazolyl, oxazolyl, isoxazolyl, oxadiazolyl, imidazolyl, pyrazolyl, isothiazolyl, triazolyl, and tetrazolyl.

In some embodiments, ring A is pyridinyl, pyrimidinyl, pyridazinyl, or pyrazinyl. In some embodiments, ring A is pyridinyl.

In some embodiments,

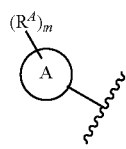

is

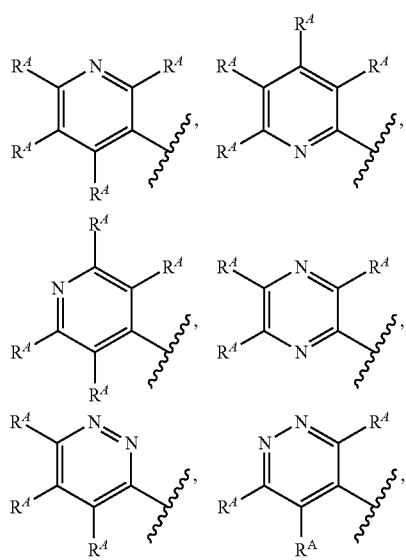

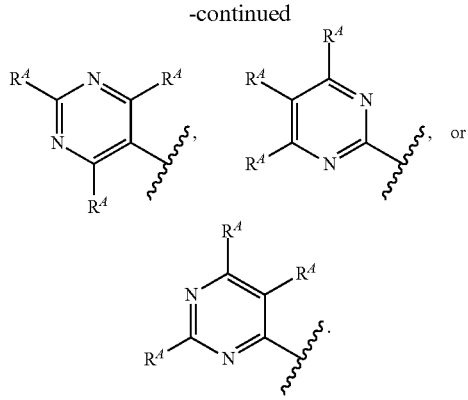

In some embodiments,

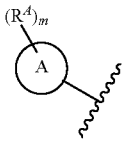

is

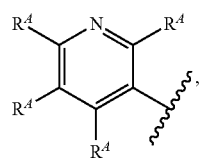

In some embodiments, ring A is monosubstituted with $R^A$. In some embodiments, ring A is disubstituted with $R^A$. In some embodiments, ring A is trisubstituted with $R^A$. In some embodiments, ring A is substituted with —CN and at least one additional $R^A$. In some embodiments, ring A is substituted with —CN and zero, one or two additional $R^A$. In some embodiments, ring A is substituted with —CN and one or two additional $R^A$. In some embodiments, ring A is substituted with —CN and one additional $R^A$.

In some embodiments, ring A is pyridinyl; each $R^A$ is independently selected from H, halogen, —CN, —OH, —S(=O)$_2$R$^{10}$, —S(=O)$_2$N(R$^9$)$_2$, —C(=O)N(R$^9$)$_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, substituted or unsubstituted phenyl or substituted or unsubstituted monocyclic heteroaryl.

In some embodiments, both $R^1$ are taken together with the carbon atom to which they are attached to form a cyclopropyl, cyclobutyl, cyclopentyl, or cyclohexyl; ring A is N-containing bicyclic heteroaryl selected from quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, azaindolyl, pyrazolopyridinyl, thiazolopyrimidinyl, triazolopyridazinyl, thiazolopyridinyl, pyridothienyl, pyrimidiothienyl and pyrrolopyrimidinyl; each $R^A$ is independently selected from H, halogen, —CN, —OH, —S(=O)$_2$R$^{10}$, —S(=O)$_2$N(R$^9$)$_2$, —C(=O)N(R$^9$)$_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, substituted or unsubstituted phenyl or substituted or unsubstituted monocyclic heteroaryl.

In some embodiments, ring A is N-containing bicyclic heteroaryl selected from quinolinyl, isoquinolinyl, quinazolinyl, quinoxalinyl, pyridopyrimidinyl, pyrazolopyrimidinyl, triazolopyridazinyl, and pyrrolopyrimidinyl.

In some embodiments, ring A is [1,2,4]triazolo[4,3-b]pyridazinyl.

In some embodiments, ring B is phenyl or monocyclic heteroaryl; each $R^4$ is independently selected from H, halogen, —CN, —NO$_2$, —OH, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl; $R^5$ is substituted or unsubstituted $C_2$-$C_{10}$alkyl, substituted or unsubstituted $C_2$-$C_{10}$fluoroalkyl, substituted or unsubstituted $C_2$-$C_{10}$alkoxy, substituted or unsubstituted $C_2$-$C_{10}$fluoroalkoxy, substituted or unsubstituted $C_2$-$C_{10}$heteroalkyl, substituted or unsubstituted $C_2$-$C_{10}$heterofluoroalkyl, or -$L^1$-$L^2$-$R^6$; $L^1$ is absent, —O—, —S—, —S(=O)—, —S(=O)$_2$—, —NH—, —C(=O)—, —C(=O)NH—, —NHC(=O)—, —NHS(=O)$_2$—, or —S(=O)$_2$NH—; $L^2$ is substituted or unsubstituted $C_1$-$C_6$alkylene, substituted or unsubstituted $C_1$-$C_6$fluoroalkylene or substituted or unsubstituted $C_1$-$C_6$heteroalkylene; $R^6$ is halogen, —CN, —NO$_2$, —OH, —OR$^9$, —SR$^9$, —S(=O)R$^{10}$, —S(=O)$_2$R$^{10}$, —S(=O)$_2$N(R$^9$)$_2$, —C(=O)R$^{10}$, —CO$_2$R$^9$, —N(R$^9$)$_2$, —C(=O)N(R$^9$)$_2$, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl.

In some embodiments, ring B is phenyl or monocyclic heteroaryl; each $R^4$ is independently selected from H, halogen, —CN, —NO$_2$, —OH, substituted or unsubstituted $C_1$-$C_4$alkyl, substituted or unsubstituted $C_1$-$C_4$fluoroalkyl, substituted or unsubstituted $C_1$-$C_4$fluoroalkoxy, and substituted or unsubstituted $C_1$-$C_4$alkoxy; $R^5$ is substituted or unsubstituted $C_2$-$C_{10}$alkyl, substituted or unsubstituted $C_2$-$C_{10}$fluoroalkyl, substituted or unsubstituted $C_2$-$C_{10}$alkoxy, substituted or unsubstituted $C_2$-$C_{10}$fluoroalkoxy, substituted or unsubstituted $C_2$-$C_{10}$heteroalkyl, substituted or unsubstituted $C_2$-$C_{10}$heterofluoroalkyl, or -$L^1$-$L^2$-$R^6$; $L^1$ is absent, —O—, or —C(=O)NH—; $L^2$ is substituted or unsubstituted $C_1$-$C_6$alkylene, substituted or unsubstituted $C_1$-$C_6$fluoroalkylene or substituted or unsubstituted $C_1$-$C_6$heteroalkylene; $R^6$ is —CN, —NO$_2$, —OH, —OR$^9$, —SR$^9$, —S(=O)R$^{10}$, —S(=O)$_2$R$^{10}$, —C(=O)R$^{10}$, —CO$_2$R$^9$, —C(=O)N(R$^9$)$_2$, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl.

In some embodiments, $L^2$ is substituted or unsubstituted $C_1$-$C_6$alkylene; $R^6$ is —CN, —OR$^9$, —SR$^9$, —S(=O)R$^{10}$, —S(=O)$_2$R$^{10}$, —C(=O)R$^{10}$, —C(=O)N(R$^9$)$_2$, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl.

In some embodiments, $R^6$ is substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl.

In some embodiments, $L^2$ is substituted or unsubstituted $C_1$-$C_6$alkylene; $R^6$ is —CN, —OR$^9$, —SR$^9$, —S(=O)R$^{10}$, —S(=O)$_2$R$^{10}$, —C(=O)R$^{10}$, or —C(=O)N(R$^9$)$_2$; each $R^9$ is independently selected from H, substituted or unsubstituted $C_1$-$C_6$alkyl, substituted or unsubstituted $C_1$-$C_6$fluoroalkyl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), and —$C_1$-$C_4$alkylene-(substituted or unsubstituted heteroaryl); or two $R^9$ groups attached to the same N atom are taken together with the N atom to which they are attached to form a substituted or unsubstituted $C_2$-$C_{10}$heterocycloalkyl; $R^{10}$ is substituted or unsubstituted $C_1$-$C_6$alkyl, substituted or unsubstituted $C_1$-$C_6$fluoroalkyl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), or —$C_1$-$C_4$alkylene-(substituted or unsubstituted heteroaryl).

In some embodiments, provided is a compound of Formula (Ia), or a pharmaceutically acceptable salt, or N-oxide thereof:

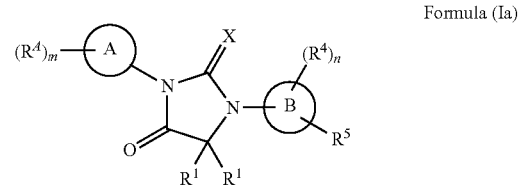

Formula (Ia)

wherein,
ring A is monocyclic heteroaryl, bicyclic heteroaryl, or naphthyl;
m is 1, 2, 3 or 4;
each $R^4$ is independently H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R, —S(=O)$_2$N(R$^9$)$_2$, —C(=O)R$^{10}$, —OC(=O)R$^{10}$, —CO$_2$R$^9$, —N(R$^9$)$_2$, —C(=O)N(R$^9$)$_2$, $C_1$-$C_6$alkyl, $C_1$-$C_6$fluoroalkyl, $C_1$-$C_6$fluoroalkoxy, $C_1$-$C_6$alkoxy, or $C_1$-$C_6$heteroalkyl;
both $R^1$ are taken together with the carbon atom to which they are attached to form a substituted or unsubstituted $C_3$-$C_6$cycloalkyl or a substituted or unsubstituted $C_2$-$C_6$heterocycloalkyl;
or each $R^1$ is independently selected from H, —OH, $C_1$-$C_6$alkyl, $C_1$-$C_6$alkoxy, and $C_1$-$C_6$fluoroalkyl;
X is S or O;
ring B is phenyl, naphthyl, monocyclic heteroaryl, or bicyclic heteroaryl;
n is 0, 1, 2, 3 or 4;
each $R^4$ is independently selected from H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, C$_1$-C$_6$alkyl, C$_1$-C$_6$fluoroalkyl, C$_1$-C$_6$fluoroalkoxy, C$_1$-C$_6$alkoxy, and C$_1$-C$_6$heteroalkyl;

R$^5$ is -L$^1$-L$^2$-R$^6$ or -L$^1$-R$^7$;

L$^1$ is absent, —O—, —S—, —S(=O)—, —S(=O)$_2$—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)$_2$—, or —S(=O)$_2$NH—;

L$^2$ is C$_1$-C$_6$alkylene, C$_1$-C$_6$fluoroalkylene or C$_1$-C$_6$heteroalkylene;

R$^6$ is halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, C$_1$-C$_6$alkyl, C$_1$-C$_6$fluoroalkyl, C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl;

R$^7$ is substituted or unsubstituted monocyclic C$_2$-C$_6$heterocycloalkyl, or substituted or unsubstituted monocyclic heteroaryl;

each R$^9$ is independently selected from H, C$_1$-C$_6$alkyl, C$_1$-C$_6$heteroalkyl, C$_1$-C$_6$fluoroalkyl, substituted or unsubstituted C$_3$-C$_6$cycloalkyl, substituted or unsubstituted C$_2$-C$_{10}$heterocycloalkyl, substituted or unsubstituted phenyl, substituted or unsubstituted monocyclic heteroaryl, —C$_1$-C$_4$alkylene-(substituted or unsubstituted C$_3$-C$_6$cycloalkyl), —C$_1$-C$_4$alkylene-(substituted or unsubstituted monocyclic C$_2$-C$_6$heterocycloalkyl), —C$_1$-C$_4$alkylene-(substituted or unsubstituted phenyl), and —C$_1$-C$_4$alkylene-(substituted or unsubstituted monocyclic heteroaryl); or two R$^9$ groups attached to the same N atom are taken together with the N atom to which they are attached to form a substituted or unsubstituted monocyclic C$_2$-C$_6$heterocycloalkyl;

R$^{10}$ is C$_1$-C$_6$alkyl, C$_1$-C$_6$heteroalkyl, C$_1$-C$_6$fluoroalkyl, a substituted or unsubstituted C$_3$-C$_6$cycloalkyl, a substituted or unsubstituted monocyclic C$_2$-C$_6$heterocycloalkyl, a substituted or unsubstituted phenyl, a substituted or unsubstituted benzyl, a substituted or unsubstituted monocyclic heteroaryl, —C$_1$-C$_4$alkylene-(substituted or unsubstituted C$_3$-C$_6$cycloalkyl), —C$_1$-C$_4$alkylene-(substituted or unsubstituted monocyclic C$_2$-C$_6$heterocycloalkyl), —C$_1$-C$_4$alkylene-(substituted or unsubstituted phenyl), or —C$_1$-C$_4$alkylene-(substituted or unsubstituted monocyclic heteroaryl);

R$^{11}$ is H or C$_1$-C$_4$alkyl.

In some embodiments, both R$^1$ are taken together with the carbon atom to which they are attached to form a substituted or unsubstituted C$_3$-C$_6$cycloalkyl; X is S; ring A is N-containing monocyclic heteroaryl; each R$^A$ is independently selected from H, halogen, —CN, —NO$_2$, —OH, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —C(=O)N(R$^9$)$_2$, C$_1$-C$_6$alkyl, C$_1$-C$_6$fluoroalkyl, C$_1$-C$_6$fluoroalkoxy, and C$_1$-C$_6$alkoxy; ring B is phenyl or monocyclic heteroaryl.

In some embodiments, both R$^1$ are taken together with the carbon atom to which they are attached to form a cyclopropyl, cyclobutyl, cyclopentyl, or cyclohexyl; ring A is pyridinyl, pyrimidinyl, pyridazinyl, or pyrazinyl.

In some embodiments, ring A is pyridinyl; each R$^A$ is independently selected from H, halogen, —CN, —OH, —S(=O)$_2$R$^{10}$, —S(=O)$_2$N(R$^9$)$_2$, —C(=O)N(R$^9$)$_2$, C$_1$-C$_6$alkyl, C$_1$-C$_6$fluoroalkyl, C$_1$-C$_6$fluoroalkoxy, and C$_1$-C$_6$alkoxy.

In some embodiments, each R$^A$ is independently selected from H, halogen, —CN, —OH, —S(=O)$_2$R$^{10}$, —S(=O)$_2$N(R$^9$)$_2$, —C(=O)N(R$^9$)$_2$, C$_1$-C$_6$alkyl, C$_1$-C$_6$fluoroalkyl, C$_1$-C$_6$fluoroalkoxy, and C$_1$-C$_6$alkoxy. In some embodiments, each R$^A$ is independently selected from H, halogen, —CN, —OH, —C(=O)N(R$^9$)$_2$, C$_1$-C$_4$alkyl, C$_1$-C$_4$fluoroalkyl, C$_1$-C$_4$fluoroalkoxy, and C$_1$-C$_4$alkoxy. In some embodiments, each R$^A$ is independently selected from H, F, Cl, —CN, —OH, —C(=O)NH$_2$, —CH$_3$, —CH$_2$H$_3$, —CF$_3$, —OCF$_3$, —OCH$_3$, —CH$_2$CH$_3$.

In some embodiments, ring B is phenyl; R$^5$ is -L$^1$-L$^2$-R$^6$; L$^1$ is absent, —O—, —S—, —S(=O)—, —S(=O)$_2$—, —NH—, —C(=O)—, —C(=O)NH—, —NHC(=O)—, —NHS(=O)$_2$—, or —S(=O)$_2$NH—; L$^2$ is C$_1$-C$_6$alkylene, C$_1$-C$_6$fluoroalkylene or C$_1$-C$_6$heteroalkylene; R$^6$ is halogen, —CN, —NO$_2$, —OH, —OR$^9$, —SR$^9$, —S(=O)R$^{10}$, —S(=O)$_2$R$^{10}$, —S(=O)$_2$N(R$^9$)$_2$, —C(=O)R$^{10}$, —CO$_2$R$^9$, —N(R$^9$)$_2$, —C(=O)N(R$^9$)$_2$, substituted or unsubstituted C$_3$-C$_6$cycloalkyl, substituted or unsubstituted C$_2$-C$_6$heterocycloalkyl, substituted or unsubstituted monocyclic heteroaryl, or substituted or unsubstituted phenyl.

In some embodiments, ring B is phenyl; each R$^A$ is independently selected from H, halogen, —CN, —NO$_2$, —OH, C$_1$-C$_4$alkyl, C$_1$-C$_4$fluoroalkyl, C$_1$-C$_4$fluoroalkoxy, and C$_1$-C$_4$alkoxy; R$^5$ is -L$^1$-L$^2$-R$^6$; L$^1$ is absent, —O—, or —C(=O)NH—; L$^2$ is C$_1$-C$_6$alkylene, C$_1$-C$_6$fluoroalkylene or C$_1$-C$_6$heteroalkylene; R$^6$ is —CN, —NO$_2$, —OH, —OR$^9$, —SR$^9$, —S(=O)R$^{10}$, —S(=O)$_2$R$^{10}$, —C(=O)R$^{10}$, —CO$_2$R$^9$, —C(=O)N(R$^9$)$_2$, substituted or unsubstituted C$_3$-C$_6$cycloalkyl, substituted or unsubstituted C$_2$-C$_6$heterocycloalkyl, substituted or unsubstituted monocyclic heteroaryl, or substituted or unsubstituted phenyl.

In some embodiments, L$^2$ is C$_1$-C$_6$alkylene; R$^6$ is —CN, —OR$^9$, —SR$^9$, —S(=O)R$^{10}$, —S(=O)$_2$R$^{10}$, —C(=O)R$^{10}$, —C(=O)N(R$^9$)$_2$, substituted or unsubstituted C$_3$-C$_6$cycloalkyl, substituted or unsubstituted C$_2$-C$_6$heterocycloalkyl, substituted or unsubstituted monocyclic heteroaryl, or substituted or unsubstituted phenyl.

In some embodiments, R$^6$ is substituted or unsubstituted C$_3$-C$_6$cycloalkyl, substituted or unsubstituted C$_2$-C$_6$heterocycloalkyl, substituted or unsubstituted monocyclic heteroaryl, or substituted or unsubstituted phenyl.

In some embodiments, if R$^6$ is substituted, then R$^6$ is substituted with 1 or 2 groups independently selected from halogen, —CN, —NH$_2$, —NH(CH$_3$), —N(CH$_3$)$_2$, —OH, —CO$_2$H, —CO$_2$(C$_1$-C$_4$alkyl), —C(=O)C$_1$-C$_4$alkyl, —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —S—C$_1$-C$_4$alkyl, or —S(=O)$_2$C$_1$-C$_4$alkyl. In some embodiments, if R$^6$ is substituted, then R$^6$ is substituted with 1 or 2 groups independently selected from halogen, —CN, —OH, —CO$_2$(C$_1$-C$_4$alkyl), —C(=O)C$_1$-C$_4$alkyl, —C(=O)NH$_2$, —C(=O)NH(C$_1$-C$_4$alkyl), —C(=O)N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, and C$_1$-C$_4$fluoroalkoxy.

In some embodiments, L$^2$ is C$_1$-C$_6$alkylene; R$^6$ is a substituted or unsubstituted C$_2$-C$_6$heterocycloalkyl. In some embodiments, L¹ is absent, —O—, or —C(=O)NH—; L² is C₁-C₆alkylene; R⁶ is a substituted or unsubstituted C₂-C₆heterocycloalkyl. In some embodiments, L¹ is —C(=O)NH—. In some embodiments, R⁶ is a substituted or unsubstituted C₃-C₆heterocycloalkyl. In some embodiments, R⁶ is a substituted or unsubstituted N-containing C₂-C₆heterocycloalkyl.

In some embodiments, ring B is phenyl; each R⁴ is independently selected from H, halogen, —CN, —NO₂, —OH, C₁-C₄alkyl, C₁-C₄fluoroalkyl, C₁-C₄fluoroalkoxy, and C₁-C₄alkoxy; R⁵ is -L¹-R⁷; L¹ is absent, —O—, —S—, —S(=O)—, —S(=O)₂—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)₂—, or —S(=O)₂NH—; R⁷ is substituted or unsubstituted monocyclic C₂-C₆heterocycloalkyl, or substituted or unsubstituted monocyclic heteroaryl.

In some embodiments, L² is C₁-C₆alkylene. In some embodiments, L² is C₁-C₄alkylene. In some embodiments, L² is —CH₂—, —CH₂CH₂—, —CH₂CH₂CH₂—, —CH₂CH₂CH₂CH₂—, —CH₂CH₂CH₂CH₂CH₂—, or —CH₂CH₂CH₂CH₂CH₂CH₂—. In some embodiments, L² is —CH₂—, —CH₂CH₂—, —CH₂CH₂CH₂—, or —CH₂CH₂CH₂CH₂—.

In some embodiments, each R⁴ is independently selected from H, halogen, —OH, C₁-C₄alkyl, C₁-C₄fluoroalkyl, C₁-C₄fluoroalkoxy, and C₁-C₄alkoxy.

In some embodiments, R⁵ is -L¹-R⁷.

In some embodiments, L¹ is absent, —O—, —S—, —S(=O)—, —S(=O)₂—, —NH—, —C(=O)—, —C(=O)NH—, or —S(=O)₂NH—. In some embodiments, L¹ is absent. In some embodiments, L¹ is —O—, —S—, —S(=O)—, —S(=O)₂—, —NH—, —C(=O)—, —C(=O)NH—, or —S(=O)₂NH—. In some embodiments, L¹ is absent. In some embodiments, L¹ is —O—. In some embodiments, L¹ is absent. In some embodiments, L¹ is —C(=O)NH—.

In some embodiments, R⁵ is -L¹-R⁷; L¹ is —O—, —S—, —S(=O)—, —S(=O)₂—, —NH—, —C(=O)—, —C(=O)NH—, or —S(=O)₂NH—; R⁷ is substituted or unsubstituted monocyclic C₂-C₆heterocycloalkyl, or substituted or unsubstituted monocyclic heteroaryl.

In some embodiments, if R⁷ is substituted, then R⁷ is substituted with 1 or 2 groups independently selected from halogen, —CN, —NH₂, —NH(CH₃), —N(CH₃)₂, —OH, —CO₂H, —CO₂(C₁-C₄alkyl), —C(=O)C₁-C₄alkyl, —C(=O)NH₂, —C(=O)NH(C₁-C₄alkyl), —C(=O)N(C₁-C₄alkyl)₂, —S(=O)₂NH₂, —S(=O)₂NH(C₁-C₄alkyl), —S(=O)₂N(C₁-C₄alkyl)₂, C₁-C₄alkyl, C₃-C₆cycloalkyl, C₁-C₄fluoroalkyl, C₁-C₄heteroalkyl, C₁-C₄alkoxy, C₁-C₄fluoroalkoxy, —S—C₁-C₄alkyl, or —S(=O)₂C₁-C₄alkyl. In some embodiments, if R⁷ is substituted, then R⁷ is substituted with 1 or 2 groups independently selected from halogen, —CN, —OH, —CO₂(C₁-C₄alkyl), —C(=O)C₁-C₄alkyl, —C(=O)NH₂, —C(=O)NH(C₁-C₄alkyl), —C(=O)N(C₁-C₄alkyl)₂, C₁-C₄alkyl, C₃-C₆cycloalkyl, C₁-C₄fluoroalkyl, C₁-C₄heteroalkyl, C₁-C₄alkoxy, and C₁-C₄fluoroalkoxy.

In some embodiments, R⁵ is -L¹-R⁷; L¹ is absent, —O—, —S—, —S(=O)—, —S(=O)₂—, —NH—, —C(=O)—, —C(=O)NH—, or —S(=O)₂NH—; R⁷ is substituted or unsubstituted monocyclic heteroaryl.

In some embodiments, the compound of Formula (I) or Formula (Ia) has the structure of Formula (II):

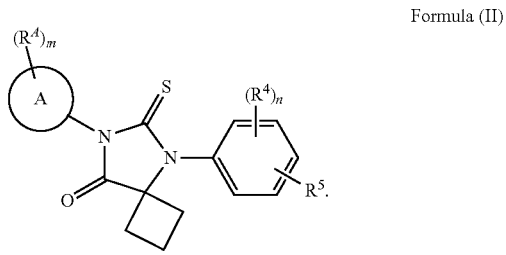

Formula (II)

In some embodiments, the compound of Formula (Ia) has the structure of Formula (II):

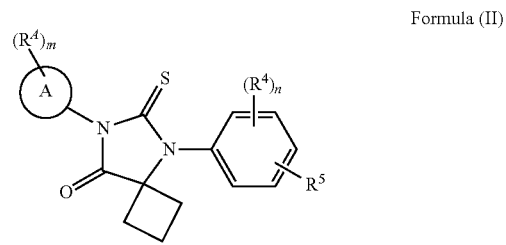

Formula (II)

wherein,

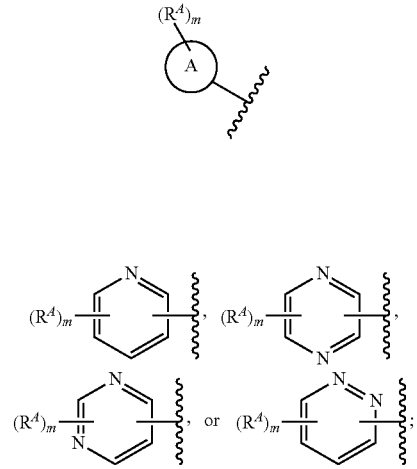

is m is 2;
one R^A is —CN, —NO₂, —S(=O)₂R¹⁰, —S(=O)₂N(R⁹)₂, —C(=O)R¹⁰, —CO₂R⁹, or —C(=O)N(R⁹)₂; and the other R^A is H, halogen, —OH, C₁-C₆alkyl, C₁-C₆fluoroalkyl, C₁-C₆fluoroalkoxy, or C₁-C₆alkoxy;
n is 0 or 1;
each R⁴ is independently selected from H, halogen, —CN, —NO₂, —OH, C₁-C₆alkyl, C₁-C₆fluoroalkyl, C₁-C₆fluoroalkoxy, and C₁-C₆alkoxy;
R⁵ is -L¹-L²-R⁶ or -L¹-R⁷;
L¹ is absent, —O—, or —C(=O)NH—;
L² is C₁-C₆alkylene, C₁-C₆fluoroalkylene or C₁-C₆heteroalkylene;
R⁶ is —CN, —NO₂, —OH, —OR⁹, —SR⁹, —S(=O)R¹⁰, —S(=O)₂R¹⁰, —C(=O)R¹⁰, —CO₂R⁹, —N(R⁹)₂, —C(=O)N(R⁹)₂, substituted or unsubstituted C₃-C₆cycloalkyl, substituted or unsubstituted C₂-C₆heterocycloalkyl, substituted or unsubstituted monocyclic heteroaryl, or substituted or unsubstituted phenyl;

R⁷ is substituted or unsubstituted monocyclic C₂-C₆heterocycloalkyl, or substituted or unsubstituted monocyclic heteroaryl.

In some embodiments,

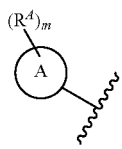

is

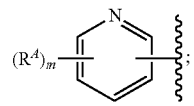

one R^A is —CN and the other R^A is H, halogen, —OH, C₁-C₄alkyl, C₁-C₄fluoroalkyl, C₁-C₄fluoroalkoxy, or C₁-C₄alkoxy; each R⁴ is independently selected from H, halogen, —OH, C₁-C₄alkyl, C₁-C₄fluoroalkyl, C₁-C₄fluoroalkoxy, and C₁-C₄alkoxy; R⁵ is -L¹-L²-R⁶ or -L¹-R⁷; L¹ is absent, —O—, or —C(=O)NH—; L² is C₁-C₆alkylene, C₁-C₆fluoroalkylene, or C₁-C₆heteroalkylene; R⁶ is —CN, —NO₂, —OH, —OR⁹, —SR⁹, —S(=O)R¹⁰, —S(=O)₂R¹⁰, —C(=O)R¹⁰, —CO₂R⁹, —C(=O)N(R⁹)₂, substituted or unsubstituted C₃-C₆cycloalkyl, substituted or unsubstituted C₂-C₆heterocycloalkyl, substituted or unsubstituted monocyclic heteroaryl, or substituted or unsubstituted phenyl; R⁷ is substituted or unsubstituted monocyclic C₂-C₆heterocycloalkyl, or substituted or unsubstituted monocyclic heteroaryl.

In some embodiments, described herein is a compound of Formula (I), or a pharmaceutically acceptable salt, solvate, N-oxide, metabolite or prodrug thereof:

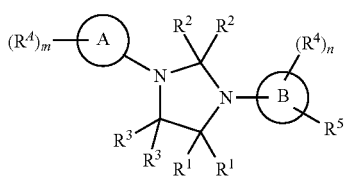

Formula (I)

wherein,
ring A is bicyclic heteroaryl, or naphthyl;
m is 0, 1, 2, or 3;
each R^A is independently selected from H, halogen, —CN, —NO₂, —OH, —OR⁹, —SR⁹, —S(=O)R¹⁰, —S(=O)₂R¹⁰, —N(R¹¹)S(=O)₂R¹⁰, —S(=O)₂N(R⁹)₂, —C(=O)R¹⁰, —OC(=O)R¹⁰, —CO₂R⁹, —N(R⁹)₂, —C(=O)N(R⁹)₂, substituted or unsubstituted C₁-C₆alkyl, substituted or unsubstituted C₁-C₆fluoroalkyl, substituted or unsubstituted C₁-C₆fluoroalkoxy, substituted or unsubstituted C₁-C₆alkoxy, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted phenyl or substituted or unsubstituted monocyclic heteroaryl;

each R¹ is independently selected from H, —OH, substituted or unsubstituted C₁-C₆alkyl, substituted or unsubstituted C₁-C₆alkoxy, and substituted or unsubstituted C₁-C₆fluoroalkyl;

or both R¹ are taken together with the carbon atom to which they are attached to form a substituted or unsubstituted C₃-C₁₀cycloalkyl or a substituted or unsubstituted C₂-C₁₀heterocycloalkyl;

each R² is H; or both R² are taken together with the carbon to which they are attached to form —C(=S)— or —C(=O)—;

each R³ is H; or both R³ are taken together with the carbon to which they are attached to form —C(=S)— or —C(=O)—; provided that each R² is not H if each R³ is H;

ring B is phenyl, naphthyl, monocyclic heteroaryl, or bicyclic heteroaryl;

n is 0, 1, or 2;

each R⁴ is independently selected from H, halogen, —CN, —NO₂, —OH, —OR⁹, —SR⁹, —S(=O)R¹⁰, —S(=O)₂R¹⁰, —N(R¹¹)S(=O)₂R¹⁰, —S(=O)₂N(R⁹)₂, —C(=O)R¹⁰, —OC(=O)R¹⁰, —CO₂R⁹, —OCO₂R¹⁰, —N(R⁹)₂, —C(=O)N(R⁹)₂, —OC(=O)N(R⁹)₂, —NR¹¹C(=O)N(R⁹)₂, —NR¹¹C(=O)R¹⁰, —NR¹¹C(=O)OR¹⁰, substituted or unsubstituted C₁-C₆alkyl, substituted or unsubstituted C₁-C₆fluoroalkyl, substituted or unsubstituted C₁-C₆fluoroalkoxy, substituted or unsubstituted C₁-C₆alkoxy, and substituted or unsubstituted C₁-C₆heteroalkyl;

R⁵ is H, halogen, —CN, —NO₂, —OH, —OR⁹, —SR⁹, —S(=O)R¹⁰, —S(=O)₂R¹⁰, —N(R¹¹)S(=O)₂R, —S(=O)₂N(R⁹)₂, —C(=O)R¹⁰, —OC(=O)R¹⁰, —CO₂R⁹, —OCO₂R¹⁰, —N(R⁹)₂, —C(=O)N(R⁹)₂, —OC(=O)N(R⁹)₂, —NR¹¹C(=O)N(R⁹)₂, —NR¹¹C(=O)R¹⁰, —NR¹¹C(=O)OR¹⁰, substituted or unsubstituted C₁-C₁₀alkyl, substituted or unsubstituted C₁-C₁₀fluoroalkyl, substituted or unsubstituted C₁-C₁₀fluoroalkoxy, C₁-C₁₀alkoxy, substituted or unsubstituted C₁-C₁₀heteroalkyl, or -L¹-L²-R⁶;

L¹ is absent, —O—, —S—, —S(=O)—, —S(=O)₂—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)₂—, or —S(=O)₂NH—;

L² is substituted or unsubstituted C₁-C₆alkylene, substituted or unsubstituted C₁-C₆fluoroalkylene or substituted or unsubstituted C₁-C₆heteroalkylene;

R⁶ is halogen, —CN, —NO₂, —OH, —OR⁹, —SR⁹, —S(=O)R¹⁰, —S(=O)₂R¹⁰, —N(R¹¹)S(=O)₂R¹⁰, —S(=O)₂N(R⁹)₂, —C(=O)R¹⁰, —OC(=O)R¹⁰, —CO₂R⁹, —OCO₂R¹⁰, —N(R⁹)₂, —C(=O)N(R⁹)₂, —OC(=O)N(R⁹)₂, —NR¹¹C(=O)N(R⁹)₂, —NR¹¹C(=O)R¹⁰, —NR¹¹C(=O)OR¹⁰, substituted or unsubstituted C₁-C₆alkyl, substituted or unsubstituted C₁-C₆fluoroalkyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted monocyclic heteroaryl, substituted or unsubstituted bicyclic heteroaryl, substituted or unsubstituted phenyl, or substituted or unsubstituted naphthyl;

each $R^9$ is independently selected from H, substituted or unsubstituted $C_1$-$C_6$alkyl, substituted or unsubstituted $C_1$-$C_6$heteroalkyl, substituted or unsubstituted $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), and —$C_1$-$C_4$alkylene-(substituted or unsubstituted heteroaryl); or two $R^9$ groups attached to the same N atom are taken together with the N atom to which they are attached to form a substituted or unsubstituted $C_2$-$C_{10}$heterocycloalkyl;

$R^{10}$ is substituted or unsubstituted $C_1$-$C_6$alkyl, substituted or unsubstituted $C_1$-$C_6$heteroalkyl, substituted or unsubstituted $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), or —$C_1$-$C_4$alkylene-(substituted or unsubstituted heteroaryl);

$R^{11}$ is H or $C_1$-$C_4$alkyl.

In some embodiments, ring A is selected from quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, azaindolyl, pyrazolopyridinyl, thiazolopyrimidinyl, triazolopyridazinyl, thiazolopyridinyl, pyridothienyl, pyrimidiothienyl, pyrrolopyrimidinyl and naphthyl.

In some embodiments, ring A is selected from quinolinyl, isoquinolinyl, quinazolinyl, quinoxalinyl, pyridopyrimidinyl, pyrazolopyrimidinyl, triazolopyridazinyl, pyrrolopyrimidinyl, and napthyl.

In some embodiments, ring A is [1,2,4]triazolo[4,3-b]pyridazinyl.

In some embodiments, described herein is a compound of Formula (I), or a pharmaceutically acceptable salt, solvate, N-oxide, metabolite or prodrug thereof:

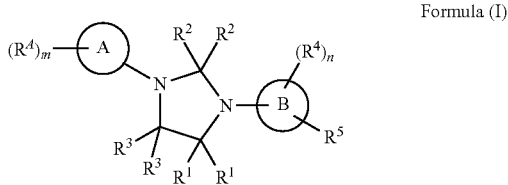

Formula (I)

wherein,
ring A is a 5-membered heteroaryl;
m is 0, 1, 2, or 3;
each $R^4$ is independently selected from H, halogen, —CN, —$NO_2$, —OH, —$OR^9$, —$SR^9$, —S(=O)$R^{10}$, —S(=O)$_2R^{10}$, —N($R^{11}$)S(=O)$_2R^{10}$, —S(=O)$_2$N($R^9$)$_2$, —C(=O)$R^{10}$, —OC(=O)$R^{10}$, —$CO_2R^9$, —N($R^9$)$_2$, —C(=O)N($R^9$)$_2$, substituted or unsubstituted $C_1$-$C_4$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl or substituted or unsubstituted monocyclic heteroaryl;

each $R^1$ is independently selected from H, —OH, substituted or unsubstituted $C_1$-$C_6$alkyl, substituted or unsubstituted $C_1$-$C_6$alkoxy, and substituted or unsubstituted $C_1$-$C_6$fluoroalkyl;

or both $R^1$ are taken together with the carbon atom to which they are attached to form a substituted or unsubstituted $C_3$-$C_{10}$cycloalkyl or a substituted or unsubstituted $C_2$-$C_{10}$heterocycloalkyl;

each $R^2$ is H; or both $R^2$ are taken together with the carbon to which they are attached to form —C(=S)— or —C(=O)—;

each $R^3$ is H; or both $R^3$ are taken together with the carbon to which they are attached to form —C(=S)— or —C(=O)—; provided that each $R^2$ is not H if each $R^3$ is H;

ring B is phenyl, naphthyl, monocyclic heteroaryl, or bicyclic heteroaryl;

n is 0, 1, or 2;

each $R^4$ is independently selected from H, halogen, —CN, —$NO_2$, —OH, —$OR^9$, —$SR^9$, —S(=O)$R^{10}$, —S(=O)$_2R^{10}$, —N($R^{11}$)S(=O)$_2R^{10}$, —S(=O)$_2$N($R^9$)$_2$, —C(=O)$R^{10}$, —OC(=O)$R^{10}$, —$CO_2R^9$, —$OCO_2R^{10}$, —N($R^9$)$_2$, —C(=O)N($R^9$)$_2$, —OC(=O)N($R^9$)$_2$, —$NR^{11}$C(=O)N($R^9$)$_2$, —$NR^{11}$C(=O)$R^{10}$, —$NR^{11}$C(=O)$OR^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, and substituted or unsubstituted $C_1$-$C_6$heteroalkyl;

$R^5$ is H, halogen, —CN, —$NO_2$, —OH, —$OR^9$, —$SR^9$, —S(=O)$R^{10}$, —S(=O)$_2R^{10}$, —N($R^{11}$)S(=O)$_2$R, —S(=O)$_2$N($R^9$)$_2$, —C(=O)$R^{10}$, —OC(=O)$R^{10}$, —$CO_2R^9$, —$OCO_2R^{10}$, —N($R^9$)$_2$, —C(=O)N($R^9$)$_2$, —OC(=O)N($R^9$)$_2$, —$NR^{11}$C(=O)N($R^9$)$_2$, —$NR^{11}$C(=O)$R^{10}$, —$NR^{11}$C(=O)$OR^{10}$, substituted or unsubstituted $C_1$-$C_{10}$alkyl, substituted or unsubstituted $C_1$-$C_{10}$fluoroalkyl, substituted or unsubstituted $C_1$-$C_{10}$fluoroalkoxy, substituted or unsubstituted $C_1$-$C_{10}$alkoxy, substituted or unsubstituted $C_1$-$C_{10}$heteroalkyl, or -$L^1$-$L^2$-$R^6$;

$L^1$ is absent, —O—, —S—, —S(=O)—, —S(=O)$_2$—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)$_2$—, or —S(=O)$_2$NH—;

$L^2$ is substituted or unsubstituted $C_1$-$C_6$alkylene, substituted or unsubstituted $C_1$-$C_6$fluoroalkylene or substituted or unsubstituted $C_1$-$C_6$heteroalkylene;

$R^6$ is halogen, —CN, —$NO_2$, —OH, —$OR^9$, —$SR^9$, —S(=O)$R^{10}$, —S(=O)$_2R^{10}$, —N($R^{11}$)S(=O)$_2R^{10}$, —S(=O)$_2$N($R^9$)$_2$, —C(=O)$R^{10}$, —OC(=O)$R^{10}$, —$CO_2R^9$, —$OCO_2R^{10}$, —N($R^9$)$_2$, —C(=O)N($R^9$)$_2$, —OC(=O)N($R^9$)$_2$, —$NR^{11}$C(=O)N($R^9$)$_2$, —$NR^{11}$C(=O)$R^{10}$, —$NR^{11}$C(=O)$OR^{10}$, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl;

each $R^9$ is independently selected from H, substituted or unsubstituted $C_1$-$C_6$alkyl, substituted or unsubstituted $C_1$-$C_6$heteroalkyl, substituted or unsubstituted $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), and —$C_1$-$C_4$alkylene-(substituted or unsubstituted heteroaryl); or two $R^9$ groups attached to the same N atom are taken together with the N atom to which they are attached to form a substituted or unsubstituted $C_2$-$C_{10}$heterocycloalkyl;

$R^{10}$ is substituted or unsubstituted $C_1$-$C_6$alkyl, substituted or unsubstituted $C_1$-$C_6$heteroalkyl, substituted or unsubstituted $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), or —$C_1$-$C_4$alkylene-(substituted or unsubstituted heteroaryl);

$R^{11}$ is H or $C_1$-$C_4$alkyl.

In some embodiments, ring A is selected from pyrrolyl, thiazolyl, oxazolyl, isoxazolyl, oxadiazolyl, imidazolyl, pyrazolyl, isothiazolyl, triazolyl, and tetrazolyl.

In some embodiments,

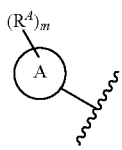

is selected from:

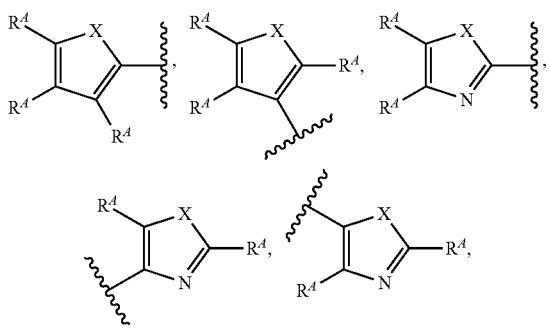

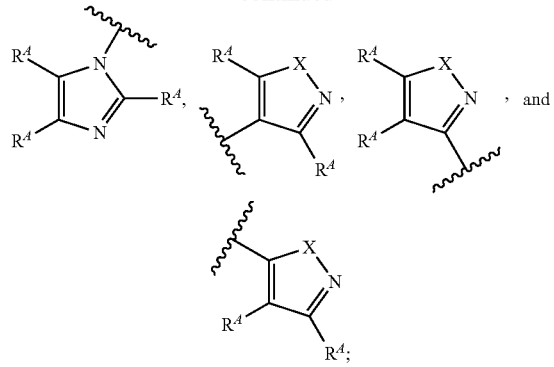

where X is O, S, or $NR^A$. In some embodiments, X is O. In some embodiments, X is S. In some embodiments, X is $NR^A$.

In some embodiments, both $R^1$ are taken together with the carbon atom to which they are attached to form a $C_3$-$C_{10}$cycloalkyl; both $R^2$ are taken together with the carbon to which they are attached to form —C(=S)—; both $R^3$ are taken together with the carbon to which they are attached to form -C(=O)—.

In some embodiments, the compound described herein has the structure of Formula (III):

Formula (III)

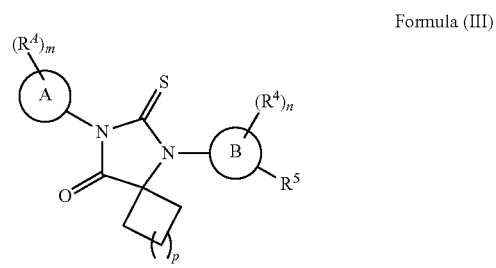

wherein, p is 0, 1, 2, or 3.

In some embodiments, each $R^A$ is independently selected from H, halogen, —CN, —$NO_2$, —OH, —S(=O)$_2R^{10}$, —S(=O)$_2$N($R^9$)$_2$, —C(=O)$R^{10}$, —$CO_2R^9$, —C(=O)N($R^9$)$_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, substituted or unsubstituted phenyl or substituted or unsubstituted monocyclic heteroaryl.

In some embodiments, each $R^4$ is independently selected from H, halogen, —CN, —$NO_2$, —OH, substituted or unsubstituted $C_1$-$C_6$alkyl, substituted or unsubstituted $C_1$-$C_6$fluoroalkyl, substituted or unsubstituted $C_1$-$C_6$fluoroalkoxy, and substituted or unsubstituted $C_1$-$C_6$alkoxy; $R^5$ is substituted or unsubstituted $C_2$-$C_{10}$alkyl, substituted or unsubstituted $C_2$-$C_{10}$fluoroalkyl, substituted or unsubstituted $C_2$-$C_{10}$alkoxy, substituted or unsubstituted $C_2$-$C_{10}$fluoroalkoxy, substituted or unsubstituted $C_2$-$C_{10}$heteroalkyl, substituted or unsubstituted $C_2$-$C_{10}$heterofluoroalkyl, or -$L^1$-$L^2$-$R^6$; $L^1$ is absent, —O—, —S—, —S(=O)—, —S(=O)$_2$—, —NH—, —C(=O)—, —C(=O)NH—, —NHC(=O)—, —NHS(=O)$_2$—, or —S(=O)$_2$NH—; $L^2$ is substituted or unsubstituted $C_1$-$C_6$alkylene, substituted or unsubstituted $C_1$-$C_6$fluoroalkylene or substituted or unsubstituted $C_1$-$C_6$heteroalkylene; $R^6$ is halogen, —CN, —NO$_2$, —OH, —OR$^9$, —SR$^9$, —S(═O)R$^{10}$, —S(═O)$_2$R$^{10}$, —S(═O)$_2$N(R$^9$)$_2$, —C(═O)R$^{10}$, —CO$_2$R$^9$, —N(R$^9$)$_2$, —C(═O)N(R$^9$)$_2$, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl.

In some embodiments, each $R^4$ is independently selected from H, halogen, —CN, —NO$_2$, —OH, substituted or unsubstituted $C_1$-$C_6$alkyl, substituted or unsubstituted $C_1$-$C_6$fluoroalkyl, substituted or unsubstituted $C_1$-$C_6$fluoroalkoxy, and substituted or unsubstituted $C_1$-$C_6$alkoxy; $R^5$ is H, halogen, —CN, —NO$_2$, —OH, —OR$^9$, —SR$^9$, —S(═O)R$^{10}$, —S(═O)$_2$R$^{10}$, —S(═O)$_2$N(R$^9$)$_2$, —C(═O)R$^{10}$, —CO$_2$R$^9$, —C(═O)N(R$^9$)$_2$, —NR$^{11}$C(═O)R$^{10}$, —NR$^{11}$C(═O)OR$^{10}$, substituted or unsubstituted $C_1$-$C_{10}$alkyl, substituted or unsubstituted $C_1$-$C_{10}$fluoroalkyl, substituted or unsubstituted $C_1$-$C_{10}$fluoroalkoxy, substituted or unsubstituted $C_1$-$C_{10}$alkoxy, substituted or unsubstituted $C_1$-$C_{10}$heteroalkyl, or -L$^1$-L$^2$-R$^6$; L$^1$ is absent, —O—, or —C(═O)NH—; L$^2$ is $C_1$-$C_6$alkylene, $C_1$-$C_6$fluoroalkylene or $C_1$-$C_6$heteroalkylene; $R^6$ is —CN, —NO$_2$, —OH, —OR$^9$, —SR$^9$, —S(═O)R$^{10}$, —S(═O)$_2$R$^{10}$, —C(═O)R$^{10}$, —CO$_2$R$^9$, —C(═O)N(R$^9$)$_2$, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl.

In some embodiments, the compound described herein has the structure of Formula (III):

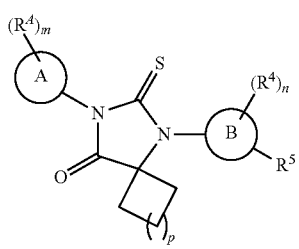

Formula (III)

wherein,
ring A is monocyclic heteroaryl, bicyclic heteroaryl, or naphthyl;
m is 1 or 2;
each $R^4$ is independently H, halogen, —CN, —NO$_2$, —OH, —OR$^9$, —SR$^9$, —S(═O)R$^{10}$, —S(═O)$_2$R$^{10}$, —N(R$^{11}$)S(═O)$_2$R$^{10}$, —S(═O)$_2$N(R$^9$)$_2$, —C(═O)R$^{10}$, —OC(═O)R$^{10}$, —CO$_2$R$^9$, —N(R$^9$)$_2$, —C(═O)N(R$^9$)$_2$, $C_1$-$C_6$alkyl, $C_1$-$C_6$fluoroalkyl, $C_1$-$C_6$fluoroalkoxy, $C_1$-$C_6$alkoxy, or $C_1$-$C_6$heteroalkyl;
ring B is phenyl, naphthyl, monocyclic heteroaryl, or bicyclic heteroaryl;
n is 0, 1 or 2;
each $R^4$ is independently selected from H, halogen, —CN, —NO$_2$, —OH, —OR$^9$, —SR$^9$, —S(═O)R$^{10}$, —S(═O)$_2$R$^{10}$, —N(R$^{11}$)S(═O)$_2$R$^{10}$, —S(═O)$_2$N(R$^9$)$_2$, —C(═O)R$^{10}$, —OC(═O)R$^{10}$, —CO$_2$R$^9$, —OCO$_2$R$^{10}$, —N(R$^9$)$_2$, —C(═O)N(R$^9$)$_2$, $C_1$-$C_6$alkyl, $C_1$-$C_6$fluoroalkyl, $C_1$-$C_6$fluoroalkoxy, $C_1$-$C_6$alkoxy, and $C_1$-$C_6$heteroalkyl;

$R^5$ is substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, -L$^1$-L$^2$-R$^6$ or -L$^1$-R$^7$;
L$^1$ is absent, —O—, —S—, —S(═O)—, —S(═O)$_2$—, —NH—, —C(═O)—, —C(═O)NH—, —NHC(═O)—, —NHC(═O)O—, —NHC(═O)NH—, —C(═O)O—, —OC(═O)—, —OC(═O)O—, —OC(═O)NH—, —NHS(═O)$_2$—, or —S(═O)$_2$NH—;
L$^2$ is $C_1$-$C_6$alkylene, $C_1$-$C_6$fluoroalkylene or $C_1$-$C_6$heteroalkylene;
$R^6$ is halogen, —CN, —NO$_2$, —OH, —OR$^9$, —SR$^9$, —S(═O)R$^{10}$, —S(═O)$_2$R$^{10}$, —N(R$^{11}$)S(═O)$_2$R$^{10}$, —S(═O)$_2$N(R$^9$)$_2$, —C(═O)R$^{10}$, —OC(═O)R$^{10}$, —CO$_2$R$^9$, —OCO$_2$R$^{10}$, —N(R$^9$)$_2$, —C(═O)N(R$^9$)$_2$, —OC(═O)N(R$^9$)$_2$, —NR$^{11}$C(═O)N(R$^9$)$_2$, —NR$^{11}$C(═O)R$^{10}$, —NR$^{11}$C(═O)OR$^{10}$, $C_1$-$C_6$alkyl, $C_1$-$C_6$fluoroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, substituted or unsubstituted phenyl, or substituted or unsubstituted naphthyl;
$R^7$ is substituted or unsubstituted $C_3$-$C_{10}$cycloalkyl, substituted or unsubstituted monocyclic $C_2$-$C_6$heterocycloalkyl, substituted or unsubstituted monocyclic phenyl, or substituted or unsubstituted monocyclic heteroaryl;
each $R^9$ is independently selected from H, $C_1$-$C_6$alkyl, $C_1$-$C_6$heteroalkyl, $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted benzyl, a substituted or unsubstituted heteroaryl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), and —$C_1$-$C_4$alkylene-(substituted or unsubstituted heteroaryl); or
two $R^9$ groups attached to the same N atom are taken together with the N atom to which they are attached to form a substituted or unsubstituted $C_2$-$C_{10}$heterocycloalkyl;
$R^{10}$ is $C_1$-$C_6$alkyl, $C_1$-$C_6$heteroalkyl, $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted benzyl, a substituted or unsubstituted heteroaryl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), or —$C_1$-$C_4$alkylene-(substituted or unsubstituted heteroaryl);
$R^{11}$ is H or $C_1$-$C_4$alkyl;
p is 0, 1, 2, or 3.

In some embodiments, $R^5$ is $C_3$-$C_6$cycloalkyl, substituted or unsubstituted $C_2$-$C_6$heterocycloalkyl, substituted or unsubstituted phenyl, substituted or unsubstituted monocyclic 5-membered or 6-membered heteroaryl, -L$_1$-L$^2$-R$^6$ or -L$^1$-R$^7$; L$^1$ is absent, —O—, or —C(═O)NH—; L$^2$ is $C_1$-$C_6$alkylene; $R^6$ is $C_3$-$C_6$cycloalkyl, substituted or unsubstituted $C_2$-$C_6$heterocycloalkyl, substituted or unsubstituted monocyclic 5-membered or 6-membered heteroaryl, or substituted or unsubstituted phenyl; $R^7$ is $C_3$-$C_6$cycloalkyl, substituted or unsubstituted monocyclic $C_2$-$C_6$heterocycloalkyl, substituted or unsubstituted monocyclic phenyl, or substituted or unsubstituted monocyclic 5-membered or 6-membered heteroaryl.

In some embodiments, described herein is a compound of Formula (IV), or a pharmaceutically acceptable salt, solvate, N-oxide, metabolite or prodrug thereof:

Formula (IV)

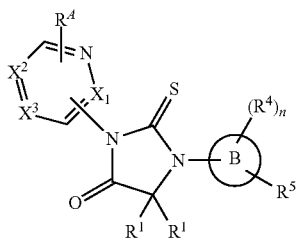

wherein, each $R^1$ is independently selected from H, —OH, substituted or unsubstituted $C_1$-$C_6$alkyl, substituted or unsubstituted $C_1$-$C_6$alkoxy, and substituted or unsubstituted $C_1$-$C_6$fluoroalkyl;

or both $R^1$ are taken together with the carbon atom to which they are attached to form a substituted or unsubstituted $C_3$-$C_{10}$cycloalkyl or a substituted or unsubstituted $C_2$-$C_{10}$heterocycloalkyl;

$X^1$ is $CR^A$ or N;

$X^2$ is $CR^A$ or N;

$X^3$ is $CR^A$ or N; provided that at least two of $X^1$, $X^2$, and $X^3$ is $CR^A$;

each $R^A$ is independently selected from H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —N(R$^9$)$_2$, —C(=O)N(R$^9$)$_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl or substituted or unsubstituted monocyclic heteroaryl;

ring B is phenyl, naphthyl, monocyclic heteroaryl, or bicyclic heteroaryl;

n is 0, 1, or 2;

$R^4$ is H, halogen, —CN, —NO$_2$, —OH, —OR$^9$, —SR$^9$, —S(=O)R$^{10}$, —S(=O)$_2$R$^{10}$, substituted or unsubstituted $C_1$-$C_6$alkyl, substituted or unsubstituted $C_1$-$C_6$fluoroalkyl, substituted or unsubstituted $C_1$-$C_6$fluoroalkoxy, substituted or unsubstituted $C_1$-$C_6$alkoxy, or substituted or unsubstituted $C_1$-$C_6$heteroalkyl;

$R^5$ is halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted $C_2$-$C_{10}$alkyl, substituted or unsubstituted $C_2$-$C_{10}$fluoroalkyl, substituted or unsubstituted $C_1$-$C_{10}$fluoroalkoxy, substituted or unsubstituted $C_1$-$C_{10}$alkoxy, substituted or unsubstituted $C_1$-$C_{10}$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, or -L$^1$-L$^2$-R$^6$;

L$^1$ is absent, —O—, —S—, —S(O)—, —S(O)$_2$—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)$_2$—, or —S(=O)$_2$NH—;

L$^2$ is substituted or unsubstituted $C_1$-$C_6$alkylene, substituted or unsubstituted $C_1$-$C_6$fluoroalkylene or substituted or unsubstituted $C_1$-$C_6$heteroalkylene;

R$^6$ is —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, or substituted or unsubstituted aryl;

each R$^9$ is independently selected from H, substituted or unsubstituted $C_1$-$C_6$alkyl, substituted or unsubstituted $C_1$-$C_6$heteroalkyl, substituted or unsubstituted $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted benzyl, a substituted or unsubstituted heteroaryl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), and —$C_1$-$C_4$alkylene-(substituted or unsubstituted heteroaryl); or two R$^9$ groups attached to the same N atom are taken together with the N atom to which they are attached to form a substituted or unsubstituted $C_2$-$C_{10}$heterocycloalkyl;

R$^{10}$ is substituted or unsubstituted $C_1$-$C_6$alkyl, substituted or unsubstituted $C_1$-$C_6$heteroalkyl, substituted or unsubstituted $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted benzyl, a substituted or unsubstituted heteroaryl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), or —$C_1$-$C_4$alkylene-(substituted or unsubstituted heteroaryl);

R$^{11}$ is H or $C_1$-$C_4$alkyl.

In some embodiments,

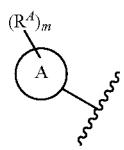

is

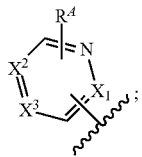

where $X^1$ is $CR^A$ or N; $X^2$ is $CR^A$ or N; $X^3$ is $CR^A$ or N; provided that at least two of $X^1$, $X^2$, and $X^3$ is $CR^A$.

In some embodiments,

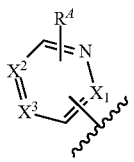

is

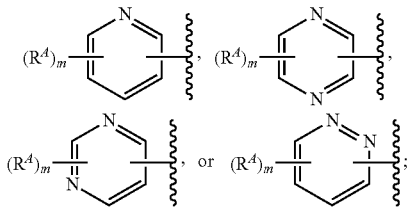

m is 0, 1, 2, 3, or 4.

In some embodiments,

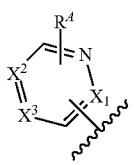

is

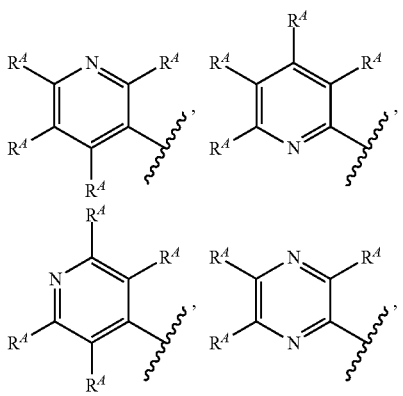

-continued

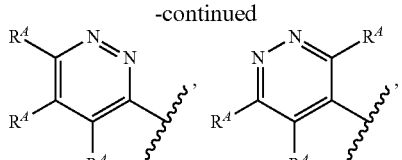

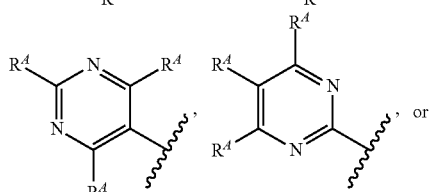

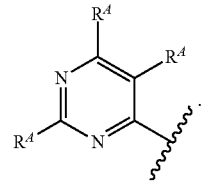

In some embodiments, the compound of Formula (IV) has the structure of Formula (V):

Formula (V)

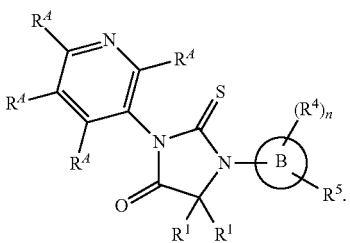

In some embodiments, ring B is phenyl; $R^4$ is H, halogen, —CN, —OH, substituted or unsubstituted $C_1$-$C_6$alkyl, substituted or unsubstituted $C_1$-$C_6$fluoroalkyl, substituted or unsubstituted $C_1$-$C_6$fluoroalkoxy, or substituted or unsubstituted $C_1$-$C_6$alkoxy; $R^5$ is halogen, —CN, —NO$_2$, —OH, —OR$^9$, —SR$^9$, —S(=O)R$^{10}$, —S(=O)$_2$R$^{10}$, —S(=O)$_2$N(R$^9$)$_2$, —C(=O)R$^{10}$, —CO$_2$R$^9$, —N(R$^9$)$_2$, substituted or unsubstituted $C_2$-$C_{10}$alkyl, substituted or unsubstituted $C_2$-$C_{10}$fluoroalkyl, substituted or unsubstituted $C_1$-$C_{10}$fluoroalkoxy, substituted or unsubstituted $C_1$-$C_{10}$alkoxy, substituted or unsubstituted $C_1$-$C_{10}$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, or -$L^1$-$L^2$-$R^6$; $L^1$ is absent, —O—, —S—, —S(O)—, —S(O)$_2$—, —NH—, —C(=O)—, —C(=O)NH—, or —S(=O)$_2$NH—; $L^2$ is substituted or unsubstituted $C_1$-$C_6$alkylene, substituted or unsubstituted $C_1$-$C_6$fluoroalkylene or substituted or unsubstituted $C_1$-$C_6$heteroalkylene; $R^6$ is —CN, —NO$_2$, —OH, —OR$^9$, —SR$^9$, —S(=O)R$^{10}$, —S(=O)$_2$R$^{10}$, —S(=O)$_2$N(R$^9$)$_2$, —CO$_2$R$^9$, —C(=O)N(R$^9$)$_2$, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, or substituted or unsubstituted aryl.

In some embodiments, each $R^A$ is independently selected from H, halogen, —CN, —NO$_2$, —OH, —S(=O)$_2$R$^{10}$, —S(=O)$_2$N(R$^9$)$_2$, —C(=O)R$^{10}$, —CO$_2$R$^9$, —C(=O)N ($R^9)_2$, substituted or unsubstituted $C_1$-$C_6$alkyl, substituted or unsubstituted $C_1$-$C_6$fluoroalkyl, substituted or unsubstituted $C_1$-$C_6$fluoroalkoxy, or substituted or unsubstituted $C_1$-$C_6$alkoxy.

In some embodiments, the compound of Formula (I), (Ia), (II), (IV) or (V) has the structure of Formula (VI):

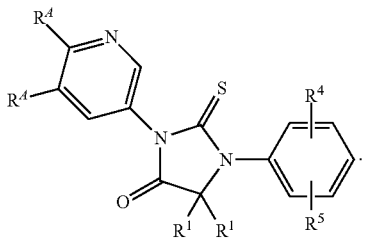

Formula (VI)

In some embodiments, the compound of Formula (I), (Ia), (II), (IV) or (V) has the structure of Formula (VI):

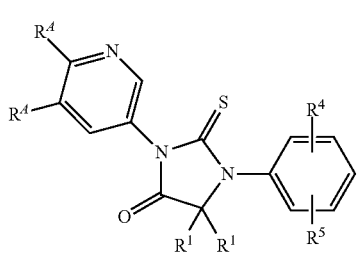

Formula (VI)

wherein,
one $R^A$ is —CN, —NO$_2$, —S(=O)$_2$R$^{10}$, —S(=O)$_2$N($R^9)_2$, —C(=O)R$^{10}$, —CO$_2$R$^9$, or —C(=O)N($R^9)_2$; and the other $R^A$ is H, halogen, —OH, $C_1$-$C_6$alkyl, $C_1$-$C_6$fluoroalkyl, $C_1$-$C_6$fluoroalkoxy, or $C_1$-$C_6$alkoxy;
both $R^1$ are taken together with the carbon atom to which they are attached to form a $C_3$-$C_6$cycloalkyl;
or each $R^1$ is independently $C_1$-$C_4$alkyl;
$R^4$ is H, halogen, —OH, $C_1$-$C_4$alkyl, $C_1$-$C_4$fluoroalkyl, $C_1$-$C_4$fluoroalkoxy, or $C_1$-$C_4$alkoxy.

In some embodiments, $R^5$ is -$L^1$-$L^2$-$R^6$ or -$L^1$-$R^7$; $L^1$ is absent, —O—, or —C(=O)NH—; $L^2$ is $C_1$-$C_6$alkylene, $C_1$-$C_6$fluoroalkylene or $C_1$-$C_6$heteroalkylene; $R^6$ is —CN, —NO$_2$, —OH, —OR$^9$, —SR$^9$, —S(=O)R$^{10}$, —S(=O)$_2$R$^{10}$, —C(=O)R$^{10}$, —CO$_2$R$^9$, —C(=O)N($R^9)_2$, substituted or unsubstituted $C_3$-$C_6$cycloalkyl, substituted or unsubstituted monocyclic $C_2$-$C_6$heterocycloalkyl, substituted or unsubstituted monocyclic heteroaryl, or substituted or unsubstituted phenyl; $R^7$ is substituted or unsubstituted monocyclic $C_2$-$C_6$heterocycloalkyl, or substituted or unsubstituted monocyclic heteroaryl.

In some embodiments, one $R^A$ is —CN; and the other $R^A$ is H, F, Cl, —OH, —CH$_3$, —CF$_3$, —OCF$_3$, —OCH$_3$ or —OCH$_2$CH$_3$. In some embodiments, one $R^A$ is —CN; and the other $R^A$ is —CH$_3$, or —CF$_3$.

In some embodiments, both $R^1$ are taken together with the carbon atom to which they are attached to form a cyclobutyl; or each $R^1$ is —CH$_3$.

In some embodiments, $R^5$ is -$L^1$-$L^2$-$R^6$ or -$L^1$-$R^7$; $L^1$ is absent, —O—, or —C(=O)NH—; $L^2$ is $C_1$-$C_6$alkylene; $R^6$ is substituted or unsubstituted $C_3$-$C_6$cycloalkyl, substituted or unsubstituted monocyclic $C_2$-$C_6$heterocycloalkyl, substituted or unsubstituted monocyclic heteroaryl, or substituted or unsubstituted phenyl; $R^7$ is substituted or unsubstituted monocyclic $C_2$-$C_6$heterocycloalkyl, or substituted or unsubstituted monocyclic heteroaryl. In some embodiments, $R^5$ is -$L^1$-$L^2$-$R^6$; $L^1$ is —C(=O)NH—; $L^2$ is $C_1$-$C_4$alkylene; substituted or unsubstituted N-containing 5-membered or 6-membered $C_2$-$C_6$heterocycloalkyl. In some embodiments, $R^5$ is -$L^1$-$R^7$; $L^1$ is absent, —O—, or —C(=O)NH—; $R^7$ is substituted or unsubstituted monocyclic 5-membered or 6-membered $C_2$-$C_6$heterocycloalkyl, or substituted or unsubstituted monocyclic 5-membered or 6-membered heteroaryl.

In some embodiments, one $R^A$ is —CN, —NO$_2$, —S(=O)$_2$R$^{10}$, —S(=O)$_2$N($R^9)_2$, —C(=O)R$^{10}$, —CO$_2$R$^9$, —C(=O)N($R^9)_2$, substituted or unsubstituted phenyl or substituted or unsubstituted monocyclic heteroaryl; and the other $R^A$ is H, halogen, —OH, substituted or unsubstituted $C_1$-$C_6$alkyl, substituted or unsubstituted $C_1$-$C_6$fluoroalkyl, substituted or unsubstituted $C_1$-$C_6$fluoroalkoxy, or substituted or unsubstituted $C_1$-$C_6$alkoxy; $R^4$ is H, halogen, —CN, —OH, substituted or unsubstituted $C_1$-$C_6$alkyl, substituted or unsubstituted $C_1$-$C_6$fluoroalkyl, substituted or unsubstituted $C_1$-$C_6$fluoroalkoxy, or substituted or unsubstituted $C_1$-$C_6$alkoxy; $R^5$ is halogen, —CN, —NO$_2$, —OH, —OR$^9$, —S(=O)$_2$R$^{10}$, —S(=O)$_2$N($R^9)_2$, —C(=O)R$^{10}$, —CO$_2$R$^9$, substituted or unsubstituted $C_2$-$C_{10}$alkyl, substituted or unsubstituted $C_2$-$C_{10}$fluoroalkyl, substituted or unsubstituted $C_1$-$C_{10}$fluoroalkoxy, substituted or unsubstituted $C_1$-$C_{10}$alkoxy, substituted or unsubstituted $C_1$-$C_{10}$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, or -$L^1$-$L^2$-$R^6$; $L^1$ is absent, —O—, or —C(=O)NH—; $L^2$ is substituted or unsubstituted $C_1$-$C_6$alkylene, substituted or unsubstituted $C_1$-$C_6$fluoroalkylene or substituted or unsubstituted $C_1$-$C_6$heteroalkylene; $R^6$ is —CN, —NO$_2$, —OH, —OR$^9$, —SR$^9$, —S(=O)R$^{10}$, —S(=O)$_2$R$^{10}$, —S(=O)$_2$N($R^9)_2$, —CO$_2$R$^9$, —C(=O)N($R^9)_2$, substituted or unsubstituted monocyclic heteroaryl, or substituted or unsubstituted phenyl.

In some embodiments, described herein is a compound of Formula (VII), or a pharmaceutically acceptable salt, solvate, N-oxide, metabolite or prodrug thereof:

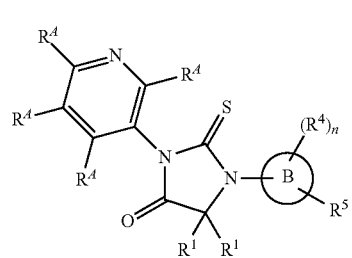

Formula (VII)

wherein,
each $R^1$ is independently selected from H, —OH, substituted or unsubstituted $C_1$-$C_6$alkyl, substituted or unsubstituted $C_1$-$C_6$alkoxy, and substituted or unsubstituted $C_1$-$C_6$fluoroalkyl;
or both $R^1$ are taken together with the carbon atom to which they are attached to form a substituted or unsubstituted $C_3$-$C_{10}$cycloalkyl or a substituted or unsubstituted $C_2$-$C_{10}$heterocycloalkyl;

each $R^A$ is independently selected from H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —N(R$^9$)$_2$, —C(=O)N(R$^9$)$_2$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, substituted or unsubstituted C$_1$-C$_6$heteroalkyl, substituted or unsubstituted cycloalkyl, substituted or unsubstituted heterocycloalkyl, substituted or unsubstituted phenyl or substituted or unsubstituted monocyclic heteroaryl;

ring B is 5-membered heteroaryl, bicyclic heteroaryl or naphthyl;

n is 0, 1, or 2;

$R^4$ is H, halogen, —CN, —NO$_2$, —OH, substituted or unsubstituted C$_1$-C$_6$alkyl, substituted or unsubstituted C$_1$-C$_6$fluoroalkyl, substituted or unsubstituted C$_1$-C$_6$fluoroalkoxy, or substituted or unsubstituted C$_1$-C$_6$alkoxy;

$R^5$ is H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted C$_2$-C$_{10}$alkyl, substituted or unsubstituted C$_2$-C$_{10}$fluoroalkyl, substituted or unsubstituted C$_1$-C$_{10}$fluoroalkoxy, substituted or unsubstituted C$_1$-C$_{10}$alkoxy, substituted or unsubstituted C$_1$-C$_{10}$heteroalkyl, substituted or unsubstituted C$_3$-C$_{10}$cycloalkyl, substituted or unsubstituted C$_2$-C$_{10}$heterocycloalkyl, substituted or unsubstituted phenyl, substituted or unsubstituted monocyclic heteroaryl, or -L$^1$-L$^2$-R$^6$;

L$^1$ is absent, —O—, —S—, —S(O)—, —S(O)$_2$—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)$_2$—, or —S(=O)$_2$NH—;

L$^2$ is substituted or unsubstituted C$_1$-C$_6$alkylene, substituted or unsubstituted C$_1$-C$_6$fluoroalkylene or substituted or unsubstituted C$_1$-C$_6$heteroalkylene;

$R^6$ is halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NRC(=O)N(R$^9$)$_2$, —NR$^{11}$C(=O)R$^{10}$, —NR$^{11}$C(=O)OR$^{10}$, substituted or unsubstituted C$_3$-C$_{10}$cycloalkyl, substituted or unsubstituted C$_2$-C$_{10}$heterocycloalkyl, substituted or unsubstituted monocyclic heteroaryl, substituted or unsubstituted bicyclic heteroaryl, or substituted or unsubstituted aryl;

each $R^9$ is independently selected from H, substituted or unsubstituted C$_1$-C$_6$alkyl, substituted or unsubstituted C$_1$-C$_6$heteroalkyl, substituted or unsubstituted C$_1$-C$_6$fluoroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted benzyl, a substituted or unsubstituted heteroaryl, —C$_1$-C$_4$alkylene-(substituted or unsubstituted C$_3$-C$_{10}$cycloalkyl), —C$_1$-C$_4$alkylene-(substituted or unsubstituted C$_2$-C$_{10}$heterocycloalkyl), —C$_1$-C$_4$alkylene-(substituted or unsubstituted aryl), and —C$_1$-C$_4$alkylene-(substituted or unsubstituted heteroaryl); or two R$^9$ groups attached to the same N atom are taken together with the N atom to which they are attached to form a substituted or unsubstituted C$_2$-C$_{10}$heterocycloalkyl;

$R^{10}$ is substituted or unsubstituted C$_1$-C$_6$alkyl, substituted or unsubstituted C$_1$-C$_6$heteroalkyl, substituted or unsubstituted C$_1$-C$_6$fluoroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted benzyl, a substituted or unsubstituted heteroaryl, —C$_1$-C$_4$alkylene-(substituted or unsubstituted C$_3$-C$_{10}$cycloalkyl), —C$_1$-C$_4$alkylene-(substituted or unsubstituted C$_2$-C$_{10}$heterocycloalkyl), —C$_1$-C$_4$alkylene-(substituted or unsubstituted aryl), or —C$_1$-C$_4$alkylene-(substituted or unsubstituted heteroaryl);

$R^{11}$ is H or C$_1$-C$_4$alkyl.

In some embodiments, described herein is a compound of Formula (VIII), or a pharmaceutically acceptable salt, solvate, N-oxide, metabolite or prodrug thereof:

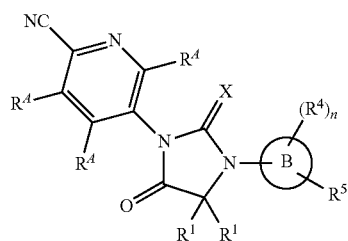

Formula (VIII)

wherein, each $R^1$ is independently selected from H, —OH, substituted or unsubstituted C$_1$-C$_6$alkyl, substituted or unsubstituted C$_1$-C$_6$alkoxy, and substituted or unsubstituted C$_1$-C$_6$fluoroalkyl;

or both R$^1$ are taken together with the carbon atom to which they are attached to form a substituted or unsubstituted C$_3$-C$_6$cycloalkyl or a substituted or unsubstituted C$_2$-C$_6$heterocycloalkyl;

X is O or S;

each $R^A$ is independently selected from H, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —N(R$^9$)$_2$, —C(=O)N(R$^9$)$_2$, C$_1$-C$_6$alkyl, C$_1$-C$_6$alkoxy, C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted phenyl or substituted or unsubstituted monocyclic heteroaryl;

ring B is phenyl, naphthyl, monocyclic heteroaryl, or bicyclic heteroaryl;

n is 0, 1, or 2;

$R^4$ is H, halogen, —CN, —NO$_2$, —OH, —OR$^9$, —SR$^9$, —S(=O)R$^{10}$, —S(=O)$_2$R$^{10}$, substituted or unsubstituted C$_1$-C$_6$alkyl, substituted or unsubstituted C$_1$-C$_6$fluoroalkyl, substituted or unsubstituted C$_1$-C$_6$fluoroalkoxy, substituted or unsubstituted C$_1$-C$_6$alkoxy, or substituted or unsubstituted C$_1$-C$_6$heteroalkyl;

R⁵ is halogen, —CN, —NO₂, —OH, —OR⁹, —SR⁹, —S(=O)R¹⁰, —S(=O)₂R¹⁰, —N(R¹¹)S(=O)₂R¹⁰, —S(=O)₂N(R⁹)₂, —C(=O)R¹⁰, —OC(=O)R¹⁰, —CO₂R⁹, —OCO₂R¹⁰, —N(R⁹)₂, —C(=O)N(R⁹)₂, —OC(=O)N(R⁹)₂, —NR¹¹C(=O)N(R⁹)₂, —NR¹¹C(=O)R¹⁰, —NR¹¹C(=O)OR¹⁰, substituted or unsubstituted $C_1$-$C_{10}$alkyl, substituted or unsubstituted $C_1$-$C_{10}$fluoroalkyl, substituted or unsubstituted $C_1$-$C_{10}$fluoroalkoxy, substituted or unsubstituted $C_1$-$C_{10}$alkoxy, substituted or unsubstituted $C_1$-$C_{10}$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, or -L¹-L²-R⁶;

L¹ is absent, —O—, —S—, —S(O)—, —S(O)₂—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)₂—, or —S(=O)₂NH—;

L² is substituted or unsubstituted $C_1$-$C_6$alkylene, substituted or unsubstituted $C_1$-$C_6$fluoroalkylene or substituted or unsubstituted $C_1$-$C_6$heteroalkylene;

R⁶ is —CN, —NO₂, —OH, —OR⁹, —SR⁹, —S(=O)R¹⁰, —S(=O)₂R¹⁰, —N(R¹¹)S(=O)₂R¹⁰, —S(=O)₂N(R⁹)₂, —C(=O)R¹⁰, —OC(=O)R¹⁰, —CO₂R⁹, —OCO₂R¹⁰, —N(R⁹)₂, —C(=O)N(R⁹)₂, —OC(=O)N(R⁹)₂, —NR¹¹C(=O)N(R⁹)₂, —NR¹¹C(=O)R¹⁰, —NR¹¹C(=O)OR¹⁰, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, or substituted or unsubstituted aryl;

each R⁹ is independently selected from H, substituted or unsubstituted $C_1$-$C_6$alkyl, substituted or unsubstituted $C_1$-$C_6$heteroalkyl, substituted or unsubstituted $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted benzyl, a substituted or unsubstituted heteroaryl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), and —$C_1$-$C_4$alkylene-(substituted or unsubstituted heteroaryl); or two R⁹ groups attached to the same N atom are taken together with the N atom to which they are attached to form a substituted or unsubstituted $C_2$-$C_{10}$heterocycloalkyl;

R¹⁰ is substituted or unsubstituted $C_1$-$C_6$alkyl, substituted or unsubstituted $C_1$-$C_6$heteroalkyl, substituted or unsubstituted $C_1$-$C_6$fluoroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted benzyl, a substituted or unsubstituted heteroaryl, —$C_1$-$C_4$alkylene-(substituted or unsubstituted $C_3$-$C_{10}$cycloalkyl), —$C_1$-$C_4$alkylene-(substituted or unsubstituted $C_2$-$C_{10}$heterocycloalkyl), —$C_1$-$C_4$alkylene-(substituted or unsubstituted aryl), or —$C_1$-$C_4$alkylene-(substituted or unsubstituted heteroaryl);

R¹¹ is H or $C_1$-$C_4$alkyl.

In some embodiments, X is S; ring B is phenyl; R⁴ is H, halogen, —CN, —OH, $C_1$-$C_6$alkyl, $C_1$-$C_6$fluoroalkyl, $C_1$-$C_6$fluoroalkoxy, or $C_1$-$C_6$alkoxy; R⁵ is halogen, —CN, —NO₂, —OH, —OR⁹, —SR⁹, —S(=O)R¹⁰, —S(=O)₂R¹⁰, —S(=O)₂N(R⁹)₂, —C(=O)R¹⁰, —CO₂R⁹, —N(R⁹)₂, —C(=O)N(R⁹)₂, substituted or unsubstituted $C_1$-$C_{10}$alkyl, substituted or unsubstituted $C_1$-$C_{10}$fluoroalkyl, substituted or unsubstituted $C_1$-$C_{10}$fluoroalkoxy, substituted or unsubstituted $C_1$-$C_{10}$alkoxy, substituted or unsubstituted $C_1$-$C_{10}$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, or -L¹-L²-R⁶; L¹ is absent, —O—, —S—, —S(O)—, —S(O)₂—, —NH—, —C(=O)—, —C(=O)NH—, or —S(=O)₂NH—; L² is substituted or unsubstituted $C_1$-$C_6$alkylene, substituted or unsubstituted $C_1$-$C_6$fluoroalkylene or substituted or unsubstituted $C_1$-$C_6$heteroalkylene; R⁶ is —CN, —NO₂, —OH, —OR⁹, —SR⁹, —S(=O)R¹⁰, —S(=O)₂R¹⁰, —S(=O)₂N(R⁹)₂, —CO₂R⁹, —C(=O)N(R⁹)₂, substituted or unsubstituted $C_3$-$C_{10}$cycloalkyl, substituted or unsubstituted $C_2$-$C_{10}$heterocycloalkyl, substituted or unsubstituted monocyclic heteroaryl, substituted or unsubstituted bicyclic heteroaryl, or substituted or unsubstituted aryl.

In some embodiments, each R⁴ is independently selected from H, halogen, —CN, —NO₂, —OH, —S(=O)₂R¹⁰, —S(=O)₂N(R⁹)₂, —C(=O)R¹⁰, —CO₂R⁹, —C(=O)N(R⁹)₂, $C_1$-$C_6$alkyl, and $C_1$-$C_6$alkoxy.

In some embodiments, described herein is a compound of Formula (VIIIa), or a pharmaceutically acceptable salt, or N-oxide thereof:

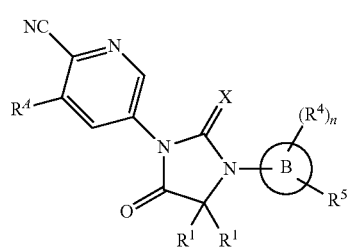

Formula (VIIIa)

wherein, both R¹ are taken together with the carbon atom to which they are attached to form a substituted or unsubstituted $C_3$-$C_6$cycloalkyl or a substituted or unsubstituted $C_2$-$C_6$heterocycloalkyl;

or each R¹ is independently H, —OH, $C_1$-$C_6$alkyl, $C_1$-$C_6$alkoxy, or $C_1$-$C_6$fluoroalkyl;

X is O or S;

R⁴ is $C_1$-$C_6$alkyl;

ring B is phenyl, naphthyl, monocyclic heteroaryl, or bicyclic heteroaryl;

n is 0, 1, or 2;

R⁴ is H, halogen, —CN, —NO₂, —OH, —OR⁹, —SR⁹, —S(=O)R¹⁰, —S(=O)₂R¹⁰, $C_1$-$C_6$alkyl, $C_1$-$C_6$fluoroalkyl, $C_1$-$C_6$fluoroalkoxy, $C_1$-$C_6$alkoxy, or $C_1$-$C_6$heteroalkyl;

$R^5$ is halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, C$_1$-C$_{10}$alkyl, C$_1$-C$_{10}$fluoroalkyl, C$_1$-C$_{10}$fluoroalkoxy, C$_1$-C$_{10}$alkoxy, C$_1$-C$_{10}$heteroalkyl, substituted or unsubstituted C$_3$-C$_{10}$cycloalkyl, substituted or unsubstituted C$_2$-C$_{10}$heterocycloalkyl, substituted or unsubstituted phenyl, substituted or unsubstituted monocyclic heteroaryl, or -L$^1$-L$^2$-R$^6$;

L$^1$ is absent, —O—, —S—, —S(O)—, —S(O)$_2$—, —NH—, —C(=O)—, —C(=O)NH—, —NHC(=O)—, —NHC(=O)O—, —NHC(=O)NH—, —C(=O)O—, —OC(=O)—, —OC(=O)O—, —OC(=O)NH—, —NHS(=O)$_2$—, or —S(=O)$_2$NH—;

L$^2$ is C$_1$-C$_6$alkylene, C$_1$-C$_6$fluoroalkylene or C$_1$-C$_6$heteroalkylene;

R$^6$ is —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, substituted or unsubstituted C$_3$-C$_{10}$cycloalkyl, substituted or unsubstituted C$_2$-C$_{10}$heterocycloalkyl, substituted or unsubstituted monocyclic heteroaryl, substituted or unsubstituted bicyclic heteroaryl, or substituted or unsubstituted aryl;

each R$^9$ is independently selected from H, C$_1$-C$_6$alkyl, C$_1$-C$_6$heteroalkyl, C$_1$-C$_6$fluoroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted benzyl, a substituted or unsubstituted heteroaryl, —C$_1$-C$_4$alkylene-(substituted or unsubstituted C$_3$-C$_{10}$cycloalkyl), —C$_1$-C$_4$alkylene-(substituted or unsubstituted C$_2$-C$_{10}$heterocycloalkyl), —C$_1$-C$_4$alkylene-(substituted or unsubstituted aryl), and —C$_1$-C$_4$alkylene-(substituted or unsubstituted heteroaryl); or two R$^9$ groups attached to the same N atom are taken together with the N atom to which they are attached to form a substituted or unsubstituted C$_2$-C$_{10}$heterocycloalkyl;

R$^{10}$ is C$_1$-C$_6$alkyl, C$_1$-C$_6$heteroalkyl, C$_1$-C$_6$fluoroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted benzyl, a substituted or unsubstituted heteroaryl, —C$_1$-C$_4$alkylene-(substituted or unsubstituted C$_3$-C$_{10}$cycloalkyl), —C$_1$-C$_4$alkylene-(substituted or unsubstituted C$_2$-C$_{10}$heterocycloalkyl), —C$_1$-C$_4$alkylene-(substituted or unsubstituted aryl), or —C$_1$-C$_4$alkylene-(substituted or unsubstituted heteroaryl);

R$^{11}$ is H or C$_1$-C$_4$alkyl.

In some embodiments, X is S; ring B is phenyl; R$^4$ is H, halogen, —CN, —OH, C$_1$-C$_6$alkyl, C$_1$-C$_6$fluoroalkyl, C$_1$-C$_6$fluoroalkoxy, or C$_1$-C$_6$alkoxy; R$^5$ is halogen, —CN, —NO$_2$, —OH, —OR$^9$, —SR$^9$, —S(=O)R$^{10}$, —S(=O)$_2$R$^{10}$, —S(=O)$_2$N(R$^9$)$_2$, —C(=O)R$^{10}$, —CO$_2$R$^9$, —N(R$^9$)$_2$, —C(=O)N(R$^9$)$_2$, C$_1$-C$_{10}$alkyl, C$_1$-C$_{10}$fluoroalkyl, C$_1$-C$_{10}$fluoroalkoxy, C$_1$-C$_{10}$alkoxy, C$_1$-C$_{10}$heteroalkyl, substituted or unsubstituted C$_3$-C$_{10}$cycloalkyl, substituted or unsubstituted C$_2$-C$_{10}$heterocycloalkyl, substituted or unsubstituted phenyl, substituted or unsubstituted monocyclic heteroaryl, or -L$^1$-L$^2$-R$^6$; L$^1$ is absent, —O—, —S—, —S(O)—, —S(O)$_2$—, —NH—, —C(=O)—, —C(=O)NH—, or —S(=O)$_2$NH—; L$^2$ is C$_1$-C$_6$alkylene, C$_1$-C$_6$fluoroalkylene or C$_1$-C$_6$heteroalkylene; R$^6$ is —CN, —NO$_2$, —OH, —OR$^9$, —SR$^9$, —S(=O)R$^{10}$, —S(=O)$_2$R$^{10}$, —S(=O)$_2$N(R$^9$)$_2$, —CO$_2$R$^9$, —C(=O)N(R$^9$)$_2$, substituted or unsubstituted C$_3$-C$_{10}$cycloalkyl, substituted or unsubstituted C$_2$-C$_{10}$heterocycloalkyl, substituted or unsubstituted monocyclic heteroaryl, substituted or unsubstituted bicyclic heteroaryl, or substituted or unsubstituted aryl.

In some embodiments, R$^4$ is C$_1$-C$_6$alkyl; both R$^1$ are taken together with the carbon atom to which they are attached to form a C$_3$-C$_6$cycloalkyl; or each R$^1$ is independently C$_1$-C$_4$alkyl.

In some embodiments, the compound of Formula (VIII) has the structure of Formula (IX):

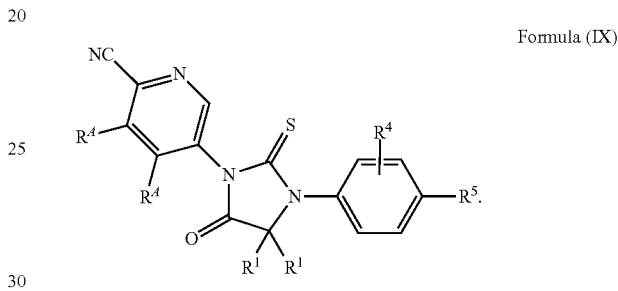

Formula (IX)

In some embodiments, each R$^4$ is independently selected from H, halogen, —OH, C$_1$-C$_6$alkyl, and C$_1$-C$_6$alkoxy.

In some embodiments, the compound of Formula (VIIIa) has the structure of Formula (IXa):

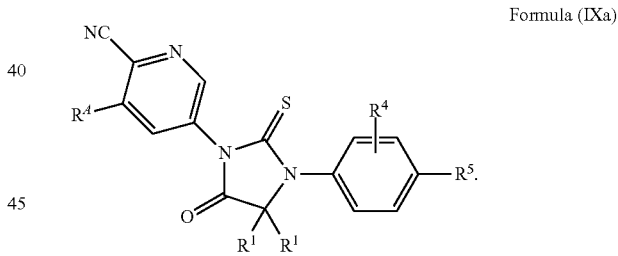

Formula (IXa)

In some embodiments, each R$^9$ is independently selected from H, C$_1$-C$_6$alkyl, C$_1$-C$_6$heteroalkyl, C$_1$-C$_6$fluoroalkyl, a substituted or unsubstituted C$_3$-C$_6$cycloalkyl, a substituted or unsubstituted C$_2$-C$_6$heterocycloalkyl, a substituted or unsubstituted phenyl, a substituted or unsubstituted benzyl, and a substituted or unsubstituted monocyclic heteroaryl; or two R$^9$ groups attached to the same N atom are taken together with the N atom to which they are attached to form a substituted or unsubstituted C$_2$-C$_6$heterocycloalkyl; R$^{10}$ is C$_1$-C$_6$alkyl, C$_1$-C$_6$heteroalkyl, C$_1$-C$_6$fluoroalkyl, a substituted or unsubstituted C$_3$-C$_6$cycloalkyl, a substituted or unsubstituted C$_2$-C$_6$heterocycloalkyl, a substituted or unsubstituted phenyl, or a substituted or unsubstituted monocyclic heteroaryl.

In some embodiments, R$^5$ is halogen, —CN, —OH, —OR$^9$, —SR$^9$, —S(=O)R$^{10}$, —S(=O)$_2$R$^{10}$, —S(=O)$_2$N(R$^9$)$_2$, —C(=O)R$^{10}$, —CO$_2$R$^9$, —N(R$^9$)$_2$, —C(=O)NH(R$^9$), C$_1$-C$_{10}$alkyl, C$_1$-C$_{10}$fluoroalkyl, C$_1$-C$_{10}$fluoroalkoxy, C$_1$-C$_{10}$alkoxy, C$_1$-C$_{10}$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, or -$L^1$-$L^2$-$R^6$; $L^1$ is absent, —O—, —S—, —S(O)—, —S(O)$_2$—, —NH—, —C(=O)—, —C(=O)NH—, or —S(=O)$_2$NH—; $L^2$ is $C_1$-$C_4$alkylene; $R^6$ is —CN, —OH, —OR$^9$, —SR$^9$, —S(=O)R$^{10}$, —S(=O)$_2$R$^{10}$, —S(=O)$_2$N(R$^9$)$_2$, —CO$_2$R$^9$, —C(=O)N(R$^9$)$_2$, substituted or unsubstituted $C_3$-$C_6$cycloalkyl, substituted or unsubstituted $C_2$-$C_6$heterocycloalkyl, substituted or unsubstituted monocyclic heteroaryl, or substituted or unsubstituted phenyl.

In some embodiments, $R^4$ is —CH$_3$; both $R^1$ are taken together with the carbon atom to which they are attached to form a cyclopropyl, cyclobutyl, cyclopentyl, or cyclohexyl; or each $R^1$ is —CH$_3$; $R^5$ is halogen, —CN, —OH, —OR$^9$, —SR$^9$, —S(=O)R$^{10}$, —S(=O)$_2$R$^{10}$, —S(=O)$_2$N(R$^9$)$_2$, —C(=O)R$^{10}$, —CO$_2$R$^9$, —N(R$^9$)$_2$, —C(=O)NH(R$^9$), $C_1$-$C_{10}$alkyl, $C_1$-$C_{10}$fluoroalkyl, $C_1$-$C_{10}$fluoroalkoxy, $C_1$-$C_{10}$alkoxy, $C_1$-$C_{10}$heteroalkyl, substituted or unsubstituted $C_3$-$C_6$cycloalkyl, substituted or unsubstituted $C_2$-$C_6$heterocycloalkyl, substituted or unsubstituted phenyl, substituted or unsubstituted monocyclic heteroaryl, or -$L^1$-$L^2$-$R^6$; $L^1$ is absent, —O—, —S—, —S(O)—, —S(O)$_2$—, —NH—, —C(=O)—, —C(=O)NH—, or —S(=O)$_2$NH—; $L^2$ is $C_1$-$C_4$alkylene; $R^6$ is substituted or unsubstituted $C_2$-$C_6$heterocycloalkyl, substituted or unsubstituted monocyclic heteroaryl, or substituted or unsubstituted phenyl.

In some embodiments, the compound of Formula (VIII) or Formula (VIIIa) has the following structure:

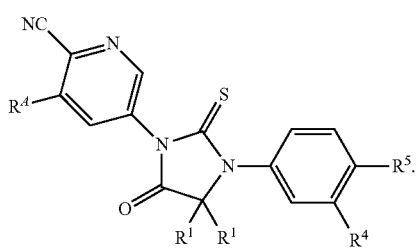

In some embodiments, $R^4$ is H, halogen, —OH, $C_1$-$C_6$alkyl, or $C_1$-$C_6$alkoxy. In some embodiments, $R^4$ is $C_1$-$C_6$alkyl. In some embodiments, $R^4$ is —CH$_3$.

In some embodiments, $R^4$ is H, halogen, —CN, —NO$_2$, —OH, —OR$^9$, —SR$^9$, —S(=O)R$^{10}$, —S(=O)$_2$R$^{10}$, $C_1$-$C_6$alkyl, $C_1$-$C_6$fluoroalkyl, $C_1$-$C_6$fluoroalkoxy, $C_1$-$C_6$alkoxy, or $C_1$-$C_6$heteroalkyl. In some embodiments, $R^4$ is halogen. In some embodiments, $R^4$ is F.

In some embodiments, $R^5$ is halogen, —CN, —OH, —OR$^9$, —SR$^9$, —S(=O)R$^{10}$, —S(=O)$_2$R$^{10}$, —S(=O)$_2$N(R$^9$)$_2$, —C(=O)R$^{10}$, —CO$_2$R$^9$, —C(=O)N(R$^9$)$_2$, $C_1$-$C_4$alkyl, $C_1$-$C_4$fluoroalkyl, $C_1$-$C_4$fluoroalkoxy, $C_1$-$C_4$alkoxy. In some embodiments, $R^5$ is —CO$_2$R$^9$ or —C(=O)N(R$^9$)$_2$. In some embodiments, $R^5$ is —CO$_2$H, —C(=O)NH$_2$ or —C(=O)NH(CH$_3$).

In some embodiments, described herein is a compound of Formula (X), or a pharmaceutically acceptable salt, solvate, N-oxide, metabolite or prodrug thereof:

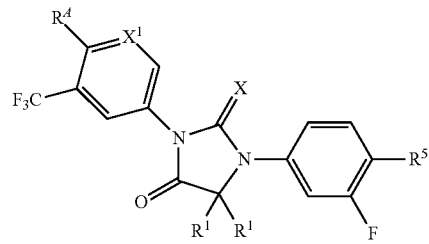

wherein,
each $R^1$ is independently selected from H and —CH$_3$;
or both $R^1$ are taken together with the carbon atom to which they are attached to form a cyclobutyl;
X is O or S;
$X^1$ is CH or N;
$R^4$ is —CN or —C(=O)NH$_2$;
$R^5$ is —CO$_2$H, or —C(=O)NH$_2$.

In some embodiments, described herein is a compound of Formula (X), or a pharmaceutically acceptable salt, solvate, N-oxide, metabolite or prodrug thereof:

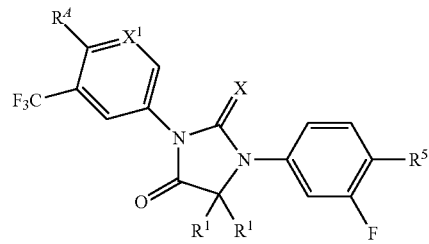

wherein,
each $R^1$ is independently selected from H and —CH$_3$;
or both $R^1$ are taken together with the carbon atom to which they are attached to form a cyclobutyl;
X is O;
$X^1$ is CH or N;
$R^4$ is —CN or —C(=O)NH$_2$;
$R^5$ is —CO$_2$H, —C(=O)NH$_2$ or —C(=O)NH(CH$_3$).

In some embodiments, described herein is a compound of Formula (X), or a pharmaceutically acceptable salt, solvate, N-oxide, metabolite or prodrug thereof:

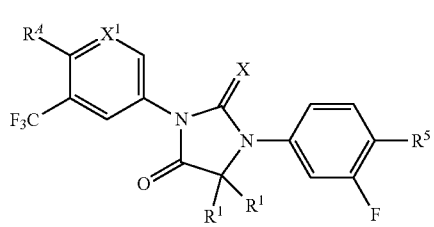

wherein,
each $R^1$ is independently selected from H and —CH$_3$;
or both $R^1$ are taken together with the carbon atom to which they are attached to form a cyclobutyl;
X is O or S;
$X^1$ is CH or N;
$R^4$ is —C(=O)NH$_2$;
$R^5$ is —CO$_2$H, —C(=O)NH$_2$ or —C(=O)NH(CH$_3$).

Throughout the specification, groups and substituents thereof can be chosen by one skilled in the field to provide stable moieties and compounds.

In one aspect, compounds described herein include compounds in Table 1, or a pharmaceutically acceptable salt thereof, or N-oxide thereof:

TABLE 1

| Cmpd. | Name | Structure | LCMS* [M + 1]+ |
|---|---|---|---|
| 1 | 5-(5-(3-Fluoro-4-hydroxyphenyl)-8-oxo-6-thioxo-5,7-diazaspiro[3.4]octan-7-yl)-3-(trifluoromethyl)picolinonitrile | 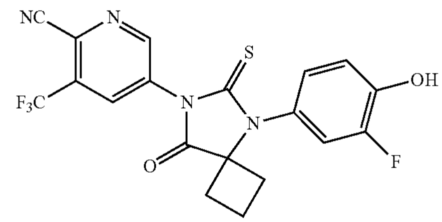 | |
| 2 | 5-(4-Hydroxyphenyl)-6-thioxo-7-(3-(trifluoromethyl)-[1,2,4]triazolo[4,3-b]pyridazin-6-yl)-5,7-diazaspiro[3.4]octan-8-one | 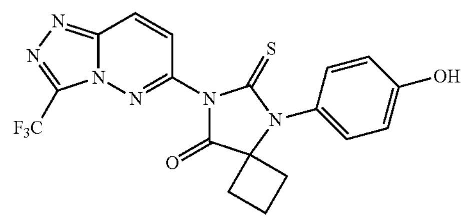 [SMILES: O=C1N(c2ccc3nnc(C(F)(F)F)n3n2)C(=S)N(c2ccc(O)cc2)C12CCC2] | 435.4 |
| 3 | Ethyl 4-(7-(6-cyano-5-(trifluoromethyl)pyridin-3-yl)-8-oxo-6-thioxo-5,7-diazaspiro[3.4]octan-5-yl)-2-fluorobenzoate | 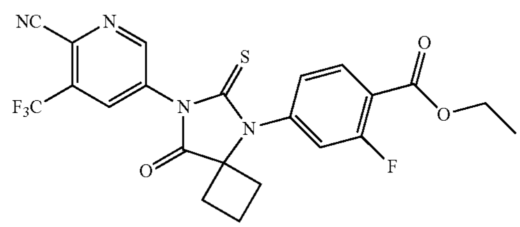 [SMILES: CCOC(=O)c1ccc(N2C(=S)N(c3cnc(C#N)c(C(F)(F)F)c3)C(=O)C23CCC3)cc1F] | |
| 4 | 5-(5-(4-Bromo-3-fluorophenyl)-8-oxo-6-thioxo-5,7-diazaspiro[3.4]octan-7-yl)-3-(trifluoromethyl)picolinonitrile | 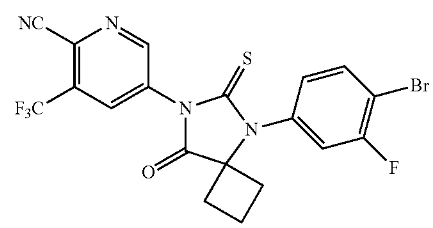 [SMILES: N#Cc1ncc(N2C(=O)C3(CCC3)N(c3ccc(Br)c(F)c3)C2=S)cc1C(F)(F)F] | 500.3 |
| 5 | 4-(7-(6-Cyano-5-methylpyridin-3-yl)-8-oxo-6-thioxo-5,7-diazaspiro[3.4]octan-5-yl)-2-fluoro-N-methylbenzamide | 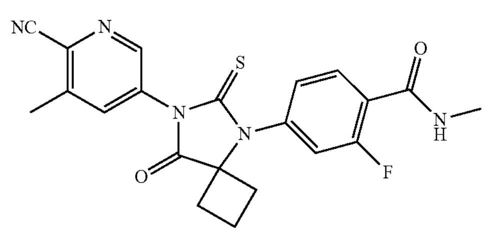 | 424.0 |
| 6 | 4-(3-(6-Cyano-5-methylpyridin-3-yl)-4-oxo-2-thioxo-1,3-diazaspiro[4.4]nonan-1-yl)-2-fluoro-N-methylbenzamide | 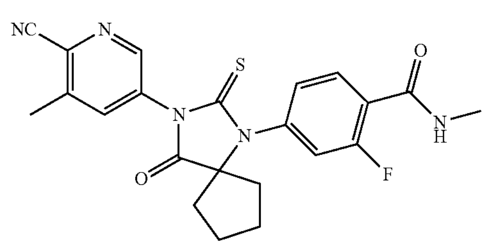 | 438.1 |

TABLE 1-continued

| Cmpd. | Name | Structure | LCMS* [M + 1]+ |
|---|---|---|---|
| 7 | 3-Methyl-5-(5-(4-(5-methylfuran-2-yl)phenyl)-8-oxo-6-thioxo-5,7-diazaspiro[3.4]octan-7-yl)picolinonitrile | 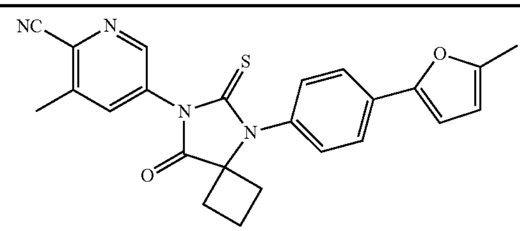 | 429.1 |
| 8 | Ethyl 5-(7-(6-cyano-5-(trifluoromethyl)pyridin-3-yl)-8-oxo-6-thioxo-5,7-diazaspiro[3.4]octan-5-yl)-2-fluorobenzoate | 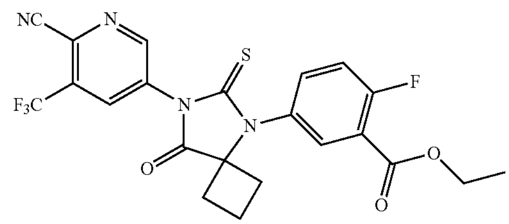 [SMILES: CCOC(=O)c1cc(N2C(=S)N(c3cnc(C#N)c(C(F)(F)F)c3)C(=O)C23CCC3)ccc1F] | 493.4 |
| 9 | 5-(5-(Naphthalen-2-yl)-8-oxo-6-thioxo-5,7-diazaspiro[3.4]octan-7-yl)-3-(trifluoromethyl)picolinonitrile | 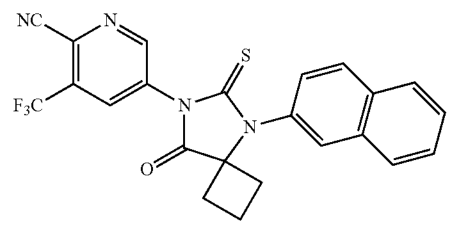 [SMILES: N#Cc1ncc(N2C(=O)C3(CCC3)N(c3ccc4ccccc4c3)C2=S)cc1C(F)(F)F] | 453.0 |
| 10 | 5-(5-(2-Cyanophenyl)-8-oxo-6-thioxo-5,7-diazaspiro[3.4]octan-7-yl)-3-(trifluoromethyl)picolinonitrile | 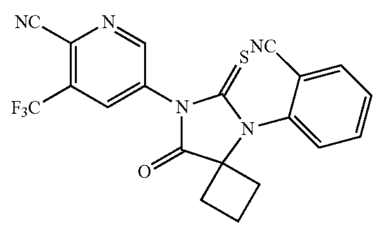 [SMILES: N#Cc1ccccc1N1C(=S)N(c2cnc(C#N)c(C(F)(F)F)c2)C(=O)C12CCC2] | 428.0 |
| 11 | 5-(5-(3-Cyanophenyl)-8-oxo-6-thioxo-5,7-diazaspiro[3.4]octan-7-yl)-3-(trifluoromethyl)picolinonitrile | 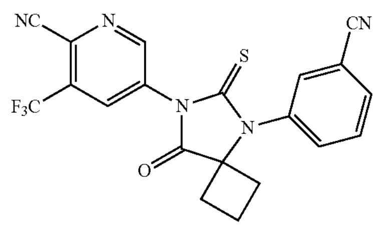 [SMILES: N#Cc1cccc(N2C(=S)N(c3cnc(C#N)c(C(F)(F)F)c3)C(=O)C23CCC3)c1] | 428.4 |
| 12 | 5-(5-(4-Cyanophenyl)-8-oxo-6-thioxo-5,7-diazaspiro[3.4]octan-7-yl)-3-(trifluoromethyl)picolinonitrile | 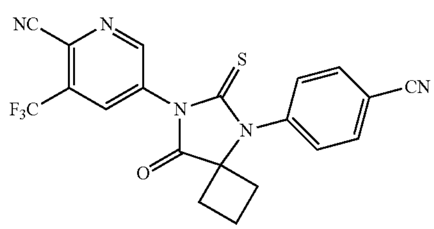 [SMILES: N#Cc1ccc(N2C(=S)N(c3cnc(C#N)c(C(F)(F)F)c3)C(=O)C23CCC3)cc1] | 428.4 |
| 13 | 5-(5-([1,1'-Biphenyl]-4-yl)-8-oxo-6-thioxo-5,7-diazaspiro[3.4]octan-7-yl)-3-(trifluoromethyl)picolinonitrile | 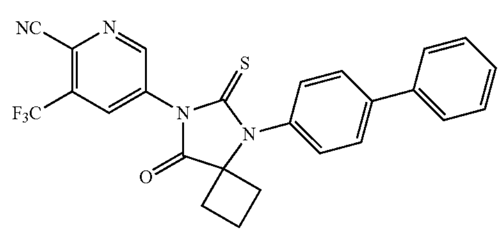 | 479.5 |

TABLE 1-continued

| Cmpd. | Name | Structure | LCMS* [M + 1]+ |
|---|---|---|---|
| 14 | 5-(5-([1,1'-Biphenyl]-3-yl)-8-oxo-6-thioxo-5,7-diazaspiro[3.4]octan-7-yl)-3-(trifluoromethyl)picolinonitrile | 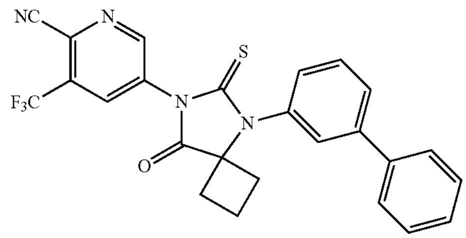 [SMILES: N#Cc1ncc(N2C(=O)C3(CCC3)N(c3cccc(-c4ccccc4)c3)C2=S)cc1C(F)(F)F] | 479.0 |
| 15 | 5-(5-([1,1'-Biphenyl]-2-yl)-8-oxo-6-thioxo-5,7-diazaspiro[3.4]octan-7-yl)-3-(trifluoromethyl)picolinonitrile | 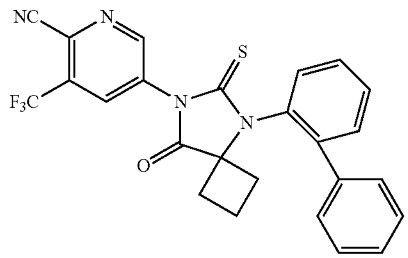 [SMILES: N#Cc1ncc(N2C(=O)C3(CCC3)N(c3ccccc3-c3ccccc3)C2=S)cc1C(F)(F)F] | 479.0 |
| 16 | 5-(8-Oxo-5-(4-(pyridin-2-yl)phenyl)-6-thioxo-5,7-diazaspiro[3.4]octan-7-yl)-3-(trifluoromethyl)picolinonitrile | 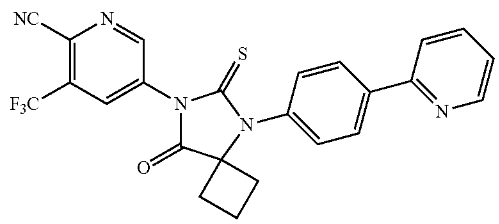 [SMILES: N#Cc1ncc(N2C(=O)C3(CCC3)N(c3ccc(-c4ccccn4)cc3)C2=S)cc1C(F)(F)F] | 480.1 |
| 17 | 5-(8-Oxo-5-(4-(pyridin-3-yl)phenyl)-6-thioxo-5,7-diazaspiro[3.4]octan-7-yl)-3-(trifluoromethyl)picolinonitrile | 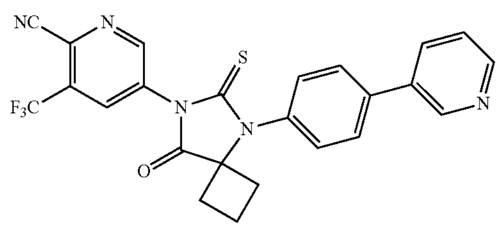 [SMILES: N#Cc1ncc(N2C(=O)C3(CCC3)N(c3ccc(-c4cccnc4)cc3)C2=S)cc1C(F)(F)F] | 480.1 |
| 18 | 5-(8-Oxo-5-(4-(pyridin-4-yl)phenyl)-6-thioxo-5,7-diazaspiro[3.4]octan-7-yl)-3-(trifluoromethyl)picolinonitrile | 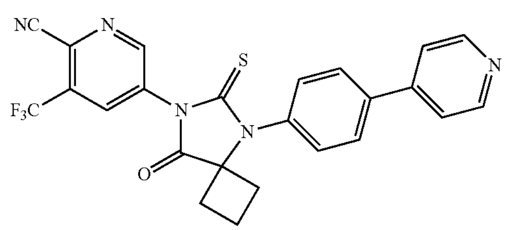 [SMILES: N#Cc1ncc(N2C(=O)C3(CCC3)N(c3ccc(-c4ccncc4)cc3)C2=S)cc1C(F)(F)F] | 480.1 |
| 19 | 5-(8-Oxo-5-(pyridin-3-yl)-6-thioxo-5,7-diazaspiro[3.4]octan-7-yl)-3-(trifluoromethyl)picolinonitrile | 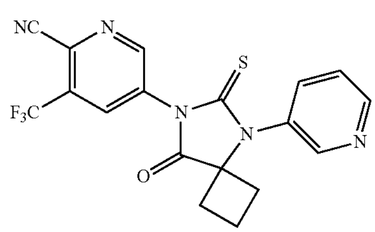 [SMILES: N#Cc1ncc(N2C(=O)C3(CCC3)N(c3cccnc3)C2=S)cc1C(F)(F)F] | 404.4 |

TABLE 1-continued

| Cmpd. | Name | Structure | LCMS* [M + 1]+ |
|---|---|---|---|
| 20 | 5-(8-Oxo-6-thioxo-5-(o-tolyl)-5,7-diazaspiro[3.4]octan-7-yl)-3-(trifluoromethyl)picolinonitrile | 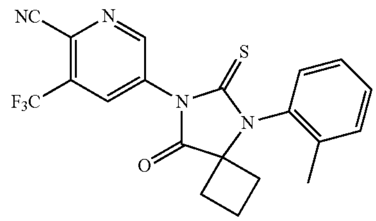 [SMILES: Cc1ccccc1N1C(=S)N(c2cnc(C#N)c(C(F)(F)F)c2)C(=O)C12CCC2] | 417.5 |
| 21 | 5-(8-Oxo-6-thioxo-5-(m-tolyl)-5,7-diazaspiro[3.4]octan-7-yl)-3-(trifluoromethyl)picolinonitrile | 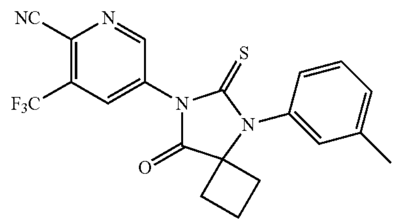 [SMILES: Cc1cccc(N2C(=S)N(c3cnc(C#N)c(C(F)(F)F)c3)C(=O)C23CCC3)c1] | 417.5 |
| 22 | 5-(8-Oxo-6-thioxo-5-(p-tolyl)-5,7-diazaspiro[3.4]octan-7-yl)-3-(trifluoromethyl)picolinonitrile | 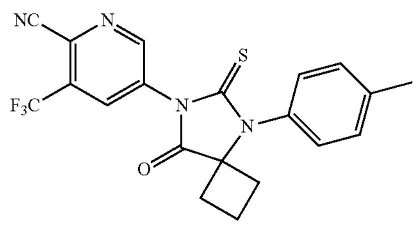 | 417.5 |
| 23[a] | 5-(8-Oxo-5-(2-phenoxyphenyl)-6-thioxo-5,7-diazaspiro[3.4]octan-7-yl)-3-(trifluoromethyl)picolinonitrile | 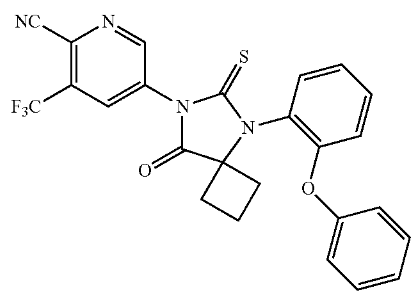 [SMILES: N#Cc1ncc(N2C(=O)C3(CCC3)N(c3ccccc3Oc3ccccc3)C2=S)cc1C(F)(F)F] | 495.5 |
| 24 | 5-(8-Oxo-5-(3-phenoxyphenyl)-6-thioxo-5,7-diazaspiro[3.4]octan-7-yl)-3-(trifluoromethyl)picolinonitrile | 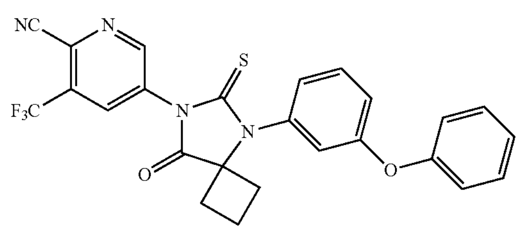 [SMILES: N#Cc1ncc(N2C(=O)C3(CCC3)N(c3cccc(Oc4ccccc4)c3)C2=S)cc1C(F)(F)F] | 495.5 |
| 25 | 5-(8-Oxo-5-(4-phenoxyphenyl)-6-thioxo-5,7-diazaspiro[3.4]octan-7-yl)-3-(trifluoromethyl)picolinonitrile | 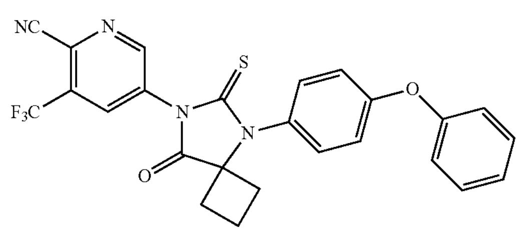 [SMILES: N#Cc1ncc(N2C(=O)C3(CCC3)N(c3ccc(Oc4ccccc4)cc3)C2=S)cc1C(F)(F)F] | 495.5 |

TABLE 1-continued

| Cmpd. | Name | Structure | LCMS* [M + 1]+ |
|---|---|---|---|
| 26 | 5-(5-(2-Fluorophenyl)-8-oxo-6-thioxo-5,7-diazaspiro[3.4]octan-7-yl)-3-(trifluoromethyl)picolinonitrile | 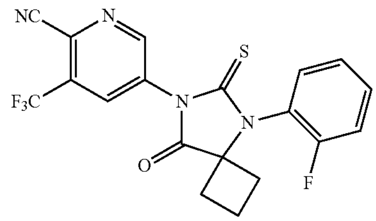 | 421.5 |
| 27 | 5-(5-(3-Fluorophenyl)-8-oxo-6-thioxo-5,7-diazaspiro[3.4]octan-7-yl)-3-(trifluoromethyl)picolinonitrile | 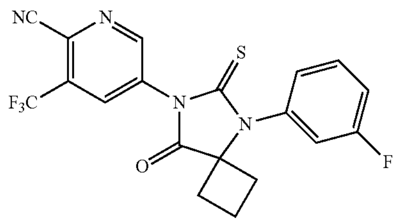 [SMILES: N#Cc1ncc(N2C(=O)C3(CCC3)N(c3cccc(F)c3)C2=S)cc1C(F)(F)F] | 421.5 |
| 28 | 5-(5-(4-Fluorophenyl)-8-oxo-6-thioxo-5,7-diazaspiro[3.4]octan-7-yl)-3-(trifluoromethyl)picolinonitrile | 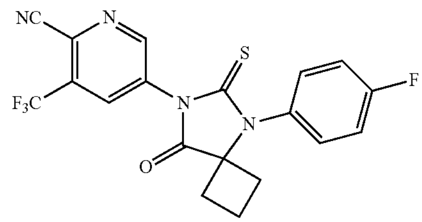 [SMILES: N#Cc1ncc(N2C(=O)C3(CCC3)N(c3ccc(F)cc3)C2=S)cc1C(F)(F)F] | 421.5 |
| 29 | 5-(5-(4-Fluoro-2-methoxyphenyl)-8-oxo-6-thioxo-5,7-diazaspiro[3.4]octan-7-yl)-3-(trifluoromethyl)picolinonitrile | 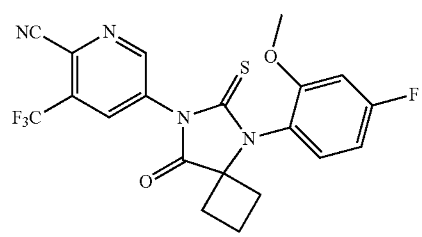 [SMILES: COc1cc(F)ccc1N1C(=S)N(c2cnc(C#N)c(C(F)(F)F)c2)C(=O)C12CCC2] | 451.5 |
| 30 | 6-Thioxo-5-(p-tolyl)-7-(3-(trifluoromethyl)-[1,2,4]triazolo[4,3-b]pyridazin-6-yl)-5,7-diazaspiro[3.4]octan-8-one | 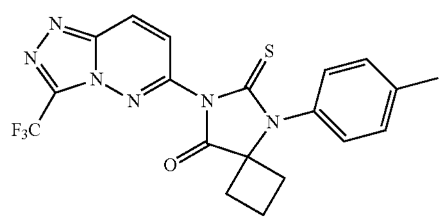 [SMILES: Cc1ccc(N2C(=S)N(c3ccc4nnc(C(F)(F)F)n4n3)C(=O)C23CCC3)cc1] | 433.5 |
| 31 | 3-Methyl-5-(8-oxo-6-thioxo-5-(p-tolyl)-5,7-diazaspiro[3.4]octan-7-yl)picolinonitrile | 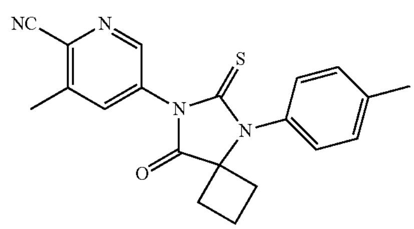 | 363.5 |
| 32 | 5-(5-(4-Fluoro-3-methoxyphenyl)-8-oxo-6-thioxo-5,7-diazaspiro[3.4]octan-7-yl)-3-(trifluoromethyl)picolinonitrile | 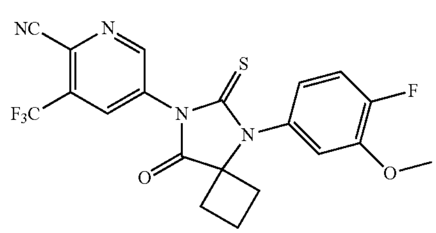 [SMILES: COc1cc(N2C(=S)N(c3cnc(C#N)c(C(F)(F)F)c3)C(=O)C23CCC3)ccc1F] | 451.0 |

TABLE 1-continued

| Cmpd. | Name | Structure | LCMS* [M + 1]+ |
|---|---|---|---|
| 33 | 5-(4,4-Dimethyl-5-oxo-2-thioxo-3-(p-tolyl)imidazolidin-1-yl)-3-(trifluoromethyl)picolinonitrile | 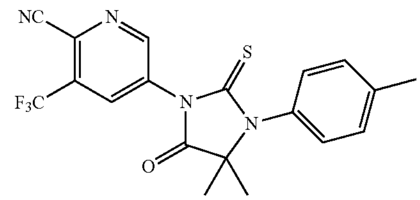 [SMILES: Cc1ccc(N2C(=S)N(c3cnc(C#N)c(C(F)(F)F)c3)C(=O)C2(C)C)cc1] | 405.5 |
| 34 | 6-(8-Oxo-6-thioxo-5-(p-tolyl)-5,7-diazaspiro[3.4]octan-7-yl)-2-(trifluoromethyl)nicotinonitrile | 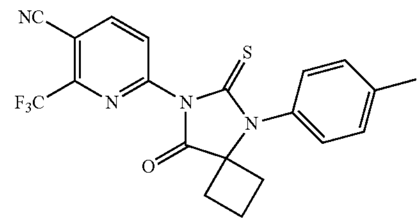 [SMILES: Cc1ccc(N2C(=S)N(c3ccc(C#N)c(C(F)(F)F)n3)C(=O)C23CCC3)cc1] | 417.5 |
| 35 | 4-(7-(5-Cyano-6-(trifluoromethyl)pyridin-2-yl)-8-oxo-6-thioxo-5,7-diazaspiro[3.4]octan-5-yl)-2-fluoro-N-methylbenzamide | 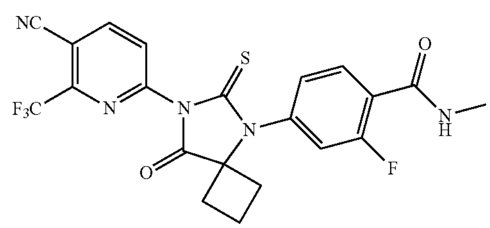 [SMILES: CNC(=O)c1ccc(N2C(=S)N(c3ccc(C#N)c(C(F)(F)F)n3)C(=O)C23CCC3)cc1F] | 478.5 |
| 36 | 5-(8-Oxo-6-thioxo-5-(p-tolyl)-5,7-diazaspiro[3.4]octan-7-yl)quinoline-8-carbonitrile | 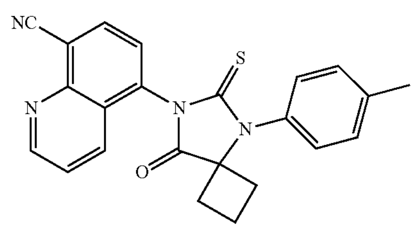 [SMILES: Cc1ccc(N2C(=S)N(c3ccc(C#N)c4ncccc34)C(=O)C23CCC3)cc1] | 399.6 |
| 37 | 4-(7-(8-Cyanoquinolin-5-yl)-8-oxo-6-thioxo-5,7-diazaspiro[3.4]octan-5-yl)-2-fluoro-N-methylbenzamide | 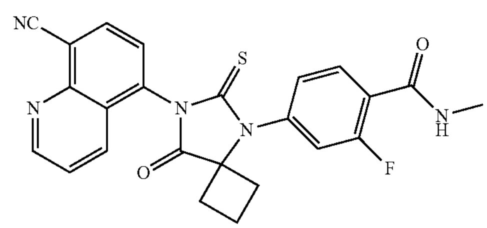 [SMILES: CNC(=O)c1ccc(N2C(=S)N(c3ccc(C#N)c4ncccc34)C(=O)C23CCC3)cc1F] | 460.6 |
| 38 | 5-(5-(4-Fluoro-2-hydroxyphenyl)-8-oxo-6-thioxo-5,7-diazaspiro[3.4]octan-7-yl)-3-(trifluoromethyl)picolinonitrile | 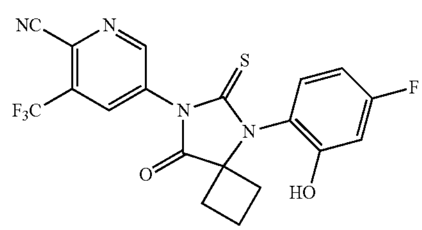 [SMILES: N#Cc1ncc(N2C(=O)C3(CCC3)N(c3ccc(F)cc3O)C2=S)cc1C(F)(F)F] | 437.5 |
| 39 | 5-(8-Oxo-5-(4-(pyridin-3-yloxy)phenyl)-6-thioxo-5,7-diazaspiro[3.4]octan-7-yl)-3-(trifluoromethyl)picolinonitrile | 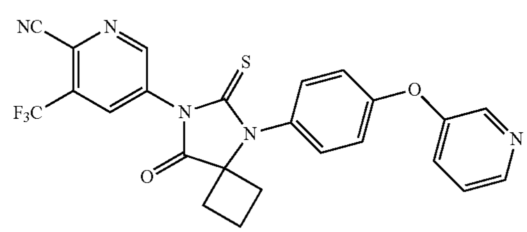 [SMILES: N#Cc1ncc(N2C(=O)C3(CCC3)N(c3ccc(Oc4cccnc4)cc3)C2=S)cc1C(F)(F)F] | 496.1 |

TABLE 1-continued

| Cmpd. | Name | Structure | LCMS* [M + 1]+ |
|---|---|---|---|
| 40 | 5-(8-Oxo-5-(4-(pyridin-4-yloxy)phenyl)-6-thioxo-5,7-diazaspiro[3.4]octan-7-yl)-3-(trifluoromethyl)picolinonitrile | 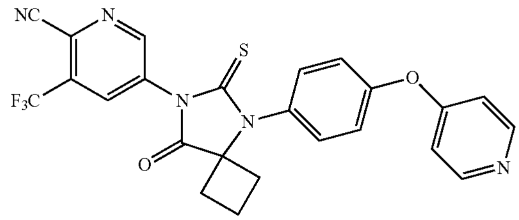 [SMILES: N#Cc1ncc(N2C(=O)C3(CCC3)N(c3ccc(Oc4ccncc4)cc3)C2=S)cc1C(F)(F)F] | 496.4 |
| 41 | 5-(8-Oxo-5-(4-(pyridin-2-yloxy)phenyl)-6-thioxo-5,7-diazaspiro[3.4]octan-7-yl)-3-(trifluoromethyl)picolinonitrile | 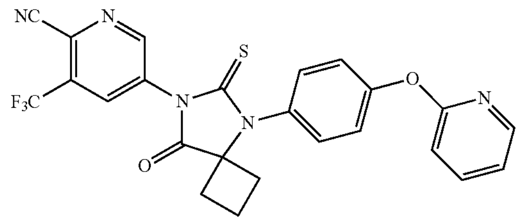 | 496.6 |
| 42 | 5-(8-Oxo-5-(4-(pyrimidin-5-yloxy)phenyl)-6-thioxo-5,7-diazaspiro[3.4]octan-7-yl)-3-(trifluoromethyl)picolinonitrile | 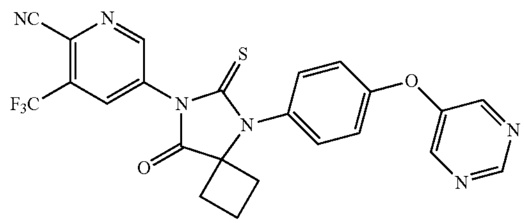 | 496.9 |
| 43 | 4-(3-(6-Cyano-5-(trifluoromethyl)pyridin-3-yl)-5,5-dimethyl-4-oxo-2-thioxoimidazolidin-1-yl)-2-fluoro-N-methylbenzamide | 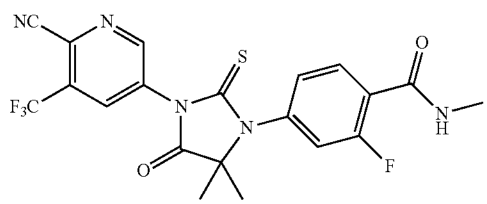 [SMILES: CNC(=O)c1ccc(N2C(=S)N(c3cnc(C#N)c(C(F)(F)F)c3)C(=O)C2(C)C)cc1F] | 466.5 |
| 44 | 5-(8-Oxo-6-thioxo-5-(4-(trifluoromethoxy)phenyl)-5,7-diazaspiro[3.4]octan-7-yl)-3-(trifluoromethyl)picolinonitrile | 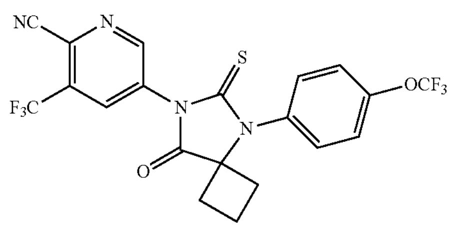 [SMILES: N#Cc1ncc(N2C(=O)C3(CCC3)N(c3ccc(OC(F)(F)F)cc3)C2=S)cc1C(F)(F)F] | 487.5 |
| 45 | 5-(8-Oxo-6-thioxo-5-(3-(trifluoromethoxy)phenyl)-5,7-diazaspiro[3.4]octan-7-yl)-3-(trifluoromethyl)picolinonitrile | 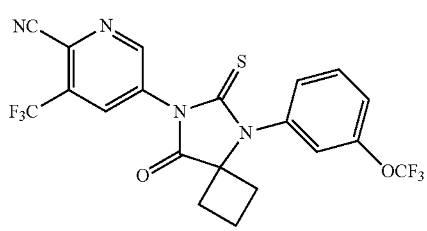 [SMILES: N#Cc1ncc(N2C(=O)C3(CCC3)N(c3cccc(OC(F)(F)F)c3)C2=S)cc1C(F)(F)F] | 487.5 |
| 46 | 5-(8-Oxo-6-thioxo-5-(4-(trifluoromethyl)phenyl)-5,7-diazaspiro[3.4]octan-7-yl)-3-(trifluoromethyl)picolinonitrile | 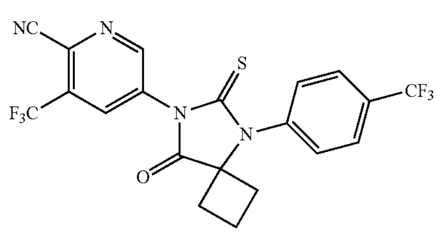 [SMILES: N#Cc1ncc(N2C(=O)C3(CCC3)N(c3ccc(C(F)(F)F)cc3)C2=S)cc1C(F)(F)F] | 471.5 |

TABLE 1-continued

| Cmpd. | Name | Structure | LCMS* [M + 1]+ |
|---|---|---|---|
| 47 | 4-(3-(6-Cyano-5-methylpyridin-3-yl)-5,5-dimethyl-4-oxo-2-thioxoimidazolidin-1-yl)-2-fluoro-N-methylbenzamide | 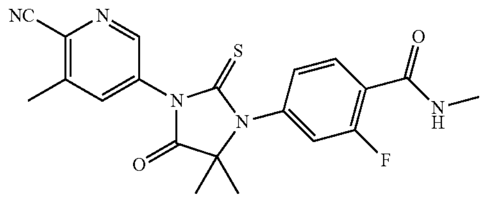 | 412.5 |
| 48 | 5-(8-Oxo-5-phenyl-6-thioxo-5,7-diazaspiro[3.4]octan-7-yl)-3-(trifluoromethyl)picolinonitrile | 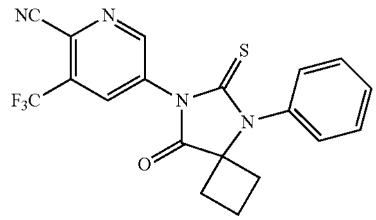 | 403.5 |
| 49 | 5-(5-(3-Fluoro-4-methylphenyl)-8-oxo-6-thioxo-5,7-diazaspiro[3.4]octan-7-yl)-3-(trifluoromethyl)picolinonitrile | 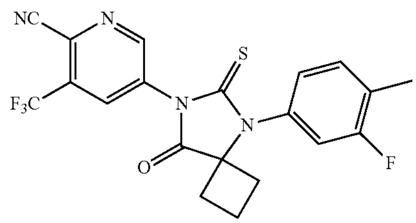 [SMILES: Cc1ccc(N2C(=S)N(c3cnc(C#N)c(C(F)(F)F)c3)C(=O)C23CCC3)cc1F] | 435.5 |
| 50 | 5-(5-(2-Fluoro-4-methylphenyl)-8-oxo-6-thioxo-5,7-diazaspiro[3.4]octan-7-yl)-3-(trifluoromethyl)picolinonitrile | 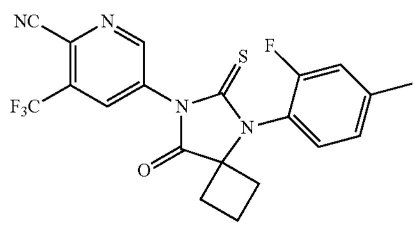 [SMILES: Cc1ccc(N2C(=S)N(c3cnc(C#N)c(C(F)(F)F)c3)C(=O)C23CCC3)c(F)c1] | 435.5 |
| 51 | 5-(5-(Isoquinolin-6-yl)-8-oxo-6-thioxo-5,7-diazaspiro[3.4]octan-7-yl)-3-(trifluoromethyl)picolinonitrile | 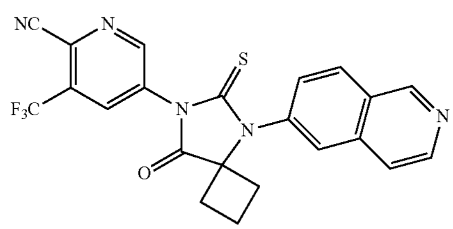 [SMILES: N#Cc1ncc(N2C(=O)C3(CCC3)N(c3ccc4cnccc4c3)C2=S)cc1C(F)(F)F] | 454.6 |
| 52 | 5-(5-(Isoquinolin-7-yl)-8-oxo-6-thioxo-5,7-diazaspiro[3.4]octan-7-yl)-3-(trifluoromethyl)picolinonitrile | 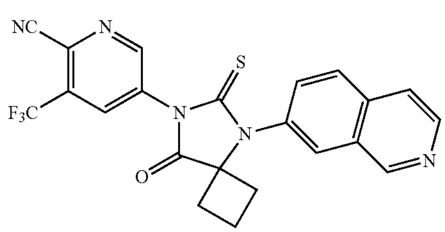 [SMILES: N#Cc1ncc(N2C(=O)C3(CCC3)N(c3ccc4ccncc4c3)C2=S)cc1C(F)(F)F] | 454.6 |
| 53 | 5-(5-Cyclohexyl-8-oxo-6-thioxo-5,7-diazaspiro[3.4]octan-7-yl)-3-(trifluoromethyl)picolinonitrile | 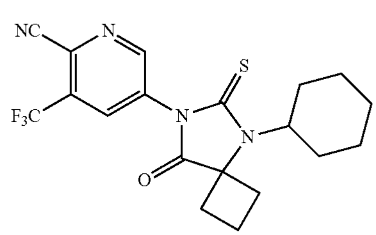 [SMILES: N#Cc1ncc(N2C(=O)C3(CCC3)N(C3CCCCC3)C2=S)cc1C(F)(F)F] | 409.6 |

TABLE 1-continued

| Cmpd. | Name | Structure | LCMS* [M + 1]+ |
|---|---|---|---|
| 54 | 5-(5-(3-Fluoro-4-hydroxyphenyl)-8-oxo-6-thioxo-5,7-diazaspiro[3.4]octan-7-yl)-3-methylpicolinonitrile | 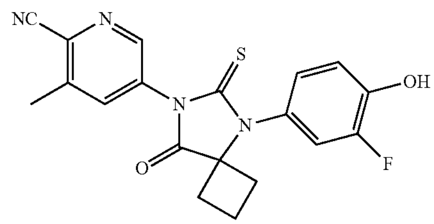 [SMILES: Cc1cc(N2C(=O)C3(CCC3)N(c3ccc(O)c(F)c3)C2=S)cnc1C#N] | 383.0 |
| 55 | 5-(5-(3-Fluoro-4-hydroxyphenyl)-8-oxo-6-thioxo-5,7-diazaspiro[3.4]octan-7-yl)quinoline-8-carbonitrile | 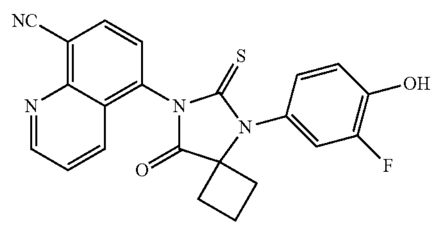 [SMILES: N#Cc1ccc(N2C(=O)C3(CCC3)N(c3ccc(O)c(F)c3)C2=S)c2cccnc12] | 419.0 |
| 56 | 5-(5-(4-Cyano-3-fluorophenyl)-8-oxo-6-thioxo-5,7-diazaspiro[3.4]octan-7-yl)-3-(trifluoromethyl)picolinonitrile | 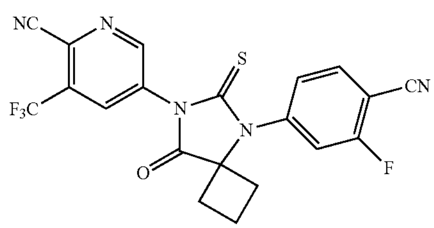 [SMILES: N#Cc1ccc(N2C(=S)N(c3cnc(C#N)c(C(F)(F)F)c3)C(=O)C23CCC3)cc1F] | 446.6 |
| 57 | 3-Chloro-5-(8-oxo-6-thioxo-5-(p-tolyl)-5,7-diazaspiro[3.4]octan-7-yl)picolinonitrile | 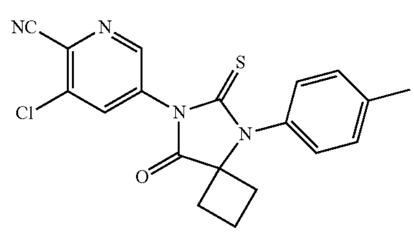 [SMILES: Cc1ccc(N2C(=S)N(c3cnc(C#N)c(Cl)c3)C(=O)C23CCC3)cc1] | 383.0 |
| 58 | 4-(7-(5-Chloro-6-cyanopyridin-3-yl)-8-oxo-6-thioxo-5,7-diazaspiro[3.4]octan-5-yl)-2-fluoro-N-methylbenzamide | 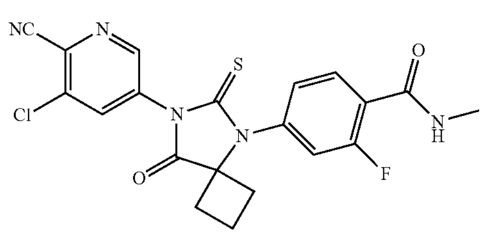 [SMILES: CNC(=O)c1ccc(N2C(=S)N(c3cnc(C#N)c(Cl)c3)C(=O)C23CCC3)cc1F] | 444.0 |
| 59 | 3-Methoxy-5-(8-oxo-6-thioxo-5-(p-tolyl)-5,7-diazaspiro[3.4]octan-7-yl)picolinonitrile | 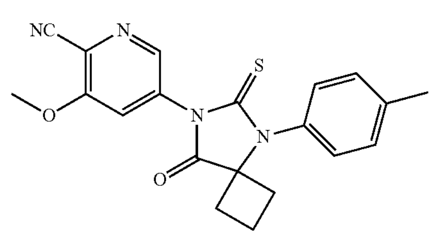 | 379.0 |

TABLE 1-continued

| Cmpd. | Name | Structure | LCMS* [M + 1]+ |
|---|---|---|---|
| 60 | 4-(7-(6-Cyano-5-methoxypyridin-3-yl)-8-oxo-6-thioxo-5,7-diazaspiro[3.4]octan-5-yl)-2-fluoro-N-methylbenzamide | 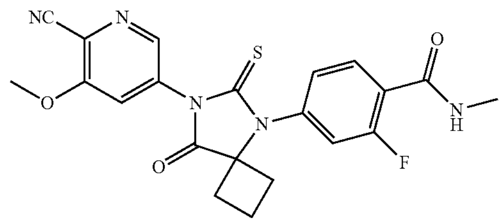 | 440.0 |
| 61 | 6-Thioxo-5-(p-tolyl)-7-(3-(trifluoromethyl)-[2,3'-bipyridin]-5-yl)-5,7-diazaspiro[3.4]octan-8-one | 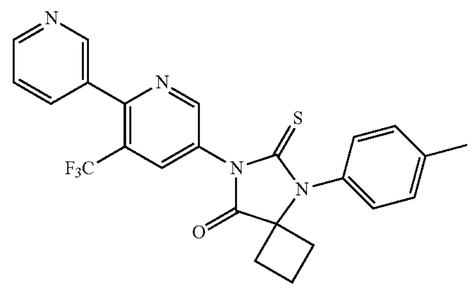 [SMILES: Cc1ccc(N2C(=S)N(c3cnc(-c4cccnc4)c(C(F)(F)F)c3)C(=O)C23CCC3)cc1] | 469.0 |
| 62 | 7-(Imidazo[1,2-a]pyridin-6-yl)-6-thioxo-5-(p-tolyl)-5,7-diazaspiro[3.4]octan-8-one | 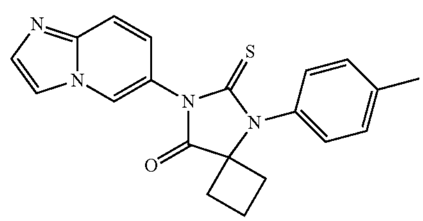 [SMILES: Cc1ccc(N2C(=S)N(c3ccc4nccn4c3)C(=O)C23CCC3)cc1] | 363.0 |
| 63 | 5-(5-(4-Hydroxyphenyl)-8-oxo-6-thioxo-5,7-diazaspiro[3.4]octan-7-yl)-3-(trifluoromethyl)picolinonitrile | 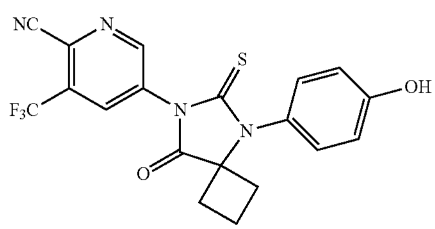 | 419.9 |
| 64 | 5-(5-(2-Fluoro-4-hydroxyphenyl)-8-oxo-6-thioxo-5,7-diazaspiro[3.4]octan-7-yl)-3-(trifluoromethyl)picolinonitrile | 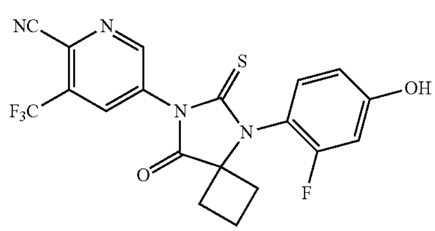 [SMILES: N#Cc1ncc(N2C(=O)C3(CCC3)N(c3ccc(O)cc3F)C2=S)cc1C(F)(F)F] | 437.8 |
| 65 | 4-(8-Oxo-6-thioxo-5-(p-tolyl)-5,7-diazaspiro[3.4]octan-7-yl)isoquinoline-1-carbonitrile | 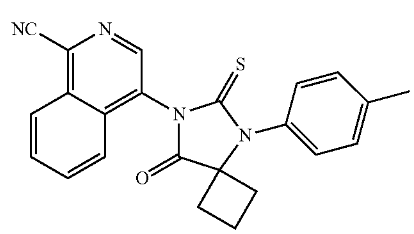 [SMILES: Cc1ccc(N2C(=S)N(c3cnc(C#N)c4ccccc34)C(=O)C23CCC3)cc1] | 399.0 |

TABLE 1-continued

| Cmpd. | Name | Structure | LCMS* [M + 1]+ |
|---|---|---|---|
| 66 | 4-(7-(1-Cyanoisoquinolin-4-yl)-8-oxo-6-thioxo-5,7-diazaspiro[3.4]octan-5-yl)-2-fluoro-N-methylbenzamide | 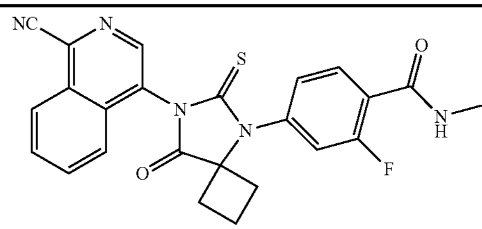 | 460.0 |
| 67 | 5-(5-(3-(Hydroxymethyl)phenyl)-8-oxo-6-thioxo-5,7-diazaspiro[3.4]octan-7-yl)-3-(trifluoromethyl)picolinonitrile | 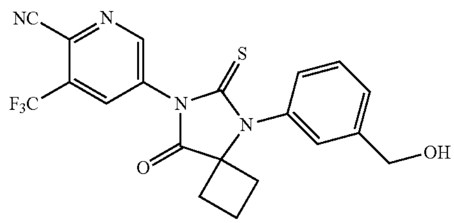 [SMILES: N#Cc1ncc(N2C(=O)C3(CCC3)N(c3cccc(CO)c3)C2=S)cc1C(F)(F)F] | 433.0 |
| 68 | 5-(5-(2-(Hydroxymethyl)phenyl)-8-oxo-6-thioxo-5,7-diazaspiro[3.4]octan-7-yl)-3-(trifluoromethyl)picolinonitrile | 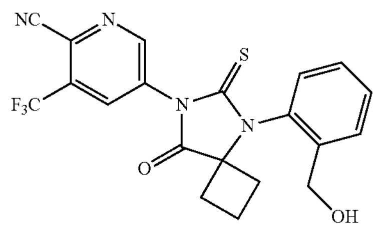 [SMILES: N#Cc1ncc(N2C(=O)C3(CCC3)N(c3ccccc3CO)C2=S)cc1C(F)(F)F] | 433.0 |
| 69 | 5-(5-(4-(Hydroxymethyl)phenyl)-8-oxo-6-thioxo-5,7-diazaspiro[3.4]octan-7-yl)-3-(trifluoromethyl)picolinonitrile | 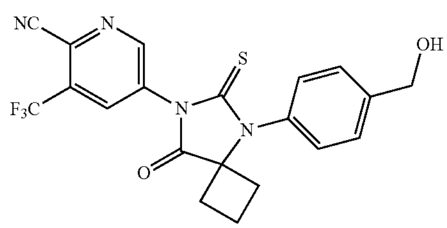 [SMILES: N#Cc1ncc(N2C(=O)C3(CCC3)N(c3ccc(CO)cc3)C2=S)cc1C(F)(F)F] | 433.1 |
| 70 | 5-(5-(4-Cyano-2-fluorophenyl)-8-oxo-6-thioxo-5,7-diazaspiro[3.4]octan-7-yl)-3-(trifluoromethyl)picolinonitrile | 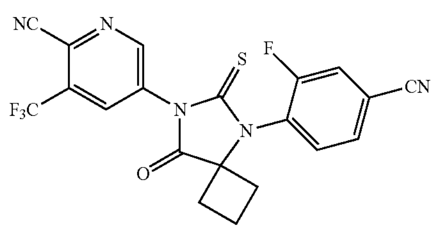 [SMILES: N#Cc1ccc(N2C(=S)N(c3cnc(C#N)c(C(F)(F)F)c3)C(=O)C23CCC3)c(F)c1] | 445.9 |
| 71 | Methyl 4-(7-(6-cyano-5-methylpyridin-3-yl)-8-oxo-6-thioxo-5,7-diazaspiro[3.4]octan-5-yl)-3-fluorobenzoate | 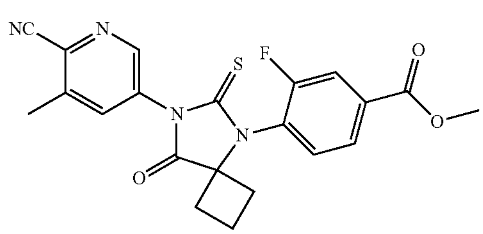 | 425.0 |
| 72 | 5-(5-(2,3-Difluorophenyl)-8-oxo-6-thioxo-5,7-diazaspiro[3.4]octan-7-yl)-3-(trifluoromethyl)picolinonitrile | 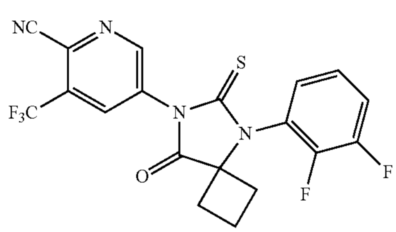 [SMILES: N#Cc1ncc(N2C(=O)C3(CCC3)N(c3cccc(F)c3F)C2=S)cc1C(F)(F)F] | 438.9 |

TABLE 1-continued

| Cmpd. | Name | Structure | LCMS* [M + 1]+ |
|---|---|---|---|
| 73 | 5-(5-(2,6-Difluorophenyl)-8-oxo-6-thioxo-5,7-diazaspiro[3.4]octan-7-yl)-3-(trifluoromethyl)picolinonitrile | 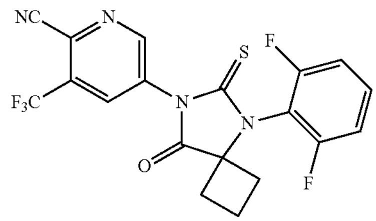 [SMILES: N#Cc1ncc(N2C(=O)C3(CCC3)N(c3c(F)cccc3F)C2=S)cc1C(F)(F)F] | 438.9 |
| 74 | 5-(5-(2,5-Difluorophenyl)-8-oxo-6-thioxo-5,7-diazaspiro[3.4]octan-7-yl)-3-(trifluoromethyl)picolinonitrile | 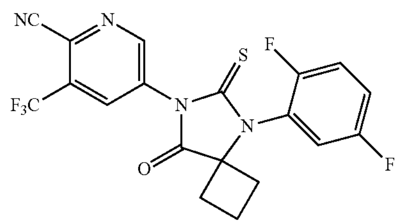 [SMILES: N#Cc1ncc(N2C(=O)C3(CCC3)N(c3cc(F)ccc3F)C2=S)cc1C(F)(F)F] | 439.0 |
| 75 | 5-(8-Oxo-6-thioxo-5-(2,3,6-trifluorophenyl)-5,7-diazaspiro[3.4]octan-7-yl)-3-(trifluoromethyl)picolinonitrile | 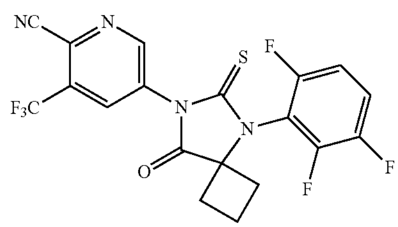 [SMILES: N#Cc1ncc(N2C(=O)C3(CCC3)N(c3c(F)ccc(F)c3F)C2=S)cc1C(F)(F)F] | 456.9 |
| 76 | 5-(5-(2,4-Difluorophenyl)-8-oxo-6-thioxo-5,7-diazaspiro[3.4]octan-7-yl)-3-(trifluoromethyl)picolinonitrile | 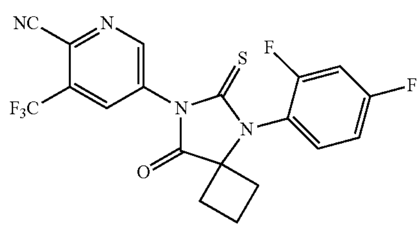 [SMILES: N#Cc1ncc(N2C(=O)C3(CCC3)N(c3ccc(F)cc3F)C2=S)cc1C(F)(F)F] | 438.9 |
| 77 | 5-(5-(4-Hydroxyphenyl)-8-oxo-6-thioxo-5,7-diazaspiro[3.4]octan-7-yl)-3-methylpicolinonitrile | 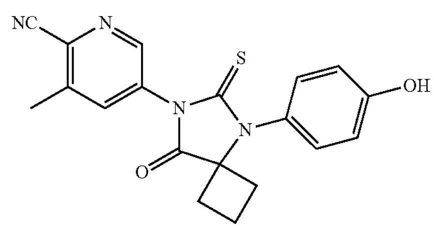 [SMILES: Cc1cc(N2C(=O)C3(CCC3)N(c3ccc(O)cc3)C2=S)cnc1C#N] | 365.0 |
| 78 | 4-(7-(6-Cyano-5-methylpyridin-3-yl)-8-oxo-6-thioxo-5,7-diazaspiro[3.4]octan-5-yl)-N-methylbenzamide | 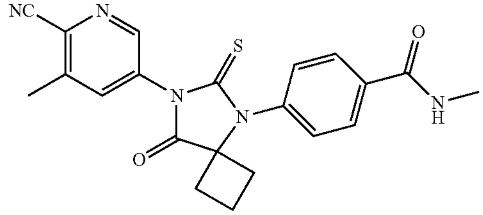 | 406.1 |

TABLE 1-continued

| Cmpd. | Name | Structure | LCMS* [M + 1]+ |
|---|---|---|---|
| 79 | 4-(7-(6-Cyano-5-(trifluoromethyl)pyridin-3-yl)-8-oxo-6-thioxo-5,7-diazaspiro[3.4]octan-5-yl)-N-methylbenzamide | 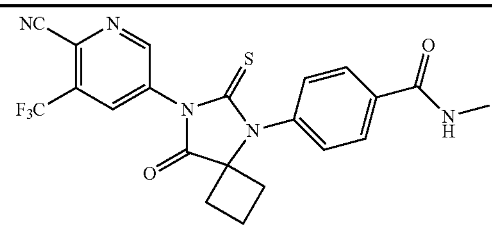 | 460.0 |
| 80 | 5-(5-(4-(Methylsulfonyl)phenyl)-8-oxo-6-thioxo-5,7-diazaspiro[3.4]octan-7-yl)-3-(trifluoromethyl)picolinonitrile | 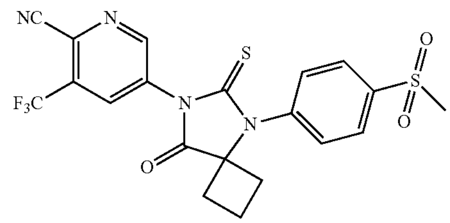 [SMILES: CS(=O)(=O)c1ccc(N2C(=S)N(c3cnc(C#N)c(C(F)(F)F)c3)C(=O)C23CCC3)cc1] | 481.0 |
| 81 | 4-(7-(6-Cyano-5-(trifluoromethyl)pyridin-3-yl)-8-oxo-6-thioxo-5,7-diazaspiro[3.4]octan-5-yl)benzenesulfonamide | 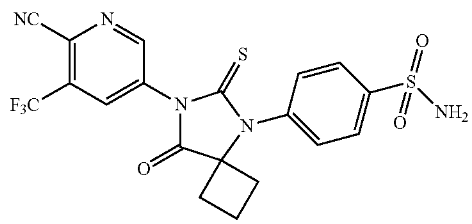 [SMILES: N#Cc1ncc(N2C(=O)C3(CCC3)N(c3ccc(S(N)(=O)=O)cc3)C2=S)cc1C(F)(F)F] | 482.0 |
| 82 | 4-(8-Oxo-6-thioxo-5-(p-tolyl)-5,7-diazaspiro[3.4]octan-7-yl)pyrazolo[1,5-a]pyridine-7-carbonitrile | 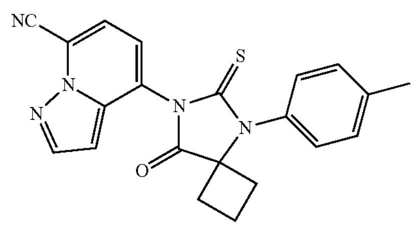 [SMILES: Cc1ccc(N2C(=S)N(c3ccc(C#N)n4nccc34)C(=O)C23CCC3)cc1] | 388.0 |
| 83 | 4-(7-(7-Cyanopyrazolo[1,5-a]pyridin-4-yl)-8-oxo-6-thioxo-5,7-diazaspiro[3.4]octan-5-yl)-2-fluoro-N-methylbenzamide | 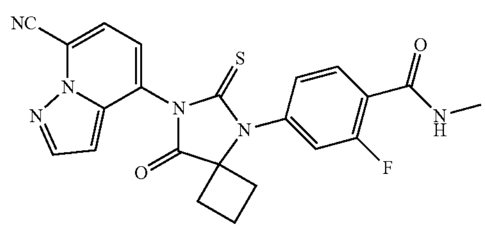 [SMILES: CNC(=O)c1ccc(N2C(=S)N(c3ccc(C#N)n4nccc34)C(=O)C23CCC3)cc1F] | 449.0 |
| 84 | 5-(5-(4-Methylbenzyl)-8-oxo-6-thioxo-5,7-diazaspiro[3.4]octan-7-yl)-3-(trifluoromethyl)picolinonitrile | 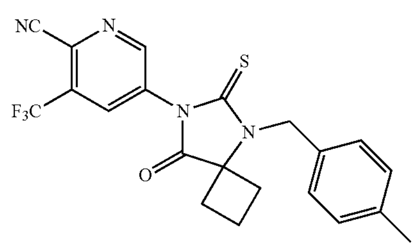 [SMILES: Cc1ccc(CN2C(=S)N(c3cnc(C#N)c(C(F)(F)F)c3)C(=O)C23CCC3)cc1] | 431.0 |
| 85 | 5-(5-(4-Methylphenethyl)-8-oxo-6-thioxo-5,7-diazaspiro[3.4]octan-7-yl)-3-(trifluoromethyl)picolinonitrile | 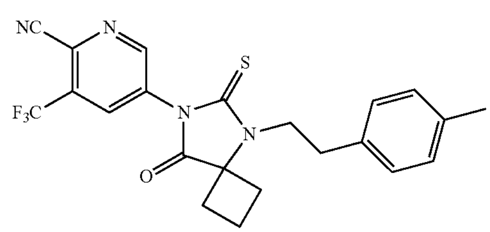 [SMILES: Cc1ccc(CCN2C(=S)N(c3cnc(C#N)c(C(F)(F)F)c3)C(=O)C23CCC3)cc1] | 445.0 |

TABLE 1-continued

| Cmpd. | Name | Structure | LCMS* [M + 1]+ |
|---|---|---|---|
| 86 | 5-(5-(4-(3-Hydroxypropyl)phenyl)-8-oxo-6-thioxo-5,7-diazaspiro[3.4]octan-7-yl)-3-(trifluoromethyl)picolinonitrile | 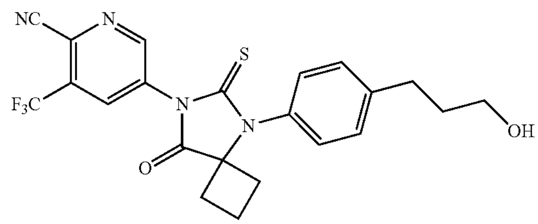 [SMILES: N#Cc1ncc(N2C(=O)C3(CCC3)N(c3ccc(CCCO)cc3)C2=S)cc1C(F)(F)F] | 461.1 |
| 87 | 5-(5-(1H-Indazol-5-yl)-8-oxo-6-thioxo-5,7-diazaspiro[3.4]octan-7-yl)-3-(trifluoromethyl)picolinonitrile | 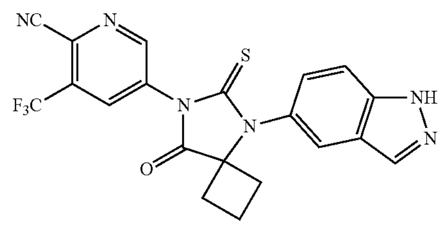 [SMILES: N#Cc1ncc(N2C(=O)C3(CCC3)N(c3ccc4[nH]ncc4c3)C2=S)cc1C(F)(F)F] | 443.7 |
| 88 | 5-(5-(1H-Indazol-6-yl)-8-oxo-6-thioxo-5,7-diazaspiro[3.4]octan-7-yl)-3-(trifluoromethyl)picolinonitrile | 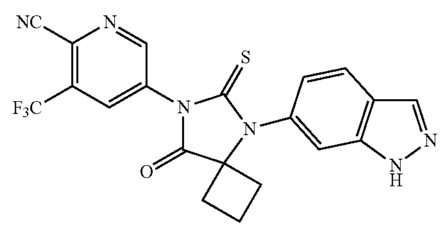 [SMILES: N#Cc1ncc(N2C(=O)C3(CCC3)N(c3ccc4cn[nH]c4c3)C2=S)cc1C(F)(F)F] | 443.7 |
| 89 | 4-(7-(6-Cyano-5-(trifluoromethyl)pyridin-3-yl)-8-oxo-6-thioxo-5,7-diazaspiro[3.4]octan-5-yl)-3-fluoro-N-methylbenzamide | 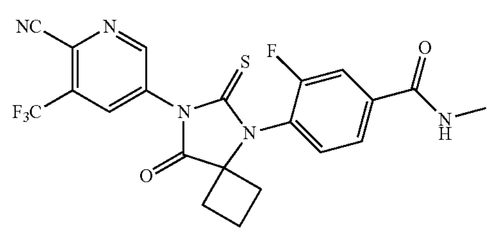 [SMILES: CNC(=O)c1ccc(N2C(=S)N(c3cnc(C#N)c(C(F)(F)F)c3)C(=O)C23CCC3)c(F)c1] | 478.3 |
| 90 | 5-(5-(4-(4-Methylpiperazin-1-yl)phenyl)-8-oxo-6-thioxo-5,7-diazaspiro[3.4]octan-7-yl)-3-(trifluoromethyl)picolinonitrile | 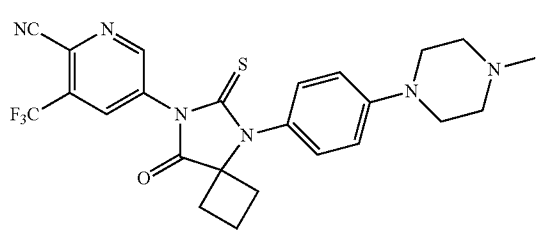 [SMILES: CN1CCN(c2ccc(N3C(=S)N(c4cnc(C#N)c(C(F)(F)F)c4)C(=O)C34CCC4)cc2)CC1] | 501.1 |
| 91 | 5-(8-Oxo-5-(4-((2-(pyridin-4-yl)ethyl)sulfonyl)phenyl)-6-thioxo-5,7-diazaspiro[3.4]octan-7-yl)-3-(trifluoromethyl)picolinonitrile | 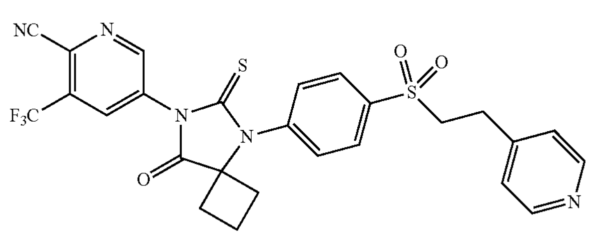 [SMILES: N#Cc1ncc(N2C(=O)C3(CCC3)N(c3ccc(S(=O)(=O)CCc4ccncc4)cc3)C2=S)cc1C(F)(F)F] | 572.1 |

TABLE 1-continued

| Cmpd. | Name | Structure | LCMS* [M + 1]+ |
|---|---|---|---|
| 92 | 5-(5-(4-((Methyl(pyridin-4-ylmethyl)amino)methyl)phenyl)-8-oxo-6-thioxo-5,7-diazaspiro[3.4]octan-7-yl)-3-(trifluoromethyl)picolinonitrile | 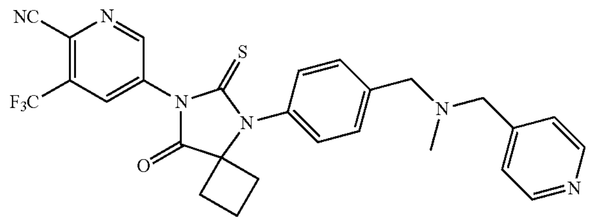 [SMILES: CN(Cc1ccncc1)Cc1ccc(N2C(=S)N(c3cnc(C#N)c(C(F)(F)F)c3)C(=O)C23CCC3)cc1] | 537.1 |
| 93 | 5-(5-(4-((4-Methylpiperazin-1-yl)methyl)phenyl)-8-oxo-6-thioxo-5,7-diazaspiro[3.4]octan-7-yl)-3-(trifluoromethyl)picolinonitrile | 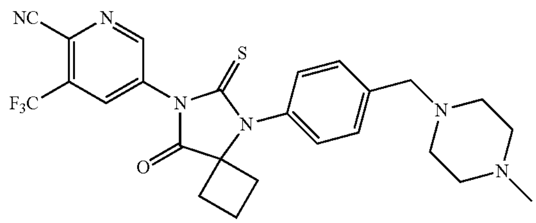 [SMILES: CN1CCN(Cc2ccc(N3C(=S)N(c4cnc(C#N)c(C(F)(F)F)c4)C(=O)C34CCC4)cc2)CC1] | 515.1 |
| 94 | 4-(8-Oxo-6-thioxo-5-(p-tolyl)-5,7-diazaspiro[3.4]octan-7-yl)-1-naphthonitrile | 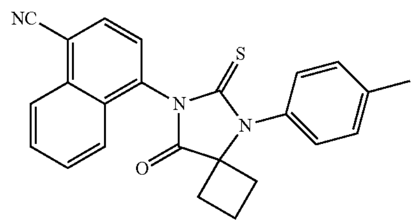 [SMILES: Cc1ccc(N2C(=S)N(c3ccc(C#N)c4ccccc34)C(=O)C23CCC3)cc1] | 398.6 |
| 95 | 4-(7-(4-Cyanonaphthalen-1-yl)-8-oxo-6-thioxo-5,7-diazaspiro[3.4]octan-5-yl)-2-fluoro-N-methylbenzamide | 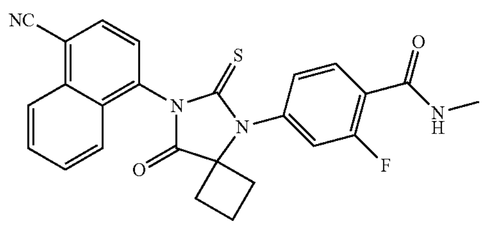 [SMILES: CNC(=O)c1ccc(N2C(=S)N(c3ccc(C#N)c4ccccc34)C(=O)C23CCC3)cc1F] | 459.5 |
| 96 | 3-Methyl-5-(5-(4-(6-methylpyridin-3-yl)phenyl)-8-oxo-6-thioxo-5,7-diazaspiro[3.4]octan-7-yl)picolinonitrile | 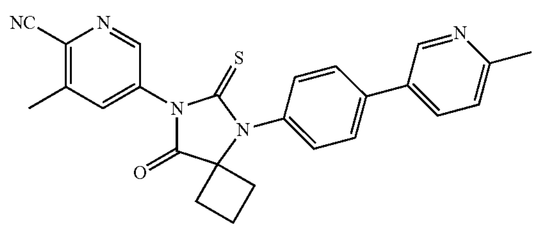 | 440.0 |
| 97 | 3-Methyl-5-(5-(4-(4-methylpyridin-3-yl)phenyl)-8-oxo-6-thioxo-5,7-diazaspiro[3.4]octan-7-yl)picolinonitrile | 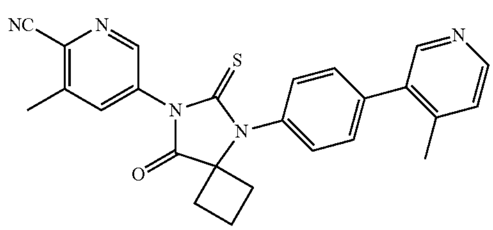 [SMILES: Cc1ccncc1-c1ccc(N2C(=S)N(c3cnc(C#N)c(C)c3)C(=O)C23CCC3)cc1] | 440.1 |
| 98 | 3-Methyl-5-(5-(4-(5-methylpyridin-3-yl)phenyl)-8-oxo-6-thioxo-5,7-diazaspiro[3.4]octan-7-yl)picolinonitrile | 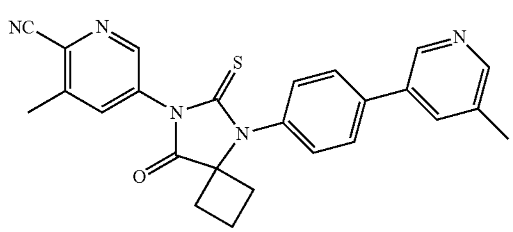 | 440.1 |

TABLE 1-continued

| Cmpd. | Name | Structure | LCMS* [M + 1]+ |
|---|---|---|---|
| 99 | 3-Methyl-5-(5-(4-(2-methylpyridin-3-yl)phenyl)-8-oxo-6-thioxo-5,7-diazaspiro[3.4]octan-7-yl)picolinonitrile | 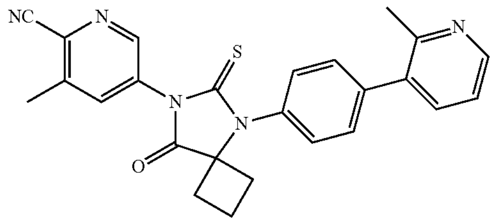 [SMILES: Cc1cc(N2C(=O)C3(CCC3)N(c3ccc(-c4cccnc4C)cc3)C2=S)cnc1C#N] | 440.0 |
| 100 | 5-(3-(4-Hydroxyphenyl)-4,4-dimethyl-5-oxo-2-thioxoimidazolidin-1-yl)-3-(trifluoromethyl)picolinonitrile | 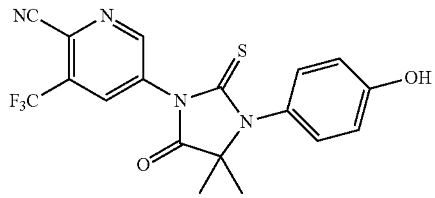 [SMILES: CC1(C)C(=O)N(c2cnc(C#N)c(C(F)(F)F)c2)C(=S)N1c1ccc(O)cc1] | 407.0 |
| 101 | 5-(3-(4-Hydroxyphenyl)-4,4-dimethyl-5-oxo-2-thioxoimidazolidin-1-yl)-3-methylpicolinonitrile | 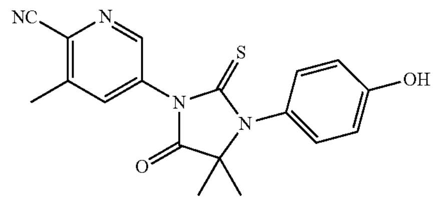 [SMILES: Cc1cc(N2C(=O)C(C)(C)N(c3ccc(O)cc3)C2=S)cnc1C#N] | 353.0 |
| 102 | 3-Methyl-5-(5-(4-(methyl(1-methylpiperidin-4-yl)amino)phenyl)-8-oxo-6-thioxo-5,7-diazaspiro[3.4]octan-7-yl)picolinonitrile | 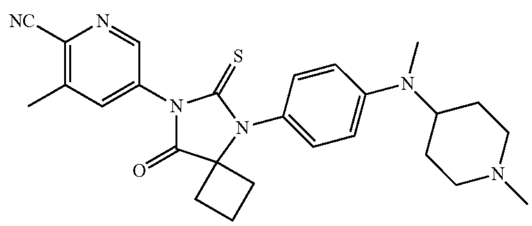 | 475.1 |
| 103 | 3-Methyl-5-(8-oxo-5-(4-(pyrimidin-5-yl)phenyl)-6-thioxo-5,7-diazaspiro[3.4]octan-7-yl)picolinonitrile | 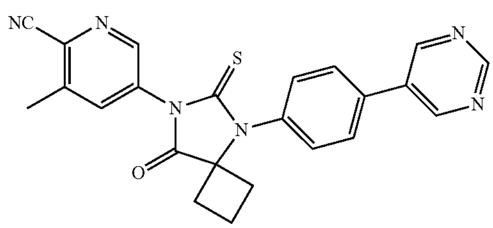 [SMILES: Cc1cc(N2C(=O)C3(CCC3)N(c3ccc(-c4cncnc4)cc3)C2=S)cnc1C#N] | 427.0 |
| 104 | 4-(7-(6-Cyano-5-methylpyridin-3-yl)-8-oxo-6-thioxo-5,7-diazaspiro[3.4]octan-5-yl)-3-fluoro-N-methylbenzamide | 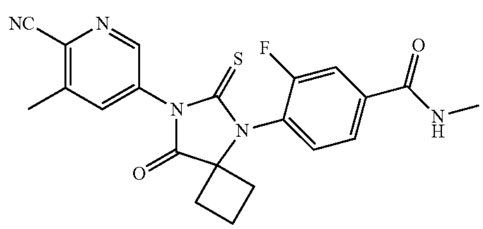 | 424.0 |
| 105 | 5-(5-(4-(5-Fluoropyridin-3-yl)phenyl)-8-oxo-6-thioxo-5,7-diazaspiro[3.4]octan-7-yl)-3-methylpicolinonitrile | 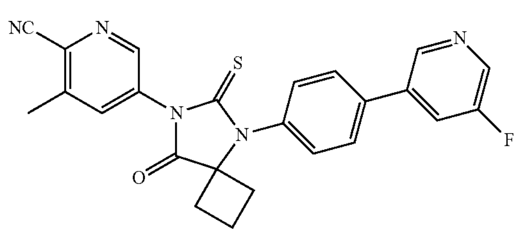 [SMILES: Cc1cc(N2C(=O)C3(CCC3)N(c3ccc(-c4cncc(F)c4)cc3)C2=S)cnc1C#N] | 444.0 |

TABLE 1-continued

| Cmpd. | Name | Structure | LCMS* [M + 1]+ |
|---|---|---|---|
| 106 | 4-(7-(6-Cyano-5-methylpyridin-3-yl)-8-oxo-6-thioxo-5,7-diazaspiro[3.4]octan-5-yl)-N,2-dimethylbenzamide | 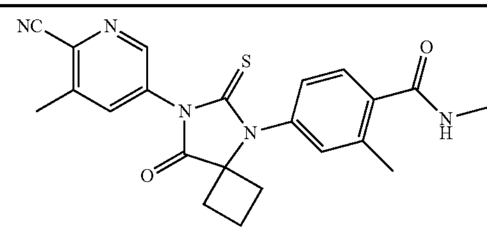 | 419.9 |
| 107 | 4-(7-(6-Cyano-5-methylpyridin-3-yl)-8-oxo-6-thioxo-5,7-diazaspiro[3.4]octan-5-yl)-2-methoxy-N-methylbenzamide | 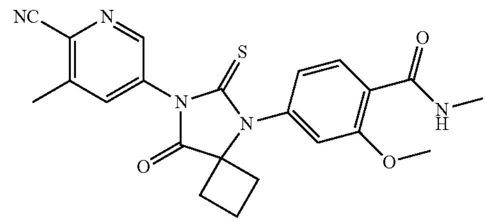 | 436.0 |
| 108 | 2-Chloro-4-(7-(6-cyano-5-methylpyridin-3-yl)-8-oxo-6-thioxo-5,7-diazaspiro[3.4]octan-5-yl)-N-methylbenzamide | 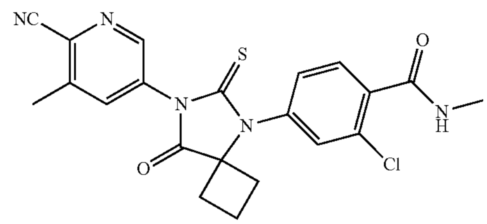 | 440.0 |
| 109 | 4-(7-(6-Cyano-5-methylpyridin-3-yl)-8-oxo-6-thioxo-5,7-diazaspiro[3.4]octan-5-yl)-N-methyl-2-(trifluoromethyl)benzamide | 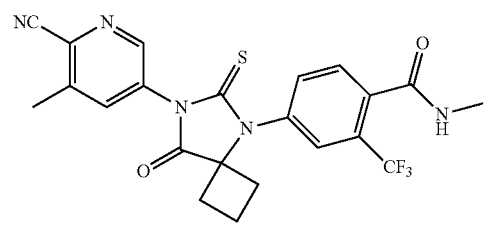 | 474.1 |
| 110 | 5-(5-(Naphthalen-1-yl)-8-oxo-6-thioxo-5,7-diazaspiro[3.4]octan-7-yl)-3-(trifluoromethyl)picolinonitrile | 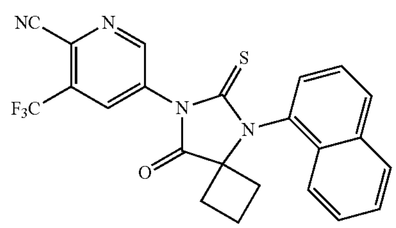 [SMILES: N#Cc1ncc(N2C(=O)C3(CCC3)N(c3cccc4ccccc34)C2=S)cc1C(F)(F)F] | 453.0 |
| 111 | 3-Methyl-5-(8-oxo-5-(1-oxoisoindolin-5-yl)-6-thioxo-5,7-diazaspiro[3.4]octan-7-yl)picolinonitrile | 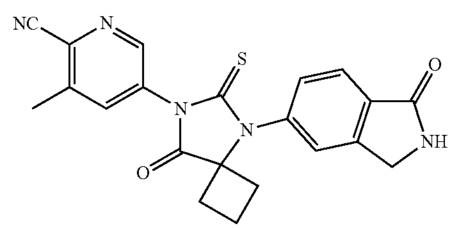 [SMILES: Cc1cc(N2C(=O)C3(CCC3)N(c3ccc4c(c3)CNC4=O)C2=S)cnc1C#N] | 404.1 |
| 112 | 3-Methyl-5-(8-oxo-5-(4-(tetrahydro-2H-pyran-4-yl)phenyl)-6-thioxo-5,7-diazaspiro[3.4]octan-7-yl)picolinonitrile | 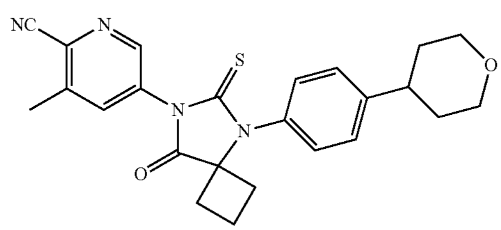 [SMILES: Cc1cc(N2C(=O)C3(CCC3)N(c3ccc(C4CCOCC4)cc3)C2=S)cnc1C#N] | 433.0 |

TABLE 1-continued

| Cmpd. | Name | Structure | LCMS* [M + 1]+ |
|---|---|---|---|
| 113 | 4-(7-(6-Cyano-5-(difluoromethyl)pyridin-3-yl)-8-oxo-6-thioxo-5,7-diazaspiro[3.4]octan-5-yl)-2-fluoro-N-methylbenzamide | 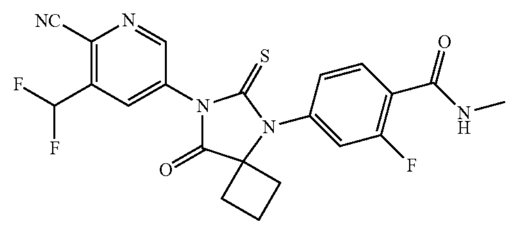 [SMILES: CNC(=O)c1ccc(N2C(=S)N(c3cnc(C#N)c(C(F)F)c3)C(=O)C23CCC3)cc1F] | 460.0 |
| 114 | 1-Methyl-4-(8-oxo-6-thioxo-5-(p-tolyl)-5,7-diazaspiro[3.4]octan-7-yl)-1H-pyrrole-2-carbonitrile | 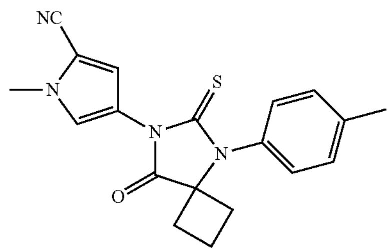 | 352.1 |
| 115 | 5-(8-Oxo-5-(4-(tetrahydro-2H-pyran-4-yl)phenyl)-6-thioxo-5,7-diazaspiro[3.4]octan-7-yl)-3-(trifluoromethyl)picolinonitrile | 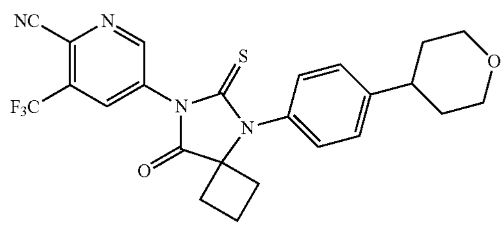 [SMILES: N#Cc1ncc(N2C(=O)C3(CCC3)N(c3ccc(C4CCOCC4)cc3)C2=S)cc1C(F)(F)F] | 487.1 |
| 116 | 5-(5-(4-(Furan-2-yl)phenyl)-8-oxo-6-thioxo-5,7-diazaspiro[3.4]octan-7-yl)-3-methylpicolinonitrile | 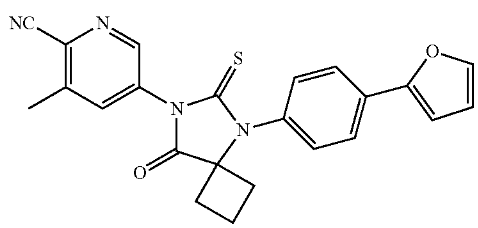 [SMILES: Cc1cc(N2C(=O)C3(CCC3)N(c3ccc(-c4ccco4)cc3)C2=S)cnc1C#N] | 415.1 |
| 117 | 5-(3-Fluoro-4-hydroxyphenyl)-6-thioxo-7-(3-(trifluoromethyl)-[1,2,4]triazolo[4,3-b]pyridazin-6-yl)-5,7-diazaspiro[3.4]octan-8-one | 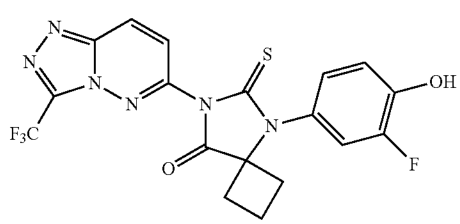 [SMILES: O=C1N(c2ccc3nnc(C(F)(F)F)n3n2)C(=S)N(c2ccc(O)c(F)c2)C12CCC2] | 453.5 |
| 118 | 5-(8-Oxo-5-(4-(piperazin-1-yl)phenyl)-6-thioxo-5,7-diazaspiro[3.4]octan-7-yl)-3-(trifluoromethyl)picolinonitrile | 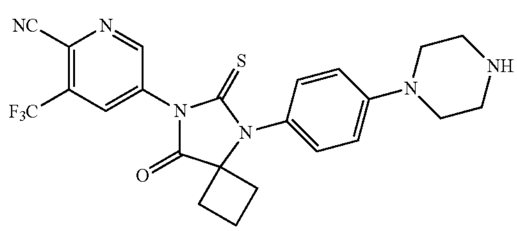 [SMILES: N#Cc1ncc(N2C(=O)C3(CCC3)N(c3ccc(N4CCNCC4)cc3)C2=S)cc1C(F)(F)F] | 487.1 |

TABLE 1-continued

| Cmpd. | Name | Structure | LCMS* [M + 1]+ |
|---|---|---|---|
| 119 | tert-Butyl 4-(4-(7-(6-cyano-5-(trifluoromethyl)pyridin-3-yl)-8-oxo-6-thioxo-5,7-diazaspiro[3.4]octan-5-yl)phenyl)piperazine-1-carboxylate | 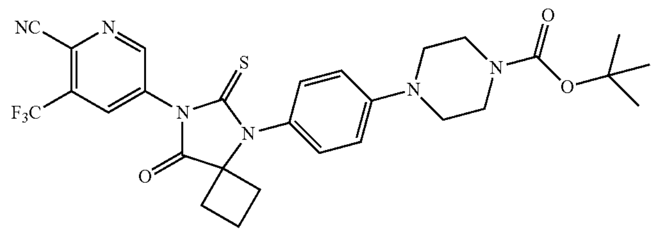 [SMILES: CC(C)(C)OC(=O)N1CCN(c2ccc(N3C(=S)N(c4cnc(C#N)c(C(F)(F)F)c4)C(=O)C34CCC4)cc2)CC1] | 587.2 |
| 120 | 4-(7-(6-Cyano-5-(trifluoromethyl)pyridin-3-yl)-8-oxo-6-thioxo-5,7-diazaspiro[3.4]octan-5-yl)-N-methylbenzenesulfonamide | 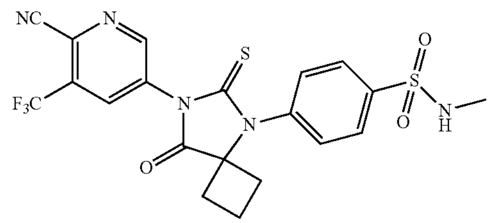 [SMILES: CNS(=O)(=O)c1ccc(N2C(=S)N(c3cnc(C#N)c(C(F)(F)F)c3)C(=O)C23CCC3)cc1] | 518.0 |
| 121 | 4-(7-(6-Cyano-5-(trifluoromethyl)pyridin-3-yl)-8-oxo-6-thioxo-5,7-diazaspiro[3.4]octan-5-yl)-N,N-dimethylbenzenesulfonamide | 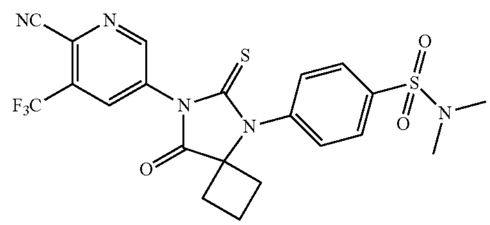 [SMILES: CN(C)S(=O)(=O)c1ccc(N2C(=S)N(c3cnc(C#N)c(C(F)(F)F)c3)C(=O)C23CCC3)cc1] | 532.0 |
| 122 | Methyl 4-(4-(7-(6-cyano-5-(trifluoromethyl)pyridin-3-yl)-8-oxo-6-thioxo-5,7-diazaspiro[3.4]octan-5-yl)phenyl)butanoate | 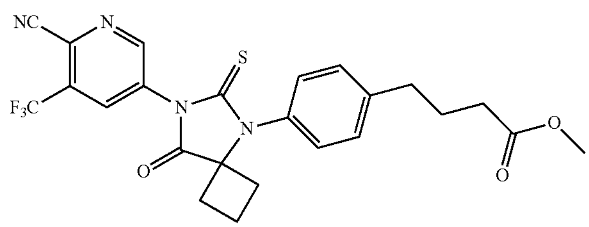 [SMILES: COC(=O)CCCc1ccc(N2C(=S)N(c3cnc(C#N)c(C(F)(F)F)c3)C(=O)C23CCC3)cc1] | 503.0 |
| 123 | 5-(5-(4-Fluoro-3-hydroxyphenyl)-8-oxo-6-thioxo-5,7-diazaspiro[3.4]octan-7-yl)-3-(trifluoromethyl)picolinonitrile | 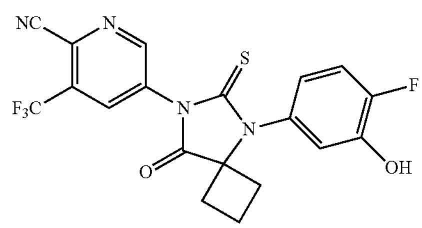 [SMILES: N#Cc1ncc(N2C(=O)C3(CCC3)N(c3ccc(F)c(O)c3)C2=S)cc1C(F)(F)F] | 437.5 |
| 124 | 5-(5-(4-(3-(4-Methylpiperazin-1-yl)propyl)phenyl)-8-oxo-6-thioxo-5,7-diazaspiro[3.4]octan-7-yl)-3-(trifluoromethyl)picolinonitrile | 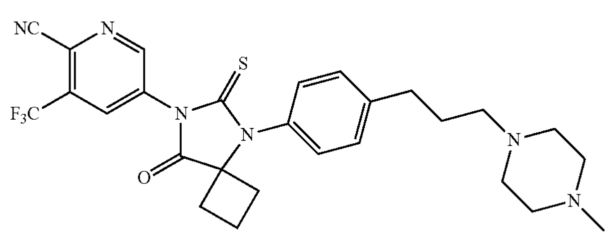 [SMILES: CN1CCN(CCCc2ccc(N3C(=S)N(c4cnc(C#N)c(C(F)(F)F)c4)C(=O)C34CCC4)cc2)CC1] | 543.1 |

TABLE 1-continued

| Cmpd. | Name | Structure | LCMS* [M + 1]+ |
|---|---|---|---|
| 125 | 5-(5-(Benzo[d]oxazol-6-yl)-8-oxo-6-thioxo-5,7-diazaspiro[3.4]octan-7-yl)-3-(trifluoromethyl)picolinonitrile | 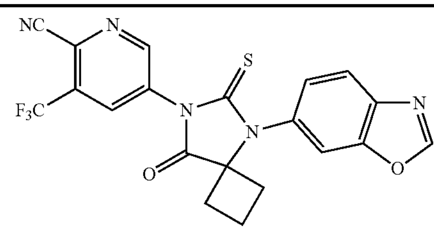 | 444.0 |
| 126 | 5-(5-(3-Fluoro-4-(2-(1-methyl-1H-pyrazol-5-yl)ethoxy)phenyl)-8-oxo-6-thioxo-5,7-diazaspiro[3.4]octan-7-yl)-3-(trifluoromethyl)picolinonitrile | 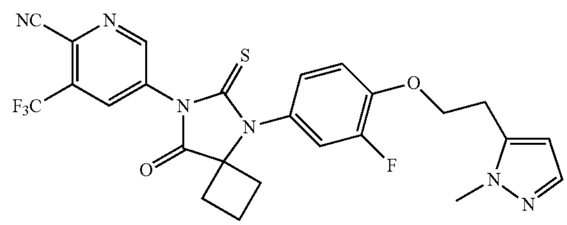 [SMILES: Cn1nccc1CCOc1ccc(N2C(=S)N(c3cnc(C#N)c(C(F)(F)F)c3)C(=O)C23CCC3)cc1F] | 545.5 |
| 127 | 5-(5-(3-Fluoro-4-(2-(pyrrolidin-1-yl)ethoxy)phenyl)-8-oxo-6-thioxo-5,7-diazaspiro[3.4]octan-7-yl)-3-(trifluoromethyl)picolinonitrile | 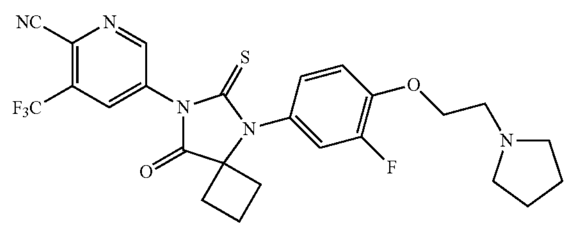 [SMILES: N#Cc1ncc(N2C(=O)C3(CCC3)N(c3ccc(OCCN4CCCC4)c(F)c3)C2=S)cc1C(F)(F)F] | 534.9 |
| 128 | 5-(5-(4-(Benzyloxy)-3-fluorophenyl)-8-oxo-6-thioxo-5,7-diazaspiro[3.4]octan-7-yl)-3-(trifluoromethyl)picolinonitrile | 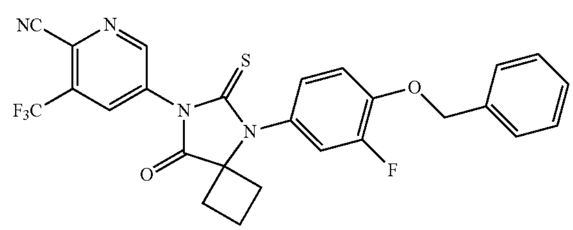 [SMILES: N#Cc1ncc(N2C(=O)C3(CCC3)N(c3ccc(OCc4ccccc4)c(F)c3)C2=S)cc1C(F)(F)F] | 527.6 |
| 129 | 5-(5-(4-((1-Methylpiperidin-4-yl)oxy)phenyl)-8-oxo-6-thioxo-5,7-diazaspiro[3.4]octan-7-yl)-3-(trifluoromethyl)picolinonitrile | 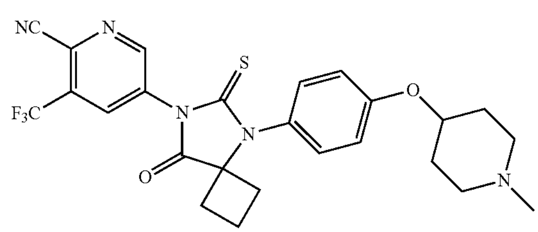 | 516.0 |
| 130 | 5-(5-(3-Fluoro-4-(2-(pyridin-2-yl)ethoxy)phenyl)-8-oxo-6-thioxo-5,7-diazaspiro[3.4]octan-7-yl)-3-(trifluoromethyl)picolinonitrile | 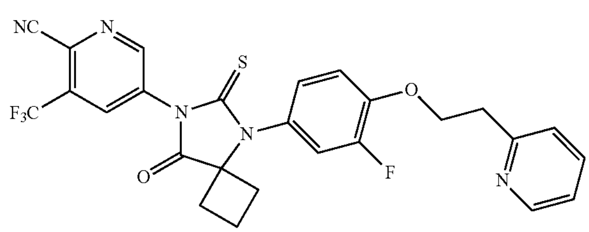 | 542.6 |
| 131 | 5-(5-(3-Fluoro-4-(2-methoxyethoxy)phenyl)-8-oxo-6-thioxo-5,7-diazaspiro[3.4]octan-7-yl)-3-(trifluoromethyl)picolinonitrile | 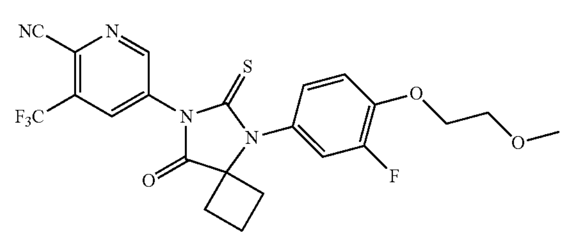 [SMILES: COCCOc1ccc(N2C(=S)N(c3cnc(C#N)c(C(F)(F)F)c3)C(=O)C23CCC3)cc1F] | 495.5 |

TABLE 1-continued

| Cmpd. | Name | Structure | LCMS* [M + 1]+ |
|---|---|---|---|
| 132 | Ethyl 2-(4-(7-(6-cyano-5-(trifluoromethyl)pyridin-3-yl)-8-oxo-6-thioxo-5,7-diazaspiro[3.4]octan-5-yl)-2-fluorophenoxy)acetate | 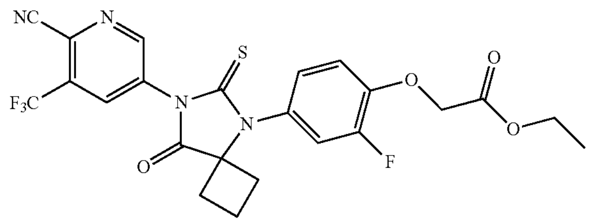 [SMILES: CCOC(=O)COc1ccc(N2C(=S)N(c3cnc(C#N)c(C(F)(F)F)c3)C(=O)C23CCC3)cc1F] | 523.5 |
| 133 | 5-(5-(3-Fluoro-4-(4-methoxybutoxy)phenyl)-8-oxo-6-thioxo-5,7-diazaspiro[3.4]octan-7-yl)-3-(trifluoromethyl)picolinonitrile | 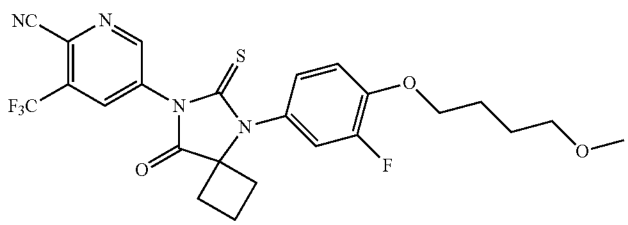 [SMILES: COCCCCOc1ccc(N2C(=S)N(c3cnc(C#N)c(C(F)(F)F)c3)C(=O)C23CCC3)cc1F] | 523.6 |
| 134 | 5-(5-(3-Fluoro-4-((4,4,5,5,5-pentafluoropentyl)oxy)phenyl)-8-oxo-6-thioxo-5,7-diazaspiro[3.4]octan-7-yl)-3-(trifluoromethyl)picolinonitrile | 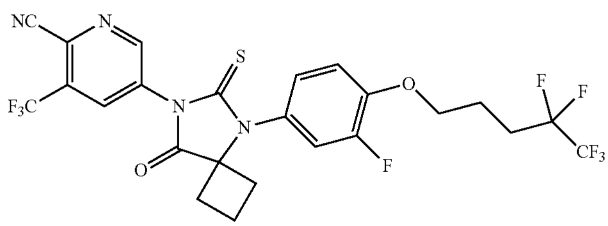 [SMILES: N#Cc1ncc(N2C(=O)C3(CCC3)N(c3ccc(OCCCC(F)(F)C(F)(F)F)c(F)c3)C2=S)cc1C(F)(F)F] | 597.7 |
| 135 | 5-(5-(4-(3-(Benzyloxy)propoxy)-3-fluorophenyl)-8-oxo-6-thioxo-5,7-diazaspiro[3.4]octan-7-yl)-3-(trifluoromethyl)picolinonitrile | 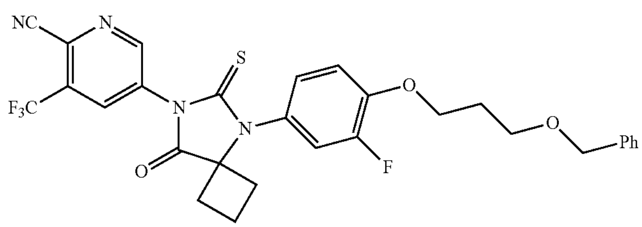 [SMILES: N#Cc1ncc(N2C(=O)C3(CCC3)N(c3ccc(OCCCOCc4ccccc4)c(F)c3)C2=S)cc1C(F)(F)F] | 585.5 |
| 136 | 5-(5-(4-(4-(Benzyloxy)butoxy)-3-fluorophenyl)-8-oxo-6-thioxo-5,7-diazaspiro[3.4]octan-7-yl)-3-(trifluoromethyl)picolinonitrile | 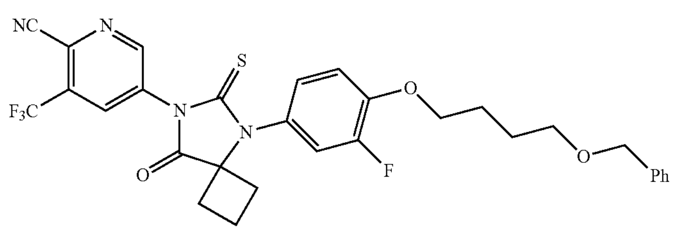 [SMILES: N#Cc1ncc(N2C(=O)C3(CCC3)N(c3ccc(OCCCCOCc4ccccc4)c(F)c3)C2=S)cc1C(F)(F)F] | 599.8 |
| 137 | 5-(5-(3-Fluoro-4-(2-methylphenethoxy)phenyl)-8-oxo-6-thioxo-5,7-diazaspiro[3.4]octan-7-yl)-3-(trifluoromethyl)picolinonitrile | 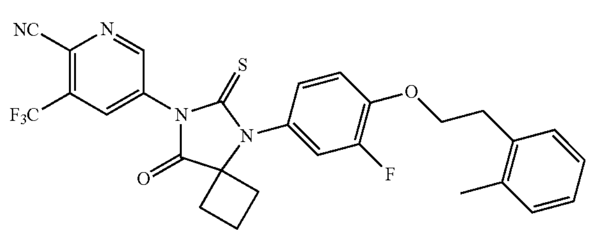 [SMILES: Cc1ccccc1CCOc1ccc(N2C(=S)N(c3cnc(C#N)c(C(F)(F)F)c3)C(=O)C23CCC3)cc1F] | 555.8 |

TABLE 1-continued

| Cmpd. | Name | Structure | LCMS* [M + 1]+ |
|---|---|---|---|
| 138 | 5-(5-(3-Fluoro-4-(3-phenylpropoxy)phenyl)-8-oxo-6-thioxo-5,7-diazaspiro[3.4]octan-7-yl)-3-(trifluoromethyl)picolinonitrile | 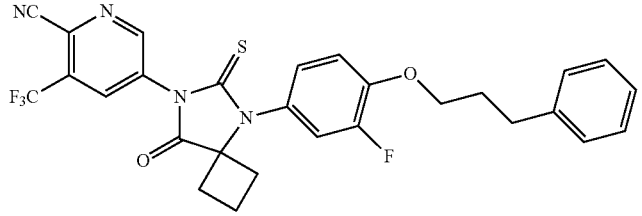 [SMILES: N#Cc1ncc(N2C(=O)C3(CCC3)N(c3ccc(OCCCc4ccccc4)c(F)c3)C2=S)cc1C(F)(F)F] | 555.8 |
| 139 | 5-(5-(3-Fluoro-4-(3,3,4,4,4-pentafluorobutoxy)phenyl)-8-oxo-6-thioxo-5,7-diazaspiro[3.4]octan-7-yl)-3-(trifluoromethyl)picolinonitrile | 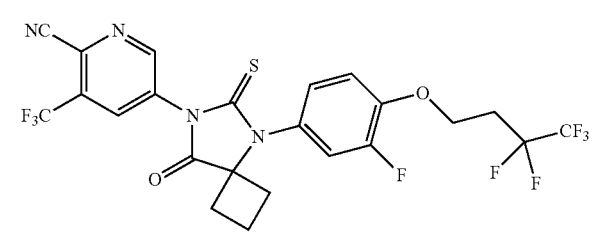 [SMILES: N#Cc1ncc(N2C(=O)C3(CCC3)N(c3ccc(OCCC(F)(F)C(F)(F)F)c(F)c3)C2=S)cc1C(F)(F)F] | 583.4 |
| 140 | 5-(5-(3-Fluoro-4-(2-(naphthalen-1-yl)ethoxy)phenyl)-8-oxo-6-thioxo-5,7-diazaspiro[3.4]octan-7-yl)-3-(trifluoromethyl)picolinonitrile | 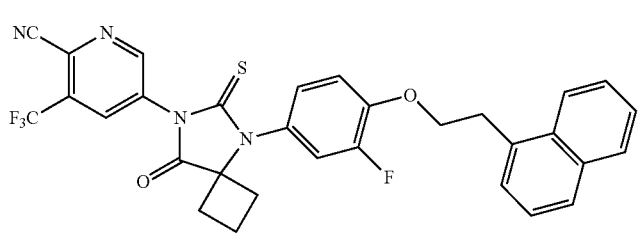 [SMILES: N#Cc1ncc(N2C(=O)C3(CCC3)N(c3ccc(OCCc4cccc5ccccc45)c(F)c3)C2=S)cc1C(F)(F)F] | 591.2 |
| 141 | 5-(5-(3-Fluoro-4-(2-(naphthalen-2-yl)ethoxy)phenyl)-8-oxo-6-thioxo-5,7-diazaspiro[3.4]octan-7-yl)-3-(trifluoromethyl)picolinonitrile | 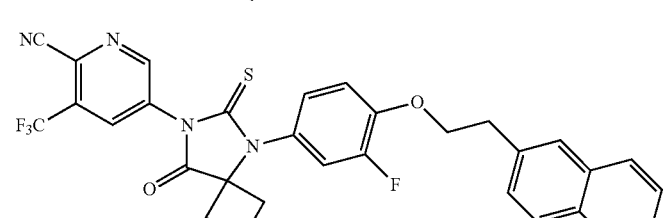 | 591.2 |
| 142 | 5-(5-(3-Fluoro-4-(2-(pyridin-4-yl)ethoxy)phenyl)-8-oxo-6-thioxo-5,7-diazaspiro[3.4]octan-7-yl)-3-(trifluoromethyl)picolinonitrile | 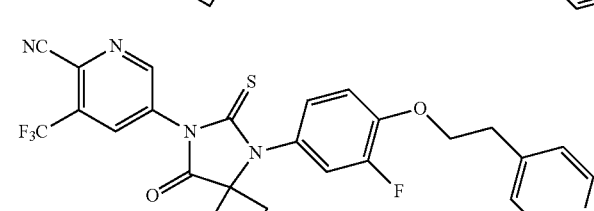 | 542.7 |
| 143 | 5-(5-(3-Fluoro-4-(2-morpholinoethoxy)phenyl)-8-oxo-6-thioxo-5,7-diazaspiro[3.4]octan-7-yl)-3-(trifluoromethyl)picolinonitrile | 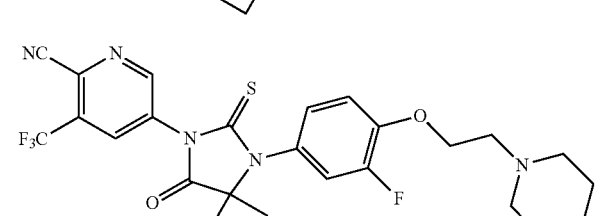 | 550.6 |
| 144 | 5-(5-(3-Fluoro-4-(2-(pyridin-3-yl)ethoxy)phenyl)-8-oxo-6-thioxo-5,7-diazaspiro[3.4]octan-7-yl)-3-(trifluoromethyl)picolinonitrile | 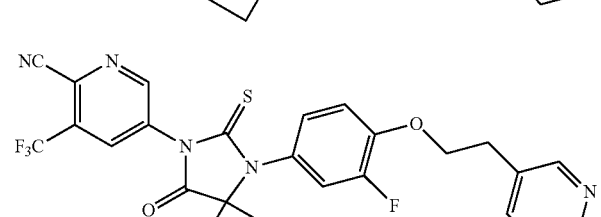 | 542.5 |

TABLE 1-continued

| Cmpd. | Name | Structure | LCMS* [M + 1]+ |
|---|---|---|---|
| 145 | 5-(5-(3-Fluoro-4-(3-(pyridin-3-yl)propoxy)phenyl)-8-oxo-6-thioxo-5,7-diazaspiro[3.4]octan-7-yl)-3-(trifluoromethyl)picolinonitrile | 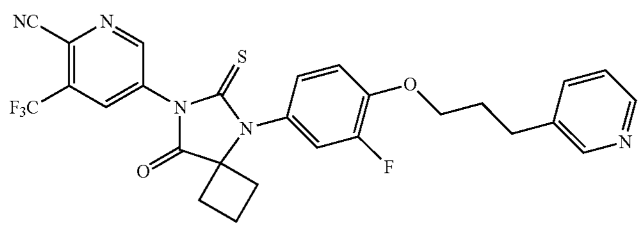 | 556.5 |
| 146 | 5-(5-(4-(2-(1H-Pyrrol-1-yl)ethoxy)-3-fluorophenyl)-8-oxo-6-thioxo-5,7-diazaspiro[3.4]octan-7-yl)-3-(trifluoromethyl)picolinonitrile | 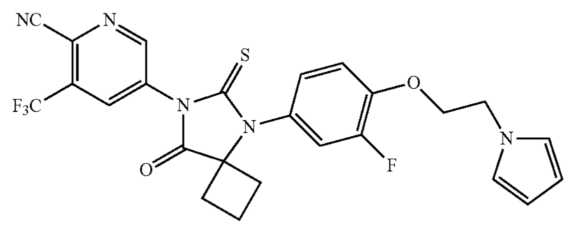 [SMILES: N#Cc1ncc(N2C(=O)C3(CCC3)N(c3ccc(OCCn4cccc4)c(F)c3)C2=S)cc1C(F)(F)F] | 530.5 |
| 147 | 5-(5-(3-Fluoro-4-(pyridin-2-ylmethoxy)phenyl)-8-oxo-6-thioxo-5,7-diazaspiro[3.4]octan-7-yl)-3-(trifluoromethyl)picolinonitrile | 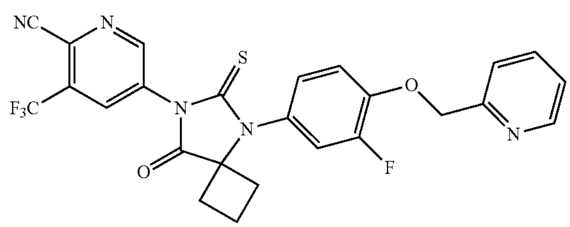 | 528.8 |
| 148 | 5-(5-(3-Fluoro-4-(pyridin-3-ylmethoxy)phenyl)-8-oxo-6-thioxo-5,7-diazaspiro[3.4]octan-7-yl)-3-(trifluoromethyl)picolinonitrile | 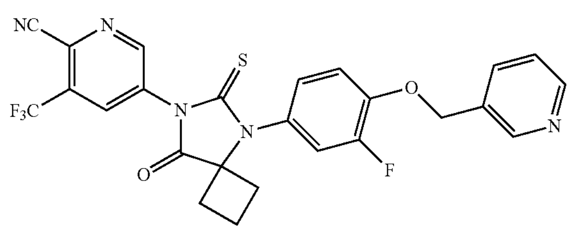 | 528.5 |
| 149 | 5-(5-(3-Fluoro-4-(2-(4-methylpiperazin-1-yl)ethoxy)phenyl)-8-oxo-6-thioxo-5,7-diazaspiro[3.4]octan-7-yl)-3-(trifluoromethyl)picolinonitrile | 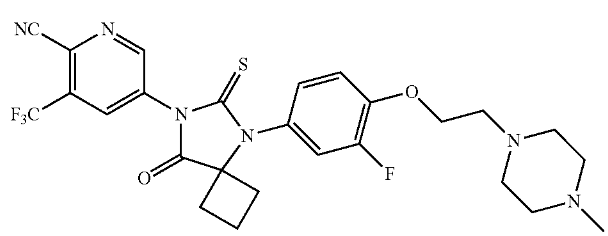 [SMILES: CN1CCN(CCOc2ccc(N3C(=S)N(c4cnc(C#N)c(C(F)(F)F)c4)C(=O)C34CCC4)cc2F)CC1] | 563.8 |
| 150 | 5-(5-(3-Fluoro-4-(3-morpholinopropoxy)phenyl)-8-oxo-6-thioxo-5,7-diazaspiro[3.4]octan-7-yl)-3-(trifluoromethyl)picolinonitrile | 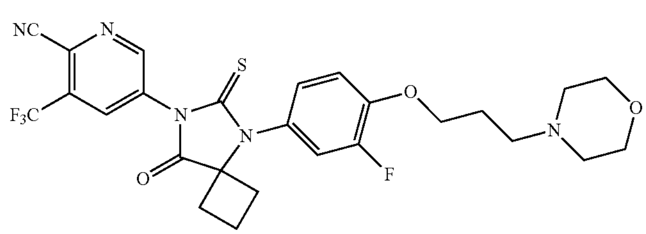 [SMILES: N#Cc1ncc(N2C(=O)C3(CCC3)N(c3ccc(OCCCN4CCOCC4)c(F)c3)C2=S)cc1C(F)(F)F] | 564.7 |

TABLE 1-continued

| Cmpd. | Name | Structure | LCMS* [M + 1]+ |
|---|---|---|---|
| 151 | 5-(5-(3-Fluoro-4-(4-((4,4,5,5,5-pentafluoropentyl)thio)butoxy)phenyl)-8-oxo-6-thioxo-5,7-diazaspiro[3.4]octan-7-yl)-3-(trifluoromethyl)picolinonitrile | 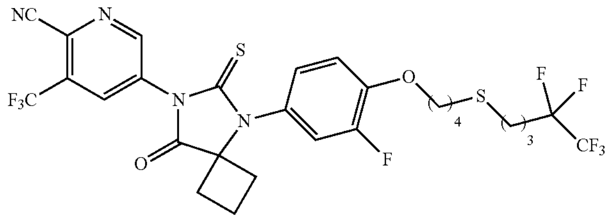 | 685.5 |
| 152 | 5-(5-(3-Fluoro-4-(4-((4,4,5,5,5-pentafluoropentyl)sulfinyl)butoxy)phenyl)-8-oxo-6-thioxo-5,7-diazaspiro[3.4]octan-7-yl)-3-(trifluoromethyl)picolinonitrile | 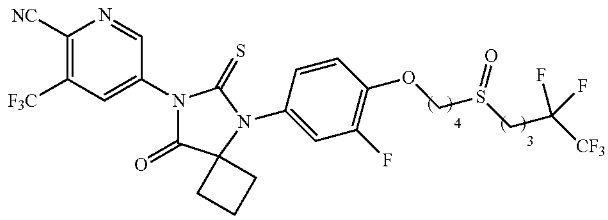 | 701.5 |
| 153 | 5-(5-(3-Fluoro-4-(3-((4,4,5,5,5-pentafluoropentyl)thio)propoxy)phenyl)-8-oxo-6-thioxo-5,7-diazaspiro[3.4]octan-7-yl)-3-(trifluoromethyl)picolinonitrile | 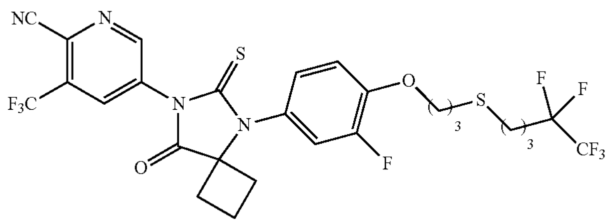 | 671.8 |
| 154 | 5-(5-(3-Fluoro-4-(3-((4,4,5,5,5-pentafluoropentyl)sulfinyl)propoxy)phenyl)-8-oxo-6-thioxo-5,7-diazaspiro[3.4]octan-7-yl)-3-(trifluoromethyl)picolinonitrile | 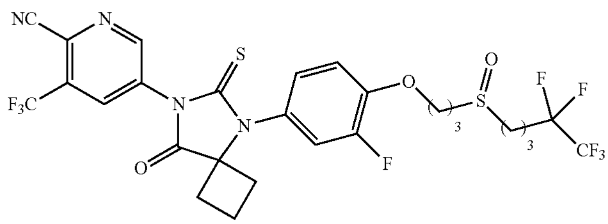 | 687.5 |
| 155 | 5-(4-(2-(Pyridin-2-yl)ethoxy)phenyl)-6-thioxo-7-(3-(trifluoromethyl)-[1,2,4]triazolo[4,3-b]pyridazin-6-yl)-5,7-diazaspiro[3.4]octan-8-one | 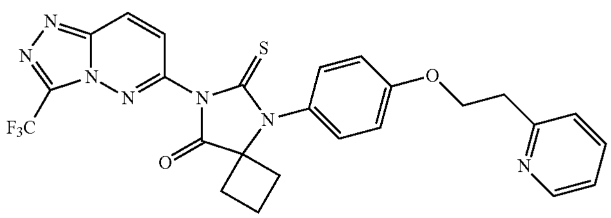 [SMILES: O=C1N(c2ccc3nnc(C(F)(F)F)n3n2)C(=S)N(c2ccc(OCCc3ccccn3)cc2)C12CCC2] | 540.6 |
| 156 | 5-(5-(3-Fluoro-4-(pyridin-4-ylmethoxy)phenyl)-8-oxo-6-thioxo-5,7-diazaspiro[3.4]octan-7-yl)-3-(trifluoromethyl)picolinonitrile | 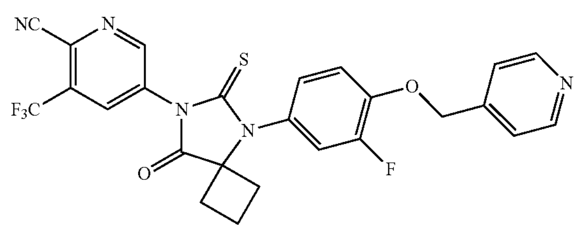 [SMILES: N#Cc1ncc(N2C(=O)C3(CCC3)N(c3ccc(OCc4ccncc4)c(F)c3)C2=S)cc1C(F)(F)F] | 528.5 |
| 157 | 5-(5-(3-Fluoro-4-(3-(4-methylpiperazin-1-yl)propoxy)phenyl)-8-oxo-6-thioxo-5,7-diazaspiro[3.4]octan-7-yl)-3-(trifluoromethyl)picolinonitrile | 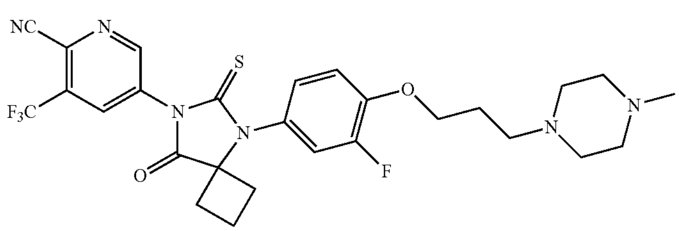 [SMILES: CN1CCN(CCCOc2ccc(N3C(=S)N(c4cnc(C#N)c(C(F)(F)F)c4)C(=O)C34CCC4)cc2F)CC1] | 577.5 |

TABLE 1-continued

| Cmpd. | Name | Structure | LCMS* [M + 1]+ |
|---|---|---|---|
| 158 | 5-(5-(4-Fluoro-3-(2-(pyridin-2-yl)ethoxy)phenyl)-8-oxo-6-thioxo-5,7-diazaspiro[3.4]octan-7-yl)-3-(trifluoromethyl)picolinonitrile | 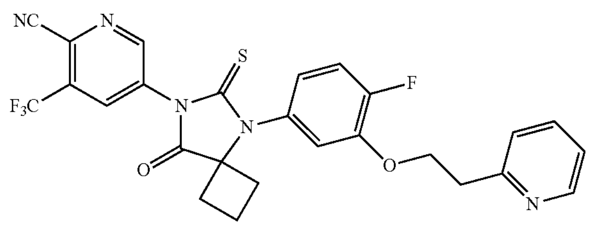 | 542.1 |
| 159 | 5-(5-(4-Fluoro-3-(2-(pyridin-3-yl)ethoxy)phenyl)-8-oxo-6-thioxo-5,7-diazaspiro[3.4]octan-7-yl)-3-(trifluoromethyl)picolinonitrile | 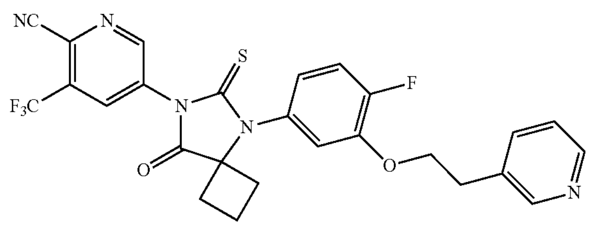 [SMILES: N#Cc1ncc(N2C(=O)C3(CCC3)N(c3ccc(F)c(OCCc4cccnc4)c3)C2=S)cc1C(F)(F)F] | 542.0 |
| 160 | 5-(5-(4-Fluoro-3-(2-(pyridin-4-yl)ethoxy)phenyl)-8-oxo-6-thioxo-5,7-diazaspiro[3.4]octan-7-yl)-3-(trifluoromethyl)picolinonitrile | 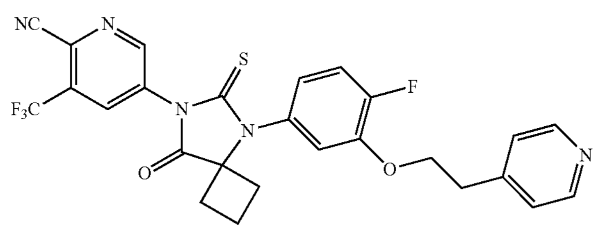 [SMILES: N#Cc1ncc(N2C(=O)C3(CCC3)N(c3ccc(F)c(OCCc4ccncc4)c3)C2=S)cc1C(F)(F)F] | 542.5 |
| 161 | 5-(5-(3-(Benzyloxy)-4-fluorophenyl)-8-oxo-6-thioxo-5,7-diazaspiro[3.4]octan-7-yl)-3-(trifluoromethyl)picolinonitrile | 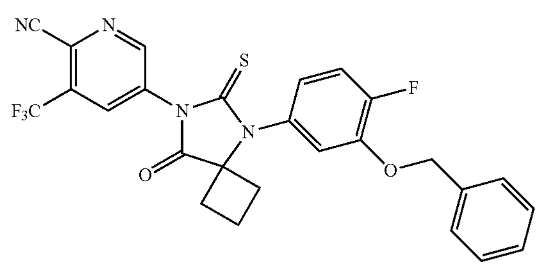 [SMILES: N#Cc1ncc(N2C(=O)C3(CCC3)N(c3ccc(F)c(OCc4ccccc4)c3)C2=S)cc1C(F)(F)F] | 527.5 |
| 162 | 5-(5-(4-Fluoro-3-phenethoxyphenyl)-8-oxo-6-thioxo-5,7-diazaspiro[3.4]octan-7-yl)-3-(trifluoromethyl)picolinonitrile | 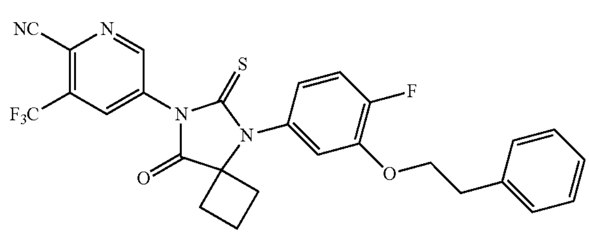 [SMILES: N#Cc1ncc(N2C(=O)C3(CCC3)N(c3ccc(F)c(OCCc4ccccc4)c3)C2=S)cc1C(F)(F)F] | 541.5 |
| 163 | 5-(5-(4-Fluoro-3-(3-phenylpropoxy)phenyl)-8-oxo-6-thioxo-5,7-diazaspiro[3.4]octan-7-yl)-3-(trifluoromethyl)picolinonitrile | 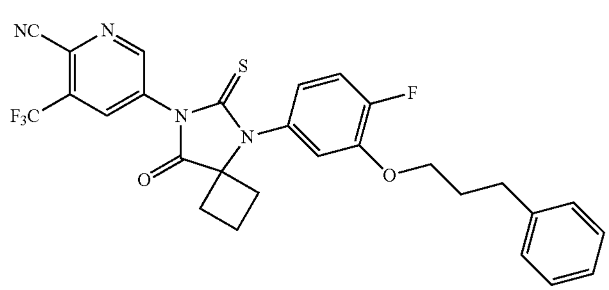 [SMILES: N#Cc1ncc(N2C(=O)C3(CCC3)N(c3ccc(F)c(OCCCc4ccccc4)c3)C2=S)cc1C(F)(F)F] | 555.5 |

TABLE 1-continued

| Cmpd. | Name | Structure | LCMS* [M + 1]+ |
|---|---|---|---|
| 164 | 5-(5-(4-Fluoro-3-(2-morpholinoethoxy)phenyl)-8-oxo-6-thioxo-5,7-diazaspiro[3.4]octan-7-yl)-3-(trifluoromethyl)picolinonitrile | 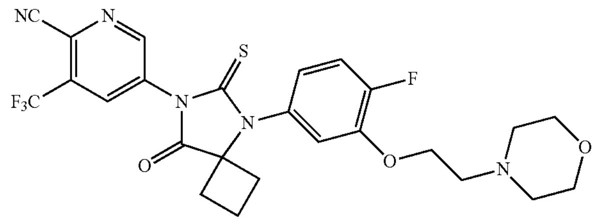 [SMILES: N#Cc1ncc(N2C(=O)C3(CCC3)N(c3ccc(F)c(OCCN4CCOCC4)c3)C2=S)cc1C(F)(F)F] | 550.1 |
| 165 | 5-(5-(4-Fluoro-3-(3-morpholinopropoxy)phenyl)-8-oxo-6-thioxo-5,7-diazaspiro[3.4]octan-7-yl)-3-(trifluoromethyl)picolinonitrile | 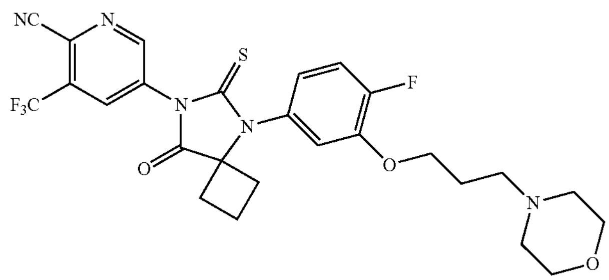 [SMILES: N#Cc1ncc(N2C(=O)C3(CCC3)N(c3ccc(F)c(OCCCN4CCOCC4)c3)C2=S)cc1C(F)(F)F] | 564.7 |
| 166 | 5-(5-(4-Fluoro-3-(2-(4-methylpiperazin-1-yl)ethoxy)phenyl)-8-oxo-6-thioxo-5,7-diazaspiro[3.4]octan-7-yl)-3-(trifluoromethyl)picolinonitrile | 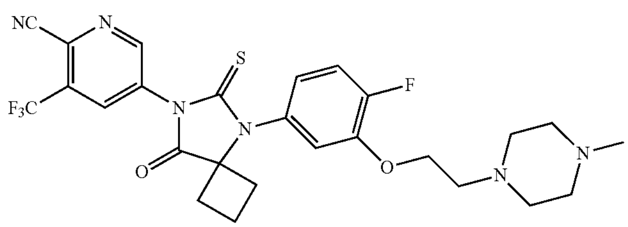 [SMILES: CN1CCN(CCOc2cc(N3C(=S)N(c4cnc(C#N)c(C(F)(F)F)c4)C(=O)C34CCC4)ccc2F)CC1] | 563.5 |
| 167 | 5-(5-(4-Fluoro-3-(3-(4-methylpiperazin-1-yl)propoxy)phenyl)-8-oxo-6-thioxo-5,7-diazaspiro[3.4]octan-7-yl)-3-(trifluoromethyl)picolinonitrile | 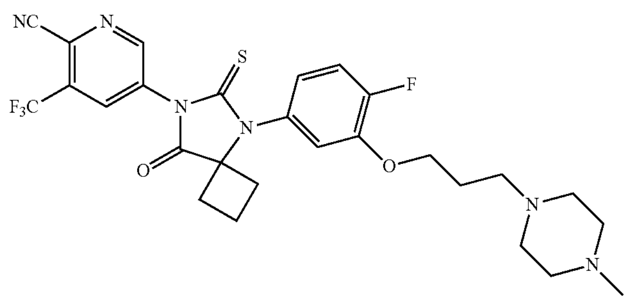 [SMILES: CN1CCN(CCCOc2cc(N3C(=S)N(c4cnc(C#N)c(C(F)(F)F)c4)C(=O)C34CCC4)ccc2F)CC1] | 577.6 |
| 168 | 5-(5-(3-Fluoro-4-(2-methoxyethoxy)phenyl)-8-oxo-6-thioxo-5,7-diazaspiro[3.4]octan-7-yl)-3-methylpicolinonitrile | 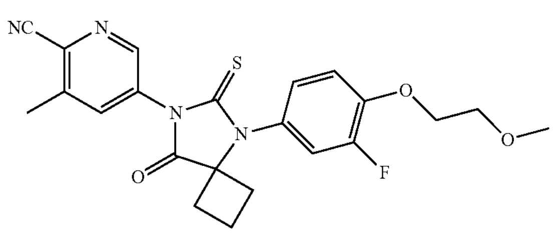 | 441.6 |
| 169 | 5-(5-(3-Fluoro-4-(2-(pyridin-2-yl)ethoxy)phenyl)-8-oxo-6-thioxo-5,7-diazaspiro[3.4]octan-7-yl)-3-methylpicolinonitrile | 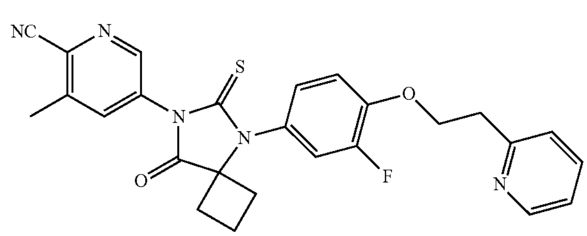 [SMILES: Cc1cc(N2C(=O)C3(CCC3)N(c3ccc(OCCc4ccccn4)c(F)c3)C2=S)cnc1C#N] | 488.7 |

TABLE 1-continued

| Cmpd. | Name | Structure | LCMS* [M + 1]+ |
|---|---|---|---|
| 170 | 5-(5-(3-Fluoro-4-(2-(4-methylpiperazin-1-yl)ethoxy)phenyl)-8-oxo-6-thioxo-5,7-diazaspiro[3.4]octan-7-yl)-3-methylpicolinonitrile | 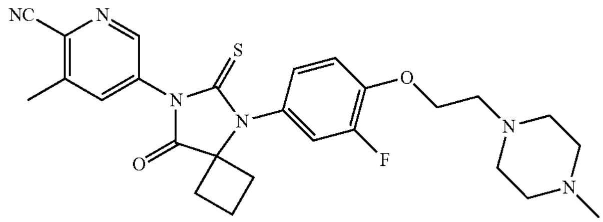 | 509.8 |
| 171 | 5-(5-(3-Fluoro-4-(2-methoxyethoxy)phenyl)-8-oxo-6-thioxo-5,7-diazaspiro[3.4]octan-7-yl)quinoline-8-carbonitrile | 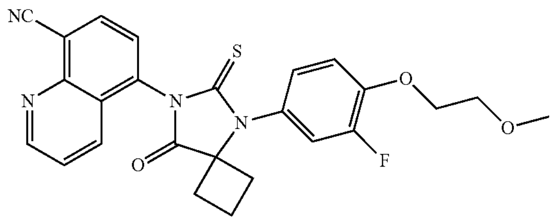 [SMILES: COCCOc1ccc(N2C(=S)N(c3ccc(C#N)c4ncccc34)C(=O)C23CCC3)cc1F] | 477.6 |
| 172 | 5-(5-(3-Fluoro-4-(2-(pyridin-2-yl)ethoxy)phenyl)-8-oxo-6-thioxo-5,7-diazaspiro[3.4]octan-7-yl)quinoline-8-carbonitrile | 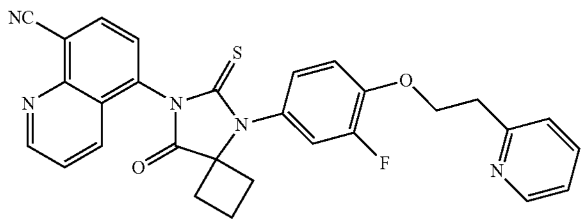 [SMILES: N#Cc1ccc(N2C(=O)C3(CCC3)N(c3ccc(OCCc4ccccn4)c(F)c3)C2=S)c2cccnc12] | 524.6 |
| 173 | 5-(5-(3-Fluoro-4-(2-(4-methylpiperazin-1-yl)ethoxy)phenyl)-8-oxo-6-thioxo-5,7-diazaspiro[3.4]octan-7-yl)quinoline-8-carbonitrile | 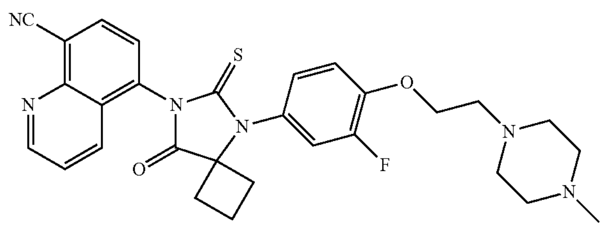 [SMILES: CN1CCN(CCOc2ccc(N3C(=S)N(c4ccc(C#N)c5ncccc45)C(=O)C34CCC4)cc2F)CC1] | 545.6 |
| 174 | 5-(5-(3-Fluoro-4-(2-(piperazin-1-yl)ethoxy)phenyl)-8-oxo-6-thioxo-5,7-diazaspiro[3.4]octan-7-yl)-3-(trifluoromethyl)picolinonitrile | 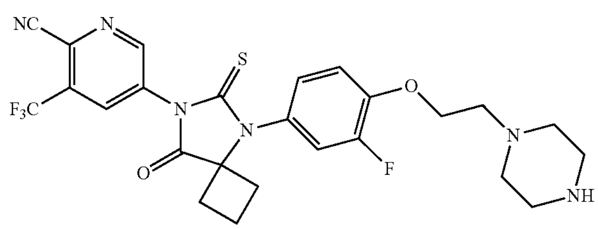 [SMILES: N#Cc1ncc(N2C(=O)C3(CCC3)N(c3ccc(OCCN4CCNCC4)c(F)c3)C2=S)cc1C(F)(F)F] | 549.9 |
| 175 | 5-(5-(3-Fluoro-4-(2-thiomorpholinoethoxy)phenyl)-8-oxo-6-thioxo-5,7-diazaspiro[3.4]octan-7-yl)-3-(trifluoromethyl)picolinonitrile | 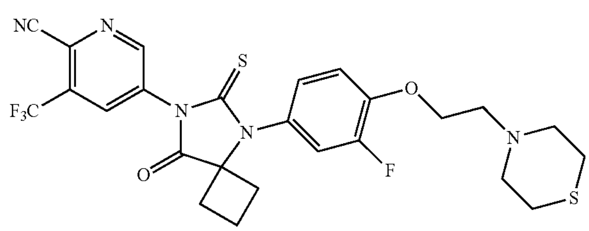 [SMILES: N#Cc1ncc(N2C(=O)C3(CCC3)N(c3ccc(OCCN4CCSCC4)c(F)c3)C2=S)cc1C(F)(F)F] | 566.8 |
| 176 | 5-(5-(3-Fluoro-4-(2-(pyrazin-2-yl)ethoxy)phenyl)-8-oxo-6-thioxo-5,7-diazaspiro[3.4]octan-7-yl)-3-(trifluoromethyl)picolinonitrile | 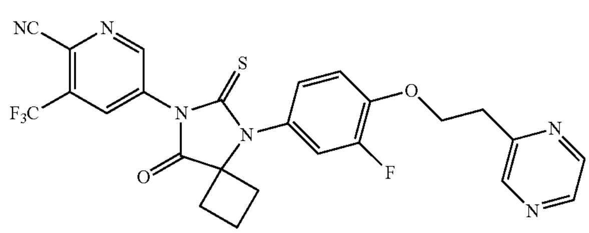 [SMILES: N#Cc1ncc(N2C(=O)C3(CCC3)N(c3ccc(OCCc4cnccn4)c(F)c3)C2=S)cc1C(F)(F)F] | 543.8 |

TABLE 1-continued

| Cmpd. | Name | Structure | LCMS* [M + 1]+ |
|---|---|---|---|
| 177 | 5-(5-(3-Fluoro-4-(2-(piperidin-1-yl)ethoxy)phenyl)-8-oxo-6-thioxo-5,7-diazaspiro[3.4]octan-7-yl)-3-(trifluoromethyl)picolinonitrile | 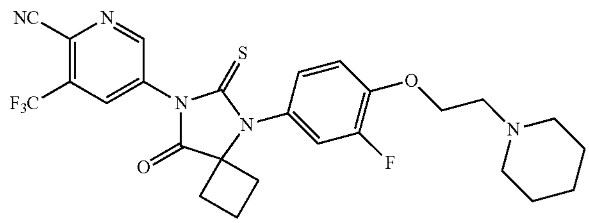 [SMILES: N#Cc1ncc(N2C(=O)C3(CCC3)N(c3ccc(OCCN4CCCCC4)c(F)c3)C2=S)cc1C(F)(F)F] | 548.8 |
| 178 | 5-(5-(4-(2-(4-Methylpiperazin-1-yl)ethoxy)phenyl)-8-oxo-6-thioxo-5,7-diazaspiro[3.4]octan-7-yl)-3-(trifluoromethyl)picolinonitrile | 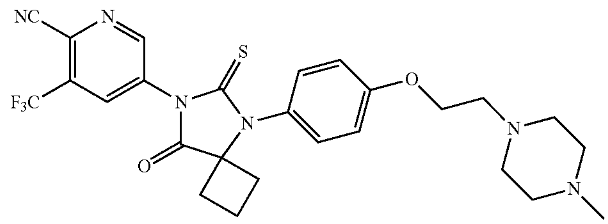 [SMILES: CN1CCN(CCOc2ccc(N3C(=S)N(c4cnc(C#N)c(C(F)(F)F)c4)C(=O)C34CCC4)cc2)CC1] | 545.8 |
| 179 | 5-(5-(4-(2-Cyclohexylethoxy)-3-fluorophenyl)-8-oxo-6-thioxo-5,7-diazaspiro[3.4]octan-7-yl)-3-(trifluoromethyl)picolinonitrile | 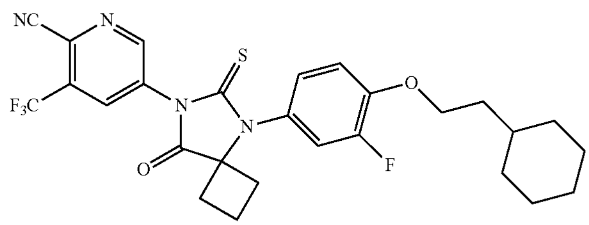 | 547.9 |
| 180 | 5-(5-(3-Fluoro-4-(2-(tetrahydro-2H-pyran-4-yl)ethoxy)phenyl)-8-oxo-6-thioxo-5,7-diazaspiro[3.4]octan-7-yl)-3-(trifluoromethyl)picolinonitrile | 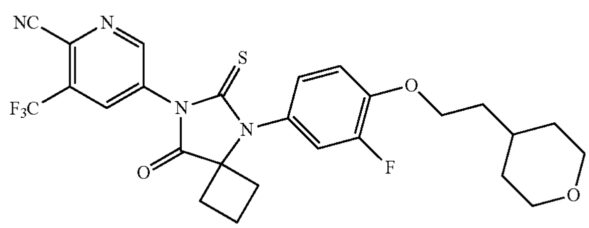 [SMILES: N#Cc1ncc(N2C(=O)C3(CCC3)N(c3ccc(OCCC4CCOCC4)c(F)c3)C2=S)cc1C(F)(F)F] | 549.8 |
| 181 | 5-(5-(2-Fluoro-4-(2-methoxyethoxy)phenyl)-8-oxo-6-thioxo-5,7-diazaspiro[3.4]octan-7-yl)-3-(trifluoromethyl)picolinonitrile | 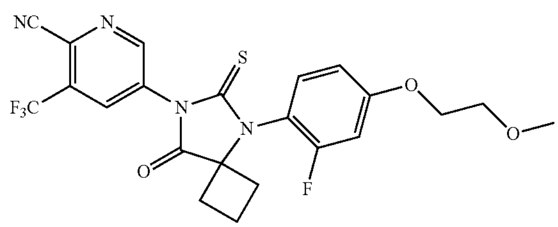 [SMILES: COCCOc1ccc(N2C(=S)N(c3cnc(C#N)c(C(F)(F)F)c3)C(=O)C23CCC3)c(F)c1] | 495.7 |
| 182 | 5-(5-(2-Fluoro-4-(2-(4-methylpiperazin-1-yl)ethoxy)phenyl)-8-oxo-6-thioxo-5,7-diazaspiro[3.4]octan-7-yl)-3-(trifluoromethyl)picolinonitrile | 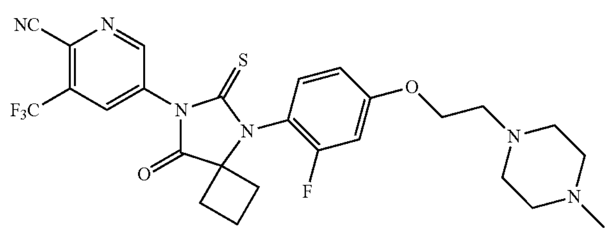 [SMILES: CN1CCN(CCOc2ccc(N3C(=S)N(c4cnc(C#N)c(C(F)(F)F)c4)C(=O)C34CCC4)c(F)c2)CC1] | 563.9 |

TABLE 1-continued

| Cmpd. | Name | Structure | LCMS* [M + 1]+ |
|---|---|---|---|
| 183 | 5-(5-(2-Fluoro-4-(2-(pyridin-2-yl)ethoxy)phenyl)-8-oxo-6-thioxo-5,7-diazaspiro[3.4]octan-7-yl)-3-(trifluoromethyl)picolinonitrile | 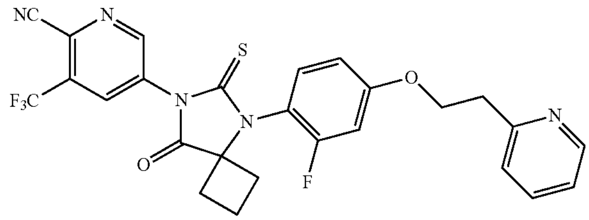 [SMILES: N#Cc1ncc(N2C(=O)C3(CCC3)N(c3ccc(OCCc4ccccn4)cc3F)C2=S)cc1C(F)(F)F] | 542.0 |
| 184 | 5-(5-(2-Fluoro-4-(3-(4-methylpiperazin-1-yl)propoxy)phenyl)-8-oxo-6-thioxo-5,7-diazaspiro[3.4]octan-7-yl)-3-(trifluoromethyl)picolinonitrile | 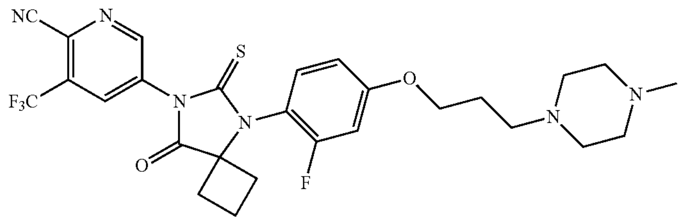 [SMILES: CN1CCN(CCCOc2ccc(N3C(=S)N(c4cnc(C#N)c(C(F)(F)F)c4)C(=O)C34CCC4)c(F)c2)CC1] | 577.1 |
| 185 | 5-(5-(3-Fluoro-4-(3-(pyrrolidin-1-yl)propoxy)phenyl)-8-oxo-6-thioxo-5,7-diazaspiro[3.4]octan-7-yl)-3-(trifluoromethyl)picolinonitrile | 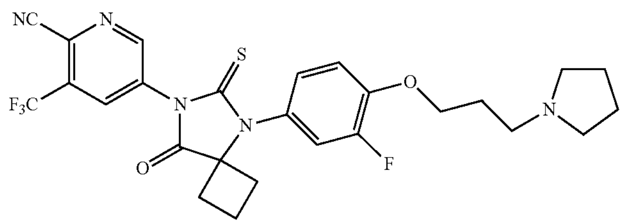 [SMILES: N#Cc1ncc(N2C(=O)C3(CCC3)N(c3ccc(OCCCN4CCCC4)c(F)c3)C2=S)cc1C(F)(F)F] | 548.1 |
| 186 | 5-(5-(4-(2-(1,1-Dioxidothiomorpholino)ethoxy)-3-fluorophenyl)-8-oxo-6-thioxo-5,7-diazaspiro[3.4]octan-7-yl)-3-(trifluoromethyl)picolinonitrile | 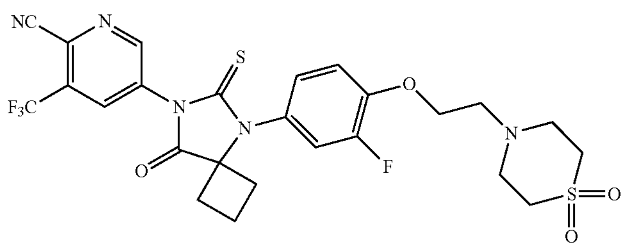 [SMILES: N#Cc1ncc(N2C(=O)C3(CCC3)N(c3ccc(OCCN4CCS(=O)(=O)CC4)c(F)c3)C2=S)cc1C(F)(F)F] | 598.0 |
| 187 | 5-(5-(2-Fluoro-4-(2-(piperidin-1-yl)ethoxy)phenyl)-8-oxo-6-thioxo-5,7-diazaspiro[3.4]octan-7-yl)-3-(trifluoromethyl)picolinonitrile | 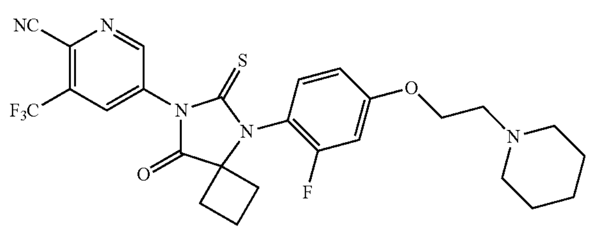 [SMILES: N#Cc1ncc(N2C(=O)C3(CCC3)N(c3ccc(OCCN4CCCCC4)cc3F)C2=S)cc1C(F)(F)F] | 548.1 |
| 188 | 5-(5-(3-Fluoro-4-phenethoxyphenyl)-8-oxo-6-thioxo-5,7-diazaspiro[3.4]octan-7-yl)-3-(trifluoromethyl)picolinonitrile | 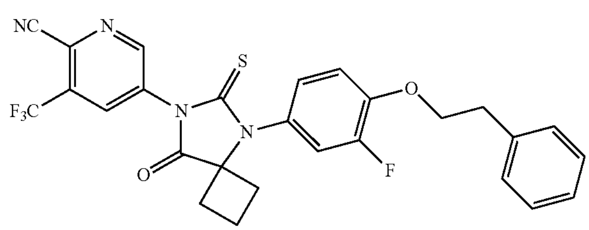 | 541.1 |

TABLE 1-continued

| Cmpd. | Name | Structure | LCMS* [M + 1]+ |
|---|---|---|---|
| 189 | 5-(5-(3-Fluoro-4-(2-(pyrimidin-2-yl)ethoxy)phenyl)-8-oxo-6-thioxo-5,7-diazaspiro[3.4]octan-7-yl)-3-(trifluoromethyl)picolinonitrile | 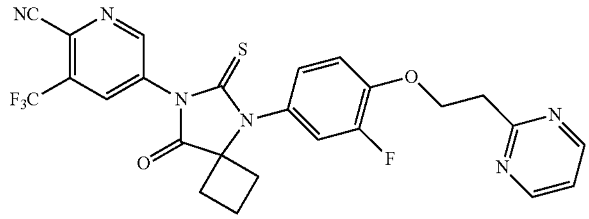 [SMILES: N#Cc1ncc(N2C(=O)C3(CCC3)N(c3ccc(OCCc4ncccn4)c(F)c3)C2=S)cc1C(F)(F)F] | 543.1 |
| 190 | 5-(5-(2-Fluoro-4-((1-methylpiperidin-4-yl)oxy)phenyl)-8-oxo-6-thioxo-5,7-diazaspiro[3.4]octan-7-yl)-3-(trifluoromethyl)picolinonitrile | 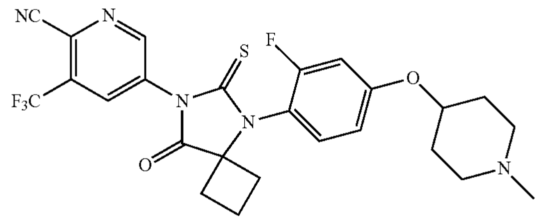 [SMILES: CN1CCC(Oc2ccc(N3C(=S)N(c4cnc(C#N)c(C(F)(F)F)c4)C(=O)C34CCC4)c(F)c2)CC1] | 534.0 |
| 191 | 3-Methyl-5-(5-(4-((1-methylpiperidin-4-yl)oxy)phenyl)-8-oxo-6-thioxo-5,7-diazaspiro[3.4]octan-7-yl)picolinonitrile | 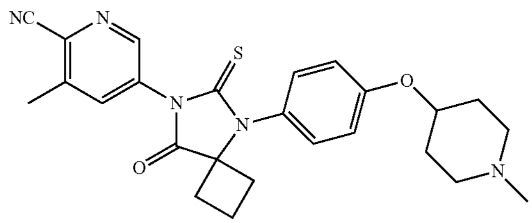 | 462.1 |
| 192 | 5-(5-(3-Fluoro-4-((1-methylpiperidin-4-yl)oxy)phenyl)-8-oxo-6-thioxo-5,7-diazaspiro[3.4]octan-7-yl)-3-methylpicolinonitrile | 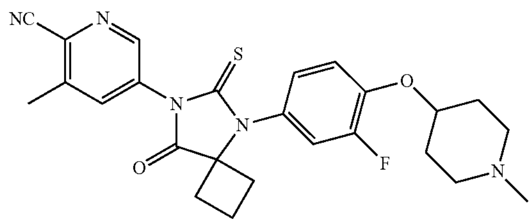 | 480.1 |
| 193 | 5-(5-(3-Fluoro-4-((1-methylpiperidin-4-yl)oxy)phenyl)-8-oxo-6-thioxo-5,7-diazaspiro[3.4]octan-7-yl)-3-(trifluoromethyl)picolinonitrile | 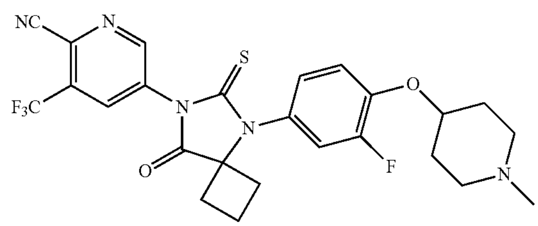 [SMILES: CN1CCC(Oc2ccc(N3C(=S)N(c4cnc(C#N)c(C(F)(F)F)c4)C(=O)C34CCC4)cc2F)CC1] | 534.2 |
| 194 | 3-Methyl-5-(8-oxo-5-(4-((tetrahydro-2H-pyran-4-yl)oxy)phenyl)-6-thioxo-5,7-diazaspiro[3.4]octan-7-yl)picolinonitrile | 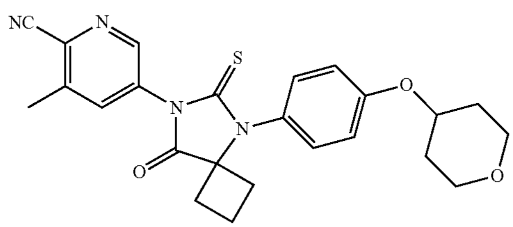 | 449.0 |
| 195 | 3-Methyl-5-(8-oxo-5-(4-((tetrahydro-2H-thiopyran-4-yl)oxy)phenyl)-6-thioxo-5,7-diazaspiro[3.4]octan-7-yl)picolinonitrile | 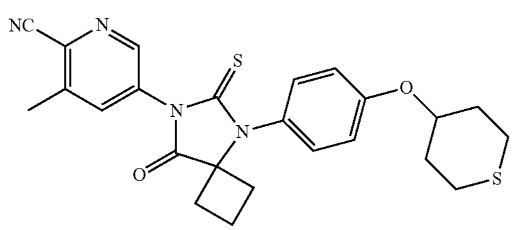 [SMILES: Cc1cc(N2C(=O)C3(CCC3)N(c3ccc(OC4CCOCC4)cc3)C2=S)cnc1C#N] | 465.0 |

TABLE 1-continued

| Cmpd. | Name | Structure | LCMS* [M + 1]+ |
|---|---|---|---|
| 196 | 5-(4,4-Dimethyl-3-(4-((1-methylpiperidin-4-yl)oxy)phenyl)-5-oxo-2-thioxoimidazolidin-1-yl)-3-(trifluoromethyl)picolinonitrile | 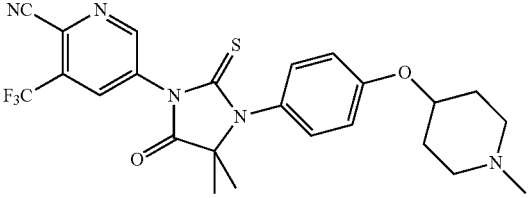 | 504.1 |
| 197 | 5-(4,4-Dimethyl-3-(4-((1-methylpiperidin-4-yl)oxy)phenyl)-5-oxo-2-thioxoimidazolidin-1-yl)-3-methylpicolinonitrile | 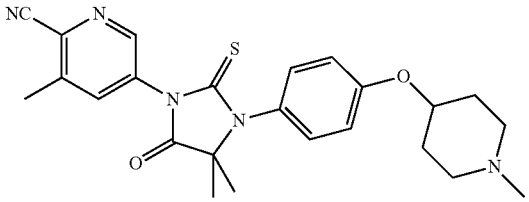 | 450.1 |
| 198 | 5-(8-Oxo-5-(4-((tetrahydro-2H-pyran-4-yl)oxy)phenyl)-6-thioxo-5,7-diazaspiro[3.4]octan-7-yl)-3-(trifluoromethyl)picolinonitrile | 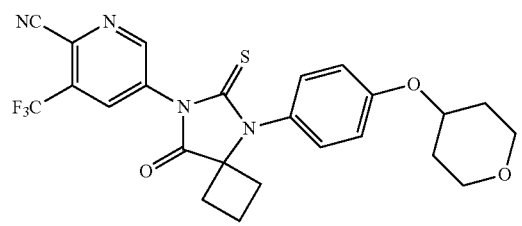 [SMILES: N#Cc1ncc(N2C(=O)C3(CCC3)N(c3ccc(OC4CCOCC4)cc3)C2=S)cc1C(F)(F)F] | 503.0 |
| 199 | 3-Methyl-5-(8-oxo-6-thioxo-5-(4-(2-(4-(2,2,2-trifluoroethyl)piperazin-1-yl)ethoxy)phenyl)-5,7-diazaspiro[3.4]octan-7-yl)picolinonitrile | 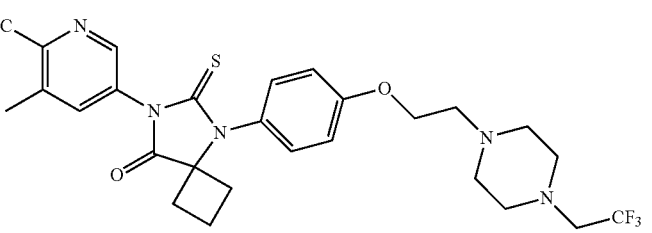 | 559.1 |
| 200 | 3-Methyl-5-(5-(4-(2-(4-methylpiperazin-1-yl)ethoxy)phenyl)-8-oxo-6-thioxo-5,7-diazaspiro[3.4]octan-7-yl)picolinonitrile | 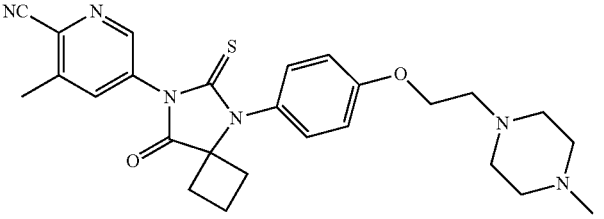 | 491.2 |
| 201 | 5-(5-(4-((1,1-Dioxidotetrahydro-2H-thiopyran-4-yl)oxy)phenyl)-8-oxo-6-thioxo-5,7-diazaspiro[3.4]octan-7-yl)-3-methylpicolinonitrile | 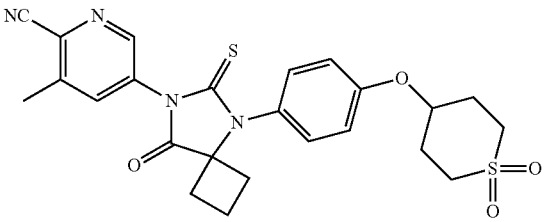 [SMILES: Cc1cc(N2C(=O)C3(CCC3)N(c3ccc(OC4CCS(=O)(=O)CC4)cc3)C2=S)cnc1C#N] | 497.0 |

TABLE 1-continued

| Cmpd. | Name | Structure | LCMS* [M + 1]+ |
|---|---|---|---|
| 202 | 5-(5-(4-(2-(4-Acetylpiperazin-1-yl)ethoxy)-3-fluorophenyl)-8-oxo-6-thioxo-5,7-diazaspiro[3.4]octan-7-yl)-3-(trifluoromethyl)picolinonitrile | 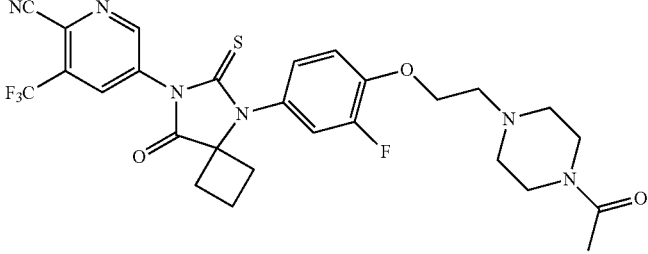 [SMILES: CC(=O)N1CCN(CCOc2ccc(N3C(=S)N(c4cnc(C#N)c(C(F)(F)F)c4)C(=O)C34CCC4)cc2F)CC1] | 591.9 |
| 203 | 5-(5-(3-Fluoro-4-methoxyphenyl)-8-oxo-6-thioxo-5,7-diazaspiro[3.4]octan-7-yl)-3-(trifluoromethyl)picolinonitrile | 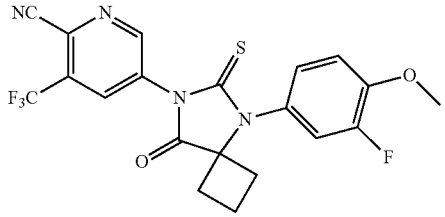 [SMILES: COc1ccc(N2C(=S)N(c3cnc(C#N)c(C(F)(F)F)c3)C(=O)C23CCC3)cc1F] | 451.4 |
| 204 | 5-(5-(4-Methoxyphenyl)-8-oxo-6-thioxo-5,7-diazaspiro[3.4]octan-7-yl)-3-(trifluoromethyl)picolinonitrile | 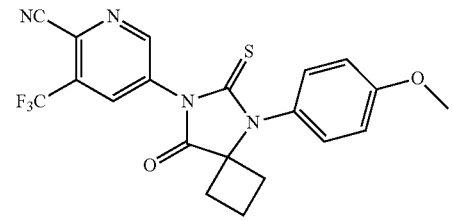 | 433.8 |
| 205 | 5-(5-(4-Methoxyphenyl)-8-oxo-6-thioxo-5,7-diazaspiro[3.4]octan-7-yl)-3-methylpicolinonitrile | 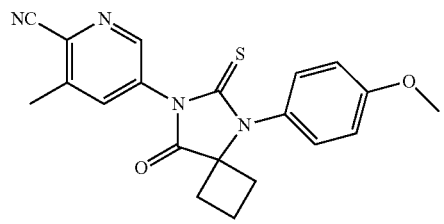 | 379.0 |
| 206 | 5-(8-Oxo-5-(4-(pyrimidin-2-yloxy)phenyl)-6-thioxo-5,7-diazaspiro[3.4]octan-7-yl)-3-(trifluoromethyl)picolinonitrile | 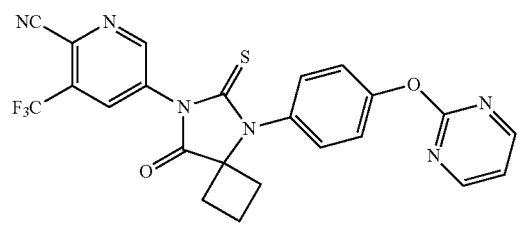 [SMILES: N#Cc1ncc(N2C(=O)C3(CCC3)N(c3ccc(Oc4ncccn4)cc3)C2=S)cc1C(F)(F)F] | 497.8 |
| 207 | 5-(8-Oxo-5-(4-(pyrazin-2-yloxy)phenyl)-6-thioxo-5,7-diazaspiro[3.4]octan-7-yl)-3-(trifluoromethyl)picolinonitrile | 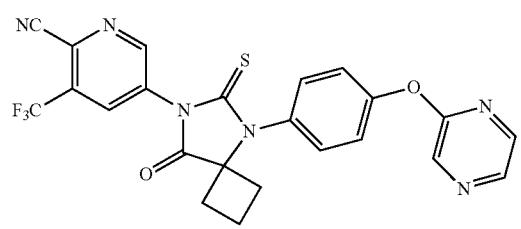 [SMILES: N#Cc1ncc(N2C(=O)C3(CCC3)N(c3ccc(Oc4cnccn4)cc3)C2=S)cc1C(F)(F)F] | 496.9 |

TABLE 1-continued

| Cmpd. | Name | Structure | LCMS* [M + 1]+ |
|---|---|---|---|
| 208 | 5-(8-Oxo-5-(4-(pyrimidin-4-yloxy)phenyl)-6-thioxo-5,7-diazaspiro[3.4]octan-7-yl)-3-(trifluoromethyl)picolinonitrile | 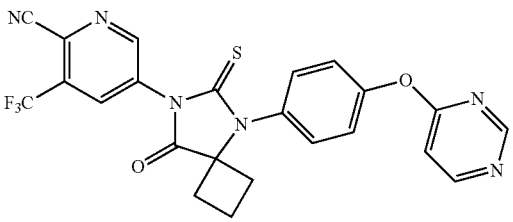 [SMILES: N#Cc1ncc(N2C(=O)C3(CCC3)N(c3ccc(Oc4ccncn4)cc3)C2=S)cc1C(F)(F)F] | 497.1 |
| 209 | 3-Methyl-5-(8-oxo-5-(4-(pyrimidin-4-yloxy)phenyl)-6-thioxo-5,7-diazaspiro[3.4]octan-7-yl)picolinonitrile | 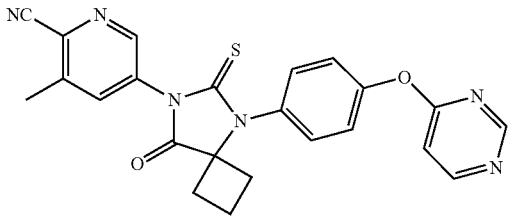 [SMILES: Cc1cc(N2C(=O)C3(CCC3)N(c3ccc(Oc4ccncn4)cc3)C2=S)cnc1C#N] | 443.0 |
| 210 | 3-Methyl-5-(8-oxo-5-(4-(piperidin-4-yloxy)phenyl)-6-thioxo-5,7-diazaspiro[3.4]octan-7-yl)picolinonitrile | 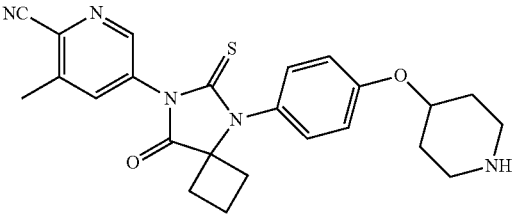 [SMILES: Cc1cc(N2C(=O)C3(CCC3)N(c3ccc(OC4CCNCC4)cc3)C2=S)cnc1C#N] | 448.1 |
| 211 | 5-(8-Oxo-5-(4-(piperidin-4-yloxy)phenyl)-6-thioxo-5,7-diazaspiro[3.4]octan-7-yl)-3-(trifluoromethyl)picolinonitrile | 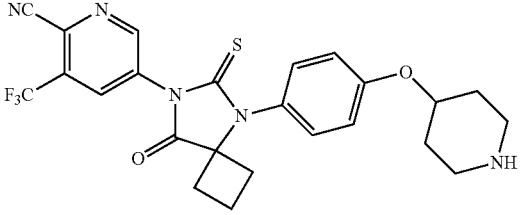 [SMILES: N#Cc1ncc(N2C(=O)C3(CCC3)N(c3ccc(OC4CCNCC4)cc3)C2=S)cc1C(F)(F)F] | 502.2 |
| 212 | 5-(8-Oxo-5-(4-((1-propionylpiperidin-4-yl)oxy)phenyl)-6-thioxo-5,7-diazaspiro[3.4]octan-7-yl)-3-(trifluoromethyl)picolinonitrile | 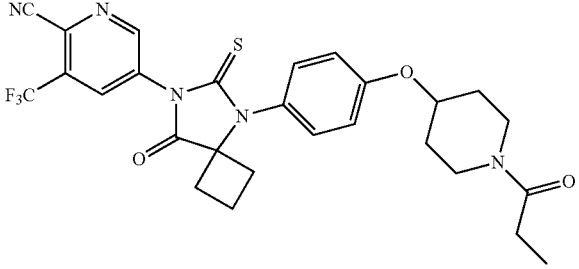 [SMILES: CCC(=O)N1CCC(Oc2ccc(N3C(=S)N(c4cnc(C#N)c(C(F)(F)F)c4)C(=O)C34CCC4)cc2)CC1] | 558.1 |
| 213 | 5-(5-(4-((1-isobutyrylpiperidin-4-yl)oxy)phenyl)-8-oxo-6-thioxo-5,7-diazaspiro[3.4]octan-7-yl)-3-(trifluoromethyl)picolinonitrile | 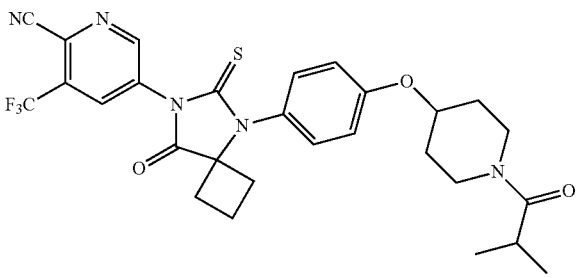 [SMILES: CC(C)C(=O)N1CCC(Oc2ccc(N3C(=S)N(c4cnc(C#N)c(C(F)(F)F)c4)C(=O)C34CCC4)cc2)CC1] | 572.1 |

TABLE 1-continued

| Cmpd. | Name | Structure | LCMS* [M + 1]+ |
|---|---|---|---|
| 214 | ethyl 4-(4-(7-(6-cyano-5-(trifluoromethyl)pyridin-3-yl)-8-oxo-6-thioxo-5,7-diazaspiro[3.4]octan-5-yl)phenoxy)piperidine-1-carboxylate | 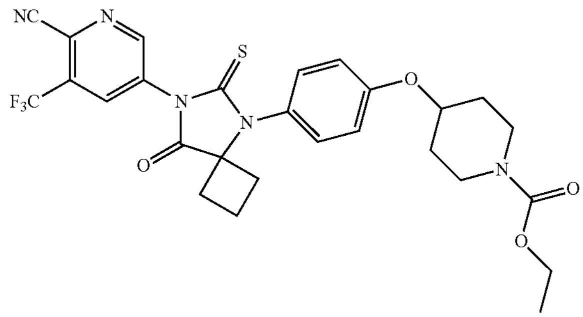 [SMILES: CCOC(=O)N1CCC(Oc2ccc(N3C(=S)N(c4cnc(C#N)c(C(F)(F)F)c4)C(=O)C34CCC4)cc2)CC1] | 574.0 |
| 215 | 5-(5-(4-((1-acetylpiperidin-4-yl)oxy)phenyl)-8-oxo-6-thioxo-5,7-diazaspiro[3.4]octan-7-yl)-3-methylpicolinonitrile | 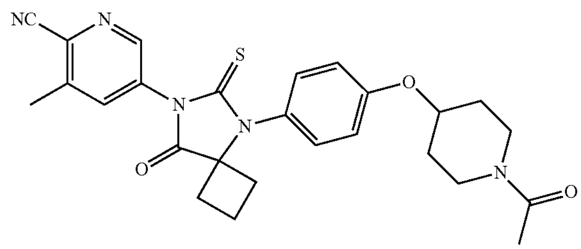 [SMILES: CC(=O)N1CCC(Oc2ccc(N3C(=S)N(c4cnc(C#N)c(C)c4)C(=O)C34CCC4)cc2)CC1] | 490.0 |
| 216 | 5-(5-(4-((1-Ethylpiperidin-4-yl)oxy)phenyl)-8-oxo-6-thioxo-5,7-diazaspiro[3.4]octan-7-yl)-3-methylpicolinonitrile | 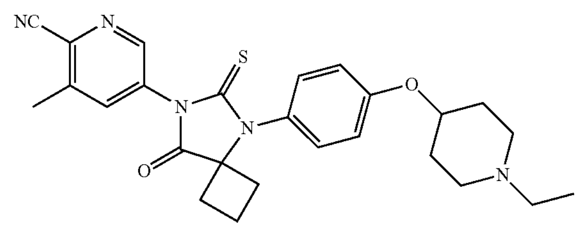 [SMILES: CCN1CCC(Oc2ccc(N3C(=S)N(c4cnc(C#N)c(C)c4)C(=O)C34CCC4)cc2)CC1] | 476.1 |
| 217 | 5-(5-(4-((1-(2-Hydroxyethyl)piperidin-4-yl)oxy)phenyl)-8-oxo-6-thioxo-5,7-diazaspiro[3.4]octan-7-yl)-3-methylpicolinonitrile | 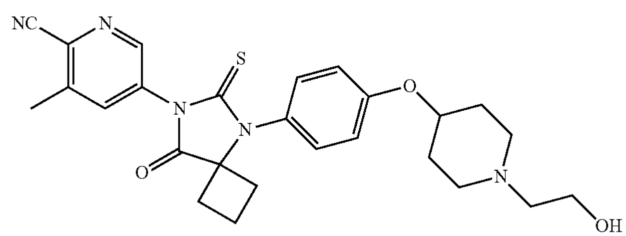 [SMILES: Cc1cc(N2C(=O)C3(CCC3)N(c3ccc(OC4CCN(CCO)CC4)cc3)C2=S)cnc1C#N] | 492.1 |
| 218 | 5-(5-(4-((1-(2-hydroxyethyl)piperidin-4-yl)oxy)phenyl)-8-oxo-6-thioxo-5,7-diazaspiro[3.4]oetan-7-yl)-3-(trifluoromethyl)picolinonitrile | 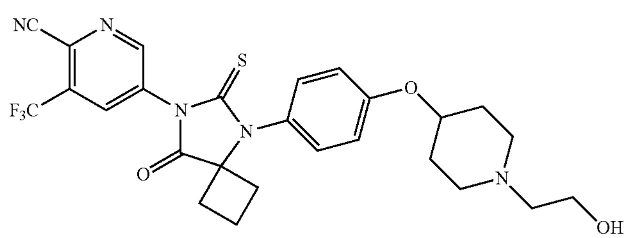 [SMILES: N#Cc1ncc(N2C(=O)C3(CCC3)N(c3ccc(OC4CCN(CCO)CC4)cc3)C2=S)cc1C(F)(F)F] | 546.1 |
| 219 | 5-(5-(4-((1-(methylsulfonyl)piperidin-4-yl)oxy)phenyl)-8-oxo-6-thioxo-5,7-diazaspiro[3.4]octan-7-yl)-3-(trifluoromethyl)picolinonitrile | 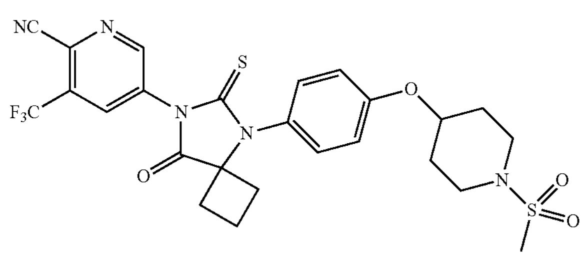 [SMILES: CS(=O)(=O)N1CCC(Oc2ccc(N3C(=S)N(c4cnc(C#N)c(C(F)(F)F)c4)C(=O)C34CCC4)cc2)CC1] | 580.1 |

TABLE 1-continued

| Cmpd. | Name | Structure | LCMS* [M + 1]+ |
|---|---|---|---|
| 220 | 5-(5-(4-((1-Isopropylpiperidin-4-yl)oxy)phenyl)-8-oxo-6-thioxo-5,7-diazaspiro[3.4]octan-7-yl)-3-(trifluoromethyl)picolinonitrile | 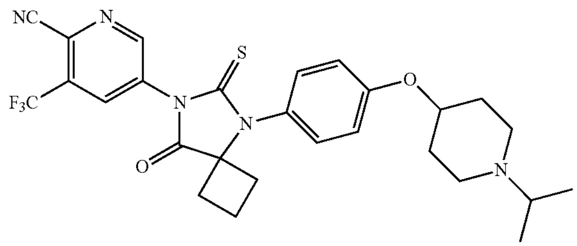 [SMILES: CC(C)N1CCC(Oc2ccc(N3C(=S)N(c4cnc(C#N)c(C(F)(F)F)c4)C(=O)C34CCC4)cc2)CC1] | 544.0 |
| 221 | Ethyl 2-(4-(4-(7-(6-cyano-5-(trifluoromethyl)pyridin-3-yl)-8-oxo-6-thioxo-5,7-diazaspiro[3.4]octan-5-yl)phenoxy)piperidin-1-yl)acetate | 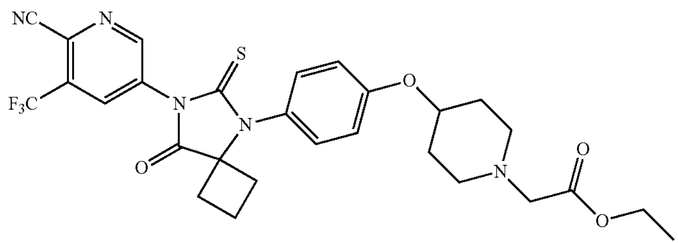 [SMILES: CCOC(=O)CN1CCC(Oc2ccc(N3C(=S)N(c4cnc(C#N)c(C(F)(F)F)c4)C(=O)C34CCC4)cc2)CC1] | 588.1 |
| 222 | 4-(4-(7-(6-Cyano-5-(trifluoromethyl)pyridin-3-yl)-8-oxo-6-thioxo-5,7-diazaspiro[3.4]octan-5-yl)phenoxy)piperidine-1-carboxamide | 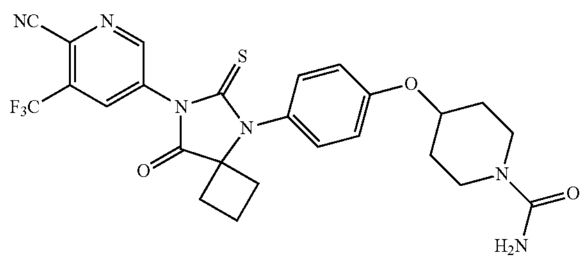 [SMILES: N#Cc1ncc(N2C(=O)C3(CCC3)N(c3ccc(OC4CCN(C(N)=O)CC4)cc3)C2=S)cc1C(F)(F)F] | 545.2 |
| 223 | 5-(5-(4-(2-Hydroxyethoxy)phenyl)-8-oxo-6-thioxo-5,7-diazaspiro[3.4]octan-7-yl)-3-methylpicolinonitrile | 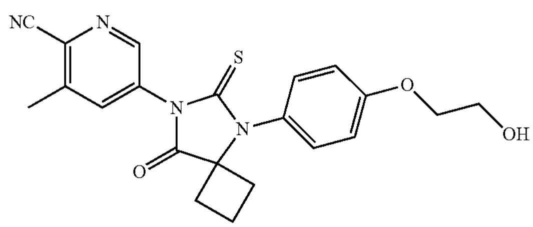 [SMILES: Cc1cc(N2C(=O)C3(CCC3)N(c3ccc(OCCO)cc3)C2=S)cnc1C#N] | 409.0 |
| 224 | 4-(7-(6-Cyano-5-(trifluoromethyl)pyridin-3-yl)-8-oxo-6-thioxo-5,7-diazaspiro[3.4]octan-5-yl)-2-fluorobenzoic acid | 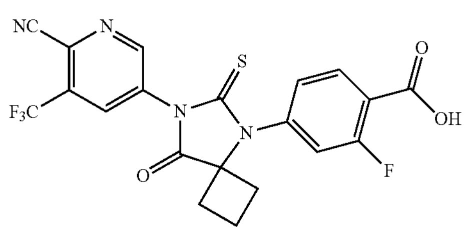 [SMILES: N#Cc1ncc(N2C(=O)C3(CCC3)N(c3ccc(C(=O)O)c(F)c3)C2=S)cc1C(F)(F)F] | 409.0 |
| 225 | 4-(7-(6-Cyano-5-methylpyridin-3-yl)-8-oxo-6-thioxo-5,7-diazaspiro[3.4]octan-5-yl)-2-fluorobenzoic acid | 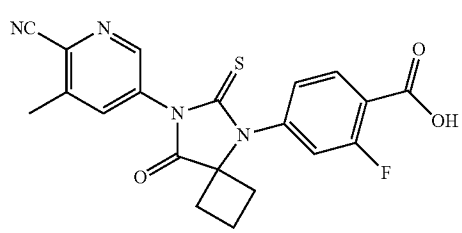 [SMILES: Cc1cc(N2C(=O)C3(CCC3)N(c3ccc(C(=O)O)c(F)c3)C2=S)cnc1C#N] | 411.0 |

TABLE 1-continued

| Cmpd. | Name | Structure | LCMS* [M + 1]+ |
|---|---|---|---|
| 226 | 5-(7-(6-Cyano-5-(trifluoromethyl)pyridin-3-yl)-8-oxo-6-thioxo-5,7-diazaspiro[3.4]octan-5-yl)-2-fluorobenzoic acid | 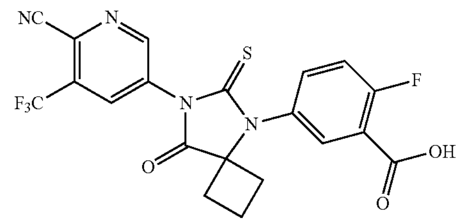 [SMILES: N#Cc1ncc(N2C(=O)C3(CCC3)N(c3ccc(F)c(C(=O)O)c3)C2=S)cc1C(F)(F)F] | 465.4 |
| 227 | 4-(4-(7-(6-Cyano-5-(trifluoromethyl)pyridin-3-yl)-8-oxo-6-thioxo-5,7-diazaspiro[3.4]octan-5-yl)phenyl)butanoic acid | 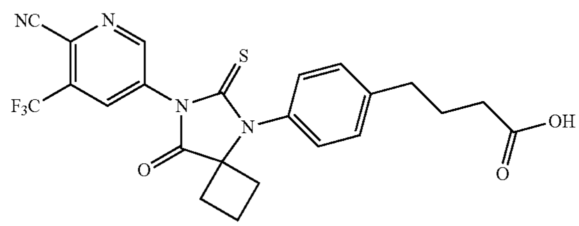 [SMILES: N#Cc1ncc(N2C(=O)C3(CCC3)N(c3ccc(CCCC(=O)O)cc3)C2=S)cc1C(F)(F)F] | 489.0 |
| 228 | 2-(4-(7-(6-Cyano-5-(trifluoromethyl)pyridin-3-yl)-8-oxo-6-thioxo-5,7-diazaspiro[3.4]octan-5-yl)-2-fluorophenoxy)acetic acid | 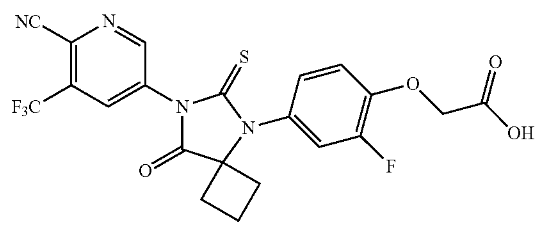 [SMILES: N#Cc1ncc(N2C(=O)C3(CCC3)N(c3ccc(OCC(=O)O)c(F)c3)C2=S)cc1C(F)(F)F] | 495.5 |
| 229 | 5-(7-(6-Carbamoyl-5-(trifluoromethyl)pyridin-3-yl)-8-oxo-6-thioxo-5,7-diazaspiro[3.4]octan-5-yl)-2-fluorobenzoic acid | 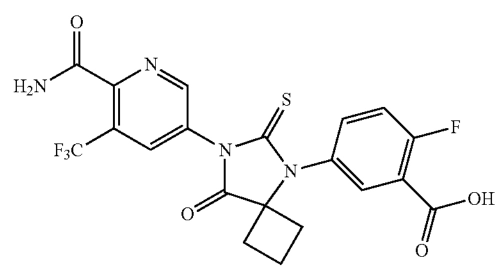 [SMILES: NC(=O)c1ncc(N2C(=O)C3(CCC3)N(c3ccc(F)c(C(=O)O)c3)C2=S)cc1C(F)(F)F] | 483.4 |
| 230 | 4-(4-(7-(6-Cyano-5-(trifluoromethyl)pyridin-3-yl)-8-oxo-6-thioxo-5,7-diazaspiro[3.4]octan-5-yl)phenyl)-N-methylbutanamide | 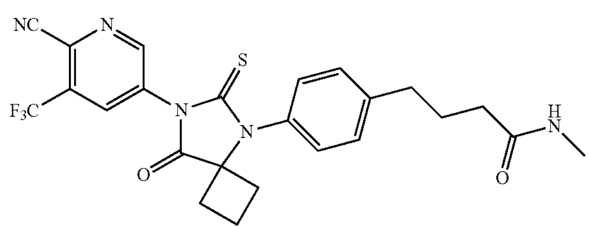 [SMILES: CNC(=O)CCCc1ccc(N2C(=S)N(c3cnc(C#N)c(C(F)(F)F)c3)C(=O)C23CCC3)cc1] | 502.0 |
| 231 | 4-(7-(6-Cyano-5-(trifluoromethyl)pyridin-3-yl)-8-oxo-6-thioxo-5,7-diazaspiro[3.4]octan-5-yl)-2-fluorobenzamide | 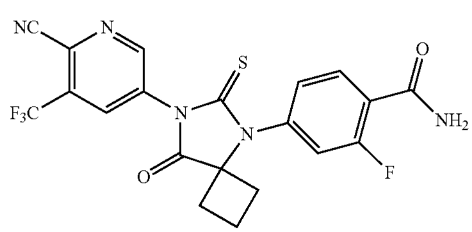 [SMILES: N#Cc1ncc(N2C(=O)C3(CCC3)N(c3ccc(C(N)=O)c(F)c3)C2=S)cc1C(F)(F)F] | 464.0 |

TABLE 1-continued

| Cmpd. | Name | Structure | LCMS* [M + 1]+ |
|---|---|---|---|
| 232 | 4-(7-(6-Cyano-5-methylpyridin-3-yl)-8-oxo-6-thioxo-5,7-diazaspiro[3.4]octan-5-yl)-2-fluorobenzamide | 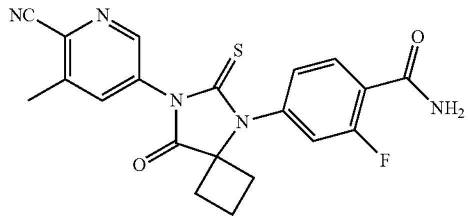 | 410.0 |
| 233 | 4-(7-(6-Cyano-5-methylpyridin-3-yl)-8-oxo-6-thioxo-5,7-diazaspiro[3.4]octan-5-yl)-2-methylbenzamide | 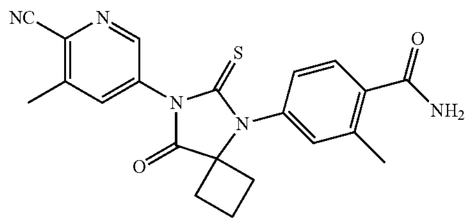 [SMILES: Cc1cc(N2C(=S)N(c3cnc(C#N)c(C)c3)C(=O)C23CCC3)ccc1C(N)=O] | 406.1 |
| 234 | 4-(7-(6-Cyano-5-(trifluoromethyl)pyridin-3-yl)-8-oxo-6-thioxo-5,7-diazaspiro[3.4]octan-5-yl)-2-fluoro-N-(2-(pyrrolidin-1-yl)ethyl)benzamide | 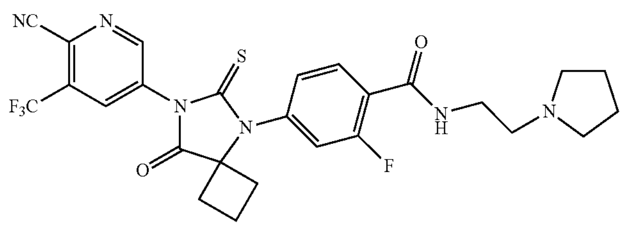 [SMILES: N#Cc1ncc(N2C(=O)C3(CCC3)N(c3ccc(C(=O)NCCN4CCCC4)c(F)c3)C2=S)cc1C(F)(F)F] | 561.1 |
| 235 | N-Benzyl-4-(7-(6-cyano-5-(trifluoromethyl)pyridin-3-yl)-8-oxo-6-thioxo-5,7-diazaspiro[3.4]octan-5-yl)-2-fluorobenzamide | 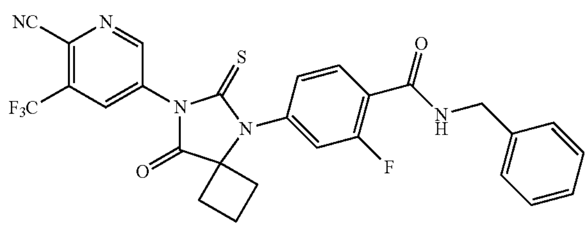 | 554.5 |
| 236 | 4-(7-(6-Cyano-5-(trifluoromethyl)pyridin-3-yl)-8-oxo-6-thioxo-5,7-diazaspiro[3.4]octan-5-yl)-2-fluoro-N-(2-(pyridin-2-yl)ethyl)benzamide | 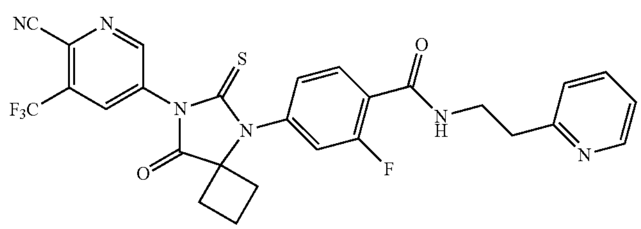 | 569.5 |
| 237 | 4-(7-(6-Cyano-5-(trifluoromethyl)pyridin-3-yl)-8-oxo-6-thioxo-5,7-diazaspiro[3.4]octan-5-yl)-2-fluoro-N-(3-(pyrrolidin-1-yl)propyl)benzamide | 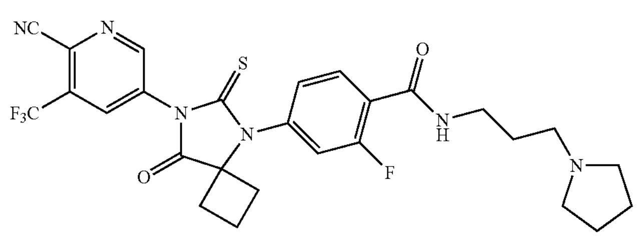 [SMILES: N#Cc1ncc(N2C(=O)C3(CCC3)N(c3ccc(C(=O)NCCCN4CCCC4)c(F)c3)C2=S)cc1C(F)(F)F] | 575.1 |
| 238 | 4-(7-(6-Cyano-5-(trifluoromethyl)pyridin-3-yl)-8-oxo-6-thioxo-5,7-diazaspiro[3.4]octan-5-yl)-2-fluoro-N-(2-(pyridin-4-yl)ethyl)benzamide | 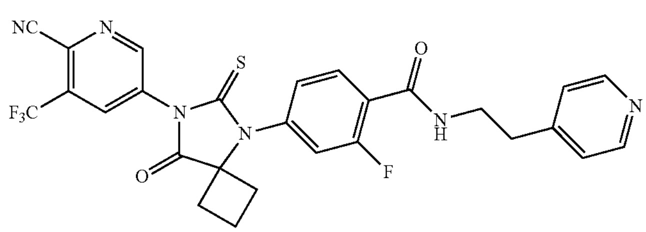 [SMILES: N#Cc1ncc(N2C(=O)C3(CCC3)N(c3ccc(C(=O)NCCc4ccncc4)c(F)c3)C2=S)cc1C(F)(F)F] | 569.5 |

TABLE 1-continued

| Cmpd. | Name | Structure | LCMS* [M + 1]+ |
|---|---|---|---|
| 239 | 5-(7-(6-Cyano-5-(trifluoromethyl)pyridin-3-yl)-8-oxo-6-thioxo-5,7-diazaspiro[3.4]octan-5-yl)-2-fluoro-N-(2-(pyridin-2-yl)ethyl)benzamide | 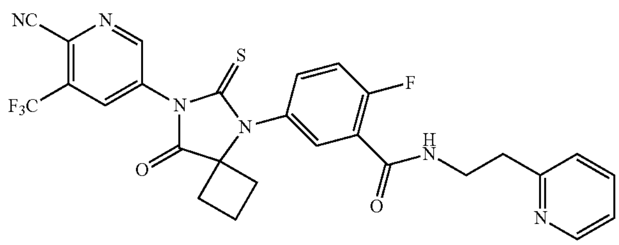 [SMILES: N#Cc1ncc(N2C(=O)C3(CCC3)N(c3ccc(F)c(C(=O)NCCc4ccccn4)c3)C2=S)cc1C(F)(F)F] | 569.5 |
| 240 | 5-(7-(6-Cyano-5-(trifluoromethyl)pyridin-3-yl)-8-oxo-6-thioxo-5,7-diazaspiro[3.4]octan-5-yl)-2-fluoro-N-(2-(pyridin-3-yl)ethyl)benzamide | 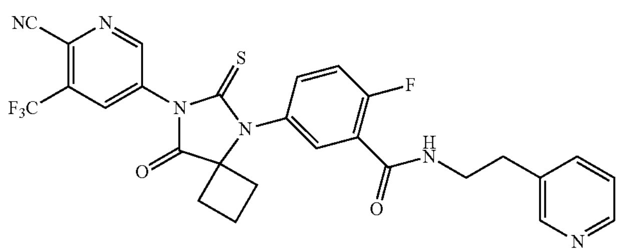 [SMILES: N#Cc1ncc(N2C(=O)C3(CCC3)N(c3ccc(F)c(C(=O)NCCc4cccnc4)c3)C2=S)cc1C(F)(F)F] | 569.5 |
| 241 | 5-(7-(6-Cyano-5-(trifluoromethyl)pyridin-3-yl)-8-oxo-6-thioxo-5,7-diazaspiro[3.4]octan-5-yl)-2-fluoro-N-(2-(pyridin-4-yl)ethyl)benzamide | 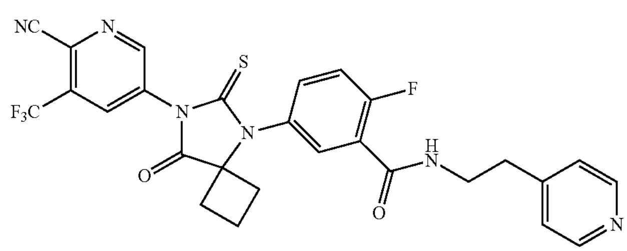 [SMILES: N#Cc1ncc(N2C(=O)C3(CCC3)N(c3ccc(F)c(C(=O)NCCc4ccncc4)c3)C2=S)cc1C(F)(F)F] | 569.5 |
| 242 | 4-(7-(6-Cyano-5-(trifluoromethyl)pyridin-3-yl)-8-oxo-6-thioxo-5,7-diazaspiro[3.4]octan-5-yl)-2-fluoro-N-(2-morpholinoethyl)benzamide | 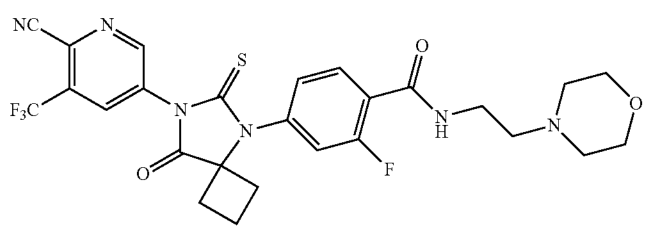 [SMILES: N#Cc1ncc(N2C(=O)C3(CCC3)N(c3ccc(C(=O)NCCN4CCOCC4)c(F)c3)C2=S)cc1C(F)(F)F] | 577.5 |
| 243 | 4-(7-(6-Cyano-5-(trifluoromethyl)pyridin-3-yl)-8-oxo-6-thioxo-5,7-diazaspiro[3.4]octan-5-yl)-2-fluoro-N-(2-(4-methylpiperazin-1-yl)ethyl)benzamide | 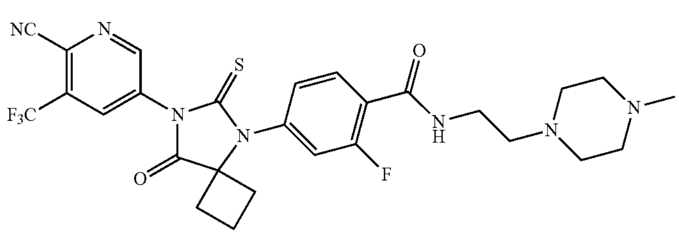 [SMILES: CN1CCN(CCNC(=O)c2ccc(N3C(=S)N(c4cnc(C#N)c(C(F)(F)F)c4)C(=O)C34CCC4)cc2F)CC1] | 590.5 |
| 244 | 4-(7-(6-Cyano-5-(trifluoromethyl)pyridin-3-yl)-8-oxo-6-thioxo-5,7-diazaspiro[3.4]octan-5-yl)-2-fluoro-N-(2-(pyridin-3-yl)ethyl)benzamide | 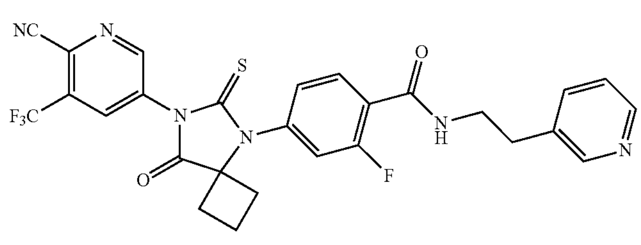 | 569.5 |

TABLE 1-continued

| Cmpd. | Name | Structure | LCMS* [M + 1]+ |
|---|---|---|---|
| 245 | Ethyl 2-(4-(7-(6-cyano-5-(trifluoromethyl)pyridin-3-yl)-8-oxo-6-thioxo-5,7-diazaspiro[3.4]octan-5-yl)-2-fluorobenzamido)acetate | 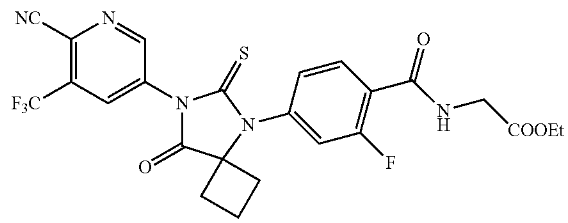 [SMILES: CCOC(=O)CNC(=O)c1ccc(N2C(=S)N(c3cnc(C#N)c(C(F)(F)F)c3)C(=O)C23CCC3)cc1F] | 550.5 |
| 246 | Ethyl 3-(4-(7-(6-cyano-5-(trifluoromethyl)pyridin-3-yl)-8-oxo-6-thioxo-5,7-diazaspiro[3.4]octan-5-yl)-2-fluorobenzamido)propanoate | 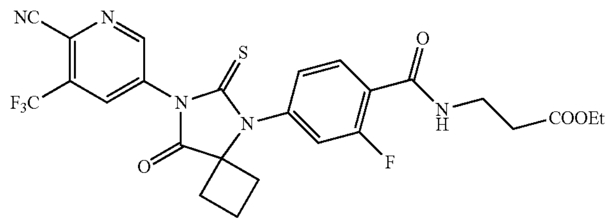 [SMILES: CCOC(=O)CCNC(=O)c1ccc(N2C(=S)N(c3cnc(C#N)c(C(F)(F)F)c3)C(=O)C23CCC3)cc1F] | 564.5 |
| 247 | Ethyl 4-(4-(7-(6-cyano-5-(trifluoromethyl)pyridin-3-yl)-8-oxo-6-thioxo-5,7-diazaspiro[3.4]octan-5-yl)-2-fluorobenzamido)butanoate | 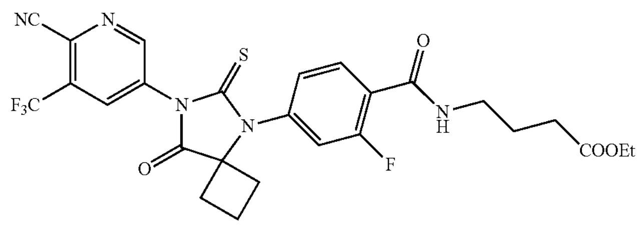 [SMILES: CCOC(=O)CCCNC(=O)c1ccc(N2C(=S)N(c3cnc(C#N)c(C(F)(F)F)c3)C(=O)C23CCC3)cc1F] | 578.5 |
| 248 | 4-(7-(6-Cyano-5-(trifluoromethyl)pyridin-3-yl)-8-oxo-6-thioxo-5,7-diazaspiro[3.4]octan-5-yl)-2-fluoro-N-(2-methoxyethyl)benzamide | 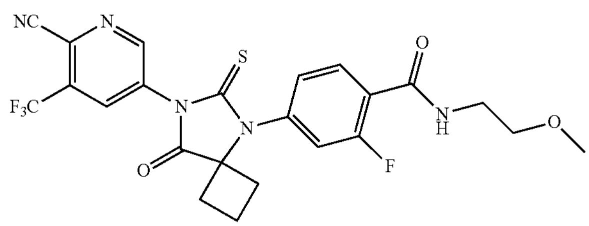 | 522.5 |
| 249 | 4-(7-(6-Cyano-5-(trifluoromethyl)pyridin-3-yl)-8-oxo-6-thioxo-5,7-diazaspiro[3.4]octan-5-yl)-2-fluoro-N-(3-methoxypropyl)benzamide | 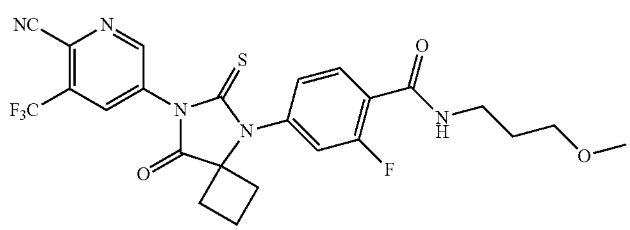 [SMILES: COCCCNC(=O)c1ccc(N2C(=S)N(c3cnc(C#N)c(C(F)(F)F)c3)C(=O)C23CCC3)cc1F] | 536.5 |
| 250 | 4-(7-(6-Cyano-5-(trifluoromethyl)pyridin-3-yl)-8-oxo-6-thioxo-5,7-diazaspiro[3.4]octan-5-yl)-2-fluoro-N-(2-methoxyethyl)-N-methylbenzamide | 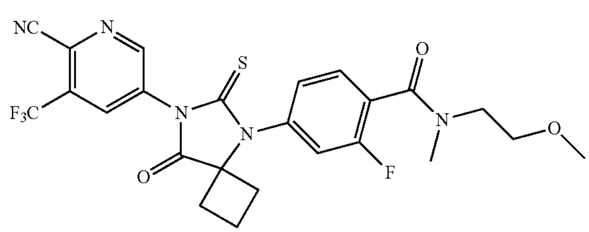 [SMILES: COCCN(C)C(=O)c1ccc(N2C(=S)N(c3cnc(C#N)c(C(F)(F)F)c3)C(=O)C23CCC3)cc1F] | 536.5 |

TABLE 1-continued

| Cmpd. | Name | Structure | LCMS* [M + 1]+ |
|---|---|---|---|
| 251 | 5-(7-(6-Cyano-5-(trifluoromethyl)pyridin-3-yl)-8-oxo-6-thioxo-5,7-diazaspiro[3.4]octan-5-yl)-2-fluoro-N-(2-(pyrrolidin-1-yl)ethyl)benzamide | 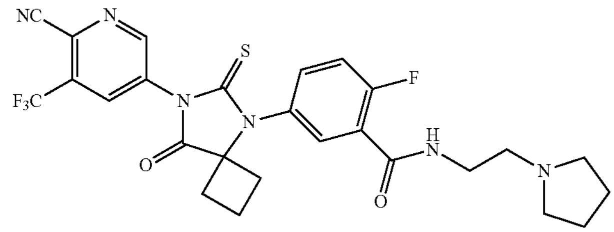 [SMILES: N#Cc1ncc(N2C(=O)C3(CCC3)N(c3ccc(F)c(C(=O)NCCN4CCCC4)c3)C2=S)cc1C(F)(F)F] | 561.6 |
| 252 | 5-(7-(6-Cyano-5-(trifluoromethyl)pyridin-3-yl)-8-oxo-6-thioxo-5,7-diazaspiro[3.4]octan-5-yl)-2-fluoro-N-(3-(pyrrolidin-1-yl)propyl)benzamide | 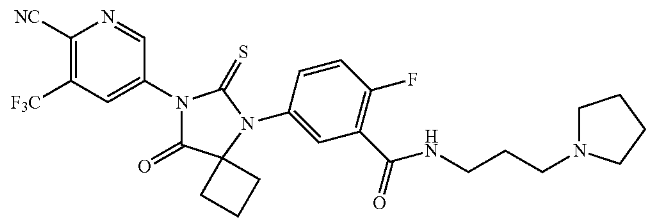 [SMILES: N#Cc1ncc(N2C(=O)C3(CCC3)N(c3ccc(F)c(C(=O)NCCCN4CCCC4)c3)C2=S)cc1C(F)(F)F] | 575.1 |
| 253 | 5-(7-(6-Cyano-5-(trifluoromethyl)pyridin-3-yl)-8-oxo-6-thioxo-5,7-diazaspiro[3.4]octan-5-yl)-2-fluoro-N-(2-morpholinoethyl)benzamide | 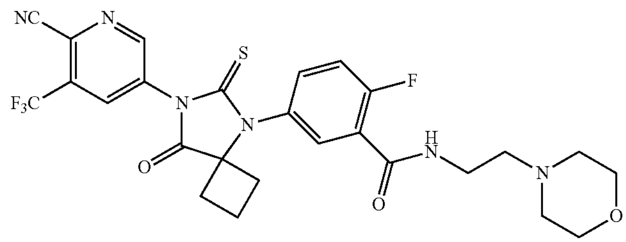 [SMILES: N#Cc1ncc(N2C(=O)C3(CCC3)N(c3ccc(F)c(C(=O)NCCN4CCOCC4)c3)C2=S)cc1C(F)(F)F] | 577.6 |
| 254 | 5-(7-(6-Cyano-5-(trifluoromethyl)pyridin-3-yl)-8-oxo-6-thioxo-5,7-diazaspiro[3.4]octan-5-yl)-2-fluoro-N-(2-(4-methylpiperazin-1-yl)ethyl)benzamide | 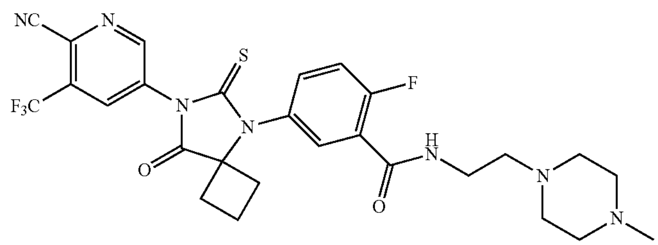 [SMILES: CN1CCN(CCNC(=O)c2cc(N3C(=S)N(c4cnc(C#N)c(C(F)(F)F)c4)C(=O)C34CCC4)ccc2F)CC1] | 590.6 |
| 255 | 4-(7-(6-Cyano-5-(trifluoromethyl)pyridin-3-yl)-8-oxo-6-thioxo-5,7-diazaspiro[3.4]octan-5-yl)-2-fluoro-N-phenylbenzamide | 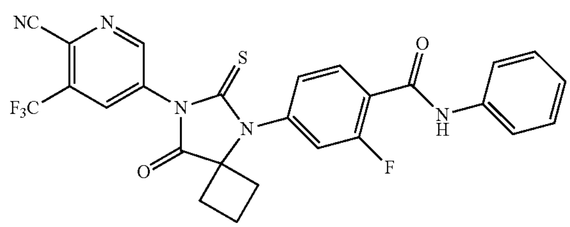 [SMILES: N#Cc1ncc(N2C(=O)C3(CCC3)N(c3ccc(C(=O)Nc4ccccc4)c(F)c3)C2=S)cc1C(F)(F)F] | 540.5 |
| 256 | N-(2-(4-Bromo-1-methyl-1H-pyrazol-5-yl)ethyl)-4-(7-(6-cyano-5-(trifluoromethyl)pyridin-3-yl)-8-oxo-6-thioxo-5,7-diazaspiro[3.4]octan-5-yl)-2-fluorobenzamide | 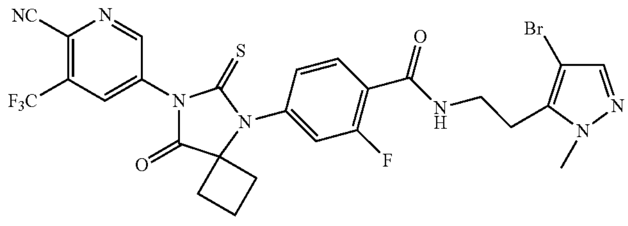 [SMILES: Cn1ncc(Br)c1CCNC(=O)c1ccc(N2C(=S)N(c3cnc(C#N)c(C(F)(F)F)c3)C(=O)C23CCC3)cc1F] | 652.2 |

TABLE 1-continued

| Cmpd. | Name | Structure | LCMS* [M + 1]+ |
|---|---|---|---|
| 257 | 4-(7-(6-Cyano-5-(trifluoromethyl)pyridin-3-yl)-8-oxo-6-thioxo-5,7-diazaspiro[3.4]octan-5-yl)-2-fluoro-N-phenethylbenzamide | 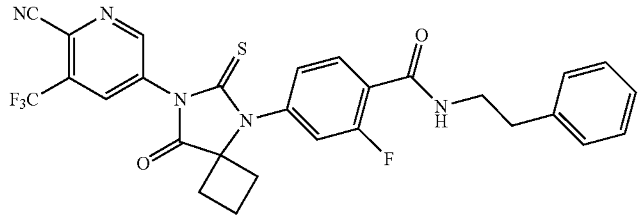 | 568.5 |
| 258 | 4-(7-(6-Cyano-5-(trifluoromethyl)pyridin-3-yl)-8-oxo-6-thioxo-5,7-diazaspiro[3.4]octan-5-yl)-2-fluoro-N-(3-phenylpropyl)benzamide | 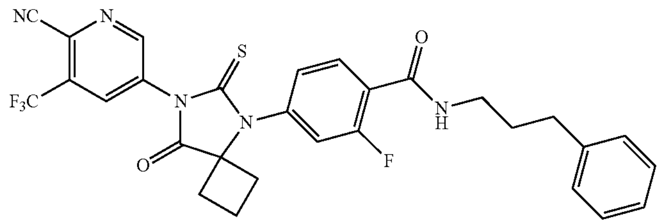 [SMILES: N#Cc1ncc(N2C(=O)C3(CCC3)N(c3ccc(C(=O)NCCCc4ccccc4)c(F)c3)C2=S)cc1C(F)(F)F] | 582.5 |
| 259 | 4-(7-(6-Cyano-5-(trifluoromethyl)pyridin-3-yl)-8-oxo-6-thioxo-5,7-diazaspiro[3.4]octan-5-yl)-2-fluoro-N-(pyridin-4-ylmethyl)benzamide | 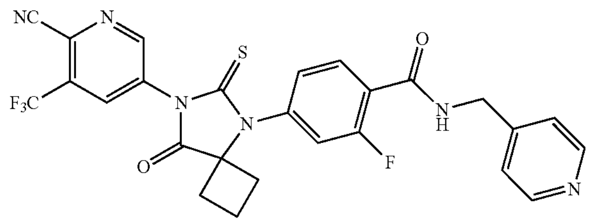 [SMILES: N#Cc1ncc(N2C(=O)C3(CCC3)N(c3ccc(C(=O)NCc4ccncc4)c(F)c3)C2=S)cc1C(F)(F)F] | 555.5 |
| 260 | 4-(7-(6-Cyano-5-(trifluoromethyl)pyridin-3-yl)-8-oxo-6-thioxo-5,7-diazaspiro[3.4]octan-5-yl)-2-fluoro-N-(thiophen-2-ylmethyl)benzamide | 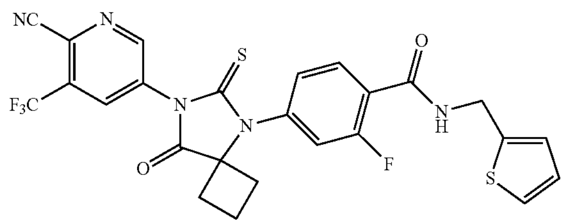 | 560.5 |
| 261 | 4-(7-(6-Cyano-5-(trifluoromethyl)pyridin-3-yl)-8-oxo-6-thioxo-5,7-diazaspiro[3.4]octan-5-yl)-2-fluoro-N-(pyridin-2-yl)benzamide | 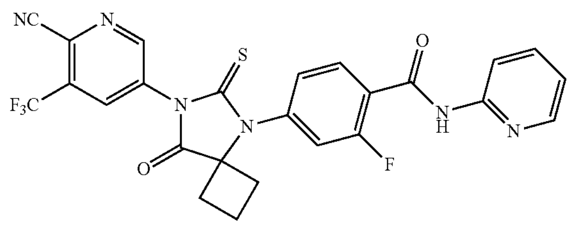 | 541.5 |
| 262 | 4-(7-(6-Cyano-5-(trifluoromethyl)pyridin-3-yl)-8-oxo-6-thioxo-5,7-diazaspiro[3.4]octan-5-yl)-2-fluoro-N-(pyridin-3-yl)benzamide | 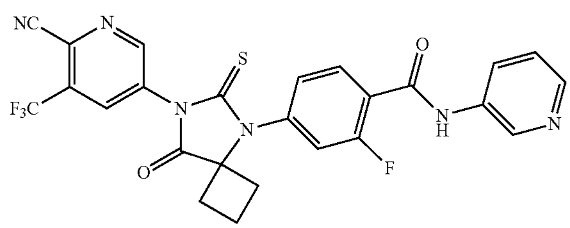 [SMILES: N#Cc1ncc(N2C(=O)C3(CCC3)N(c3ccc(C(=O)Nc4cccnc4)c(F)c3)C2=S)cc1C(F)(F)F] | 541.4 |
| 263 | 4-(7-(6-Cyano-5-(trifluoromethyl)pyridin-3-yl)-8-oxo-6-thioxo-5,7-diazaspiro[3.4]octan-5-yl)-2-fluoro-N-(pyridin-4-yl)benzamide | 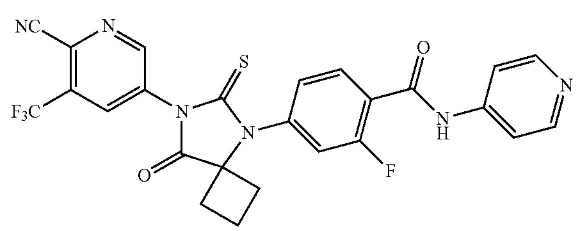 [SMILES: N#Cc1ncc(N2C(=O)C3(CCC3)N(c3ccc(C(=O)Nc4ccncc4)c(F)c3)C2=S)cc1C(F)(F)F] | 541.4 |

TABLE 1-continued

| Cmpd. | Name | Structure | LCMS* [M + 1]+ |
|---|---|---|---|
| 264 | 4-(7-(6-Cyano-5-(trifluoromethyl)pyridin-3-yl)-8-oxo-6-thioxo-5,7-diazaspiro[3.4]octan-5-yl)-2-fluoro-N-(pyridin-2-ylmethyl)benzamide | 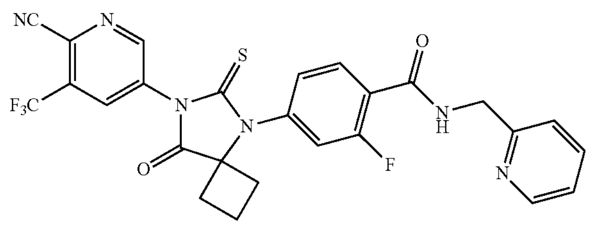 | 555.9 |
| 265 | 4-(7-(6-Cyano-5-(trifluoromethyl)pyridin-3-yl)-8-oxo-6-thioxo-5,7-diazaspiro[3.4]octan-5-yl)-2-fluoro-N-(pyridin-3-ylmethyl)benzamide | 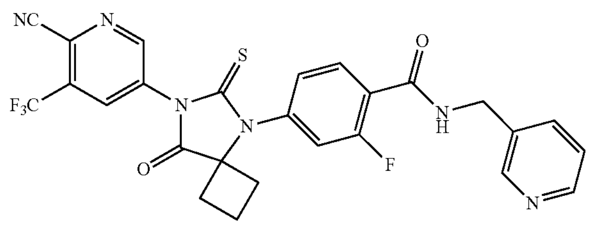 | 556.1 |
| 266 | 4-(7-(6-Cyano-5-(trifluoromethyl)pyridin-3-yl)-8-oxo-6-thioxo-5,7-diazaspiro[3.4]octan-5-yl)-2-fluoro-N-(furan-2-ylmethyl)benzamide | 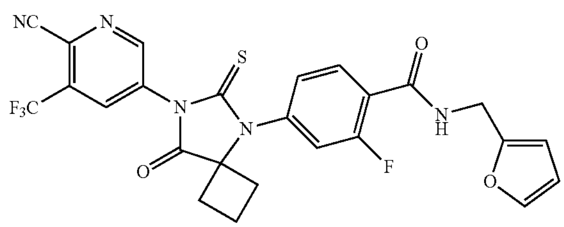 | 544.4 |
| 267 | 4-(7-(6-Cyano-5-(trifluoromethyl)pyridin-3-yl)-8-oxo-6-thioxo-5,7-diazaspiro[3.4]octan-5-yl)-N-cyclopentyl-2-fluorobenzamide | 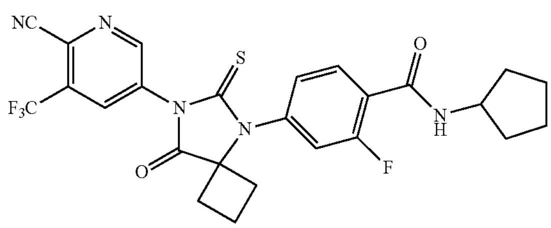 [SMILES: N#Cc1ncc(N2C(=O)C3(CCC3)N(c3ccc(C(=O)NC4CCCC4)c(F)c3)C2=S)cc1C(F)(F)F] | 532.5 |
| 268 | 4-(7-(6-Cyano-5-(trifluorometliyl)pyridin-3-yl)-8-oxo-6-thioxo-5,7-diazaspiro[3.4]octan-5-yl)-2-fluoro-N-(3-morpholinopropyl)benzamide | 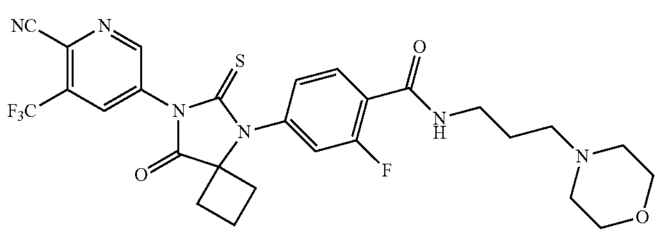 [SMILES: N#Cc1ncc(N2C(=O)C3(CCC3)N(c3ccc(C(=O)NCCCN4CCOCC4)c(F)c3)C2=S)cc1C(F)(F)F] | 591.0 |
| 269 | 4-(7-(6-Cyano-5-(trifluoromethyl)pyridin-3-yl)-8-oxo-6-thioxo-5,7-diazaspiro[3.4]octan-5-yl)-2-fluoro-N-(3-(4-methylpiperazin-1-yl)propyl)benzamide | 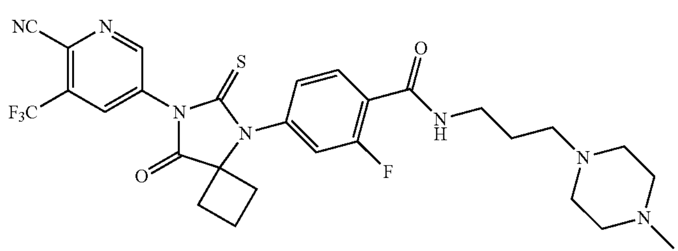 [SMILES: CN1CCN(CCCNC(=O)c2ccc(N3C(=S)N(c4cnc(C#N)c(C(F)(F)F)c4)C(=O)C34CCC4)cc2F)CC1] | 604.0 |

TABLE 1-continued

| Cmpd. | Name | Structure | LCMS* [M + 1]+ |
|---|---|---|---|
| 270 | 5-(5-(3-Fluoro-4-(pyrrolidine-1-carbonyl)phenyl)-8-oxo-6-thioxo-5,7-diazaspiro[3.4]octan-7-yl)-3-(trifluoromethyl)picolinonitrile | 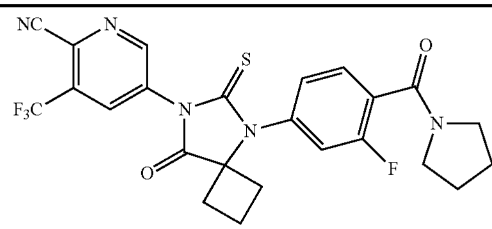 | 518.0 |
| 271 | 5-(5-(3-Fluoro-4-(morpholine-4-carbonyl)phenyl)-8-oxo-6-thioxo-5,7-diazaspiro[3.4]octan-7-yl)-3-(trifluoromethyl)picolinonitrile | 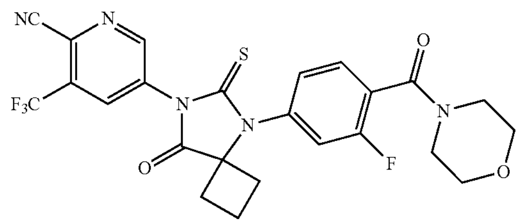 [SMILES: N#Cc1ncc(N2C(=O)C3(CCC3)N(c3ccc(C(=O)N4CCOCC4)c(F)c3)C2=S)cc1C(F)(F)F] | 534.0 |
| 272 | 4-(7-(6-Cyano-5-methylpyridin-3-yl)-8-oxo-6-thioxo-5,7-diazaspiro[3.4]octan-5-yl)-2-fluoro-N-phenylbenzamide | 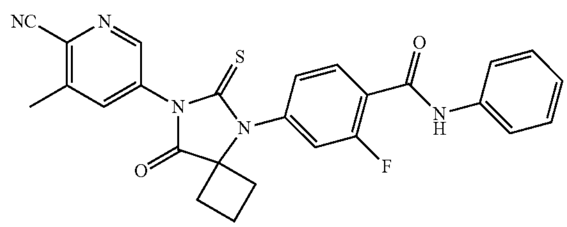 [SMILES: Cc1cc(N2C(=O)C3(CCC3)N(c3ccc(C(=O)Nc4ccccc4)c(F)c3)C2=S)cnc1C#N] | 486.8 |
| 273 | N-Benzyl-4-(7-(6-cyano-5-methylpyridin-3-yl)-8-oxo-6-thioxo-5,7-diazaspiro[3.4]octan-5-yl)-2-fluorobenzamide | 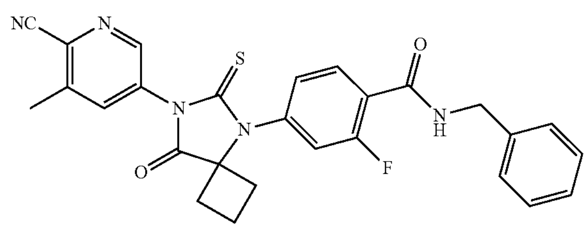 [SMILES: Cc1cc(N2C(=O)C3(CCC3)N(c3ccc(C(=O)NCc4ccccc4)c(F)c3)C2=S)cnc1C#N] | 500.8 |
| 274 | 4-(7-(6-Cyano-5-methylpyridin-3-yl)-8-oxo-6-thioxo-5,7-diazaspiro[3.4]octan-5-yl)-2-fluoro-N-(thiophen-2-ylmethyl)benzamide | 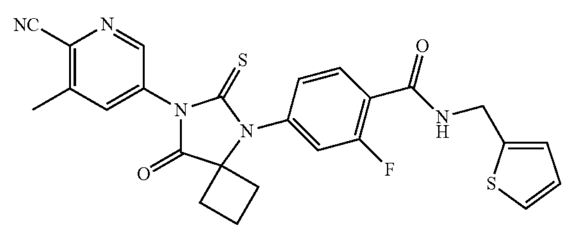 [SMILES: Cc1cc(N2C(=O)C3(CCC3)N(c3ccc(C(=O)NCc4cccs4)c(F)c3)C2=S)cnc1C#N] | 506.8 |
| 275 | 4-(7-(6-Cyano-5-methylpyridin-3-yl)-8-oxo-6-thioxo-5,7-diazaspiro[3.4]octan-5-yl)-2-fluoro-N-(3-(pyrrolidin-1-yl)propyl)benzamide | 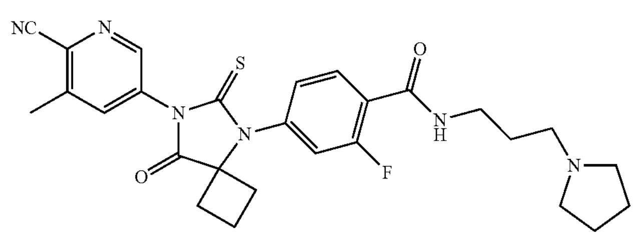 [SMILES: Cc1cc(N2C(=O)C3(CCC3)N(c3ccc(C(=O)NCCCN4CCCC4)c(F)c3)C2=S)cnc1C#N] | 521.9 |
| 276 | 4-(7-(6-Cyano-5-(trifluoromethyl)pyridin-3-yl)-8-oxo-6-thioxo-5,7-diazaspiro[3.4]octan-5-yl)-2-fluoro-N-(1-methylpiperidin-4-yl)benzamide | 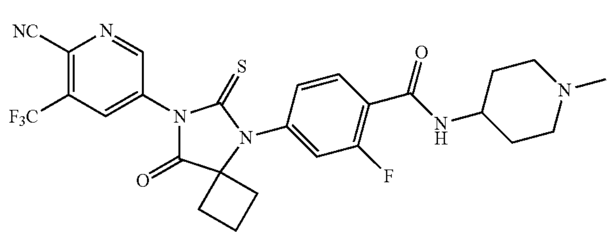 [SMILES: CN1CCC(NC(=O)c2ccc(N3C(=S)N(c4cnc(C#N)c(C(F)(F)F)c4)C(=O)C34CCC4)cc2F)CC1] | 561.1 |

TABLE 1-continued

| Cmpd. | Name | Structure | LCMS* [M + 1]+ |
|---|---|---|---|
| 277 | N-Butyl-4-(7-(6-cyano-5-(trifluoromethyl)pyridin-3-yl)-8-oxo-6-thioxo-5,7-diazaspiro[3.4]octan-5-yl)-2-fluorobenzamide | 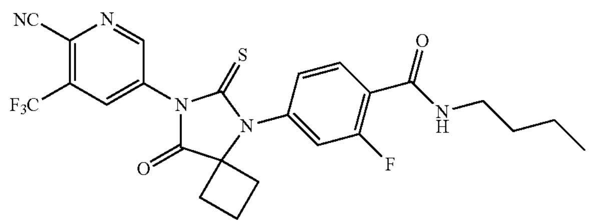 [SMILES: CCCCNC(=O)c1ccc(N2C(=S)N(c3cnc(C#N)c(C(F)(F)F)c3)C(=O)C23CCC3)cc1F] | 520.0 |
| 278 | 4-(7-(6-Cyano-5-(trifluoromethyl)pyridin-3-yl)-8-oxo-6-thioxo-5,7-diazaspiro[3.4]octan-5-yl)-2-fluoro-N-propylbenzamide | 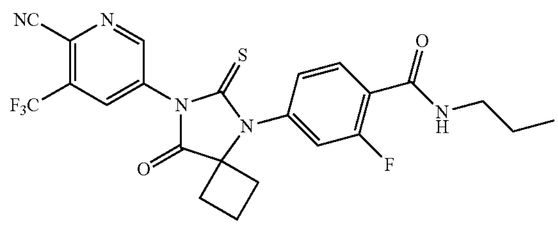 [SMILES: CCCNC(=O)c1ccc(N2C(=S)N(c3cnc(C#N)c(C(F)(F)F)c3)C(=O)C23CCC3)cc1F] | 506.1 |
| 279 | 4-(7-(6-Cyano-5-(trifluoromethyl)pyridin-3-yl)-8-oxo-6-thioxo-5,7-diazaspiro[3.4]octan-5-yl)-2-fluoro-N-isopropylbenzamide | 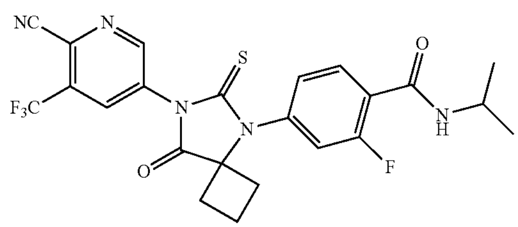 [SMILES: CC(C)NC(=O)c1ccc(N2C(=S)N(c3cnc(C#N)c(C(F)(F)F)c3)C(=O)C23CCC3)cc1F] | 506.1 |
| 280 | 4-(7-(6-Cyano-5-(trifluoromethyl)pyridin-3-yl)-8-oxo-6-thioxo-5,7-diazaspiro[3.4]octan-5-yl)-2-fluoro-N-isobutylbenzamide | 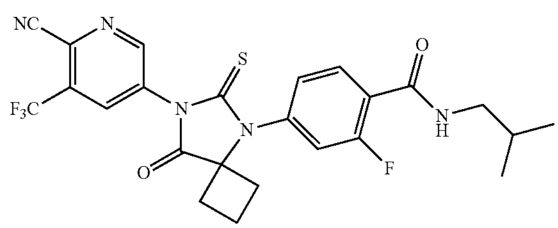 [SMILES: CC(C)CNC(=O)c1ccc(N2C(=S)N(c3cnc(C#N)c(C(F)(F)F)c3)C(=O)C23CCC3)cc1F] | 520.0 |
| 281 | 4-(7-(6-Cyano-5-(trifluoromethyl)pyridin-3-yl)-8-oxo-6-thioxo-5,7-diazaspiro[3.4]octan-5-yl)-2-fluoro-N-(prop-2-yn-1-yl)benzamide | 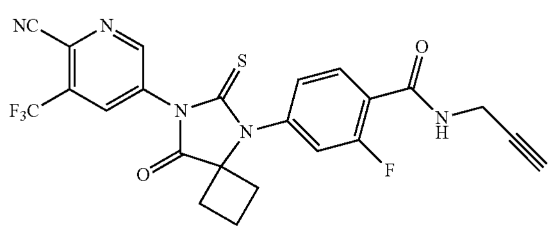 [SMILES: C#CCNC(=O)c1ccc(N2C(=S)N(c3cnc(C#N)c(C(F)(F)F)c3)C(=O)C23CCC3)cc1F] | 502.0 |
| 282 | 4-(7-(6-Cyano-5-(trifluoromethyl)pyridin-3-yl)-8-oxo-6-thioxo-5,7-diazaspiro[3.4]octan-5-yl)-2-fluoro-N-isopentylbenzamide | 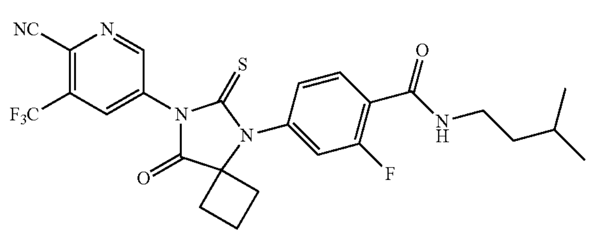 [SMILES: CC(C)CCNC(=O)c1ccc(N2C(=S)N(c3cnc(C#N)c(C(F)(F)F)c3)C(=O)C23CCC3)cc1F] | 532.1 |

TABLE 1-continued

| Cmpd. | Name | Structure | LCMS* [M + 1]+ |
|---|---|---|---|
| 283 | 4-(7-(6-Cyano-5-(trifluoromethyl)pyridin-3-yl)-8-oxo-6-thioxo-5,7-diazaspiro[3.4]octan-5-yl)-N-(cyclopentylmethyl)-2-fluorobenzamide | 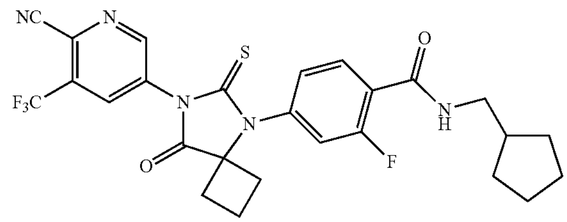 [SMILES: N#Cc1ncc(N2C(=O)C3(CCC3)N(c3ccc(C(=O)NCC4CCCC4)c(F)c3)C2=S)cc1C(F)(F)F] | 546.0 |
| 284 | 4-(7-(6-Cyano-5-(trifluoromethyl)pyridin-3-yl)-8-oxo-6-thioxo-5,7-diazaspiro[3.4]octan-5-yl)-N-cyclopropyl-2-fluorobenzamide | 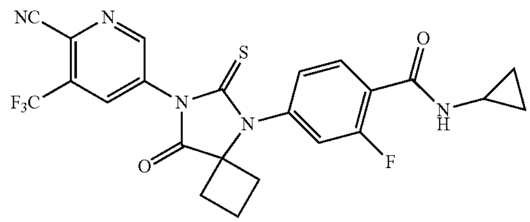 [SMILES: N#Cc1ncc(N2C(=O)C3(CCC3)N(c3ccc(C(=O)NC4CC4)c(F)c3)C2=S)cc1C(F)(F)F] | 504.0 |
| 285 | 4-(7-(6-Cyano-5-(trifluoromethyl)pyridin-3-yl)-8-oxo-6-thioxo-5,7-diazaspiro[3.4]octan-5-yl)-2-fluoro-N-(2-hydroxy-2-methylpropyl)benzamide | 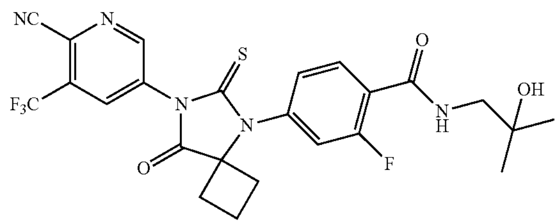 [SMILES: CC(C)(O)CNC(=O)c1ccc(N2C(=S)N(c3cnc(C#N)c(C(F)(F)F)c3)C(=O)C23CCC3)cc1F] | 519.0 (—OH) |
| 286 | N-(tert-Butyl)-4-(7-(6-cyano-5-(trifluoromethyl)pyridin-3-yl)-8-oxo-6-thioxo-5,7-diazaspiro[3.4]octan-5-yl)-2-fluorobenzamide | 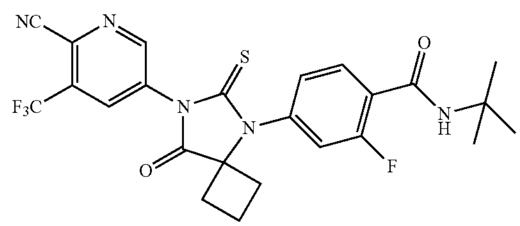 | 520.0 |
| 287 | N-(2-Chlorobenzyl)-4-(7-(6-cyano-5-(trifluoromethyl)pyridin-3-yl)-8-oxo-6-thioxo-5,7-diazaspiro[3.4]octan-5-yl)-2-fluorobenzamide | 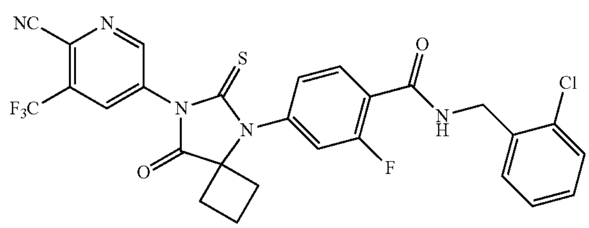 [SMILES: N#Cc1ncc(N2C(=O)C3(CCC3)N(c3ccc(C(=O)NCc4ccccc4Cl)c(F)c3)C2=S)cc1C(F)(F)F] | 588.4 |
| 288 | N-(3-Chlorobenzyl)-4-(7-(6-cyano-5-(trifluoromethyl)pyridin-3-yl)-8-oxo-6-thioxo-5,7-diazaspiro[3.4]octan-5-yl)-2-fluorobenzamide | 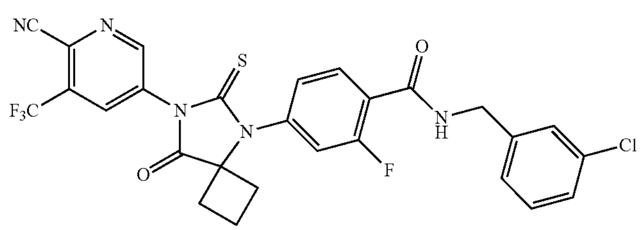 [SMILES: N#Cc1ncc(N2C(=O)C3(CCC3)N(c3ccc(C(=O)NCc4cccc(Cl)c4)c(F)c3)C2=S)cc1C(F)(F)F] | 588.4 |
| 289 | N-(4-Chlorobenzyl)-4-(7-(6-cyano-5-(trifluoromethyl)pyridin-3-yl)-8-oxo-6-thioxo-5,7-diazaspiro[3.4]octan-5-yl)-2-fluorobenzamide | 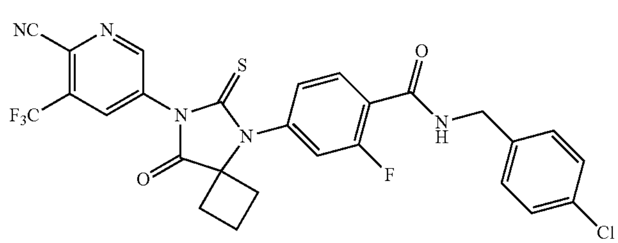 [SMILES: N#Cc1ncc(N2C(=O)C3(CCC3)N(c3ccc(C(=O)NCc4ccc(Cl)cc4)c(F)c3)C2=S)cc1C(F)(F)F] | 588.4 |

TABLE 1-continued

| Cmpd. | Name | Structure | LCMS* [M + 1]+ |
|---|---|---|---|
| 290 | 4-(7-(6-Cyano-5-(trifluoromethyl)pyridin-3-yl)-8-oxo-6-thioxo-5,7-diazaspiro[3.4]octan-5-yl)-2-fluoro-N-(pyrazin-2-ylmethyl)benzamide | 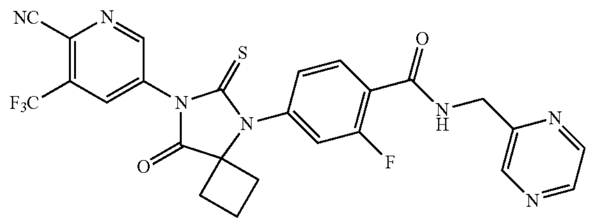 [SMILES: N#Cc1ncc(N2C(=O)C3(CCC3)N(c3ccc(C(=O)NCc4cnccn4)c(F)c3)C2=S)cc1C(F)(F)F] | 556.1 |
| 291 | 4-(7-(6-Cyano-5-(trifluoromethyl)pyridin-3-yl)-8-oxo-6-thioxo-5,7-diazaspiro[3.4]octan-5-yl)-2-fluoro-N-((5-methylfuran-2-yl)methyl)benzamide | 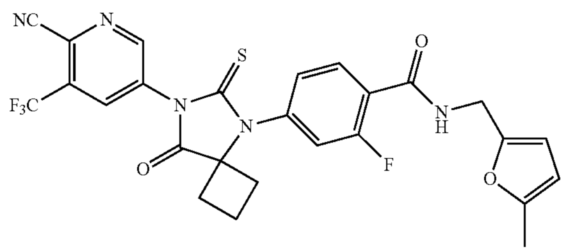 [SMILES: Cc1ccc(CNC(=O)c2ccc(N3C(=S)N(c4cnc(C#N)c(C(F)(F)F)c4)C(=O)C34CCC4)cc2F)o1] | 558.2 |
| 292 | 4-(4-(7-(6-Cyano-5-(trifluoromethyl)pyridin-3-yl)-8-oxo-6-thioxo-5,7-diazaspiro[3.4]octan-5-yl)phenyl)-N-phenylbutanamide | 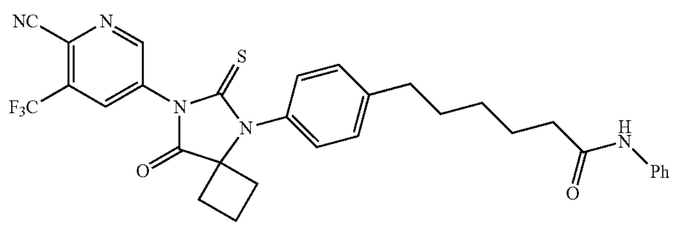 [SMILES: N#Cc1ncc(N2C(=O)C3(CCC3)N(c3ccc(CCCCCC(=O)Nc4ccccc4)cc3)C2=S)cc1C(F)(F)F] | 564.0 |
| 293 | 4-(7-(6-Cyano-5-methylpyridin-3-yl)-8-oxo-6-thioxo-5,7-diazaspiro[3.4]octan-5-yl)-2-fluoro-N-(4-fluorobenzyl)benzamide | 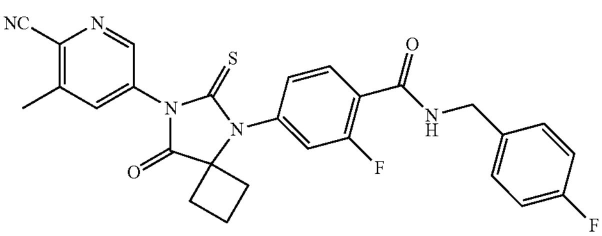 [SMILES: Cc1cc(N2C(=O)C3(CCC3)N(c3ccc(C(=O)NCc4ccc(F)cc4)c(F)c3)C2=S)cnc1C#N] | 518.1 |
| 294 | N-(2-Chlorophenyl)-4-(7-(6-cyano-5-methylpyridin-3-yl)-8-oxo-6-thioxo-5,7-diazaspiro[3.4]octan-5-yl)-2-fluorobenzamide | 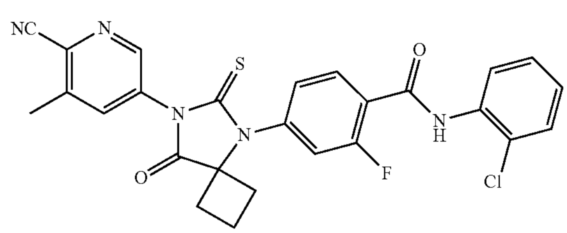 [SMILES: Cc1cc(N2C(=O)C3(CCC3)N(c3ccc(C(=O)Nc4ccccc4Cl)c(F)c3)C2=S)cnc1C#N] | 520.1 |
| 295 | N-(3-Chlorophenyl)-4-(7-(6-cyano-5-methylpyridin-3-yl)-8-oxo-6-thioxo-5,7-diazaspiro[3.4]octan-5-yl)-2-fluorobenzamide | 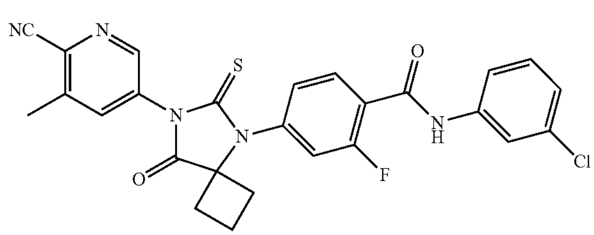 [SMILES: Cc1cc(N2C(=O)C3(CCC3)N(c3ccc(C(=O)Nc4cccc(Cl)c4)c(F)c3)C2=S)cnc1C#N] | 520.1 |

TABLE 1-continued

| Cmpd. | Name | Structure | LCMS* [M + 1]+ |
|---|---|---|---|
| 296 | N-(4-Chlorophenyl)-4-(7-(6-cyano-5-methylpyridin-3-yl)-8-oxo-6-thioxo-5,7-diazaspiro[3.4]octan-5-yl)-2-fluorobenzamide | 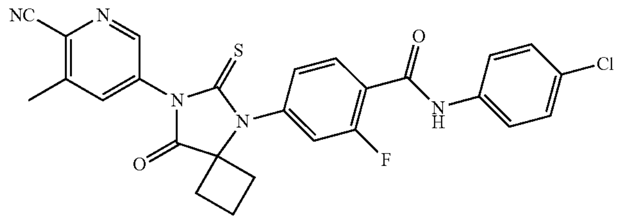 [SMILES: Cc1cc(N2C(=O)C3(CCC3)N(c3ccc(C(=O)Nc4ccc(Cl)cc4)c(F)c3)C2=S)cnc1C#N] | 520.1 |
| 297 | 4-(7-(6-Cyano-5-methylpyridin-3-yl)-8-oxo-6-thioxo-5,7-diazaspiro[3.4]octan-5-yl)-2-fluoro-N-(2-fluorophenyl)benzamide | 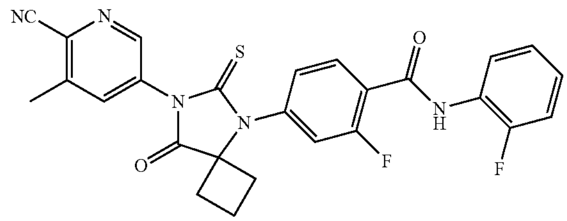 | 504.2 |
| 298 | 4-(7-(6-Cyano-5-methylpyridin-3-yl)-8-oxo-6-thioxo-5,7-diazaspiro[3.4]octan-5-yl)-2-fluoro-N-(3-fluorophenyl)benzamide | 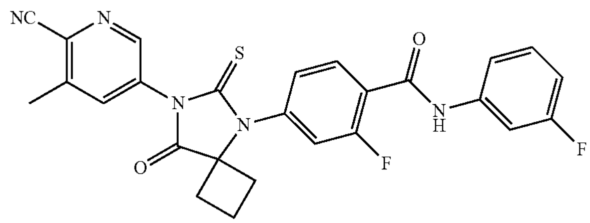 [SMILES: Cc1cc(N2C(=O)C3(CCC3)N(c3ccc(C(=O)Nc4cccc(F)c4)c(F)c3)C2=S)cnc1C#N] | 504.1 |
| 299 | 4-(7-(6-Cyano-5-methylpyridin-3-yl)-8-oxo-6-thioxo-5,7-diazaspiro[3.4]octan-5-yl)-2-fluoro-N-(4-fluorophenyl)benzamide | 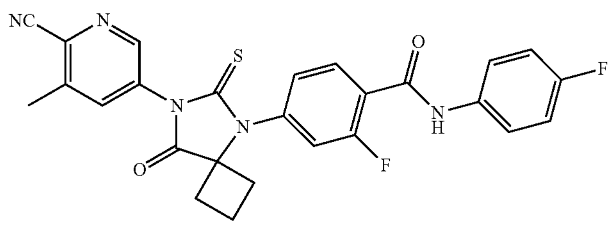 [SMILES: Cc1cc(N2C(=O)C3(CCC3)N(c3ccc(C(=O)Nc4ccc(F)cc4)c(F)c3)C2=S)cnc1C#N] | 503.1 |
| 300 | 4-(7-(6-cyano-5-methylpyridin-3-yl)-8-oxo-6-thioxo-5,7-diazaspiro[3.4]octan-5-yl)-2-fluoro-N-(oxazol-2-yl)benzamide | 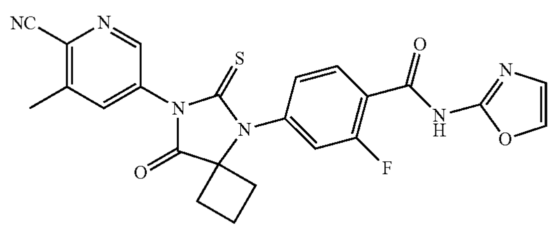 | 477.1 |
| 301 | 4-(7-(6-Cyano-5-methylpyridin-3-yl)-8-oxo-6-thioxo-5,7-diazaspiro[3.4]octan-5-yl)-2-fluoro-N-(thiazol-2-yl)benzamide | 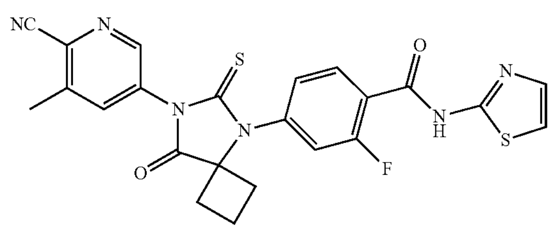 [SMILES: Cc1cc(N2C(=O)C3(CCC3)N(c3ccc(C(=O)Nc4ncco4)c(F)c3)C2=S)cnc1C#N] | 493.1 |
| 302 | 4-(7-(6-Cyano-5-methylpyridin-3-yl)-8-oxo-6-thioxo-5,7-diazaspiro[3.4]octan-5-yl)-2-fluoro-N-(1-methyl-1H-pyrazol-5-yl)benzamide | 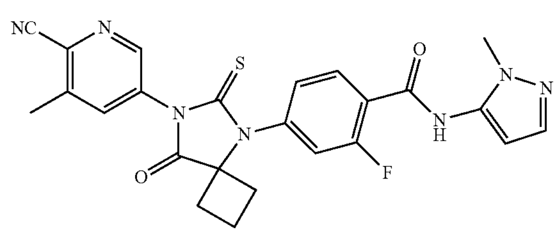 [SMILES: Cc1cc(N2C(=O)C3(CCC3)N(c3ccc(C(=O)Nc4ccnn4C)c(F)c3)C2=S)cnc1C#N] | 490.9 |

TABLE 1-continued

| Cmpd. | Name | Structure | LCMS* [M + 1]+ |
|---|---|---|---|
| 303 | 4-(7-(6-Cyano-5-methylpyridin-3-yl)-8-oxo-6-thioxo-5,7-diazaspiro[3.4]octan-5-yl)-2-fluoro-N-(1-methyl-1H-pyrazol-3-yl)benzamide | 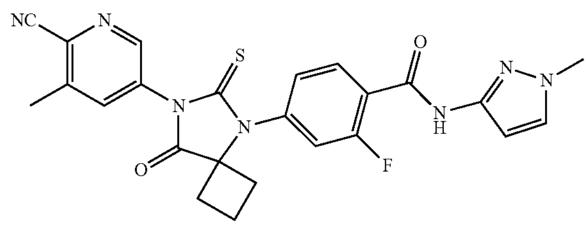 | 490.2 |
| 304 | 4-(7-(6-Cyano-5-methylpyridin-3-yl)-8-oxo-6-thioxo-5,7-diazaspiro[3.4]octan-5-yl)-2-fluoro-N-(6-methylpyridin-3-yl)benzamide | 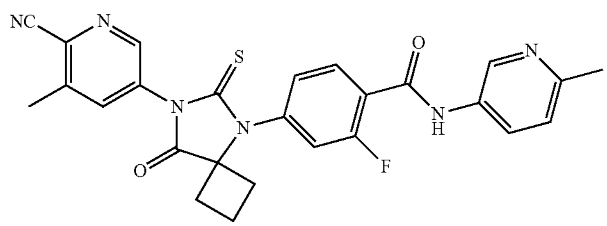 | 501.2 |
| 305 | 4-(7-(6-Cyano-5-methylpyridin-3-yl)-8-oxo-6-thioxo-5,7-diazaspiro[3.4]octan-5-yl)-2-fluoro-N-(5-fluoropyridin-3-yl)benzamide | 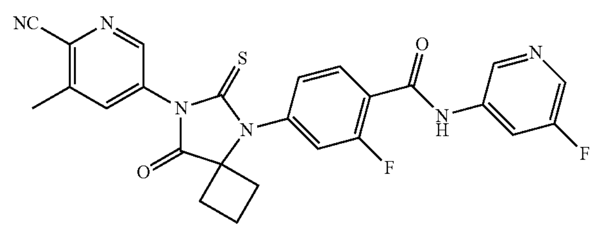 | 505.1 |
| 306 | 4-(7-(6-Cyano-5-(trifluoromethyl)pyridin-3-yl)-8-oxo-6-thioxo-5,7-diazaspiro[3.4]octan-5-yl)-2-fluoro-N-(3-hydroxypropyl)benzamide | 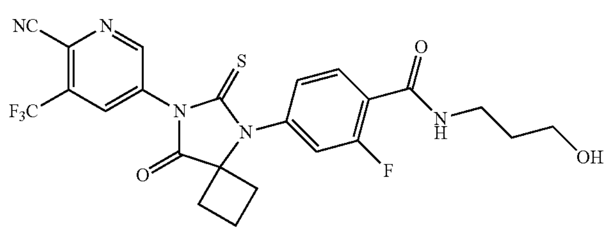 [SMILES: N#Cc1ncc(N2C(=O)C3(CCC3)N(c3ccc(C(=O)NCCCO)c(F)c3)C2=S)cc1C(F)(F)F] | 521.9 |
| 307 | 4-(7-(6-Cyano-5-(trifluoromethyl)pyridin-3-yl)-8-oxo-6-thioxo-5,7-diazaspiro[3.4]octan-5-yl)-N-(3-(cyclopentyl(methyl)amino)propyl)-2-fluorobenzamide | 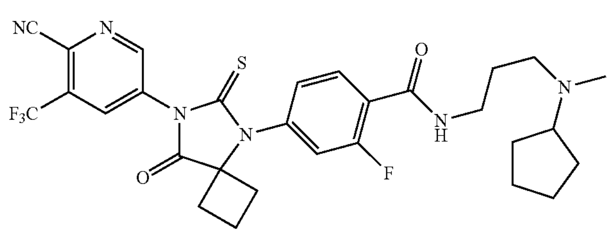 [SMILES: CN(CCCNC(=O)c1ccc(N2C(=S)N(c3cnc(C#N)c(C(F)(F)F)c3)C(=O)C23CCC3)cc1F)C1CCCC1] | 603.2 |
| 308 | 4-(7-(6-Cyano-5-(trifluoromethyl)pyridin-3-yl)-8-oxo-6-thioxo-5,7-diazaspiro[3.4]octan-5-yl)-2-fluoro-N-(3-(2-oxopyrrolidin-1-yl)propyl)benzamide | 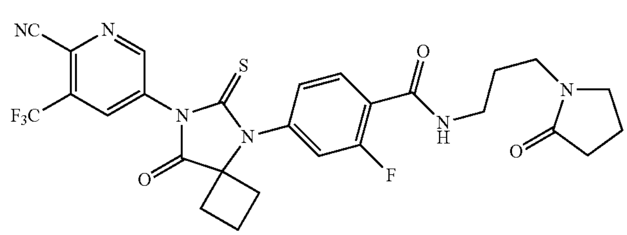 [SMILES: N#Cc1ncc(N2C(=O)C3(CCC3)N(c3ccc(C(=O)NCCCN4CCCC4=O)c(F)c3)C2=S)cc1C(F)(F)F] | 589.0 |

TABLE 1-continued

| Cmpd. | Name | Structure | LCMS* [M + 1]+ |
|---|---|---|---|
| 309 | 5-(5-(3-Fluoro-4-(2-(4-methylpiperazin-1-yl)-2-oxoethoxy)phenyl)-8-oxo-6-thioxo-5,7-diazaspiro[3.4]octan-7-yl)-3-(trifluoromethyl)picolinonitrile | 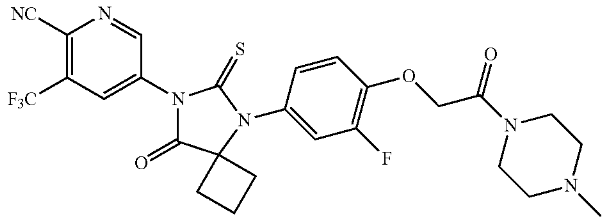 [SMILES: CN1CCN(C(=O)COc2ccc(N3C(=S)N(c4cnc(C#N)c(C(F)(F)F)c4)C(=O)C34CCC4)cc2F)CC1] | 577.1 |
| 310 | 4-(7-(6-Cyano-5-methylpyridin-3-yl)-8-oxo-6-thioxo-5,7-diazaspiro[3.4]octan-5-yl)-2-fluoro-N-(tetrahydro-2H-pyran-4-yl)benzamide | 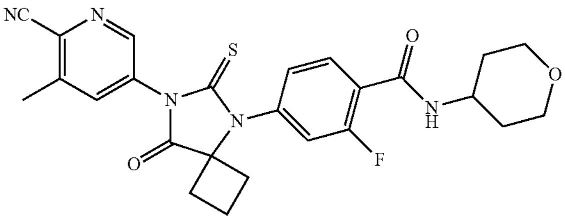 [SMILES: Cc1cc(N2C(=O)C3(CCC3)N(c3ccc(C(=O)NC4CCOCC4)c(F)c3)C2=S)cnc1C#N] | 494.1 |
| 311 | 4-(7-(6-Cyano-5-methylpyridin-3-yl)-8-oxo-6-thioxo-5,7-diazaspiro[3.4]octan-5-yl)-2-fluoro-N-((tetrahydro-2H-pyran-4-yl)methyl)benzamide | 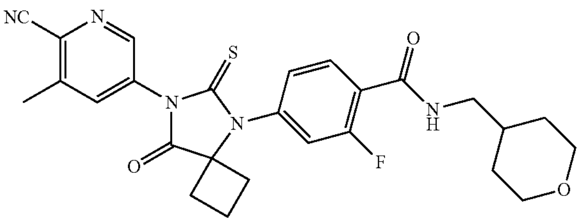 [SMILES: Cc1cc(N2C(=O)C3(CCC3)N(c3ccc(C(=O)NCC4CCOCC4)c(F)c3)C2=S)cnc1C#N] | 508.0 |
| 312 | 4-(7-(6-Cyano-5-(trifluoromethyl)pyridin-3-yl)-6,8-dioxo-5,7-diazaspiro[3.4]octan-5-yl)-2-fluoro-N-methylbenzamide | 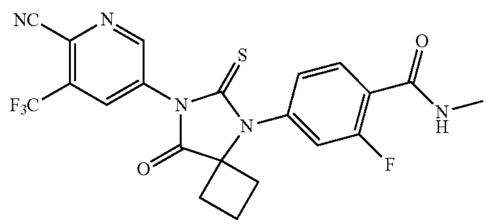 [SMILES: CNC(=O)c1ccc(N2C(=S)N(c3cnc(C#N)c(C(F)(F)F)c3)C(=O)C23CCC3)cc1F] | 462.6 |
| 313 | 4-(7-(6-Cyano-5-(trifluoromethyl)pyridin-3-yl)-8-oxo-6-thioxo-5,7-diazaspiro[3.4]octan-5-yl)-N-(3-(3,3-difluoropyrrolidin-1-yl)propyl)-2-fluorobenzamide | 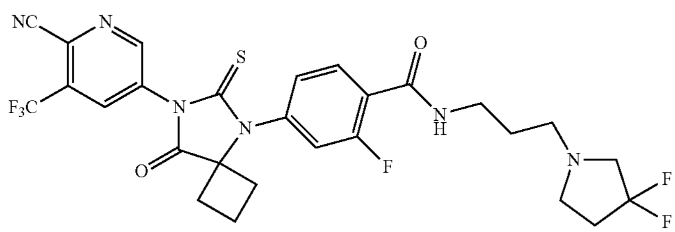 [SMILES: N#Cc1ncc(N2C(=O)C3(CCC3)N(c3ccc(C(=O)NCCCN4CCC(F)(F)C4)c(F)c3)C2=S)cc1C(F)(F)F] | 611.1 |

*mass spectrometric data

Compounds disclosed herein are AR modulators. In specific embodiments, compounds disclosed herein are AR inverse agonists, AR antagonists, AR degraders, AR trafficking modulators and/or AR DNA-binding inhibitors. In some embodiments, compounds disclosed herein are AR inverse agonists. In some embodiments, compounds disclosed herein are AR antagonists. In some embodiments, compounds disclosed herein are AR degraders. In some embodiments, compounds disclosed herein are AR trafficking modulators. In some embodiments, compounds disclosed herein are AR DNA-binding inhibitors. The overall profile of an AR modulator for the treatment of prostate cancer includes one or more of the foregoing profiles of an AR modulator.

In some embodiments, compounds disclosed herein have the following properties: full AR antagonist in prostate cancer cells, inverse AR agonist in prostate cancer cells, no AR agonist activity in prostate cancer cells, AR Degrader activity in prostate cancer cells, no antagonist or agonist or degrader activity in non-prostate cancer cells, inhibition of prostate cancer growth.

In some embodiments, compounds disclosed herein have the following properties: full AR antagonist in prostate cancer cells, inverse AR agonist in prostate cancer cells, no AR agonist activity in prostate cancer cells, AR Degrader activity in prostate cancer cells, and inhibition of prostate cancer growth.

In some embodiments, compounds disclosed herein have the following properties: full AR antagonist in prostate cancer cells, inverse AR agonist in prostate cancer cells, no AR agonist activity in prostate cancer cells, inhibition of prostate cancer growth In some embodiments, compounds disclosed herein have the following properties: full AR antagonist in prostate cancer cells, no AR agonist activity in prostate cancer cells, inhibition of prostate cancer growth In some embodiments, compounds disclosed herein have the following properties: AR Trafficking Modulator, no AR agonist activity in prostate cancer cells, no antagonist or agonist or degrader activity in non-prostate cancer cells, inhibition of prostate cancer growth In some embodiments, compounds disclosed herein have the following properties: AR Trafficking Modulator, no AR agonist activity in prostate cancer cells, inhibition of prostate cancer growth.

In some embodiments, the compound of Formula (I), (Ia), (II), (III), (IV), (V), (VI), (VII), (VIII), (VIIIa), (IX), (IXa) or (X) has minimal pro-convulsant activity and/or minimal impact on seizure threshold.

In some embodiments, the compound of Formula (I), (Ia), (II), (III), (IV), (V), (VI), (VII), (VIII), (VIIIa), (IX), (IXa) or (X) displays minimal modulation of the GABA-gated chloride channel.

In some embodiments, the compound of Formula (I), (Ia), (II), (III), (IV), (V), (VI), (VII), (VIII), (VIIIa), (IX), (IXa) or (X) displays minimal binding to the GABA-gated chloride channel.

In some embodiments, the compound of Formula (I), (Ia), (II), (III), (IV), (V), (VI), (VII), (VIII), (VIIIa), (IX), (IXa) or (X) has minimal antagonism of the GABA-gated chloride channel.

In some embodiments, the compound of Formula (I), (Ia), (II), (III), (IV), (V), (VI), (VII), (VIII), (VIIIa), (IX), (IXa) or (X) is an androgen receptor modulator with minimal interaction with a GABA-gated chloride channel.

In some embodiments, the compound of Formula (I), (Ia), (II), (III), (IV), (V), (VI), (VII), (VIII), (VIIIa), (IX), (IXa) or (X) is an androgen receptor modulator with minimal interaction with the $GABA_A$-gated chloride channel.

GABA assays are known and include, but are not limited to, those described in Ashok K. Mehta and Maharaj K. Ticku "Characterization of the Picrotoxin Site of $GABA_A$ Receptors" *Current Protocols in Pharmacology* (2000) 1.18.1-1.18.17; Copyright © 2000 by John Wiley & Sons, Inc., which is herein incorporated by reference.

In some embodiments, described herein is a method of treating cancer in a mammal comprising administering to the mammal a therapeutically effective amount of a compound, wherein the compound: a) is an androgen receptor inverse agonist; androgen receptor antagonist; is an androgen receptor degrader; is an androgen receptor trafficking modulator; is an androgen receptor DNA-binding inhibitor; or combinations thereof; and b) has minimal pro-convulsant activity and/or minimal impact on seizure threshold; displays minimal modulation of the GABA-gated chloride channel; displays minimal binding to the GABA-gated chloride channel; has minimal antagonism of the GABA-gated chloride channel; has minimal interaction with a GABA-gated chloride channel; or combinations thereof.

In some embodiments, the compound has minimal interaction with the $GABA_A$-gated chloride channel. In some embodiments, the cancer is prostate cancer. In some embodiments, the cancer is hormone refractory prostate cancer. In some embodiments, the compound is a compound of Formula (I), (Ia), (II), (III), (IV), (V), (VI), (VII), (VIII), (VIIIa), (IX), (IXa) or (X), or a pharmaceutically acceptable salt thereof or N-oxide thereof.

In some embodiments, described herein is a method of identifying an androgen receptor modulator comprising: 1) testing a compound for androgen receptor modulatory activity in an appropriate assay; and 2) testing the same compound for activity on the GABA-gated chloride channel in an appropriate in vitro or in vivo assay; wherein the compound is an androgen receptor modulator if it exhibits activity in 1) and exhibits any one of the following in 2): displays minimal modulation of the GABA-gated chloride channel; displays minimal binding to the GABA-gated chloride channel; has minimal antagonism of the GABA-gated chloride channel; or has minimal interaction with the GABA-gated chloride channel.

Synthesis of Compounds

Compounds of Formula (I), (Ia), (II), (III), (IV), (V), (VI), (VII), (VIII), (VIIIa), (IX), (IXa) and (X) described herein are synthesized using standard synthetic techniques or using methods known in the art in combination with methods described herein. In additions, solvents, temperatures and other reaction conditions presented herein may vary.

The starting material used for the synthesis of the compounds of Formula (I), (Ia), (II), (III), (IV), (V), (VI), (VII), (VIII), (VIIIa), (IX), (IXa) and (X) are either synthesized or obtained from commercial sources, such as, but not limited to, Sigma-Aldrich, Fluka, Acros Organics, Alfa Aesar, and the like. The compounds described herein, and other related compounds having different substituents are synthesized using techniques and materials described herein or otherwise known, including those found in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999). General methods for the preparation of compounds can be modified by the use of appropriate reagents and conditions for the introduction of the various moieties found in the formulae as provided herein.

In some embodiments, the compounds of Formula (I), (Ia), (II), (III), (IV), (V), (VI), (VII), (VIII), (VIIIa), (IX), (IXa) and (X) are prepared as outlined in the following Scheme.

Scheme 1:

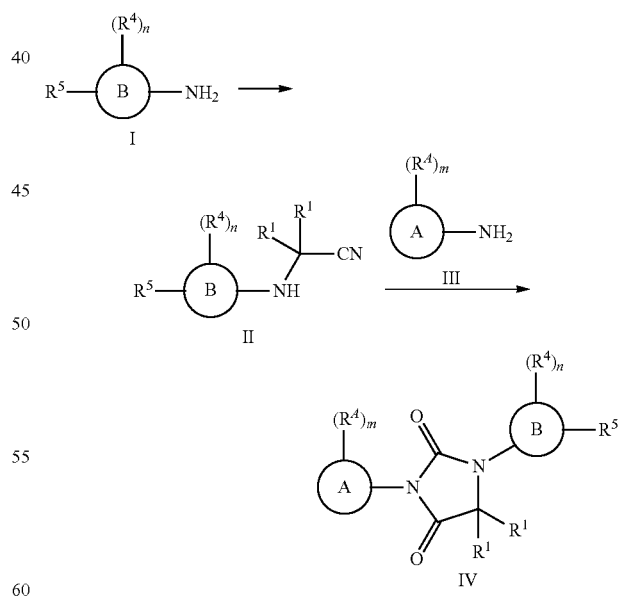

In some embodiments, amines of structure I are treated with ketones or aldehydes $R^1$—C(=O)—$R^1$ in the presence of NaCN, in a suitable solvent to provide compounds of structure II. In some embodiments, the suitable solvent is acetic acid. In some embodiments, the reaction is performed at a temperature from about 25° C. to about 80° C.

In some embodiments, compounds of structure II are treated with thiophosgene and compounds of structure III in a suitable solvent, followed by treated with an acid to provide thiohydantions of structure IV. In some embodiments, the suitable solvent is dimethylacetamide. In some embodiments, the reaction is heated to about 60° C. In some embodiments, treatment with an acid encompasses treatment with hydrochloric acid. In some embodiments, treatment with an acid encompasses treatment with HCl, MeOH, at reflux for 2 h.

In some embodiments, compounds disclosed herein are prepared as outlined in Scheme 2.

Scheme 2

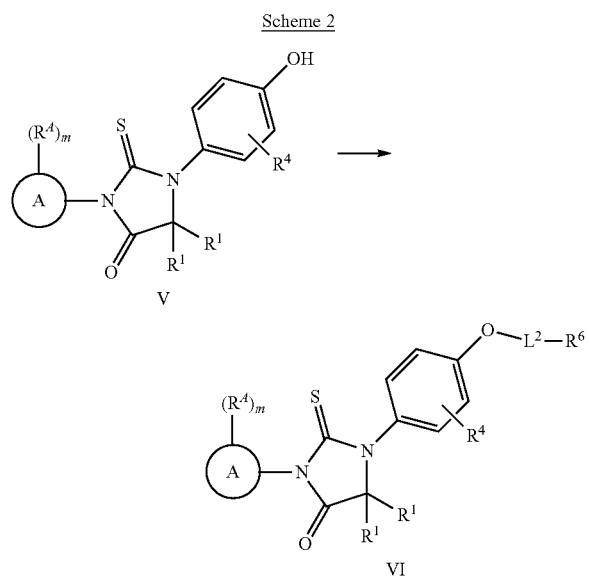

In some embodiments, compounds of structure V are elaborated into compounds of structure VI by reacting compounds of structure V with electrophiles or nucleophiles in the presence of a coupling agent. For example, in some embodiments, compounds of structure V are treated with compounds such as $R^6$-$L^2$-OH in the presence of DIAD and PPh$_3$ in a suitable solvent to provide compounds of structure VI. In some embodiments, the suitable solvent is tetrahydrofuran.

In some embodiments, compounds disclosed herein are prepared as outlined in Scheme 3.

Scheme 3

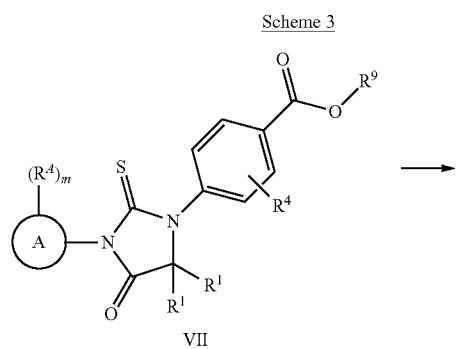

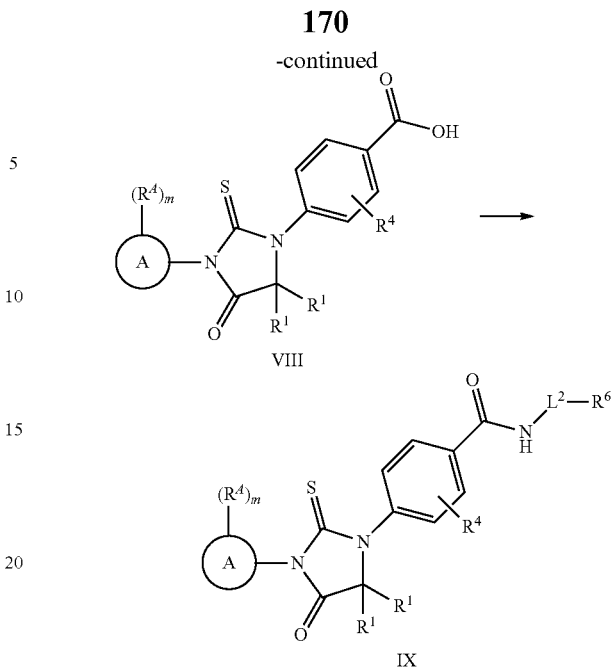

Treatment of esters of structure VII with a suitable base in a suitable solvent provides carboxylic acids of structure VIII. In some embodiments, the suitable base is lithium hydroxide. In some embodiments, the suitable solvent is tetrahydrofuran. Carboxylic acids of structure VIII are then coupled with a variety of agents to provide compounds disclosed herein. In some embodiments, carboxylic acids of structure VIII are treated with amines $R^6$-$L^2$-NH$_2$ in the presence of a coupling reagent to provide amides of structure IX. In some embodiments, carboxylic acids of structure VIII are treated with alcohols $R^6$-$L^2$-OH in the presence of a coupling reagent to provide esters as described herein. In some embodiments, the coupling reagent is EDC, DCC, BOP, HATU or the like. In some embodiments, the coupling reaction is performed in a solvent selected from dichloromethane, dichloroethane, tetrahydrofuran, dimethoxyethane, dimethylformamide or the like in the presence of a base. Suitable bases include, but are not limited to, triethylamine, diisopropylethylamine, N-methylmorpholine, pyridine or the like.

In one aspect, compounds of Formula (I), (Ia), (II), (III), (IV), (V), (VI), (VII), (VIII), (VIIIa), (IX), (IXa) and (X) are synthesized as outlined in the Examples.

Throughout the specification, groups and substituents thereof are chosen by one skilled in the field to provide stable moieties and compounds.

A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Further Forms of Compounds

In one aspect, compounds of Formula (I), (Ia), (II), (III), (IV), (V), (VI), (VII), (VIII), (VIIIa), (IX), (IXa) and (X) possess one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds of Formula (I), (Ia), (II), (III), (IV), (V), (VI), (VII), (VIII), (VIIIa), (IX), (IXa) and (X) are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

The methods and compositions described herein include the use of amorphous forms as well as crystalline forms (also known as polymorphs). In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design prodrugs of the compound is possible. (see, for example, Nogrady (1985) *Medicinal Chemistry A Biochemical Approach*, Oxford University Press, New York, pages 388-392; Silverman (1992), *The Organic Chemistry of Drug Design and Drug Action*, Academic Press, Inc., San Diego, pages 352-401, Rooseboom et al., *Pharmacological Reviews*, 56:53-102, 2004; Aesop Cho, "Recent Advances in Oral Prodrug Discovery", *Annual Reports in Medicinal Chemistry, Vol.* 41, 395-407, 2006; T. Higuchi and V. Stella, *Pro-drugs as Novel Delivery Systems*, Vol. 14 of the A.C.S. Symposium Series).

Prodrug forms of the herein described compounds, wherein the prodrug is metabolized in vivo to produce a compound of Formula (I), (Ia), (II), (III), (IV), (V), (VI), (VII), (VIII), (VIIIa), (IX), (IXa) or (X) as set forth herein are included within the scope of the claims. In some cases, some of the herein-described compounds may be a prodrug for another derivative or active compound.

In some embodiments, sites on the aromatic ring portion of compounds of Formula (I), (Ia), (II), (III), (IV), (V), (VI), (VII), (VIII), (VIIIa), (IX), (IXa) and (X) are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^3H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula (I), (Ia), (II), (III), (IV), (V), (VI), (VII), (VIII), (VIIIa), (IX), (IXa) or (X) with acids. Pharmaceutically acceptable salts are also obtained by reacting a compound of Formula (I), (Ia), (II), (III), (IV), (V), (VI), (VII), (VIII), (VIIIa), (IX), (IXa) or (X) with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Compounds described herein, such as compounds of Formula (I), (Ia), (II), (III), (IV), (V), (VI), (VII), (VIII), (VIIIa), (IX), (IXa) and (X), may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group may be a saturated alkyl group or the alkyl group may be an unsaturated alkyl group. The alkyl moiety, whether saturated or unsaturated, may be branched or straight chain. The "alkyl" group may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, and the like. In some embodiments, an alkyl is a $C_1$-$C_6$alkyl.

The term "alkylene" refers to a divalent alkyl radical. Any of the above mentioned monovalent alkyl groups may be an alkylene by abstraction of a second hydrogen atom from the alkyl. In one aspect, an alkelene is a $C_1$-$C_{10}$alkylene. In another aspect, an alkylene is a $C_1$-$C_6$alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and the like.

An "alkoxy" group refers to a (alkyl)O— group, where alkyl is as defined herein.

The term "alkylamine" refers to the —N(alkyl)$_x$H$_y$ group, where x and y are selected from the group x=1, y=1 and x=2, y=0.

The term "aromatic" refers to a planar ring having a delocalized π-electron system containing 4n+2π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from heterocyclic rings in which the ring backbone contains at least one atom which is different from carbon.

As used herein, the term "aryl" refers to an aromatic ring wherein each of the atoms forming the ring is a carbon atom. Aryl rings are formed by five, six, seven, eight, nine, or more than nine carbon atoms. Aryl groups are optionally substituted. In one aspect, an aryl is a phenyl or a naphthalenyl. In one aspect, an aryl is a phenyl. In one aspect, an aryl is a $C_6$-$C_{10}$aryl. Depending on the structure, an aryl group can be a monoradical or a diradical (i.e., an arylene group). Exemplary arylenes include, but are not limited to, phenyl-1,2-ene, phenyl-1,3-ene, and phenyl-1,4-ene.

The term "cycloalkyl" refers to a monocyclic or polycyclic aliphatic, non-aromatic radical, wherein each of the atoms forming the ring (i.e. skeletal atoms) is a carbon atom. Cycloalkyls may be saturated, or partially unsaturated. Cycloalkyls may be fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, and cyclooctyl. Cycloalkyl groups may be substituted or unsubstituted. Depending on the structure, a cycloalkyl group can be a monoradical or a diradical (i.e., an cycloalkylene group, such as, but not limited to, cyclopropan-1,1-diyl, cyclobutan-1,1-diyl, cyclopentan-1,1-diyl, cyclohexan-1,1-diyl, cyclohexan-1,4-diyl, cycloheptan-1,1-diyl, and the like). In one aspect, a cycloalkyl is a $C_3$-$C_6$cycloalkyl.

The term "halo" or, alternatively, "halogen" or "halide" means fluoro, chloro, bromo or iodo.

The term "haloalkyl" refers to an alkyl group in which one or more hydrogen atoms are replaced by one or more halide atoms. In one aspect, a haloalkyl is a $C_1$-$C_6$haloalkyl.

The term "haloalkylene" refers to an alkylene group in which one or more hydrogen atoms are replaced by one or more halide atoms. In one aspect, a haloalkylene is a $C_1$-$C_6$haloalkylene.

The term "fluoroalkyl" refers to an alkyl in which one or more hydrogen atoms are replaced by a fluorine atom. In one aspect, a fluoralkyl is a $C_1$-$C_6$fluoroalkyl.

The term "fluoroalkylene" refers to an alkylene in which one or more hydrogen atoms are replaced by a fluorine atom. In one aspect, a fluoralkylene is a $C_1$-$C_6$fluoroalkylene.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. In one aspect, a heteroalkyl is a $C_1$-$C_6$heteroalkyl.

The term "heteroalkylene" refers to an alkylene group in which one or more skeletal atoms of the alkyl are selected from an atom other than carbon, e.g., oxygen, nitrogen, sulfur, phosphorus or combinations thereof. In one aspect, a heteroalkylene is a $C_1$-$C_6$heteroalkylene. Exemplary heteroalkylenes include, but are not limited to, —OCH$_2$—, —OCH(CH$_3$)—, —OC(CH$_3$)$_2$—, —OCH$_2$CH$_2$—, —OCH$_2$CH$_2$CH$_2$—, —CH$_2$O—, —CH(CH$_3$)O—, —C(CH$_3$)$_2$O—, —CH$_2$CH$_2$O—, —CH$_2$OCH$_2$—, —CH$_2$OCH$_2$CH$_2$—, —CH$_2$CH$_2$OCH$_2$—, —SCH$_2$—, —SCH(CH$_3$)—, —SC(CH$_3$)$_2$—, —SCH$_2$CH$_2$—, —CH$_2$S—, —CH(CH$_3$)S—, —C(CH$_3$)$_2$S—, —CH$_2$CH$_2$S—, —CH$_2$SCH$_2$—, —CH$_2$SCH$_2$CH$_2$—, —CH$_2$CH$_2$SCH$_2$—, —SO$_2$CH$_2$—, —SO$_2$CH(CH$_3$)—, —SO$_2$C(CH$_3$)$_2$—, —SO$_2$CH$_2$CH$_2$—, —CH$_2$SO$_2$—, —CH(CH$_3$)SO$_2$—, —C(CH$_3$)$_2$SO$_2$—, —CH$_2$CH$_2$SO$_2$—, —CH$_2$SO$_2$CH$_2$—, —CH$_2$SO$_2$CH$_2$CH$_2$—, —CH$_2$CH$_2$SO$_2$CH$_2$—, —NHCH$_2$—, —NHCH(CH$_3$)—, —NHC(CH$_3$)$_2$—, —NHCH$_2$CH$_2$—, —CH$_2$NH—, —CH(CH$_3$)NH—, —C(CH$_3$)$_2$NH—, —CH$_2$CH$_2$NH—, —CH$_2$NHCH$_2$—, —CH$_2$NHCH$_2$CH$_2$—, —CH$_2$CH$_2$NHCH$_2$—, and the like.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C— attached (or C-linked) or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may be substituted with one or two oxo (═O) moieties, such as pyrrolidin-2-one.

The terms "heteroaryl" or, alternatively, "heteroaromatic" refers to an aryl group that includes one or more ring heteroatoms selected from nitrogen, oxygen and sulfur. Illustrative examples of heteroaryl groups include the following moieties:

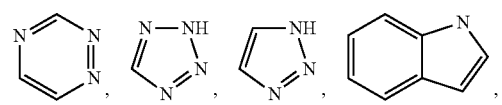

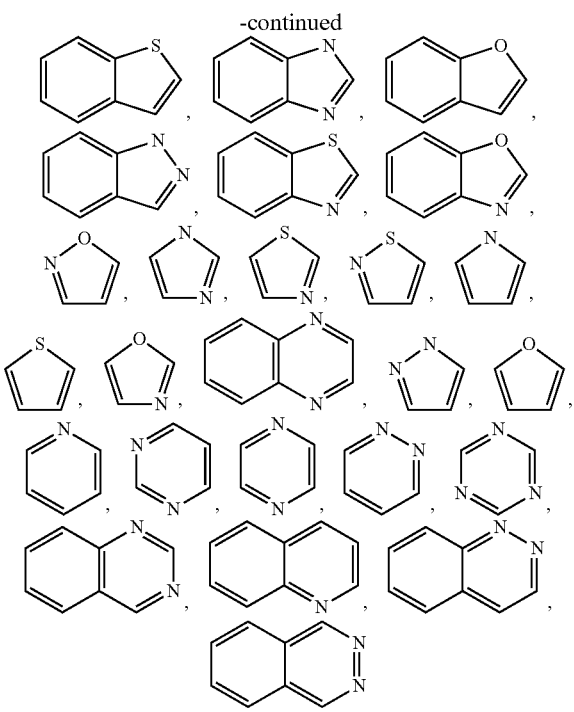

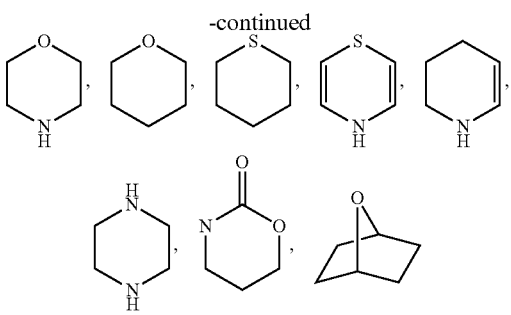

and the like. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. In some embodiments, a heteroaryl contains 0-3 N atoms in the ring. In some embodiments, a heteroaryl contains 1-3 N atoms in the ring. In some embodiments, a heteroaryl contains 0-3 N atoms, 0-1 O atoms, and 0-1 S atoms in the ring. In some embodiments, a heteroaryl is a monocyclic or bicyclic heteroaryl. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl. Depending on the structure, a heteroaryl group can be a monoradical or a diradical (i.e., a heteroarylene group).

A "heterocycloalkyl" or "heteroalicyclic" group refers to a cycloalkyl group that includes at least one heteroatom selected from nitrogen, oxygen and sulfur. The radicals may be fused with an aryl or heteroaryl. Illustrative examples of heterocycloalkyl groups, also referred to as non-aromatic heterocycles, include:

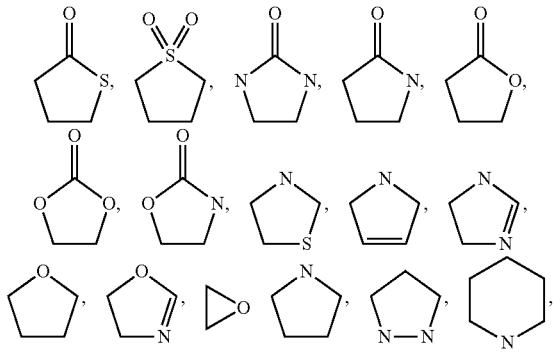

and the like. In some embodiments, the heterocycloalkyl is selected from oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. In some embodiments, the heterocycloalkyl is pyrrolidinyl, tetrahydrofuranyl, tetrahydrothienyl, tetrahydropyranyl, tetrahydrothiopyranyl, piperidinyl, morpholinyl, thiomorpholinyl, or piperazinyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

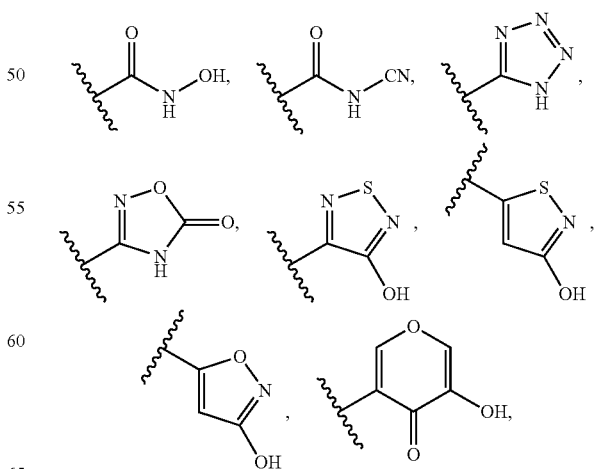

and the like.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, nitro, haloalkyl, fluoroalkyl, fluoroalkoxy, and amino, including mono- and di-substituted amino groups, and the protected derivatives thereof. By way of example optional substituents are independently selected from halide, —CN, —NO$_2$, and -LR, wherein each L is independently selected from a bond, —O—, —C(=O)—, —C(=O)O—, —S—, —S(=O)—, —S(=O)$_2$—, —NH—, —NHC(=O)—, —C(=O)NH—, S(=O)$_2$NH—, —NHS(=O)$_2$, —OC(=O)NH—, —NHC(=O)O—, or —(C$_1$-C$_6$alkylene)-; and each R is selected from H, alkyl, fluoroalkyl, heteroalkyl, cycloalkyl, aryl, heteroaryl, or heterocycloalkyl. In some embodiments, optional substituents are independently selected from halogen, —CN, —NH$_2$, —NH(CH$_3$), —N(CH$_3$)$_2$, —OH, alkyl, fluoroalkyl, heteroalkyl, cycloalkyl, heterocycloalkyl, aryl, heteroaryl, alkoxy, aryloxy, alkylthio, arylthio, alkylsulfoxide, arylsulfoxide, alkylsulfone, and arylsulfone. In some embodiments, optional substituents are independently selected from halogen, —CN, —NH$_2$, —NH(CH$_3$), —N(CH$_3$)$_2$, —OH, —CO$_2$H, —CO$_2$alkyl, —C(=O)alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, —S-alkyl, or —S(=O)$_2$alkyl. In some embodiments, optional substituents are independently selected from halogen, —CN, —NH$_2$, —NH(CH$_3$), —N(CH$_3$)$_2$, —OH, —CO$_2$H, —CO$_2$alkyl, —C(=O)alkyl, —C(=O)NH$_2$, —C(=O)NH(alkyl), —C(=O)N(alkyl)$_2$, alkyl, cycloalkyl, fluoroalkyl, heteroalkyl, alkoxy, and fluoroalkoxy. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —CH$_2$CF$_3$, —OCH$_3$, —OCH$_2$CH$_3$, and —OCF$_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, stereoselective synthesis and/or the separation of stereoisomers by chiral chromatographic columns.

The methods and formulations described herein include the use of N-oxides (if appropriate), crystalline forms (also known as polymorphs), or pharmaceutically acceptable salts of compounds having the structure of Formula (I), (Ia), (II), (III), (IV), (V), (VI), (VII), (VIII), (VIIIa), (IX), (IXa) or (X), as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, AR trafficking modulator, AR DNA-binding inhibitor. In some embodiments, a modulator is an antagonist. In some embodiments, a modulator is an inverse agonist, antagonist, degrader, AR trafficking modulator and/or a DNA binding inhibitor.

The term "antagonist" as used herein, refers to a small-molecule agent that binds to a nuclear hormone receptor and subsequently decreases the agonist induced transcriptional activity of the nuclear hormone receptor.

The term "agonist" as used herein, refers to a molecule agent that binds to a nuclear hormone receptor and subsequently increases nuclear hormone receptor transcriptional activity in the absence of a known agonist.

The term "inverse agonist" as used herein, refers to a molecule agent that binds to a nuclear hormone receptor and subsequently decreases the basal level of nuclear hormone receptor transcriptional activity that is present in the absence of a known agonist.

The term "degrader" as used herein, refers to a small molecule agent that binds to a nuclear hormone receptor and subsequently lowers the steady state protein levels of said receptor.

The term "AR trafficking modulator" as used herein, refers to a molecule agent that binds to a nuclear hormone receptor and subsequently alters the normal subcellular location of the receptor thereby interfering with its function and signaling.

The term "DNA-binding inhibitor" as used herein, refers to a molecule agent that binds to a nuclear hormone receptor and subsequently prevents DNA binding of the receptor thereby interfering with its function and signaling.

The term "AR-dependent", as used herein, refers to diseases or conditions that would not occur, or would not occur to the same extent, in the absence of androgen receptors.

The term "AR-mediated", as used herein, refers to diseases or conditions that might occur in the absence of androgen receptors but can occur in the presence of androgen receptors.

"Selective" with respect to androgen receptors means that the compound preferentially binds to androgen receptors versus other nuclear receptors. In some embodiments, a selective androgen receptor modulator preferentially binds to androgen receptors and displays little, if any, affinity to other nuclear receptors.

The term "cancer" as used herein refers to an abnormal growth of cells which tend to proliferate in an uncontrolled way and, in some cases, to metastasize (spread).

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), (Ia), (II), (III), (IV), (V), (VI), (VII), (VIII), (VIIIa), (IX), (IXa) or (X) and a co-agent, are both administered to a patient simultaneously in the form of a single entity or dosage. The term "non-fixed combination" means that the active ingredients, e.g. a compound of Formula (I), (Ia), (II), (III), (IV), (V), (VI), (VII), (VIII), (VIIIa), (IX), (IXa) or (X) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula (I), (Ia), (II), (III), (IV), (V), (VI), (VII), (VIII), (VIIIa), (IX), (IXa) or (X) and at least one pharmaceutically acceptable inactive ingredient. In some embodiments, the compounds described herein are administered as pharmaceutical compositions in which a compound of Formula (I), (Ia), (II), (III), (IV), (V), (VI), (VII), (VIII), (VIIIa), (IX), (IXa) or (X) is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I), (Ia), (II), (III), (IV), (V), (VI), (VII), (VIII), (VIIIa), (IX), (IXa) or (X) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to a mammal.

A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound of Formula (I), (Ia), (II), (III), (IV), (V), (VI), (VII), (VIII), (VIIIa), (IX), (IXa) or (X) are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), (Ia), (II), (III), (IV), (V), (VI), (VII), (VIII), (VIIIa), (IX), (IXa) or (X) as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

The pharmaceutical compositions described herein, which include a compound of Formula (I), (Ia), (II), (III), (IV), (V), (VI), (VII), (VIII), (VIIIa), (IX), (IXa) or (X) are formulated into any suitable dosage form, including but not limited to, aqueous oral dispersions, liquids, gels, syrups, elixirs, slurries, suspensions, solid oral dosage forms, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In some embodiments, the push-fit capsules do not include any other ingredient besides the capsule shell and the active ingredient. In soft capsules, the active compounds are dissolved or suspended in suitable liquids, such as fatty oils, liquid paraffin, or liquid polyethylene glycols. In some embodiments, stabilizers are added.

All formulations for oral administration are in dosages suitable for such administration.

In one aspect, solid oral soage forms are prepared by mixing a compound of Formula (I), (Ia), (II), (III), (IV), (V), (VI), (VII), (VIII), (VIIIa), (IX), (IXa) or (X) with one or more of the following: antioxidants, flavoring agents, and carrier materials such as binders, suspending agents, disintegration agents, filling agents, surfactants, solubilizers, stabilizers, lubricants, wetting agents, and diluents.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In still other embodiments, the pharmaceutical formulation is in the form of a tablet. In other embodiments, pharmaceutical formulations of the compound of Formula (I), (Ia), (II), (III), (IV), (V), (VI), (VII), (VIII), (VIIIa), (IX), (IXa) or (X) is in the form of a capsule.

In some embodiments, solid dosage forms, e.g., tablets, effervescent tablets, and capsules, are prepared by mixing particles of a compound of Formula (I), (Ia), (II), (III), (IV), (V), (VI), (VII), (VIII), (VIIIa), (IX), (IXa) or (X) with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

In some embodiments, tablets will include a film surrounding the final compressed tablet. In some embodiments, the film coating can provide a delayed release of the compound of Formula (I), (Ia), (II), (III), (IV), (V), (VI), (VII), (VIII), (VIIIa), (IX), (IXa) or (X) from the formulation. In other embodiments, the film coating aids in patient compliance (e.g., Opadry® coatings or sugar coating). Film coatings including Opadry® typically range from about 1% to about 3% of the tablet weight.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

In various embodiments, the particles of the compound of Formula (I), (Ia), (II), (III), (IV), (V), (VI), (VII), (VIII), (VIIIa), (IX), (IXa) or (X) and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In other embodiments, a powder including a compound of Formula (I), (Ia), (II), (III), (IV), (V), (VI), (VII), (VIII), (VIIIa), (IX), (IXa) or (X) is formulated to include one or more pharmaceutical excipients and flavors. Such a powder is prepared, for example, by mixing the the compound of Formula (I), (Ia), (II), (III), (IV), (V), (VI), (VII), (VIII), (VIIIa), (IX), (IXa) or (X) and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared. Effervescent salts have been used to disperse medicines in water for oral administration.

In some embodiments, the pharmaceutical solid oral dosage forms are formulated to provide a controlled release of the compound of Formula (I), (Ia), (II), (III), (IV), (V), (VI), (VII), (VIII), (VIIIa), (IX), (IXa) or (X). Controlled release refers to the release of the compound of Formula (I), (Ia), (II), (III), (IV), (V), (VI), (VII), (VIII), (VIIIa), (IX), (IXa) or (X) from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules, which include a compound of Formula (I), (Ia), (II), (III), (IV), (V), (VI), (VII), (VIII), (VIIIa), (IX), (IXa) or (X) that are coated or uncoated.

Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. Exemplary pulsatile dosage forms and methods of their manufacture are disclosed in U.S. Pat. Nos. 5,011,692, 5,017,381, 5,229,135, 5,840,329 and 5,837,284. In one embodiment, the pulsatile dosage form includes at least two groups of particles, (i.e. multiparticulate) each containing the formulation described herein. The first group of particles provides a substantially immediate dose of the compound of Formula (I), (Ia), (II), (III), (IV), (V), (VI), (VII), (VIII), (VIIIa), (IX), (IXa) or (X) upon ingestion by a mammal. The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or known in the art.

In some embodiments, pharmaceutical formulations are provided that include particles of a compound of Formula (I), (Ia), (II), (III), (IV), (V), (VI), (VII), (VIII), (VIIIa), (IX), (IXa) or (X) and at least one dispersing agent or suspending agent for oral administration to a subject. The formulations may be a powder and/or granules for suspension, and upon admixture with water, a substantially uniform suspension is obtained.

In one aspect, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the compound of Formula (I), (Ia), (II), (III), (IV), (V), (VI), (VII), (VIII), (VIIIa), (IX), (IXa) or (X), the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

Buccal formulations that include a compound of Formula (I), (Ia), (II), (III), (IV), (V), (VI), (VII), (VIII), (VIIIa), (IX), (IXa) or (X) are administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

In some embodiments, compounds of Formula (I), (Ia), (II), (III), (IV), (V), (VI), (VII), (VIII), (VIIIa), (IX), (IXa) or (X) are prepared as transdermal dosage forms. In one embodiments, the transdermal formulations described herein include at least three components: (1) a formulation of a compound of Formula (I), (Ia), (II), (III), (IV), (V), (VI), (VII), (VIII), (VIIIa), (IX), (IXa) or (X); (2) a penetration enhancer; and (3) an aqueous adjuvant. In some embodiments the transdermal formulations include additional components such as, but not limited to, gelling agents, creams and ointment bases, and the like. In some embodiments, the transdermal formulation further include a woven or nonwoven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of compounds described herein employ transdermal delivery devices and transdermal delivery patches and can be lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the compounds described herein can be accomplished by means of iontophoretic patches and the like. In one aspect, transdermal patches provide controlled delivery of the compound of Formula (I), (Ia), (II), (III), (IV), (V), (VI), (VII), (VIII), (VIIIa), (IX), (IXa) or (X). In one aspect, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In one aspect, a compound of Formula (I), (Ia), (II), (III), (IV), (V), (VI), (VII), (VIII), (VIIIa), (IX), (IXa) or (X) is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. In some embodiments, formulations suitable for subcutaneous injection also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. In some cases it is desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein are formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

Methods of Dosing and Treatment Regimens

In one embodiment, the compounds of Formula (I), (Ia), (II), (III), (IV), (V), (VI), (VII), (VIII), (VIIIa), (IX), (IXa) and (X) are used in the preparation of medicaments for the treatment of diseases or conditions in a mammal that would benefit from a reduction of androgen receptor activity. Methods for treating any of the diseases or conditions described herein in a mammal in need of such treatment, involves administration of pharmaceutical compositions that include at least one compound of Formula (I), (Ia), (II), (III), (IV), (V), (VI), (VII), (VIII), (VIIIa), (IX), (IXa) or (X) or a pharmaceutically acceptable salt, active metabolite, prodrug, or pharmaceutically acceptable solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), (Ia), (II), (III), (IV), (V), (VI), (VII), (VIII), (VIIIa), (IX), (IXa) or (X) in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously (or over a short period of time) or at appropriate intervals, for example as two, three, four or more sub-doses per day.

In one embodiment, the daily dosages appropriate for the compound of Formula (I), (Ia), (II), (III), (IV), (V), (VI), (VII), (VIII), (VIIIa), (IX), (IXa) or (X) described herein are from about 0.01 to about 10 mg/kg per body weight. In specific embodiments, an indicated daily dosage in a large mammal, including, but not limited to, humans, is in the range from about 0.5 mg to about 1000 mg, conveniently administered in divided doses, including, but not limited to, up to four times a day. In one embodiment, the daily dosage is administered in extended release form. In certain embodiments, suitable unit dosage forms for oral administration comprise from about 1 to 500 mg active ingredient. In other embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

Combination Treatments

In certain instances, it is appropriate to administer at least one compound of Formula (I), (Ia), (II), (III), (IV), (V), (VI), (VII), (VIII), (VIIIa), (IX), (IXa) or (X) in combination with another therapeutic agent.

In one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formula (I), (Ia), (II), (III), (IV), (V), (VI), (VII), (VIII), (VIIIa), (IX), (IXa) or (X) is co-administered with a second therapeutic agent, wherein the compound of Formula (I), (Ia), (II), (III), (IV), (V), (VI), (VII), (VIII), (VIIIa), (IX), (IXa) or (X) and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula (I), (Ia), (II), (III), (IV), (V), (VI), (VII), (VIII), (VIIIa), (IX), (IXa) or (X) is initiated prior to, during, or after treatment with a second agent described herein, and continues until any time during treatment with the second agent or after termination of treatment with the second agent. It also includes treatments in which a compound of Formula (I), (Ia), (II), (III), (IV), (V), (VI), (VII), (VIII), (VIIIa), (IX), (IXa) or (X) and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors. These factors include the disease, disorder or condition from which the subject suffers, as well as the age, weight, sex, diet, and medical condition of the subject. Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills). In one embodiment, one of the therapeutic agents is given in multiple doses, and in another, two (or more if present) are given as multiple doses. In some embodiments of non-simultaneous administration, the timing between the multiple doses vary from more than zero weeks to less than four weeks. In addition, the combination methods, compositions and formulations are not to be limited to the use of only two agents; the use of multiple therapeutic combinations is also envisioned.

The compounds of Formula (I), (Ia), (II), (III), (IV), (V), (VI), (VII), (VIII), (VIIIa), (IX), (IXa) and (X), as well as combination therapies that include compounds of Formula (I), (Ia), (II), (III), (IV), (V), (VI), (VII), (VIII), (VIIIa), (IX), (IXa) and (X), are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Exemplary Agent for Use in Combination Therapy

In some embodiments, methods for treatment of androgen receptor-dependent or androgen receptor-mediated conditions or diseases, such as proliferative disorders, including cancer, comprises administration to a mammal a compound of Formula (I), (Ia), (II), (III), (IV), (V), (VI), (VII), (VIII), (VIIIa), (IX), (IXa) or (X) in combination with at least one additional agent selected, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In one aspect, the compound of Formula (I), (Ia), (II), (III), (IV), (V), (VI), (VII), (VIII), (VIIIa), (IX), (IXa) or (X) is administered or formulated in combination with one or more anti-cancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, trastuzumab, BAY 11-7082, PKC412, or PD184352, paclitaxel, and analogs of paclitaxel. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with the compounds of Formula (I), (Ia), (II), (III), (IV), (V), (VI), (VII), (VIII), (VIIIa), (IX), (IXa) and (X) include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents for use in combination with the compounds of Formula (I), (Ia), (II), (III), (IV), (V), (VI), (VII), (VIII), (VIIIa), (IX), (IXa) and (X) include one or more of the following: abiraterone, adriamycin, dactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Yet other anticancer agents for use in combination with the compounds of Formula (I), (Ia), (II), (III), (IV), (V), (VI), (VII), (VIII), (VIIIa), (IX), (IXa) and (X) include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate, or pyrimidine analogs (e.g., Cytarabine), purine analogs (e.g., mercaptopurine, thioguanine, pentostatin).

Examples of natural products for use in combination with the compounds of Formula (I), (Ia), (II), (III), (IV), (V), (VI), (VII), (VIII), (VIIIa), (IX), (IXa) and (X) include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with the compounds of Formula (I), (Ia), (II), (III), (IV), (V), (VI), (VII), (VIII), (VIIIa), (IX), (IXa) and (X) include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.).

In some embodiments, compounds of Formula (I), (Ia), (II), (III), (IV), (V), (VI), (VII), (VIII), (VIIIa), (IX), (IXa) and (X) are used to treat cancer in combination with: an antiestrogen (e.g., tamoxifen), an antiandrogen (e.g., bicalutamide, flutamide), gonadotropin releasing hormone analog (e.g., leuprolide).

Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules include without limitation the following marketed drugs and drugs in development: Erbulozole, Dolastatin 10, Mivobulin isethionate, Vincristine, NSC-639829, Discodermolide, ABT-751, Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride, Epothilones (such as Epothilone A, Epothilone B, Epothilone C, Epothilone D, Epothilone E, Epothilone F, Epothilone B N-oxide, Epothilone A N-oxide, 16-aza-epothilone B, 21-aminoepothilone B, 21-hydroxyepothilone D, 26-fluoroepothilone, Auristatin PE, Soblidotin, Vincristine sulfate, Cryptophycin 52, Vitilevuamide, Tubulysin A, Canadensol, Centaureidin, Oncocidin A1 Fijianolide B, Laulimalide, Narcosine, Nascapine, Hemiasterlin, Vanadocene acetylacetonate, Indanocine Eleutherobins (such as Desmethyleleutherobin, Desaetyleleutherobin, Isoeleutherobin A, and Z-Eleutherobin), Caribaeoside, Caribaeolin, Halichondrin B, Diazonamide A, Taccalonolide A, Diozostatin, (−)-Phenylahistin, Myoseverin B, Resverastatin phosphate sodium.

In one aspect, a compound of Formula (I), (Ia), (II), (III), (IV), (V), (VI), (VII), (VIII), (VIIIa), (IX), (IXa) or (X) is co-administered with thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

In some embodiments, a compound of Formula (I), (Ia), (II), (III), (IV), (V), (VI), (VII), (VIII), (VIIIa), (IX), (IXa) or (X) is used in combination with anti-emetic agents to treat nausea or emesis, which may result from the use of a compound of Formula (I), (Ia), (II), (III), (IV), (V), (VI), (VII), (VIII), (VIIIa), (IX), (IXa) or (X), anti-cancer agent(s) and/or radiation therapy.

Anti-emetic agents include, but are not limited to: neurokinin-1 receptor antagonists, 5HT3 receptor antagonists (such as ondansetron, granisetron, tropisetron, Palonosetron, and zatisetron), $GABA_B$ receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

In some embodiments, a compound of Formula (I), (Ia), (II), (III), (IV), (V), (VI), (VII), (VIII), (VIIIa), (IX), (IXa) or (X) is used in combination with an agent useful in the treatment of anemia. Such an anemia treatment agent is, for example, a continuous eythropoiesis receptor activator (such as epoetin-α).

In some embodiments, a compound of Formula (I), (Ia), (II), (III), (IV), (V), (VI), (VII), (VIII), (VIIIa), (IX), (IXa) or (X) is used in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In some embodiments, a compound of Formula (I), (Ia), (II), (III), (IV), (V), (VI), (VII), (VIII), (VIIIa), (IX), (IXa) or (X) is administered with corticosteroids. Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In one embodiment, a compound of Formula (I), (Ia), (II), (III), (IV), (V), (VI), (VII), (VIII), (VIIIa), (IX), (IXa) or (X) is administered to a mammal in combination with a non-steroidal anti-inflammatory drug (NSAID). NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

In some embodiments, compounds of Formula (I), (Ia), (II), (III), (IV), (V), (VI), (VII), (VIII), (VIIIa), (IX), (IXa) and (X) are coadministered with analgesics.

In some embodiments, a compound of Formula (I), (Ia), (II), (III), (IV), (V), (VI), (VII), (VIII), (VIIIa), (IX), (IXa) or (X) is used in combination with radiation therapy (or radiotherapy). Radiation therapy is the treatment of cancer and other diseases with ionizing radiation. Radiation therapy can be used to treat localized solid tumors, such as cancers of the skin, tongue, larynx, brain, breast, prostate, colon, uterus and/or cervix. It can also be used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to α, β, and γ radiation and ultraviolet light.

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

EXAMPLES

These examples are provided for illustrative purposes only and not to limit the scope of the claims provided herein.

Synthesis of Compounds

Intermediate 1

5-Amino-3-(trifluoromethyl)picolinonitrile

Step 1: 5-Iodo-3-(trifluoromethyl)pyridin-2-ol

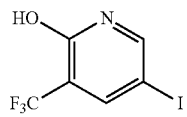

A mixture of 5-iodo-3-(trifluoromethyl)pyridin-2-ol (21.4 g, 0.13 mmol) and NIS (29.5 g, 0.13 mmol) in acetonitrile (300 mL) was heated to 80° C. for 6 h. The reaction mixture was cooled to room temperature and a saturated solution of sodium bicarbonate was added. The solid that precipitated was filtered off and acetonitrile was removed in vacuo. The aqueous layer was extracted with EtOAc (4×), the organics were combined, washed with an aqueous saturated solution of sodium thiosulfate, dried over sodium sulfate, and concentrated to dryness to afford 24 g of 5-iodo-3-(trifluoromethyl)pyridin-2-ol as a yellow solid. $^1$H NMR (300 MHz, DMSO-$d_6$) δ 12.57 (s, 1H), 8.01 (s, 1H), 7.99 (s, 1H).

Step 2: 2-Chloro-5-iodo-3-(trifluoromethyl)pyridine

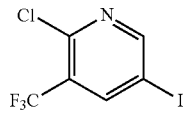

A mixture of 5-iodo-3-(trifluoromethyl)pyridin-2-ol (53 g, 0.18 mmol) and POCl$_3$ (67 mL, 0.73 mmol) in DMF (50 mL) was heated to 110° C. for 4 h. The reaction mixture was cooled to room temperature and then slowly poured into an ice/water bath. The brown solid was filtered and washed with water. It was then dissolved in DCM, washed with an aqueous saturated solution of sodium thiosulfate (2×), dried over sodium sulfate, and concentrated to dryness to afford 47 g of 2-chloro-5-iodo-3-(trifluoromethyl)pyridine as a pale yellow solid. $^1$H NMR (300 MHz, DMSO-$d_6$) δ 8.79 (d, 1H), 8.29 (d, 1H).

Step 3: 6-Chloro-N-(4-methoxybenzyl)-5-(trifluoromethyl)pyridin-3-amine

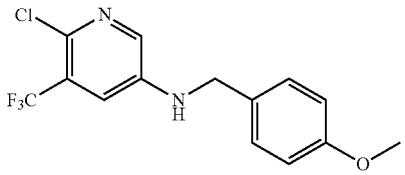 [SMILES: COc1ccc(CNc2cnc(Cl)c(C(F)(F)F)c2)cc1]

An oil bath was preheated to 130° C. A mixture of 2-chloro-5-iodo-3-(trifluoromethyl)pyridine (47 g, 152.8 mmol), (4-methoxyphenyl)methanamine (23.8 mL, 183.4 mmol), Xantphos (2.6 g, 4.58 mmol) and NaOtBu (22 g, 229.2 mmol) in toluene (500 mL) was stirred at room temperature while bubbling nitrogen for 5 min. Pd$_2$(dba)$_3$ (2.8 g, 3.05 mmol) was then added and the reaction mixture was refluxed for 2 h. The mixture was cooled to room temperature and it was filtered through a pad of celite. The pad of celite was washed with toluene and the filtrate was concentrated. The residue obtained was dissolved in EtOAc, the organic layer was washed with water (4×), and it was then evaporated to dryness. The dark oil obtained was dissolved in DCM and hexanes was added with swirling until a brown solid precipitated. The brown solid was filtered, washed with hexanes, and dried to afford 38.8 g (80%) of 6-chloro-N-(4-methoxybenzyl)-5-(trifluoromethyl)pyridin-3-amine as a brown solid. $^1$H NMR (300 MHz, DMSO-$d_6$) δ 7.96 (d, 1H), 7.38 (d, 1H), 7.29 (d, 2H), 7.07 (t, 1H), 6.92 (d, 2H), 4.29 (d, 2H), 3.73 (s, 3H). The filtrate was purified by column chromatography on Silica Gel eluting with 0 to 50% EtOAc/Hexanes to afford an additional 4 g of 6-chloro-N-(4-methoxybenzyl)-5-(trifluoromethyl)pyridin-3-amine as an orange solid (Total yield: 42.8 g).

Step 4: 5-((4-Methoxybenzyl)amino)-3-(trifluoromethyl)picolinonitrile

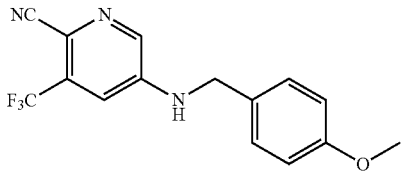 [SMILES: COc1ccc(CNc2cnc(C#N)c(C(F)(F)F)c2)cc1]

An oil bath was preheated to 180° C. A mixture of 6-chloro-N-(4-methoxybenzyl)-5-(trifluoromethyl)pyridin-3-amine (19.45 g, 61.55 mmol), Zn(CN)$_2$ (8.7 g, 73.86 mmol), and dppf (6.8 g, 12.31 mmol) in DMF (250 mL) was stirred at room temperature while bubbling nitrogen for 5 min. Pd$_2$(dba)$_3$ (2.8 g, 3.07 mmol, 0.05 eq.) was then added and the reaction mixture was placed inside the pre-heated bath. The bath temperature dropped to 160° C. The mixture started refluxing when the bath temperature reached 170° C. (takes 20 min). Refluxed for 10 min. The reaction mixture was cooled to room temperature and it was filtered through a pad of celite. The pad of celite was washed with EtOAc. The solvent was removed using a rotovap hooked up to a high vac. pump. The black residue was partitioned between EtOAc and water. An orange solid (some dppf by-product)

precipitated and was filtered and washed with EtOAc. The organic layer was washed with brine (2×), dried over sodium sulfate, and concentrated to dryness. The black residue was dissolved in DCM and loaded onto a silica gel plug. The plug was washed with DCM (to get rid of some of the fast eluting impurities) followed by 1:1 EtOAc/hexanes (to move the desired). The fractions containing the desired were combined, evaporated to dryness and the residue obtained was purified by column chromatography on silica gel eluting with 0 to 50% EtOAc/hexanes to afford 15 g of 5-((4-methoxybenzyl)amino)-3-(trifluoromethyl)picolinonitrile as reddish thick oily residue. $^1$H NMR (300 MHz, DMSO-$d_6$) δ 8.28 (s, 1H), 8.01 (t, 1H), 7.31 (m, 3H), 6.92 (d, 2H), 4.41 (d, 2H), 3.73 (s, 3H).

Step 5: 5-Amino-3-(trifluoromethyl)picolinonitrile

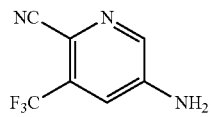 [SMILES: N#Cc1ncc(N)cc1C(F)(F)F]

5-((4-Methoxybenzyl)amino)-3-(trifluoromethyl)picolinonitrile (15 g, 49.02 mmol) was taken up in DCM (30 mL) and TFA (50 mL) was added. The resulting reaction mixture was stirred at room temperature for 3 h (until done by LC-MS). The solvent and TFA were removed in vacuo and MeOH was added to the residue. The beige solid that was not soluble in MeOH was filtered and washed with MeOH. The filtrate was evaporated to dryness and the residue was partitioned between EtOAc and a saturated solution of sodium bicarbonate. The organic layer was washed two more times with a saturated aqueous sodium bicarbonate, dried over sodium sulfate, and evaporated to dryness. The residue was dissolved in DCM and hexanes with swirling until a yellow solid precipitated. This solid was filtered and washed with hexanes to afford 7.2 g of 5-amino-3-(trifluoromethyl)picolinonitrile as a pale yellow solid. $^1$H NMR (300 MHz, DMSO-$d_6$) δ 8.17 (d, 1H), 7.28 (d, 1H), 6.99 (bs, 2H).

Intermediate 2

5-Amino-3-methylpicolinonitrile

Step 1: 3-Methyl-5-nitropicolinonitrile

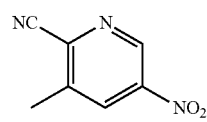

A mixture of tetrabutylammonium nitrate (17 g, 55.1 mmol) and trifluoroacetic anhydride (7.6 mL, 55.1 mmol) in DCM (50 mL) was slowly added to a cooled (0° C.) solution of 3-methylpicolinonitrile (5 g, 42.4 mmol) in DCM (100 mL) and the resulting mixture was stirred for 3 days (temperature allowed to warm to room temperature). A saturated solution of sodium bicarbonate (80 mL) was added and the mixture was stirred at room temperature for 1 h. The two layers were separated and the aqueous was extracted with DCM (2×). The organics were combined, dried over sodium sulfate, and concentrated to dryness. The residue was purified by column chromatography on silica gel eluting with 0 to 50% EtOAc/hexanes to afford 2.9 g of 3-methyl-5-nitropicolinonitrile as a pale yellow solid. $^1$H NMR (300 MHz, DMSO-$d_6$) δ 9.32 (s, 1H), 8.83 (s, 1H), 2.64 (s, 3H).

Step 2: 5-Amino-3-methylpicolinonitrile

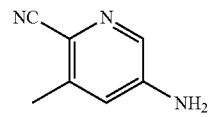

A mixture of 3-methyl-5-nitropicolinonitrile (2.9 g, 17.8 mmol) and Pd/C (cat.) in MeOH (60 mL) was hydrogenated overnight with a balloon of hydrogen. Pd/C was removed through a pad of celite and the filtrate was evaporated to dryness to afford 2.2 g of 5-amino-3-methylpicolinonitrile as a greenish solid. $^1$H NMR (300 MHz, DMSO-$d_6$) δ 7.83 (s, 1H), 6.79 (s, 1H), 6.32 (s, 2H), 2.29 (s, 3H).

Intermediate 3

3-(Trifluoromethyl)-[1,2,4]triazolo[4,3-b]pyridazin-6-amine

Step 1: 6-Chloro-3-(trifluoromethyl)-[1,2,4]triazolo[4,3-b]pyridazine

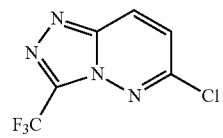

A mixture of 3-chloro-6-hydrazinylpyridazine (3.3 g, 22.8 mmol) in TFA (60 mL) was heated to 85° C. for 18 h. The reaction mixture was cooled to room temperature and TFA was removed in vacuo. The residue was partitioned between DCM and saturated aqueous sodium bicarbonate and the organic layer was washed with a saturated solution of sodium bicarbonate (3×), dried over sodium sulfate, and evaporated to dryness to afford 2.8 g of 6-chloro-3-(trifluoromethyl)-[1,2,4]triazolo[4,3-b]pyridazine as a beige solid. $^1$H NMR (300 MHz, DMSO-$d_6$) δ 8.72 (d, 1H), 7.78 (d, 1H).

Step 2: 3-(Trifluoromethyl)-[1,2,4]triazolo[4,3-b]pyridazin-6-amine

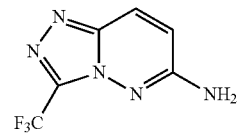

A mixture of 6-chloro-3-(trifluoromethyl)-[1,2,4]triazolo[4,3-b]pyridazine (1.14 g, 5.1 mmol) and ammonium hydroxide (10 mL) in THF (10 mL) was heated to 60° C. for 18 h. The reaction mixture was cooled to room temperature and water and EtOAc were added. The aqueous layer was extracted with EtOAc (4×), the organics were combined, dried over sodium sulfate, and evaporated to dryness to afford 1 g of 3-(trifluoromethyl)-[1,2,4]triazolo[4,3-b]pyridazin-6-amine as beige solid. ¹H NMR (300 MHz, DMSO-d₆) δ 8.12 (d, 1H), 7.23 (s, 2H), 6.97 (d, 1H).

Intermediate 4

6-Amino-2-(trifluoromethyl)nicotinonitrile

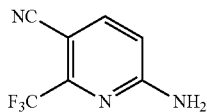 [SMILES: N#Cc1ccc(N)nc1C(F)(F)F]

A mixture of 5-bromo-6-(trifluoromethyl)pyridin-2-amine (3.0 g, 12.3 mmol), Zn(CN)₂ (0.81 g, 6.9 mmol), Pd₂(dba)₃ (0.57 g, 0.6 mmol), and Xantphos (0.72 g, 1.2 mmol) in DMA (12 mL) was placed in a sealed tube. The mixture was degassed with argon and stirred at 160° C. for 20 h. The mixture was poured into water and extracted with EtOAc (2×). The combined organic layers were dried over magnesium sulfate and concentrated to dryness. The residue was purified by column chromatography on silica gel eluting with 3:1 EtOAc/hexanes to afford 1.9 g of 6-amino-2-(trifluoromethyl)nicotinonitrile as a solid. ¹H NMR (400 MHz, CDCl₃) δ 7.74 (d, 1H), 6.67 (d, 1H).

Intermediate 5

3-(Trifluoromethyl)-[2,3'-bipyridin]-5-amine

Step 1: N-(4-Methoxybenzyl)-3-(trifluoromethyl)-[2,3'-bipyridin]-5-amine

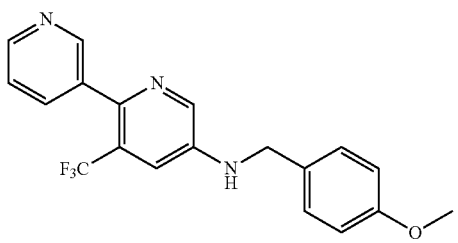 [SMILES: COc1ccc(CNc2cnc(-c3cccnc3)c(C(F)(F)F)c2)cc1]

To a solution of 6-chloro-N-(4-methoxybenzyl)-5-(trifluoromethyl)pyridin-3-amine (Intermediate 1, Step 3, 1.2 g, 3.8 mmol) and 3-(diethylboryl)pyridine (0.613 g, 4.17 mmol) in 1,4-dioxane (100 mL) was added K₃PO₄ (2.52 g, 9.48 mmol). The mixture was degassed then flushed with nitrogen before Pd₂(dba)₃ (173 mg, 0.02 mmol) and Xantphos (0.218 mg, 0.04 mmol) were added. The mixture was heated at 105° C. overnight. The reaction mixture was cooled to room temperature and filtered. The filtrate was concentrated in vacuo and the residue was purified by column chromatography on silica gel using EtOAc/PE=1/to afford 1 g of N-(4-methoxybenzyl)-3-(trifluoromethyl)-[2,3'-bipyridin]-5-amine.

Step 2: 3-(Trifluoromethyl)-[2,3'-bipyridin]-5-amine

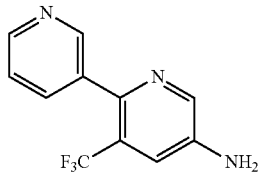 [SMILES: Nc1cnc(-c2cccnc2)c(C(F)(F)F)c1]

The title compound was synthesized as described for Intermediate 1, Step 5 using N-(4-methoxybenzyl)-3-(trifluoromethyl)-[2,3'-bipyridin]-5-amine as the starting material. ¹H NMR (300 MHz, CDCl₃) δ 8.71 (dd, 1H), 8.64 (dd, 1H), 8.30 (dd, 1H), 7.78 (m, 1H), 7.35 (m, 1H), 7.32 (d, 1H), 4.05 (s, 2H).

Intermediate 6

Isothiocyanate Method A

5-Isothiocyanato-3-methylpicolinonitrile

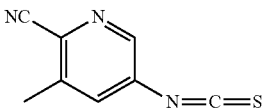

Thiophosgene (0.24 mL, 3.1 mmol) was added to a stirred biphasic solution of 5-amino-3-methylpicolinonitrile (Intermediate 2, 275 mg, 2.07 mmol) in CHCl₃ (6 mL)/water (10 mL) and the resulting orange mixture was stirred at room temperature overnight. The two layers were separated and the aqueous layer was extracted with DCM (3×). The organics were combined, washed with a saturated solution of sodium bicarbonate (2×), dried over sodium sulfate, and evaporated to dryness to afford 300 mg of 5-isothiocyanato-3-methylpicolinonitrile as an orange solid. ¹H NMR (300 MHz, DMSO-d₆) δ 8.66 (s, 1H), 8.06 (s, 1H), 2.5 (s, 3H).

Intermediate 7

6-Isothiocyanato-2-(trifluoromethyl)nicotinonitrile

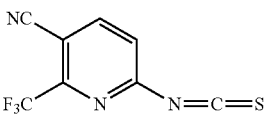 [SMILES: N#Cc1ccc(N=C=S)nc1C(F)(F)F]

A mixture of 6-amino-2-(trifluoromethyl)nicotinonitrile (648 mg, 3.5 mmol) and thiophosgene (0.4 mL, 5.2 mmol) in DCE (8 mL) was heated to 80° C. overnight. The mixture was cooled to room temperature and diluted with DCM/water. The two layers were separated and the aqueous layer was extracted with DCM (3×). The organics were combined, washed with a saturated solution of sodium bicarbonate (2×), dried over sodium sulfate, and evaporated to dryness to afford 521 mg of 6-isothiocyanato-2-(trifluoromethyl)nicotinonitrile (70% pure) as a brown oil. $^1$H NMR (300 MHz, DMSO-$d_6$) δ 8.73 (d, 1H), 7.93 (d, 1H).

Intermediate 8

6-Isothiocyanato-3-(trifluoromethyl)-[1,2,4]triazolo[4,3-b]pyridazine

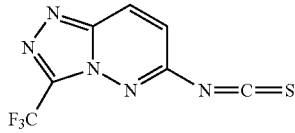

Thiophosgene (1 mL, 12.7 mmol) was added to a solution of 3-(trifluoromethyl)-[1,2,4]triazolo[4,3-b]pyridazin-6-amine (860 mg, 4.23 mmol) in pyridine (10 mL) and THF (15 mL) and the resulting dark mixture was stirred at room temperature for 2 h. The dark mixture was partitioned between EtOAc and 1M HCl. The organic layer was washed with 1M HCl (2×), dried over sodium sulfate, and evaporated to dryness to afford 545 mg (60% pure) of 6-isothiocyanato-3-(trifluoromethyl)-[1,2,4]triazolo[4,3-b]pyridazine as a dark purple solid. LCMS [M+1]$^+$ 278.5 (OMe adduct).

Intermediate 9

Isothiocyanate Method B

4-Isothiocyanatoisoquinoline-1-carbonitrile

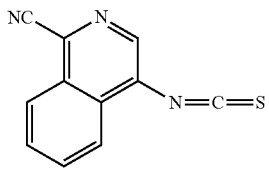 [SMILES: N#Cc1ncc(N=C=S)c2ccccc12]

A mixture of 4-aminoisoquinoline-1-carbonitrile (500 mg, 2.95 mmol) and thiophosgene (0.34 mL, 4.44 mmol) in DMA (5 mL) was stirred at room temperature overnight. The mixture was diluted with EtOAc/water. The two layers were separated and the aqueous layer was extracted with EtOAc (3×). The organics were combined, washed with a saturated solution of sodium bicarbonate (2×), dried over sodium sulfate, and evaporated to dryness to afford 553 mg of 4-isothiocyanatoisoquinoline-1-carbonitrile as an orange oil. $^1$H NMR (300 MHz, DMSO-$d_6$) δ 8.88 (s, 1H), 8.32 (d, 1H), 8.23 (d, 1H), 8.12 (td, 1H), 8.05 (td, 1H).

Isothiocyanate Intermediates 10-16 were synthesized from the appropriate amines (amines were either commercially available, synthesized in the Intermediates section, or synthesized from published procedures) according to the conditions indicated (see footnotes).

| Intermediate # | Name | Structure |
|---|---|---|
| 10[a] | 5-Isothiocyanato-3-(trifluoromethyl)picolinonitrile | 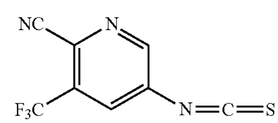 |
| 11[a] | 3-Chloro-5-isothiocyanatopicolinonitrile | 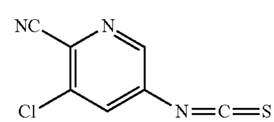 [SMILES: N#Cc1ncc(N=C=S)cc1Cl] |
| 12[a] | 5-Isothiocyanato-3-methoxypicolinonitrile | 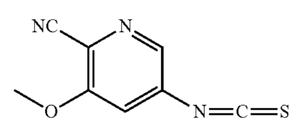 |
| 13[a] | 5-Isothiocyanatoquinoline-8-carbonitrile | 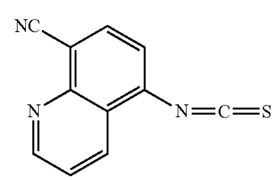 [SMILES: N#Cc1ccc(N=C=S)c2cccnc12] |
| 14[a] | 6-Isothiocyanatoimidazo[1,2-a]pyridine | 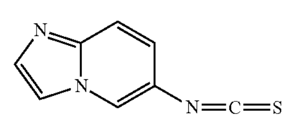 [SMILES: S=C=Nc1ccc2nccn2c1] |

-continued

| Intermediate # | Name | Structure |
|---|---|---|
| 15[a] | 5-Isothiocyanato-3-(trifluoromethyl)-2,3'-bipyridine | 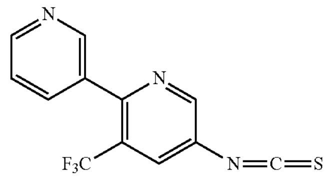 |
| 16[b] | 4-Isothiocyanatopyrazolo[1,5-a]pyridine-7-carbonitrile | 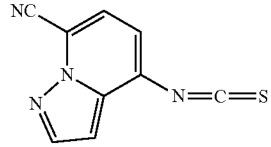 [SMILES: N#Cc1ccc(N=C=S)c2ccnn12] |

[a]Isothiocyanate method A,
[b]Isothiocyanate method B

Intermediate 17

4-((2-(Pyridin-4-yl)ethyl)sulfonyl)aniline

Step 1: 4-(2-((4-Nitrophenyl)thio)ethyl)pyridine

A mixture of 2-(pyridin-4-yl)ethanethiol hydrochloride (3.84 g, 21.8 mmol, 4-fluoro-1-nitrobenzene (6.12 g, 43.3 mmol), and $K_2CO_3$ (9.0 g, 65.1 mmol) in acetonitrile (150 mL) was refluxed overnight. The reaction mixture was filtered and the filtrate was concentrated to dryness. The residue was purified by column chromatography on silica gel (EtOAc/PE=1/1) to afford 2.0 g of 4-(2-((4-nitrophenyl)thio)ethyl)pyridine as a light yellow solid. $^1$H NMR (300 MHz, $CDCl_3$) δ 8.55 (d, 2H), 8.14 (d, 2H), 7.34 (d, 2H), 7.15 (d, 2H), 3.30 (t, 2H), 3.01 (t, 2H).

Step 2: 4-(2-((4-Nitrophenyl)sulfonyl)ethyl)pyridine $H_2O_2$ (30%, 5 mL) was added dropwise to a solution of 4-(2-((4-nitrophenyl)thio)ethyl)pyridine (338 mg, 1.30 mmol) in acetic acid (20 mL) heated at 60° C. and the resulting mixture was stirred at 60° C. for 30 min. The mixture was poured into a sat. $Na_2CO_3$ (100 mL) and extracted with DCM. The organic layer was dried over sodium sulfate and concentrated to dryness. The residue was purified by column chromatography on silica gel (EA/PE=1/3) to afford 270 mg of 4-(2-((4-nitrophenyl)sulfonyl)ethyl)pyridine as a white solid. $^1$H NMR (300 MHz, $CDCl_3$) δ 8.51 (d, 2H), 8.42 (dd, 2H), 7.13 (dd, 2H), 7.08 (d, 2H), 3.45-3.40 (m, 2H), 3.14-3.08 (m, 2H).

Step 3: 4-((2-(Pyridin-4-yl)ethyl)sulfonyl)aniline

A mixture of 4-(2-((4-nitrophenyl)sulfonyl)ethyl)pyridine (210 mg, 0.76 mmol) and 10% Pd/C (100 mg) in EtOH (100 mL) was stirred at room temperature for 3 h under $H_2$ atmosphere (balloon). The reaction mixture was filtered and the filtrate was concentrated to dryness. The residue was purified by column chromatography on silica gel (MeOH/DCM=1/50) to afford 100 mg of 4-((2-(pyridin-4-yl)ethyl)sulfonyl)aniline as a white solid. $^1$H NMR (300 MHz, $CDCl_3$) δ 8.48 (m, 2H), 7.67 (m, 2H), 7.05 (m, 2H), 6.70 (m, 2H), 4.23 (bs, 2H), 3.34-3.28 (m, 2H), 3.07-3.01 (m, 2H).

Intermediate 18

4-((Methyl(pyridin-4-ylmethyl)amino)methyl)aniline

Step 1: N-(4-Nitrobenzyl)-1-(pyridin-4-yl)methanamine

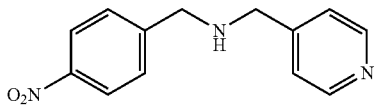 [SMILES: O=[N+]([O-])c1ccc(CNCc2ccncc2)cc1]

A mixture of 4-nitrobenzaldehyde (3.0 g, 19.8 mmol), 4-pyridylmethylamine (2.36 g, 21.8 mmol), and $NaBH_3CN$ (1.75 g, 27.7 mmol) in 1,2-dichloroethane (40.0 mL) was stirred at room temperature for 36 h and then concentrated to dryness. The residue was partitioned between water and EtOAc. The aqueous layer was extracted with EtOAc (3×). The combined organics were washed with brine (2×), dried over sodium sulfate, and concentrated. The residue was purified by column chromatography on silica gel (MeOH/DCM=1/400) to afford 1.3 g of N-(4-nitrobenzyl)-1-(pyridin-4-yl)methanamine as brown oil.

Step 2: N-Methyl-N-(4-nitrobenzyl)-1-(pyridin-4-yl)methanamine

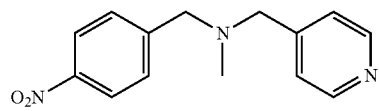 [SMILES: CN(Cc1ccncc1)Cc1ccc([N+](=O)[O-])cc1]

The title compound was synthesized as described in the previous step using N-(4-nitrobenzyl)-1-(pyridin-4-yl)methanamine and (HCHO)n as the starting materials.

Step 3: 4-((Methyl(pyridin-4-ylmethyl)amino)methyl)aniline

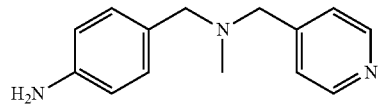 [SMILES: CN(Cc1ccncc1)Cc1ccc(N)cc1]

The title compound was synthesized as described for Intermediate 17, Step 3 using N-methyl-N-(4-nitrobenzyl)-1-(pyridin-4-yl)methanamine as the starting material.

Intermediate 19 (Aminonitrile Synthesis Method A)

1-((3-Fluoro-4-hydroxyphenyl)amino)cyclobutanecarbonitrile

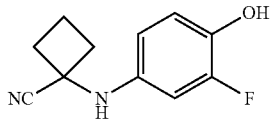 [SMILES: N#CC1(Nc2ccc(O)c(F)c2)CCC1]

Sodium cyanide (2.5 g, 50.8 mmol) was added to a mixture of 4-amino-2-fluorophenol (4.3 g, 33.9 mmol) and cyclobutanone (3.8 mL, 50.8 mmol) in acetic acid (99%, 30 mL) hooked up to a NaOH scrubber and the resulting mixture was stirred at room temperature for 6 h. The mixture was poured in water and the aqueous layer was extracted with EtOAc (3×). The organics were combined, washed with a saturated solution of sodium bicarbonate (4×), dried over sodium sulfate, and evaporated to dryness. The residue was purified by column chromatography on silica gel eluting with 0 to 50% EtOAc/hexanes to afford 4.8 g of 1-((3-fluoro-4-hydroxyphenyl)amino)cyclobutanecarbonitrile as a beige solid. $^1$H NMR (300 MHz, DMSO-$d_6$) δ 8.98 (s, 1H), 6.80 (t, 1H), 6.36 (dd, 1H), 6.28 (m, 2H), 2.71-2.62 (m, 2H), 2.35-2.25 (m, 2H), 2.12-2.00 (m, 2H).

Intermediate 20 (Aminonitrile Synthesis Method B)

Ethyl 4-((1-cyanocyclobutyl)amino)-2-fluorobenzoate

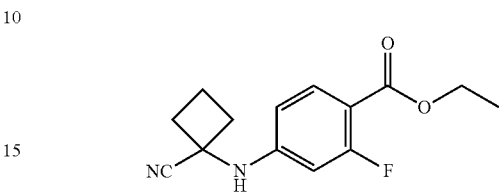

Sodium cyanide (1.3 g, 26.6 mmol) was added to a mixture of ethyl 4-amino-2-fluorobenzoate (3.25 g, 17.8 mmol) and cyclobutanone (2 mL, 26.6 mmol) in acetic acid (99%, 40 mL) hooked up to a NaOH scrubber and the resulting mixture was heated to 80° C. overnight. The mixture was cooled to room temperature and poured in water. The pink precipitate was filtered, washed with water, and redissolved in DCM (100 mL). The organic layer was washed with a saturated solution of sodium bicarbonate (4×), dried over sodium sulfate, and evaporated to dryness to afford 3.9 g of ethyl 4-((1-cyanocyclobutyl)amino)-2-fluorobenzoate as an orange solid. $^1$H NMR (300 MHz, CDCl$_3$) δ 7.87 (t, 1H), 6.43 (dd, 1H), 6.34 (dd, 1H), 4.55 (s, 1H), 4.36 (q, 2H), 2.91-2.82 (m, 2H), 2.46-2.30 (m, 2H), 2.28-2.13 (m, 2H), 1.39 (t, 3H).

Intermediate 21 (Aminonitrile Synthesis Method C)

4-((1-Cyanocyclobutyl)amino)-2-fluoro-N-methylbenzamide

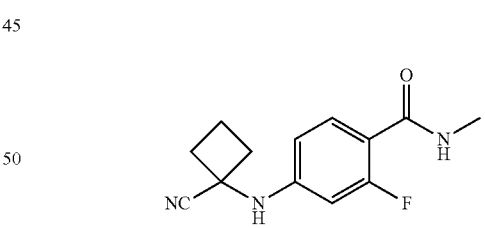

Sodium cyanide (5.8 g, 119 mmol) was added to a mixture of 4-amino-2-fluoro-N-methylbenzamide (5 g, 29.8 mmol) and cyclobutanone (4.4 mL, 59.5 mmol) in AcOH (90%, 25 mL) and EtOH (25 mL) hooked up to a NaOH scrubber and the resulting mixture was heated to 80° C. overnight. The mixture was cooled to room temperature and poured in water. The yellow precipitate was filtered, washed with water, and dried to afford 6.5 g of 4-((1-cyanocyclobutyl)amino)-2-fluoro-N-methylbenzamide as a pale yellow solid. $^1$H NMR (300 MHz, DMSO-$d_6$) δ 7.81 (t, 1H), 7.56 (t, 1H), 7.37 (s, 1H), 6.46 (dd, 1H), 6.30 (dd, 1H), 2.80-2.71 (m, 5H), 2.41-2.31 (m, 2H), 2.13-2.00 (m, 2H)

Intermediate 22 (Aminonitrile Synthesis Method D)

1-((2,6-Difluorophenyl)amino)cyclobutanecarbonitrile

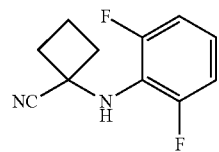 [SMILES: N#CC1(Nc2c(F)cccc2F)CCC1]

A mixture of 2,6-difluoroaniline (0.5 g, 3.9 mmol), TMSCN (0.72 mL, 5.8 mmol), and cyclobutanone (0.43 mL, 5.8 mmol) was heated to 90° C. overnight. The mixture was poured in water and the aqueous layer was extracted with EtOAc (3×). The organics were combined, washed with brine. (2×), dried over sodium sulfate, and evaporated to dryness. The residue was purified by column chromatography on silica gel eluting with 0 to 20% EtOAc/hexanes to afford 0.7 g of 1-((2,6-difluorophenyl)amino)cyclobutanecarbonitrile as a colorless oil. $^1$H NMR (300 MHz, DMSO-$d_6$) δ 7.07-7.01 (m, 2H), 6.91-6.81 (m, 1H), 6.15 (s, 1H), 2.65-2.56 (m, 2H), 2.52-2.42 (m, 2H), 2.01-1.91 (m, 2H).

Intermediate 23 (Aminonitrile Synthesis Method E)

4-((2-Cyanopropan-2-yl)amino)-2-fluoro-N-methylbenzamide

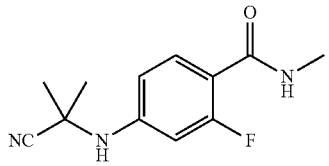 [SMILES: CNC(=O)c1ccc(NC(C)(C)C#N)cc1F]

A mixture of 4-amino-2-fluoro-N-methylbenzamide (2 g, 11.9 mmol), TMSCN (2.2 mL, 17.9 mmol), TMSOTf (0.1 mL, 0.6 mmol), and acetone (10 mL, 140 mmol) in DCM (20 mL) was stirred at room temperature overnight. The white solid was filtered, washed with a small amount of DCM, and dried to afford 1.12 g of 4-((2-cyanopropan-2-yl)amino)-2-fluoro-N-methylbenzamide as a white solid. $^1$H NMR (300 MHz, DMSO-$d_6$) δ 7.79 (t, 1H), 7.56 (t, 1H), 6.88 (s, 1H), 6.67 (dd, 1H), 6.54 (dd, 1H), 2.75 (d, 3H), 1.67 (s, 6H).

Intermediate 24

1-(4-(Pyridin-4-yloxy)phenylamino)cyclobutanecarbonitrile

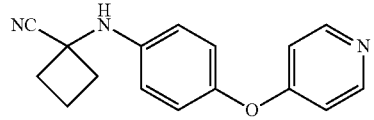 [SMILES: N#CC1(Nc2ccc(Oc3ccncc3)cc2)CCC1]

Sodium cyanide (395 mg, 8.06 mmol) was added to a mixture of 4-(pyridin-4-yloxy)aniline (500 mg, 2.69 mmol) and cyclobutanone (376 mg, 5.37 mmol) in AcOH (99%, 6 mL) in a microwave vial. The reaction mixture was irradiated with microwaves (Biotage) at 120° C. for 30 min. The slightly yellowish solution was concentrated to dryness. The residue was diluted with water and extracted with EtOAc (2×). The combined organic layers were dried over MgSO$_4$ and concentrated to dryness to afford 463 mg (65%) of 1-(4-(pyridin-4-yloxy)phenylamino)-cyclobutanecarbonitrile as a yellow oil. $^1$H NMR (400 MHz, CDCl$_3$) δ 8.46-8.38 (m, 2H), 7.02-6.94 (m, 2H), 6.79 (m, 2H), 6.72-6.64 (m, 2H), 2.86-2.74 (m, 2H), 2.46-2.34 (m, 2H), 2.22 (m, 2H)

Intermediate 25

2-((4-Hydroxyphenyl)amino)-2-methylpropanenitrile

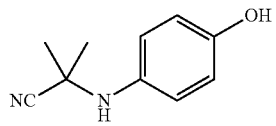

A mixture of 4-aminophenol (1 g, 9.17 mmol) and magnesium sulfate (4 g) in 2-hydroxy-2-methylpropanenitrile (10 mL) was heated to 80° C. for 2 h. Ice/water was added to a cooled mixture and it was stirred for 30 min. The white solid that precipitated was filtered, washed with water, and dried to afford 1.2 g (74%) of 2-((4-hydroxyphenyl)amino)-2-methylpropanenitrile as a white solid. $^1$H NMR (400 MHz, CDCl$_3$) δ 8.89 (s, 1H), 6.78 (d, 2H), 6.65 (d, 2H), 5.21 (s, 1H), 1.52 (s, 6H).

Intermediates 26-107 were synthesized from the appropriate amines (amines were either commercially available, synthesized in the Intermediates section, or synthesized from published procedures) and ketones, according to the conditions indicated (see footnotes).

| Intermediate # | Name | Structure |
|---|---|---|
| 26 [a] | 1-((2-Fluoro-4-hydroxyphenyl)amino)cyclobutanecarbonitrile | 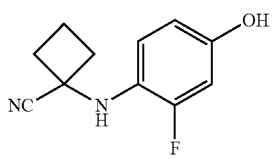 [SMILES: N#CC1(Nc2ccc(O)cc2F)CCC1] |
| 27 [b] | 1-((4-Fluoro-3-methoxyphenyl)amino)cyclobutanecarbonitrile | 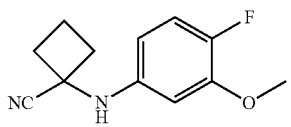 [SMILES: COc1cc(NC2(C#N)CCC2)ccc1F] |

-continued

| Intermediate # | Name | Structure |
|---|---|---|
| 28 [b] | 1-([1,1'-Biphenyl]-2-ylamino)cyclobutanecarbonitrile | 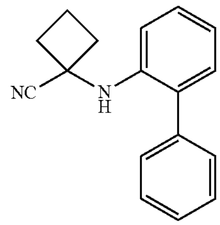 [SMILES: N#CC1(Nc2ccccc2-c2ccccc2)CCC1] |
| 29 [b] | 1-([1,1'-Biphenyl]-3-ylamino)cyclobutanecarbonitrile | 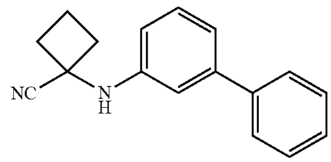 [SMILES: N#CC1(Nc2cccc(-c3ccccc3)c2)CCC1] |
| 30 [b] | 1-([1,1'-Biphenyl]-4-ylamino)cyclobutanecarbonitrile | 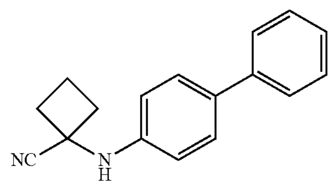 [SMILES: N#CC1(Nc2ccc(-c3ccccc3)cc2)CCC1] |
| 31 [b] | 1-(Naphthalen-1-ylamino)cyclobutanecarbonitrile | 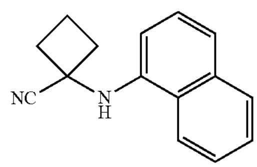 [SMILES: N#CC1(Nc2cccc3ccccc23)CCC1] |
| 32 [b] | 1-(Naphthalen-2-ylamino)cyclobutanecarbonitrile | 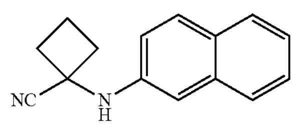 [SMILES: N#CC1(Nc2ccc3ccccc3c2)CCC1] |
| 33 [b] | Ethyl 5-((1-cyanocyclobutyl)amino)-2-fluorobenzoate | 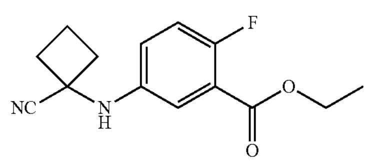 [SMILES: CCOC(=O)c1cc(NC2(C#N)CCC2)ccc1F] |
| 34 [b] | 2-((1-Cyanocyclobutyl)amino)benzonitrile | 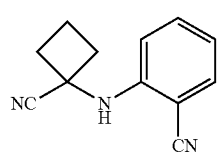 [SMILES: N#Cc1ccccc1NC1(C#N)CCC1] |
| 35 [b] | 3-((1-Cyanocyclobutyl)amino)benzonitrile | 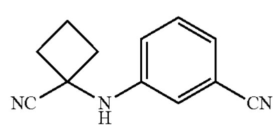 [SMILES: N#Cc1cccc(NC2(C#N)CCC2)c1] |
| 36 [b] | 4-((1-Cyanocyclobutyl)amino)benzonitrile | 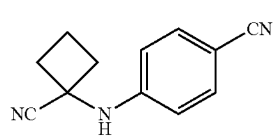 [SMILES: N#Cc1ccc(NC2(C#N)CCC2)cc1] |

-continued

| Intermediate # | Name | Structure |
|---|---|---|
| 37 [b] | 1-(Pyridin-3-ylamino)cyclobutanecarbonitrile | 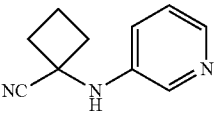 [SMILES: N#CC1(Nc2cccnc2)CCC1] |
| 38 [c] | 1-(o-Tolylamino)cyclobutanecarbonitrile | 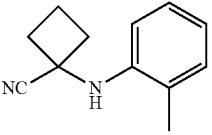 |
| 39 [c] | 1-(m-Tolylamino)cyclobutanecarbonitrile | 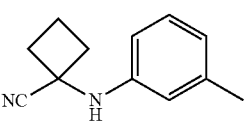 |
| 40 [c] | 1-(p-Tolylamino)cyclobutanecarbonitrile | 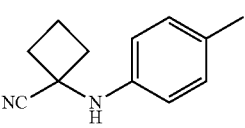 |
| 41 [b] | 1-((4-Fluoro-2-methoxyphenyl)amino)cyclobutanecarbonitrile | 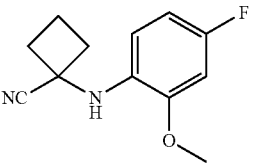 [SMILES: COc1cc(F)ccc1NC1(C#N)CCC1] |
| 42 [b] | 1-((4-Fluoro-2-hydroxyphenyl)amino)cyclobutanecarbonitrile | 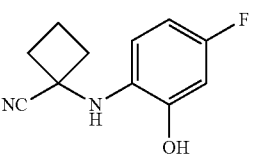 [SMILES: N#CC1(Nc2ccc(F)cc2O)CCC1] |
| 43 [d] | 1-((2-Phenoxyphenyl)amino)cyclobutanecarbonitrile | 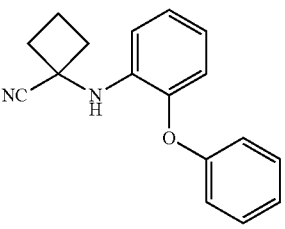 [SMILES: N#CC1(Nc2ccccc2Oc2ccccc2)CCC1] |
| 44 [b] | 1-((3-Phenoxyphenyl)amino)cyclobutanecarbonitrile | 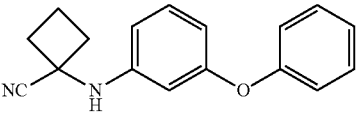 [SMILES: N#CC1(Nc2cccc(Oc3ccccc3)c2)CCC1] |
| 45 [b] | 1-((4-Phenoxyphenyl)amino)cyclobutanecarbonitrile | 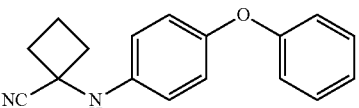 |
| 46 [d] | 1-((4-Methylbenzyl)amino)cyclobutanecarbonitrile | 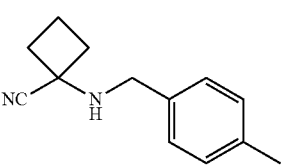 |

-continued

| Intermediate # | Name | Structure |
|---|---|---|
| 47 [d] | 1-((4-Methylphenethyl)amino)cyclobutanecarbonitrile | 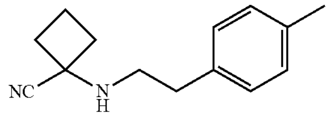 [SMILES: Cc1ccc(CCNC2(C#N)CCC2)cc1] |
| 48 [d] | 1-((4-(Pyridin-3-yloxy)phenyl)amino)cyclobutanecarbonitrile | 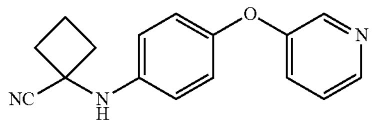 [SMILES: N#CC1(Nc2ccc(Oc3cccnc3)cc2)CCC1] |
| 49 [b] | 1-((4-(Pyridin-2-yloxy)phenyl)amino)cyclobutanecarbonitrile | 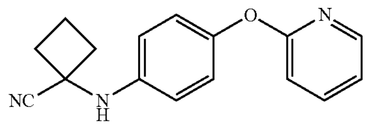 [SMILES: N#CC1(Nc2ccc(Oc3ccccn3)cc2)CCC1] |
| 50 [b] | 1-((4-(Pyrimidin-5-yloxy)phenyl)amino)cyclobutanecarbonitrile | 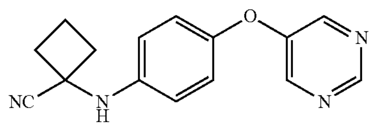 [SMILES: N#CC1(Nc2ccc(Oc3cncnc3)cc2)CCC1] |
| 51 [b] | 1-((3-(Trifluoromethoxy)phenyl)amino)cyclobutanecarbonitrile | 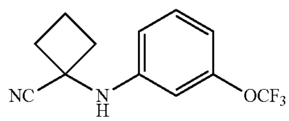 [SMILES: N#CC1(Nc2cccc(OC(F)(F)F)c2)CCC1] |
| 52 [b] | 1-((4-(Trifluoromethoxy)phenyl)amino)cyclobutanecarbonitrile | 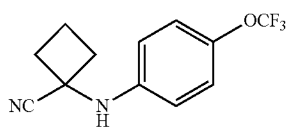 [SMILES: N#CC1(Nc2ccc(OC(F)(F)F)cc2)CCC1] |
| 53 [b] | 1-((2-Fluorophenyl)amino)cyclobutanecarbonitrile | 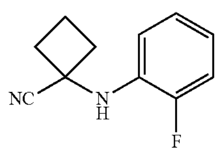 [SMILES: N#CC1(Nc2ccccc2F)CCC1] |
| 54 [b] | 1-((3-Fluorophenyl)amino)cyclobutanecarbonitrile | 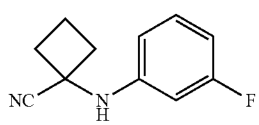 [SMILES: N#CC1(Nc2cccc(F)c2)CCC1] |
| 55 [b] | 1-((4-Fluorophenyl)amino)cyclobutanecarbonitrile | 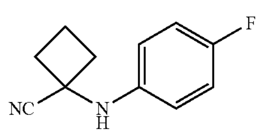 [SMILES: N#CC1(Nc2ccc(F)cc2)CCC1] |
| 56 [c] | 1-((4-(Trifluoromethyl)phenyl)amino)cyclobutanecarbonitrile | 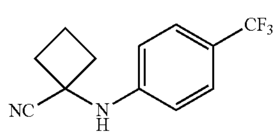 [SMILES: N#CC1(Nc2ccc(C(F)(F)F)cc2)CCC1] |
| 57 [b] | 1-(Phenylamino)cyclobutanecarbonitrile | 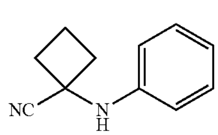 [SMILES: N#CC1(Nc2ccccc2)CCC1] |

| Intermediate # | Name | Structure |
|---|---|---|
| 58 [b] | 1-((3-Fluoro-4-methylphenyl)amino)cyclobutanecarbonitrile | 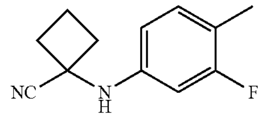 |
| 59 [b] | 1-((2-Fluoro-4-methylphenyl)amino)cyclobutanecarbonitrile | 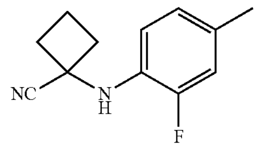 |
| 60 [b] | 1-(Cyclohexylamino)cyclobutanecarbonitrile | 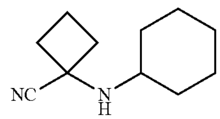 [SMILES: N#CC1(NC2CCCCC2)CCC1] |
| 61 [b] | 1-((4-(Methylsulfonyl)phenyl)amino)cyclobutane-carbonitrile | 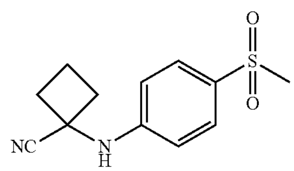 [SMILES: CS(=O)(=O)c1ccc(NC2(C#N)CCC2)cc1] |
| 62 [b] | 4-((1-Cyanocyclobutyl)amino)benzenesulfonamide | 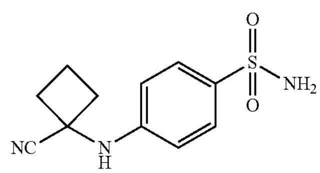 [SMILES: N#CC1(Nc2ccc(S(N)(=O)=O)cc2)CCC1] |
| 63 [b] | 1-(Isoquinolin-6-ylamino)cyclobutanecarbonitrile | 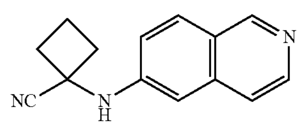 [SMILES: N#CC1(Nc2ccc3cnccc3c2)CCC1] |
| 64 [b] | 1-(Isoquinolin-7-ylamino)cyclobutanecarbonitrile | 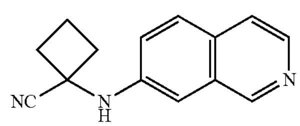 [SMILES: N#CC1(Nc2ccc3ccncc3c2)CCC1] |
| 65 [b] | 4-((1-Cyanocyclobutyl)amino)-2-fluorobenzonitrile | 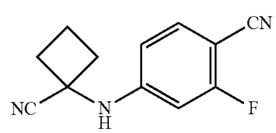 [SMILES: N#Cc1ccc(NC2(C#N)CCC2)cc1F] |
| 66 [b] | 4-((1-Cyanocyclobutyl)amino)-3-fluorobenzonitrile | 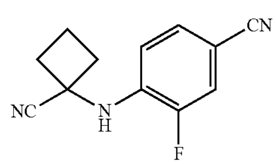 [SMILES: N#Cc1ccc(NC2(C#N)CCC2)c(F)c1] |
| 67 [c] | 1-((2-(Hydroxymethyl)phenyl)amino)cyclobutane-carbonitrile | 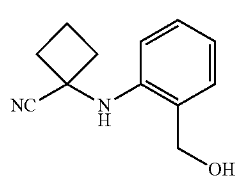 [SMILES: N#CC1(Nc2ccccc2CO)CCC1] |

| Intermediate # | Name | Structure |
|---|---|---|
| 68 [c] | 1-((3-(Hydroxymethyl)phenyl)amino)cyclobutane-carbonitrile | 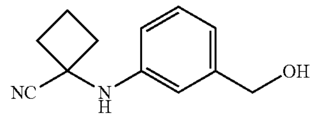 [SMILES: N#CC1(Nc2cccc(CO)c2)CCC1] |
| 69 [c] | 1-((4-(Hydroxymethyl)phenyl)amino)cyclobutane-carbonitrile | 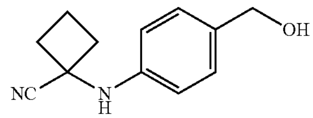 [SMILES: N#CC1(Nc2ccc(CO)cc2)CCC1] |
| 70 [b] | 4-((1-Cyanocyclobutyl)amino)-3-fluoro-N-methylbenzamide | 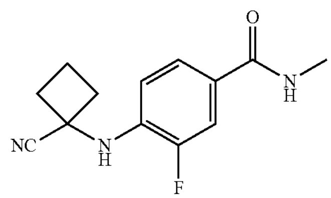 [SMILES: CNC(=O)c1ccc(NC2(C#N)CCC2)c(F)c1] |
| 71 [e] | Methyl 4-((1-cyanocyclobutyl)amino)-3-fluorobenzoate | 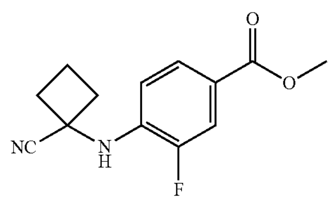 [SMILES: COC(=O)c1ccc(NC2(C#N)CCC2)c(F)c1] |
| 72 [d] | 1-((2,3-Difluorophenyl)amino)cyclobutanecarbonitrile | 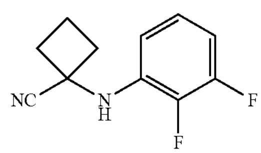 [SMILES: N#CC1(Nc2cccc(F)c2F)CCC1] |
| 73 [d] | 1-((2,5-Difluorophenyl)amino)cyclobutanecarbonitrile | 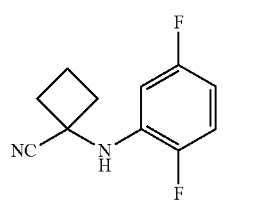 [SMILES: N#CC1(Nc2cc(F)ccc2F)CCC1] |
| 74 [d] | 1-((2,3,6-Trifluorophenyl)amino)cyclobutanecarbonitrile | 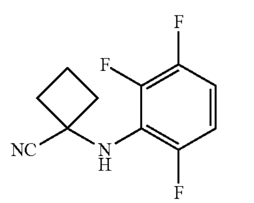 [SMILES: N#CC1(Nc2c(F)ccc(F)c2F)CCC1] |
| 75 [d] | 1-((2,4-Difluorophenyl)amino)cyclobutanecarbonitrile | 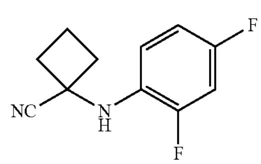 [SMILES: N#CC1(Nc2ccc(F)cc2F)CCC1] |
| 76 [c] | 2-Methyl-2-(p-tolylamino)propanenitrile | 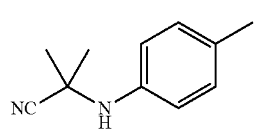 |

-continued

| Intermediate # | Name | Structure |
|---|---|---|
| 77 [c] | 1-((1H-Indazol-5-yl)amino)cyclobutanecarbonitrile | 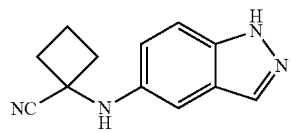 [SMILES: N#CC1(Nc2ccc3[nH]ncc3c2)CCC1] |
| 78 [c] | 1-((1H-Indazol-6-yl)amino)cyclobutanecarbonitrile | 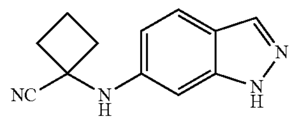 [SMILES: N#CC1(Nc2ccc3cn[nH]c3c2)CCC1] |
| 79 [e] | 1-(Benzo[d]oxazol-6-ylamino)cyclobutanecarbonitrile | 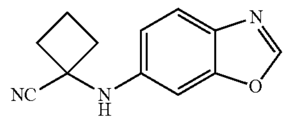 [SMILES: N#CC1(Nc2ccc3ncoc3c2)CCC1] |
| 80 [b] | 4-(4-((1-Cyanocyclobutyl)amino)phenyl)butanoic acid | 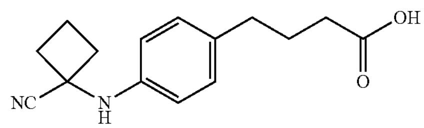 [SMILES: N#CC1(Nc2ccc(CCCC(=O)O)cc2)CCC1] |
| 81 [b] | 1-((4-(3-Hydroxypropyl)phenyl)amino)cyclobutanecarbonitrile | 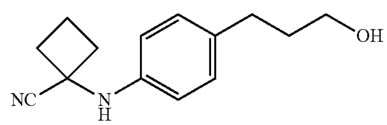 [SMILES: N#CC1(Nc2ccc(CCCO)cc2)CCC1] |
| 82 [e] | 1-((4-(4-Methylpiperazin-1-yl)phenyl)amino)cyclobutanecarbonitrile | 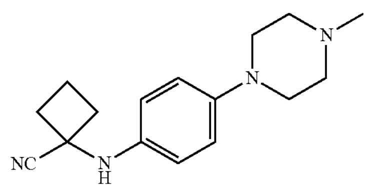 [SMILES: CN1CCN(c2ccc(NC3(C#N)CCC3)cc2)CC1] |
| 83 [e] | 1-((4-(Pyridin-4-yl)phenyl)amino)cyclobutanecarbonitrile | 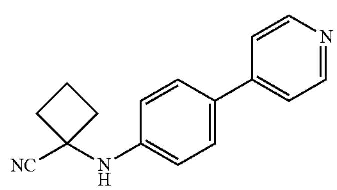 [SMILES: N#CC1(Nc2ccc(-c3ccncc3)cc2)CCC1] |
| 84 [e] | 1-((4-(Pyridin-4-yl)phenyl)amino)cyclobutanecarbonitrile | 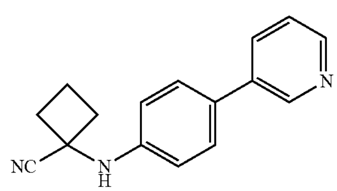 [SMILES: N#CC1(Nc2ccc(-c3cccnc3)cc2)CCC1] |
| 85 [e] | 1-((4-(pyridin-2-yl)phenyl)amino)cyclobutanecarbonitrile | 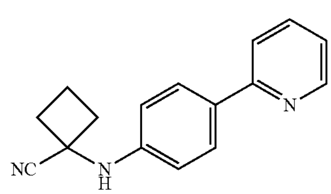 [SMILES: N#CC1(Nc2ccc(-c3ccccn3)cc2)CCC1] |

-continued

| Intermediate # | Name | Structure |
|---|---|---|
| 86 [e] | tert-Butyl 4-(4-((1-cyanocyclobutyl)amino)phenyl)piperazine-1-carboxylate | 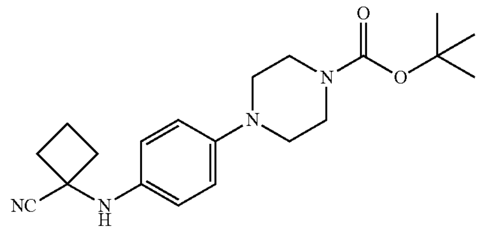 [SMILES: CC(C)(C)OC(=O)N1CCN(c2ccc(NC3(C#N)CCC3)cc2)CC1] |
| 87 [e] | 1-((4-((2-(Pyridin-4-yl)ethyl)sulfonyl)phenyl)amino)cyclobutanecarbonitrile | 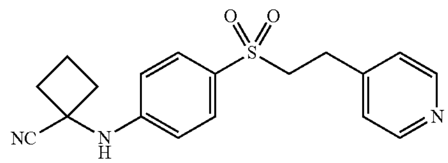 [SMILES: N#CC1(Nc2ccc(S(=O)(=O)CCc3ccncc3)cc2)CCC1] |
| 88 [e] | 1-((4-((Methyl(pyridin-4-ylmethyl)amino)methyl)phenyl)amino)cyclobutanecarbonitrile | 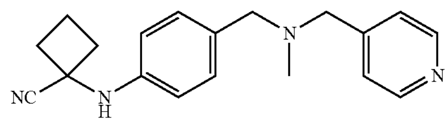 [SMILES: CN(Cc1ccncc1)Cc1ccc(NC2(C#N)CCC2)cc1] |
| 89 [e] | 1-((4-((4-Methylpiperazin-1-yl)methyl)phenyl)amino)cyclobutanecarbonitrile | 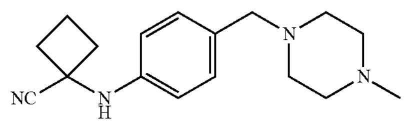 [SMILES: CN1CCN(Cc2ccc(NC3(C#N)CCC3)cc2)CC1] |
| 90 [b] | 1-((4-Bromo-3-fluorophenyl)amino)cyclobutanecarbonitrile | 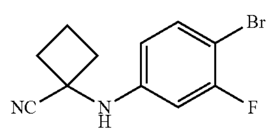 [SMILES: N#CC1(Nc2ccc(Br)c(F)c2)CCC1] |
| 91 [c] | 1-((4-(6-Methylpyridin-3-yl)phenyl)amino)cyclobutanecarbonitrile | 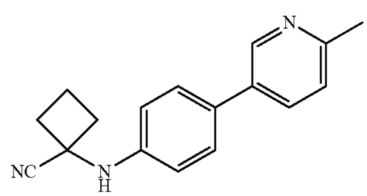 [SMILES: Cc1ccc(-c2ccc(NC3(C#N)CCC3)cc2)cn1] |
| 92 [c] | 1-((4-(4-Methylpyridin-3-yl)phenyl)amino)cyclobutanecarbonitrile | 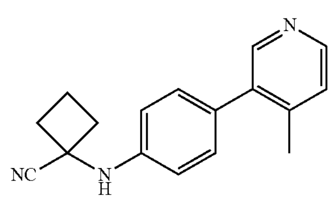 [SMILES: Cc1ccncc1-c1ccc(NC2(C#N)CCC2)cc1] |
| 93 [c] | 1-((4-(5-Methylpyridin-3-yl)phenyl)amino)cyclobutanecarbonitrile | 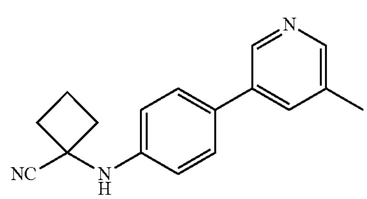 [SMILES: Cc1cncc(-c2ccc(NC3(C#N)CCC3)cc2)c1] |
| 94 [c] | 1-((4-(2-Methylpyridin-3-yl)phenyl)amino)cyclobutanecarbonitrile | 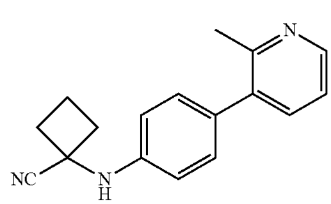 [SMILES: Cc1ncccc1-c1ccc(NC2(C#N)CCC2)cc1] |

| Intermediate # | Name | Structure |
|---|---|---|
| 95 [a] | 1-((4-(Methyl(1-methylpiperidin-4-yl)amino)phenyl)amino)cyclobutanecarbonitrile | 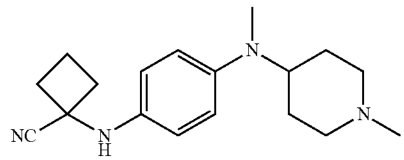 [SMILES: CN1CCC(N(C)c2ccc(NC3(C#N)CCC3)cc2)CC1] |
| 96 [c] | 1-((4-(Pyrimidin-5-yl)phenyl)amino)cyclobutanecarbonitrile | 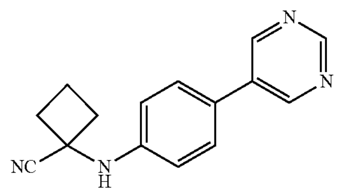 [SMILES: N#CC1(Nc2ccc(-c3cncnc3)cc2)CCC1] |
| 97 [c] | 1-((4-(5-Fluoropyridin-3-yl)phenyl)amino)cyclobutanecarbonitrile | 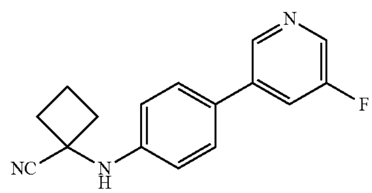 [SMILES: N#CC1(Nc2ccc(-c3cncc(F)c3)cc2)CCC1] |
| 98 [c] | 4-((1-Cyanocyclobutyl)amino)-N,2-dimethylbenzamide | 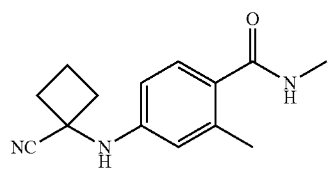 [SMILES: CNC(=O)c1ccc(NC2(C#N)CCC2)cc1C] |
| 99 [c] | 4-((1-Cyanocyclobutyl)amino)-2-methoxy-N-methylbenzamide | 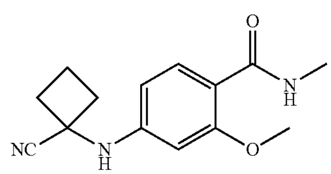 [SMILES: CNC(=O)c1ccc(NC2(C#N)CCC2)cc1OC] |
| 100 [c] | 2-Chloro-4-((1-cyanocyclobutyl)amino)-N-methylbenzamide | 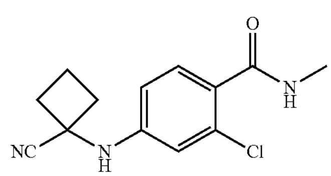 [SMILES: CNC(=O)c1ccc(NC2(C#N)CCC2)cc1Cl] |
| 101 [c] | 1-((4-(Tetrahydro-2H-pyran-4-yl)phenyl)amino)cyclobutanecarbonitrile | 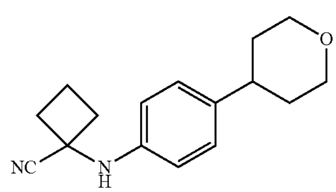 [SMILES: N#CC1(Nc2ccc(C3CCOCC3)cc2)CCC1] |
| 102 [c] | 4-((1-Cyanocyclobutyl)amino)-N-methyl-2-(trifluoromethyl)benzamide | 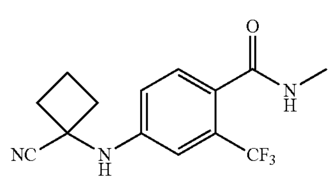 [SMILES: CNC(=O)c1ccc(NC2(C#N)CCC2)cc1C(F)(F)F] |

| Intermediate # | Name | Structure |
|---|---|---|
| 103 [c] | 4-((1-Cyanocyclopentyl)amino)-2-fluoro-N-methylbenzamide | 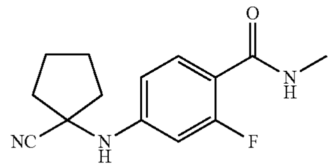 [SMILES: CNC(=O)c1ccc(NC2(C#N)CCCC2)cc1F] |
| 104 [c] | 1-((1-Oxoisoindolin-5-yl)amino)cyclobutanecarbonitrile | 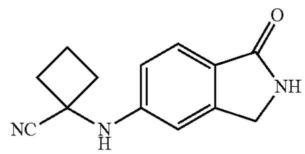 [SMILES: N#CC1(Nc2ccc3c(c2)CNC3=O)CCC1] |
| 105 [e] | 1-((4-(Furan-2-yl)phenyl)amino)cyclobutanecarbonitrile | 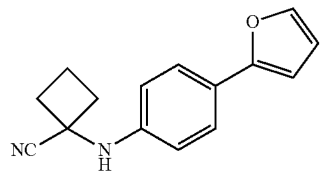 [SMILES: N#CC1(Nc2ccc(-c3ccco3)cc2)CCC1] |
| 106 [e] | 1-((4-(5-Methylfuran-2-yl)phenyl)amino)cyclobutanecarbonitrile | 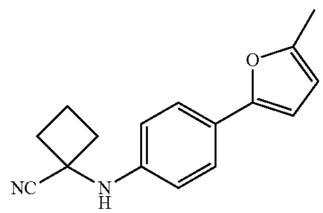 [SMILES: Cc1ccc(-c2ccc(NC3(C#N)CCC3)cc2)o1] |
| 107 [a] | 1-((4-Hydroxyphenyl)amino)cyclobutanecarbonitrile | 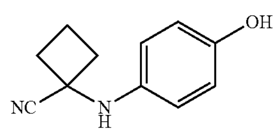 [SMILES: N#CC1(Nc2ccc(O)cc2)CCC1] |

[a] Aminonitrile synthesis method A,
[b] Aminonitrile synthesis method B,
[c] Aminonitrile synthesis method C,
[d] Aminonitrile synthesis method D,
[e] Aminonitrile synthesis method E.

Intermediate 108

4-((4,4,5,5,5-Pentafluoropentyl)thio)butan-1-ol

Step 1: 4-(Benzyloxy)butyl methanesulfonate

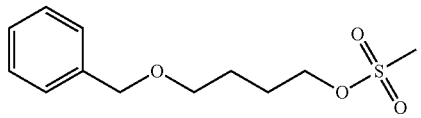 [SMILES: CS(=O)(=O)OCCCCOCc1ccccc1]

Methanesulfonyl chloride (1 mL, 13.3 mmol) was added to a cooled (0° C.) solution of 4-(benzyloxy)butan-1-ol (2 g, 11.1 mmol) and triethylamine (1.9 mL, 13.3 mmol) in DCM (20 mL) and it was stirred at 0° C. for 1 h. HCl (1M) was added to the reaction mixture and the aqueous layer was extracted with DCM (2x). The organics were combined, dried over sodium sulfate, and evaporated to dryness to afford 4-(benzyloxy)butyl methanesulfonate as a yellow oil. LCMS [M+1]$^+$ 259.5.

Step 2: 4,4,5,5,5-Pentafluoropentyl 4-methylbenzenesulfonate

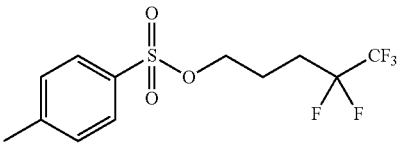 [SMILES: Cc1ccc(S(=O)(=O)OCCCC(F)(F)C(F)(F)F)cc1]

A mixture of 4,4,5,5,5-pentafluoropentan-1-ol (1 g, 5.6 mmol), p-toluenesulfonylchloride (1.3 g, 6.8 mmol), and triethylamine (1.2 mL, 8.4 mmol) in DCM (20 mL) was stirred at room temperature for 18 h. Water was added to the reaction mixture, the two layers were separated, and the aqueous layer was extracted with DCM (2x). The organics were combined, dried over sodium sulfate, and evaporated to dryness. The residue was purified by column chromatography on silica gel eluting with 0 to 20% EtOAc/hexanes to afford 1.7 g of 4,4,5,5,5-pentafluoropentyl 4-methylbenzenesulfonate as a colorless oil.

Step 3:
2-(4,4,5,5,5-Pentafluoropentyl)isothiouronium 4-methylbenzenesulfonate

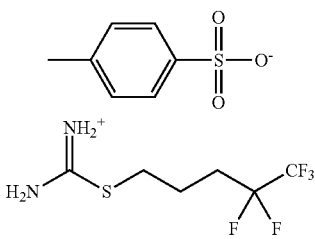

A mixture of 4,4,5,5,5-pentafluoropentyl 4-methylbenzenesulfonate (1.7 g, 5.1 mmol) and thiourea (430 mg, 5.6 mmol) in ethanol (20 mL) was refluxed for 18 h. The mixture was cooled to room temperature and most of the ethanol was removed in vacuo. Hexanes and Et₂O were added until a white precipitate started to form and the mixture was allowed to sit at room temperature for 30 min. The white solid was filtered, washed with hexanes, and dried to afford 1.7 g of 2-(4,4,5,5,5-pentafluoropentyl)isothiouronium 4-methylbenzenesulfonate as a white solid. LCMS [M+1]⁺ 237.4.

Step 4: (4-(Benzyloxy)butyl)(4,4,5,5,5-pentafluoropentyl)sulfane

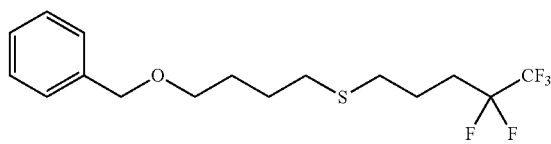 [SMILES: FC(F)(F)C(F)(F)CCCSCCCCOCc1ccccc1]

A mixture of 4-(benzyloxy)butyl methanesulfonate (759 mg, 2.9 mmol), 2-(4,4,5,5,5-pentafluoropentyl)isothiouronium 4-methylbenzenesulfonate (1.2 g, 2.9 mmol), NaOH (5M, 5 mL) in DMF (20 mL) was stirred at room temperature for 4 h. EtOAc was added to the reaction mixture and the organic layer was washed with brine (2×), dried over sodium sulfate, and evaporated to dryness. The residue was purified by column chromatography on silica gel eluting with 0 to 20% EtOAc/hexanes to afford 960 mg of (4-(benzyloxy)butyl)(4,4,5,5,5-pentafluoropentyl)sulfane as a yellow oil. LCMS [M+1]⁺ 357.5.

Step 5:
4-((4,4,5,5,5-Pentafluoropentyl)thio)butan-1-ol

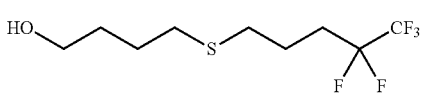 [SMILES: OCCCCSCCCC(F)(F)C(F)(F)F]

BBr₃ (1M in DCM, 2.9 mL, 2.9 mmol) was added dropwise to a solution of (4-(benzyloxy)butyl)(4,4,5,5,5-pentafluoropentyl)sulfane (340 mg, 0.95 mmol) in DCM (5 mL) cooled to −78° C. The temperature was allowed to warm up to room temperature and the mixture was stirred for 18 h. Water was slowly added and the reaction mixture was stirred for 10 min. The two layers were separated and the aqueous layer was extracted with DCM (3×). The organics were combined, dried over sodium sulfate, and evaporated to dryness. The residue was purified by column chromatography on silica gel eluting with 50 to 100% EtOAc/hexanes to afford 171 mg of 4-((4,4,5,5,5-pentafluoropentyl)thio)butan-1-ol as a colorless oil.

Intermediate 109

4-((4,4,5,5,5-Pentafluoropentyl)sulfinyl)butan-1-ol

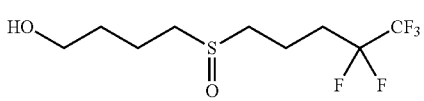

m-CPBA (64 mg, 0.37 mmol) was added to a cooled (0° C.) solution of 4-((4,4,5,5,5-pentafluoropentyl)thio)butan-1-ol (76 mg, 0.28 mmol) in DCM (3 mL) and it was stirred at 0° C. for 30 min. The reaction mixture was warmed to room temperature and was partitioned between a saturated solution of sodium bicarbonate and DCM. The organic layer was dried over sodium sulfate, and evaporated to dryness. The residue was purified by column chromatography on silica gel eluting with 0 to 10% MeOH/DCM to afford 52 mg of 4-((4,4,5,5,5-pentafluoropentyl)sulfinyl)butan-1-ol as a white solid.

Intermediate 110

5-Amino-3-(difluoromethyl)picolinonitrile

Step 1: (5-Bromo-2-chloropyridin-3-yl)methanol

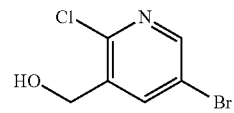

To a mixture of NaBH₄ (5.8 g, 152.6 mmol, 4 eq) and anhydrous CaCl₂ (16.9 g, 152.6 mmol) in dry DCM (100 mL) at 0° C., was added slowly methyl 5-bromo-2-chloronicotinate (9.5 g, 38.15 mmol). The resulting mixture was stirred at room temperature for 12 h. Water was added to the reaction mixture at 0° C. The organic layer was separated, dried over sodium sulfate, and concentrated in vacuo, to afford 6.8 g (crude) of (5-bromo-2-chloropyridin-3-yl)methanol, which was used in the next step without further purification. LCMS [M+H]⁺ 223.1.

Step 2: 5-Bromo-2-chloronicotinaldehyde

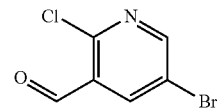

To a solution of (5-bromo-2-chloropyridin-3-yl)methanol (6.8 g, 30.6 mmol) in DCM (200 mL), was added Dess- Martin periodinane (32.4 g, 76.6 mmol) at 0° C. The resulting mixture was stirred at room temperature for 12 h. The reaction mixture was concentrated in vacuo and the residue was purified by column chromatography on silica gel (0 to 30% EtOAc in petroleum ether) to afford 5.05 g of 5-bromo-2-chloronicotinaldehyde. LCMS [M+H]+ 221.1.

Step 3:
5-Bromo-2-chloro-3-(difluoromethyl)pyridine

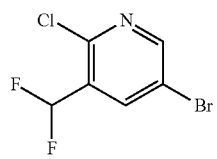

To a solution of 5-bromo-2-chloronicotinaldehyde (5.05 g, 23.2 mmol) in DCM (30 mL), were added ethanol (0.13 mL, 2.32 mmol) and DAST (7.51 g, 46.4 mmol) at room temperature. The resulting mixture was stirred for 2 h at that temperature. To the reaction mixture was slowly added saturated aqueous sodium bicarbonate (100 mL). The organic layer was separated, dried over sodium sulfate, and concentrated in vacuo. The residue was purified by column chromatography on silica gel (0 to 50% EtOAc in petroleum ether) to afford 3.80 g of 5-bromo-2-chloro-3-(difluoromethyl)pyridine. LCMS [M+H]+ 243.1.

Step 4: 5-Amino-3-(difluoromethyl)picolinonitrile

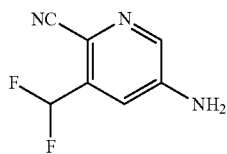 [SMILES: N#Cc1ncc(N)cc1C(F)F]

The title compound was synthesized as described in Intermediate 1 (Steps 3-5) using 5-bromo-2-chloro-3-(difluoromethyl)pyridine as the starting material. $^1$H NMR (400 MHz, DMSO-$d_6$) δ 8.09 (d, 1H), 7.28-7.01 (m, 2H), 6.80 (s, 2H). LCMS [M+H]+ 170.1.

Example 1

Synthesis of Compound 1 (Thiohydantoin Synthesis Method A)

5-(5-(3-Fluoro-4-hydroxyphenyl)-8-oxo-6-thioxo-5, 7-diazaspiro[3.4]octan-7-yl)-3-trifluoromethyl)picolinonitrile

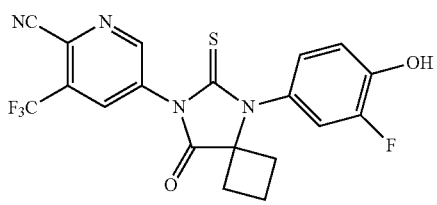 [SMILES: N#Cc1ncc(N2C(=O)C3(CCC3)N(c3ccc(O)c(F)c3)C2=S)cc1C(F)(F)F]

Thiophosgene (1.3 mL, 16.04 mmol) was added to a mixture of 5-amino-3-(trifluoromethyl) picolinonitrile (Intermediate 1, 3 g, 16.0 mmol) and 1-((3-fluoro-4-hydroxyphenyl)amino)cyclobutane-carbonitrile (Intermediate 19, 3.3 g, 16.0 mmol) in DMA (40 mL) and the mixture was heated to 60° C. for 18 h. MeOH (60 mL) and HCl (2M, 40 mL) were added and the mixture was refluxed for 2 h. The mixture was cooled to room temperature and slowly poured into an ice/water bath. The brown solid was filtered, washed with water, dried, and purified by column chromatography on silica gel eluting with 0 to 50% EtOAc/hexanes to afford 3 g of 5-(5-(3-fluoro-4-hydroxyphenyl)-8-oxo-6-thioxo-5,7-diazaspiro[3.4]octan-7-yl)-3-(trifluoromethyl)picolinonitrile as a beige solid. $^1$H NMR (300 MHz, DMSO-$d_6$) δ 10.44 (s, 1H), 9.21 (d, 1H), 8.74 (d, 1H), 7.27-7.05 (m, 3H), 2.64-2.42 (m, 4H), 2.01-1.91 (m, 1H), 1.61-1.54 (m, 1H).

Example 2

Synthesis of Compound 2 (Thiohydantoin Synthesis Method B)

5-(4-Hydroxyphenyl)-6-thioxo-7-(3-(trifluoromethyl)-[1,2,4]triazol[4,3-b]pyridazin-6-yl)-5,7-diazaspiro[3.4]octan-8-one

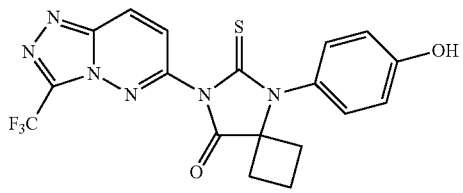 [SMILES: O=C1N(c2ccc3nnc(C(F)(F)F)n3n2)C(=S)N(c2ccc(O)cc2)C12CCC2]

A mixture of 6-isothiocyanato-3-(trifluoromethyl)-[1,2,4]triazolo[4,3-b]pyridazine (Intermediate 8, 545 mg, 2.22 mmol) and 1-((4-hydroxyphenyl)amino)cyclobutanecarbonitrile (Intermediate 25, 418 mg, 2.22 mmol) in DMA (15 mL) was heated to 60° C. for 2 h. MeOH (10 mL) and HCl (2M, 10 mL) were added and the mixture was refluxed for 1 h. The mixture was cooled to room temperature and slowly poured into an ice/water bath. The dark brown solid was filtered, washed with water, dried, and purified by reverse phase HPLC (Acetonitrile/water:TFA) to afford 5-(4-hydroxyphenyl)-6-thioxo-7-(3-(trifluoromethyl)-[1,2,4]triazolo[4,3-b]pyridazin-6-yl)-5,7-diazaspiro[3.4]octan-8-one as a light brown solid. LCMS [M+1]+ 435.4.

Example 3

Synthesis of Compound

Ethyl 4-(7-(6-cyano-5-(trifluoromethyl)pyridin-3-yl)-8-oxo-6-thioxo-5,7-diazaspiro[3.4]octan-5-yl)-2-fluorobenzoate

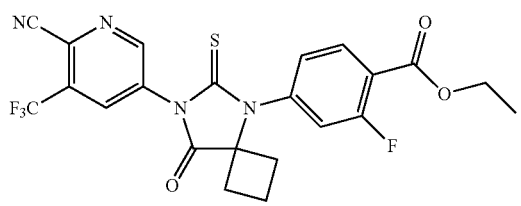 [SMILES: CCOC(=O)c1ccc(N2C(=S)N(c3cnc(C#N)c(C(F)(F)F)c3)C(=O)C23CCC3)cc1F]

A mixture of thiophosgene (0.55 mL, 5.35 mmol), 5-amino-3-(trifluoromethyl)picolinonitrile (Intermediate 1, 1 g, 5.35 mmol), and ethyl 4-((1-cyanocyclobutyl)amino)-2-fluorobenzoate (Intermediate 20, 1.4 g, 5.35 mmol) in DMA (25 mL) was heated to 70° C. overnight. MeOH (20 mL) and HCl (2M, 20 mL) were added and the mixture was refluxed for 2 h then cooled to room temperature. Water/ice was added and the aqueous layer was extracted with DCM (4×). The organics were combined, dried over sodium sulfate, and evaporated to dryness. The residue was purified by column chromatography on silica gel eluting with 0 to 50% EtOAc/hexanes to afford 1 g of ethyl 4-(7-(6-cyano-5-(trifluoromethyl)pyridin-3-yl)-8-oxo-6-thioxo-5,7-diazaspiro[3.4]octan-5-yl)-2-fluorobenzoate as a yellow foam. $^1$H NMR (300 MHz, DMSO-d$_6$) δ 9.21 (s, 1H), 8.74 (s, 1H), 8.13 (m, 1H), 7.53 (d, 1H), 7.45 (d, 1H), 4.37 (q, 2H), 2.65-2.62 (m, 2H), 2.56-2.45 (m, 2H), 2.05-1.91 (m, 1H), 1.61-1.57 (m, 1H), 1.34 (t, 3H).

Example 4

Synthesis of Compound 4

5-(5-(4-Bromo-3-fluorophenyl)-8-oxo-6-thioxo-5,7-diazaspiro[3.4]octan-7-yl)-3-(trifluoromethyl)picolinonitrile

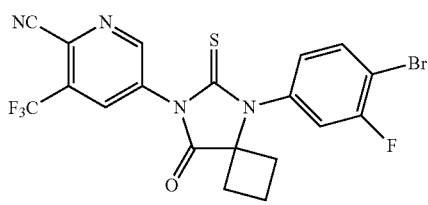 [SMILES: N#Cc1ncc(N2C(=O)C3(CCC3)N(c3ccc(Br)c(F)c3)C2=S)cc1C(F)(F)F]

Thiophosgene (0.36 mL, 4.67 mmol) was added dropwise to a solution of 5-amino-3-(trifluoromethyl)picolinonitrile (Intermediate 1, 795 mg, 4.25 mmol) and 1-((4-bromo-3-fluorophenyl)amino)cyclobutanecarbonitrile (Intermediate 90, 1.14 g, 4.25 mmol) in DMA (30 mL). The resulting mixture was heated to 60° C. overnight. MeOH (8 mL) and HCl (2M, 8 mL) were added and the mixture was refluxed for 2 h then cooled to room temperature. Water was slowly added until a light brown solid precipitated. The solid was filtered, washed with water, dried, dissolved in MeOH, and absorbed on silica gel. Purification by column chromatography on silica gel eluting with 10% EtOAc/hexanes afforded 616 mg of 5-(5-(4-bromo-3-fluorophenyl)-8-oxo-6-thioxo-5,7-diazaspiro[3.4]octan-7-yl)-3-(trifluoromethyl)picolinonitrile as a white solid. $^1$H NMR (300 MHz, DMSO-d$_6$) δ 9.21 (d, 1H), 8.74 (d, 1H), 8.00 (t, 1H), 7.55 (dd, 1H), 7.28 (dd, 1H), 2.67-2.59 (m, 2H), 2.55-2.45 (m, 2H), 1.99-1.95 (m, 1H), 1.61-1.56 (m, 1H).

Example 5

Synthesis of Compound 5

4-(7-(6-Cyano-5-methylpyridin-3-yl)-8-oxo-6-thioxo-5,7-diazaspiro[3.4]octan-5-yl)-2-fluoro-N-methylbenzamide

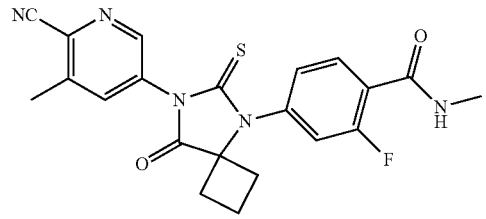

A mixture of 5-isothiocyanato-3-methylpicolinonitrile (Intermediate 6, 2.9 g, 16.57 mmol) and 4-((1-cyanocyclobutyl)amino)-2-fluoro-N-methylbenzamide (Intermediate 21, 2.7 g, 11.05 mmol) in DMA was heated to 65° C. overnight. MeOH (50 mL) and HCl (2M, 70 mL) were added and the mixture was heated to 105° C. for 1 h then cooled to room temperature. Water was slowly added until a yellow solid precipitated and the mixture was stirred at room temperature for 3 h. The solid was filtered, washed with water, dissolved in DCM, dried over sodium sulfate, and absorbed on silica gel. Purification by column chromatography on silica gel eluting with 0 to 100% EtOAc/hexanes afforded a pale yellow solid. This solid was triturated in MeOH, filtered, and dried to afford 1.39 g (29%) of 4-(7-(6-cyano-5-methylpyridin-3-yl)-8-oxo-6-thioxo-5,7-diazaspiro[3.4]octan-5-yl)-2-fluoro-N-methylbenzamide as a white solid. $^1$H NMR (300 MHz, DMSO-d$_6$) δ 8.64 (d, 1H), 8.40 (m, 1H), 8.06 (d, 1H), 7.75 (t, 1H), 7.43 (dd, 1H), 7.32 (dd, 1H), 2.73 (d, 3H), 2.59-2.53 (m, 2H), 2.52 (s, 3H), 2.44-2.23 (m, 2H), 1.91-1.88 (m, 1H), 1.52-1.48 (m, 1H). LCMS [M+1]$^+$ 424.0.

Example 6

Synthesis of Compound 6

4-(3-(6-Cyano-5-methylpyridin-3-yl)-4-oxo-2-thioxo-1,3-diazaspiro[4.4]nonan-1-yl)-2-fluoro-N-methylbenzamide

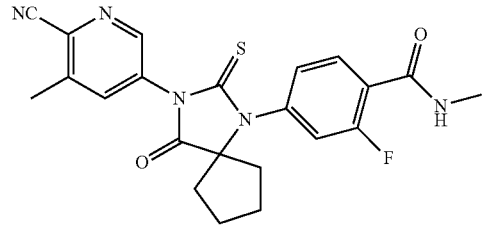

Thiophosgene (0.35 mL) was added dropwise to a solution of 4-((1-cyanocyclopentyl)amino)-2-fluoro-N-methylbenzamide (Intermediate 103, 400 mg, 1.53 mmol) and 5-amino-3-methylpicolinonitrile (Intermediate 2, 303 mg, 2.28 mmol) in DMA (30 mL) under N$_2$ atmosphere. The resulting mixture was stirred at 60° C. overnight. MeOH (22 mL) and HCl (2M, 11 mL) were added and the mixture was refluxed for 2 h then cooled to room temperature. The reaction mixture was poured into water (75 mL) and extracted with EtOAc. The organic layer was dried over sodium sulfate and concentrated in vacuo. The residue was purified by column chromatography on silica gel (1:5 EtOAc/petroleum ether), to afford 300 mg of 4-(3-(6-cyano-5-methylpyridin-3-yl)-4-oxo-2-thioxo-1,3-diazaspiro[4.4]nonan-1-yl)-2-fluoro-N-methylbenzamide as a light yellow solid. $^1$H NMR (400 MHz, DMSO-d$_6$) δ 8.74 (s, 1H), 8.47 (m, 1H), 8.17 (s, 1H), 7.78 (m, 1H), 7.55 (d, 1H), 7.41 (d, 1H), 2.81 (d, 3H), 2.60 (s, 3H), 2.29-2.21 (m, 4H), 1.72 (m, 2H), 1.41 (m, 2H). LCMS [M+1]$^+$ 438.1.

Example 7

Synthesis of Compound 7

3-Methyl-5-(5-(4-(5-methylfuran-2-yl)phenyl)-8-oxo-6-thioxo-5,7-diazaspiro[3.4]octan-7-yl)picolinonitrile

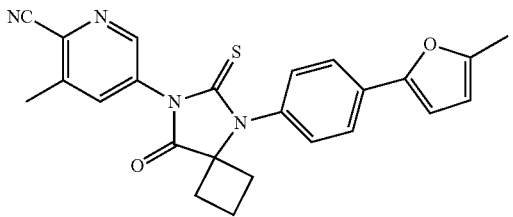

Thiophosgene (0.1 mL) was added dropwise to a solution of 1-((4-(5-methylfuran-2-yl)phenyl)amino)cyclobutanecarbonitrile (Intermediate 106, 280 mg, 1.11 mmol) and 5-amino-3-methylpicolinonitrile (Intermediate 2, 177 mg, 1.33 mmol) in DMA (20 mL). The resulting mixture was stirred at 60° C. overnight. MeOH (16 mL) and HCl (2M, 8 mL) were added and the mixture was refluxed for 2 h then cooled to room temperature. The reaction mixture was poured into water (200 mL) and extracted with EtOAc. The organic layer was washed with brine, dried over Sodium sulfate and concentrated in vacuo. The residue was purified by column chromatography on silica gel (1:3 EtOAc/petroleum ether), to afford 140 mg of 3-methyl-5-(5-(4-(5-methylfuran-2-yl)phenyl)-8-oxo-6-thioxo-5,7-diazaspiro[3.4]octan-7-yl)picolinonitrile. $^1$HNMR (400 MHz, DMSO-d$_6$) δ 8.74 (s, 1H), 8.16 (s, 1H), 7.86 (d, 2H), 7.46 (d, 2H), 6.98 (d, 1H), 6.28 (d, 1H), 2.63 (m, 2H), 2.60 (s, 3H), 2.51-2.43 (m, 2H), 2.38 (s, 3H), 1.97 (m, 1H), 1.57 (m, 1H). LCMS [M+1]$^+$ 429.1.

Compounds 8 to 117 were synthesized from the appropriate amines (amines were either commercially available, synthesized in the Intermediates section, or synthesized from literature procedures) and amino cyanohydrins, according to the conditions indicated (see footnotes): 8$^a$, 9$^a$, 10$^a$, 11$^a$, 12$^a$, 13$^a$, 14$^a$, 15$^a$, 16$^a$, 17$^b$, 18$^b$, 19$^a$, 20$^a$, 21$^a$, 22$^a$, 23$^a$, 24$^b$, 25$^b$, 26$^b$, 27$^b$, 28$^b$, 29$^a$, 30$^b$, 31$^b$, 32$^a$, 33$^a$, 34$^b$, 35$^b$, 36$^b$, 37$^b$, 38$^b$, 39$^b$, 40$^b$, 41$^b$, 42$^a$, 43$^a$, 44$^b$, 45$^b$, 46$^a$, 47$^b$, 48$^b$, 49$^b$, 50$^b$, 51$^b$, 52$^b$, 53$^b$, 54$^b$, 55$^b$, 56$^a$, 57$^b$, 58$^b$, 59$^b$, 60$^b$, 61$^b$, 62$^b$, 63$^a$, 64$^a$, 65$^a$, 66$^b$, 67$^a$, 68$^a$, 69$^a$, 70$^a$, 71$^a$, 72$^a$, 73$^a$, 74$^a$, 75$^a$, 76$^a$, 77$^a$, 78$^a$, 79$^a$, 80$^b$, 81$^b$, 82$^b$, 83$^b$, 84$^b$, 85$^b$, 86$^b$, 87$^b$, 88$^a$, 89$^b$, 90$^b$, 91$^b$, 92$^b$, 93$^b$, 94$^a$, 95$^a$, 96$^a$, 97$^a$, 98$^a$, 99$^a$, 100$^a$, 101$^a$, 102$^a$, 103$^a$, 104$^a$, 105$^a$, 106$^a$, 107$^a$, 108$^a$, 109$^b$, 110$^a$, 111$^b$, 112$^a$, 113$^a$, 114$^a$, 115$^a$, 116$^b$, 117$^b$. $^a$ Thiohydantoin synthesis method A. $^b$ Thiohydantoin synthesis method B.

Example 8

Synthesis of Compound 118

5-(8-Oxo-5-(4-(piperazin-1-yl)phenyl)-6-thioxo-5,7-diazaspiro[3.4]octan-7-yl)-3-(trifluoromethyl)picolinonitrile

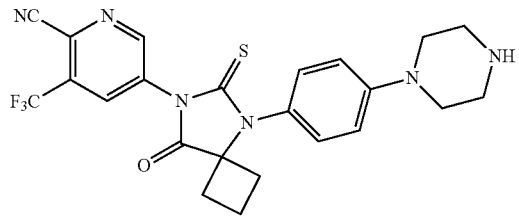 [SMILES: N#Cc1ncc(N2C(=O)C3(CCC3)N(c3ccc(N4CCNCC4)cc3)C2=S)cc1C(F)(F)F]

A mixture of tert-butyl 4-(4-(1-cyanocyclobutylamino)phenyl)piperazine-1-carboxylate (Intermediate 86, 0.25 g, 0.70 mmol) and 5-isothiocyanato-3-(trifluoromethyl)picolinonitrile (Intermediate 10, 241 mg, 1.05 mmol) in DMA (5 mL) was heated to 80° C. for 12 h. 2M HCl/MeOH=1/1 (10 mL) was added then and the resulting mixture was heated at 100 OC for 2 h. The reaction mixture was cooled to room temperature and diluted with EtOAc. The organic layer was washed with water (3×), dried over sodium sulfate, and concentrated in vacuo. The residue was purified by Prep-HPLC (20% acetonitrile in water) to afford 75 mg of 5-(8-oxo-5-(4-(piperazin-1-yl)phenyl)-6-thioxo-5,7-diazaspiro[3.4]octan-7-yl)-3-(trifluoromethyl)picolinonitrile. $^1$H NMR (DMSO-d$_6$, 300 MHz) δ 9.26 (s, 1H), 9.19 (m, 1H), 8.74 (m, 1H), 7.25 (d, 2H), 7.15 (d, 2H), 3.48 (m, 4H), 3.22 (m, 4H), 2.60-2.49 (m, 2H), 2.48-2.40 (m, 2H), 1.95 (m, 1H), 1.63 (m, 1H). LCMS [M+H]$^+$ 487.1.

Example 9

Synthesis of Compound 119 tert-Butyl 4-(4-(7-(6-cyano-5-(trifluoromethyl)pyridin-3-yl)-8-oxo-6-thioxo-5,7-diazaspiro[3.4]octan-5-yl)phenyl)piperazine-1-carboxylate

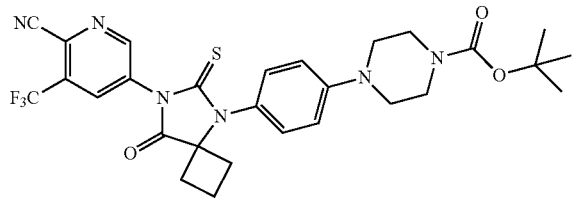 [SMILES: CC(C)(C)OC(=O)N1CCN(c2ccc(N3C(=S)N(c4cnc(C#N)c(C(F)(F)F)c4)C(=O)C34CCC4)cc2)CC1]

To a solution of 5-(8-oxo-5-(4-(piperazin-1-yl)phenyl)-6-thioxo-5,7-diazaspiro[3.4]octan-7-yl)-3-(trifluoromethyl)picolinonitrile (15 mg, 0.031 mmol) in dry DCM (2 mL) was added TEA (6 µl, 0.062 mmol) and (Boc)$_2$O (10 mg, 0.046 mmol). The mixture was stirred at room temperature for 3 h and then concentrated. The residue was purified by column chromatography on silica gel (0 to 20% EtOAc in petroleum ether) to afford 10 mg of tert-butyl 4-(4-(7-(6-cyano-5-(trifluoromethyl)pyridin-3-yl)-8-oxo-6-thioxo-5,7-diazaspiro[3.4]octan-5-yl)phenyl)piperazine-1-carboxylate. $^1$H NMR (CDCl$_3$, 300 MHz) δ 9.10 (d, 1H), 8.36 (d, 1H), 7.18 (d, 2H), 7.04 (d, 2H), 3.60 (m, 4H), 3.27 (m, 4H), 2.63-2.60 (m, 4H), 2.24-1.97 (m, 1H), 1.71-1.63 (m, 1H), 1.49 (s, 9H).

Example 10

Synthesis of Compound 120

4-(7-(6-Cyano-5-(trifluoromethyl)pyridin-3-yl)-8-oxo-6-thioxo-5,7-diazaspiro[3.4]octan-5-yl)-N-methylbenzenesulfonamide

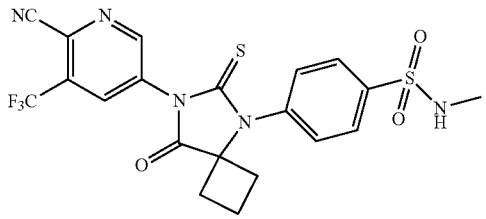

A mixture of 4-(7-(6-cyano-5-(trifluoromethyl)pyridin-3-yl)-8-oxo-6-thioxo-5,7-diazaspiro-[3.4]octan-5-yl)benzenesulfonamide (Compound 81, 97 mg, 0.20 mmol), methyl tosylate (37 mg, 0.20 mmol), and Cs$_2$CO$_3$ (65 mg, 0.20 mmol) in acetonitrile (1 mL) was heated at 50° C. for 20 h in a sealed tube. After being cooled room temperature, the reaction mixture was diluted with water and extracted with EtOAc (3×). The organic layer was dried over magnesium sulfate and concentrated to give a residue that was purified by column chromatography on silica gel (hexanes:DCM:acetone=5:9:1) to afford 30 mg of 4-(7-(6-cyano-5-(trifluoromethyl)pyridin-3-yl)-8-oxo-6-thioxo-5,7-diazaspiro[3.4]-octan-5-yl)-N-methylbenzenesulfonamide as a white solid. $^1$H NMR (400 MHz, CDCl$_3$) δ 9.11 (s, 1H), 8.37 (s, 1H), 8.10 (dd, 2H), 7.58-7.49 (m, 2H), 4.52 (d, 1H), 2.80 (m, 3H), 2.78-2.69 (m, 2H), 2.63-2.47 (m, 2H), 2.29 (m, 1H), 1.74 (m, 1H). LCMS [M+1+Na]$^+$ 518.0.

Example 11

Synthesis of Compound 121

4-(7-(6-Cyano-5-(trifluoromethyl)pyridin-3-yl)-8-oxo-6-thioxo-5,7-diazaspiro[3.4]octan-5-yl)-N,N-dimethylbenzenesulfonamide

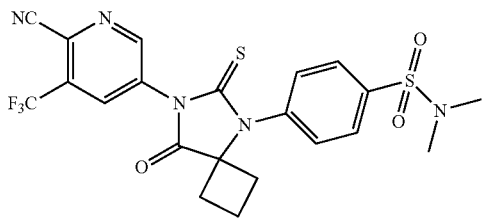

The title compound was obtained as a side product from the procedure described for Example 10. $^1$H NMR (400 MHz, CDCl$_3$) δ 9.11 (s, 1H), 8.37 (s, 1H), 8.02 (dd, 2H), 7.52 (dd, 2H), 2.84 (s, 6H), 2.83-2.68 (m, 2H), 2.55 (m, 2H), 2.37-2.21 (m, 1H), 1.80-1.64 (m, 1H). LCMS [M+Na]$^+$ 532.0.

Example 12

Synthesis of Compound 122

Methyl 4-(4-(7-(6-cyano-5-(trifluoromethyl)pyridin-3-yl)-8-oxo-6-thioxo-5,7-diazaspiro[3.4]octan-5-yl)phenyl)butanoate

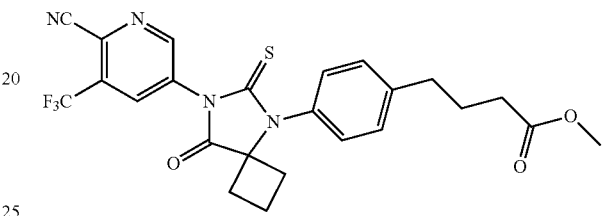

A mixture of 5-isothiocyanato-3-trifluoromethylpyridine-2-carbonitrile (Intermediate 10, 582 mg, 2.54 mmol) and 4-(4-(1-cyanocyclobutylamino)phenyl)butanoic acid (Intermediate 80, 410 mg, 1.59 mmol) in DMF (3 mL) was stirred at room temperature overnight. To this mixture were added methanol (4 mL) and HCl (2M, 2 mL) and the resulting mixture was refluxed for 3 h. After being cooled room temperature, the reaction mixture was poured into cold water and extracted with EtOAc (3×). The organic layers were dried over magnesium sulfate and concentrated to dryness. Column chromatography of the residue on silica gel (Hexane:EtOAc=4:1) afforded 256 mg of methyl 4-(4-(7-(6-cyano-5-(trifluoromethyl)-pyridin-3-yl)-8-oxo-6-thioxo-5,7-diazaspiro[3.4]octan-5-yl)phenyl)butanoate as a white solid. $^1$H NMR (400 MHz, CDCl$_3$) δ 9.11 (d, 1H), 8.38 (d, 1H), 7.42 (d, 2H), 7.36-7.19 (m, 2H), 3.70 (s, 3H), 2.87-2.75 (m, 2H), 2.75-2.53 (m, 4H), 2.42 (t, 2H), 2.26 (m, 1H), 2.05 (m, 2H), 1.78-1.61 (m, 1H). LCMS [M+1]$^+$ 503.0.

Example 13

Synthesis of Compound 123

5-(5-(4-Fluoro-3-hydroxyphenyl)-8-oxo-6-thioxo-5,7-diazaspiro[3.4]octan-7-yl)-3-(trifluoromethyl)picolinonitrile

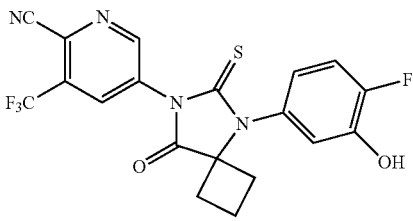 [SMILES: N#Cc1ncc(N2C(=O)C3(CCC3)N(c3ccc(F)c(O)c3)C2=S)cc1C(F)(F)F]

Trimethylsilyl iodide (7.0 ml, 51.1 mmol) was added to a solution of 5-(5-(4-fluoro-3-methoxyphenyl)-8-oxo-6-thioxo-5,7-diazaspiro[3.4]octan-7-yl)-3-(trifluoromethyl)picolinonitrile (Compound 32, 3 g, 5.1 mmol) in acetonitrile (50 mL) and the mixture was refluxed for 24 h. The mixture was cooled to room temperature, poured into water, and extracted with EtOAc (3×). The organics were combined, washed with sat'd solution of NaHSO$_3$, dried over MgSO$_4$, and evaporated to dryness. The residue was purified by column chromatography on silica gel eluting with EtOAc/Hexane=1/5 to afford 1.1 g of 5-(5-(4-fluoro-3-hydroxyphenyl)-8-oxo-6-thioxo-5,7-diazaspiro[3.4]octan-7-yl)-3-(trifluoromethyl)picolinonitrile. $^1$H NMR (400 MHz, CDCl$_3$) δ 9.10 (d, 1H), 8.38 (d, 1H), 7.27-7.22 (m, 1H), 6.93 (dd, 1H), 6.78 (m, 1H), 2.74-2.55 (m, 1H), 2.23 (m, 1H), 1.80-1.59 (m, 4H).

Example 14

Synthesis of Compound 124

5-(5-(4-(3-(4-Methylpiperazin-1-yl)propyl)phenyl)-8-oxo-6-thioxo-5,7-diazaspiro[3.4]octan-7-yl)-3-(trifluoromethyl)picolinonitrile

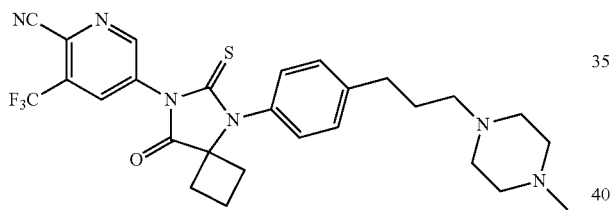

A solution of 5-(5-(4-(3-hydroxypropyl)phenyl)-8-oxo-6-thioxo-5,7-diazaspiro[3.4]octan-7-yl)-3-(trifluoromethyl)picolinonitrile (Compound 86, 66 mg, 0.14 mmol) and methanesulfonyl chloride (0.033 mL, 0.42 mmol) in DCM (2 mL) was stirred at room temperature for 2 h. The solution was washed with water (2×) and brine, dried over magnesium sulfate and concentrated to give 80 mg of the corresponding mesylate without purification. The mesylate (45 mg, 0.084 mmol), methyl piperazine (0.02 mL, 0.17 mmol) and triethylamine (0.04 mL, 0.25 mmol) in dichloromethane was stirred at room temperature overnight, then at reflux for 16 h. The mixture was partitioned between water and DCM and the aqueous was further extracted with DCM (2×). The combined organics were washed with brine, dried (MgSO$_4$) and concentrated. Purification by silica gel chromatography (0 to 80% EtOAc/hexanes) afforded 20 mg of 5-(5-(4-(3-(4-methylpiperazin-1-yl)propyl)phenyl)-8-oxo-6-thioxo-5,7-diazaspiro[3.4]octan-7-yl)-3-(trifluoromethyl)picolinonitrile as a beige solid. $^1$H NMR (300 MHz, DMSO-d$_6$) δ 9.23 (d, 1H), 8.77 (d, 1H), 7.45 (d, 2H), 7.31 (d, 2H), 2.76-2.57 (m, 4H), 2.49-2.23 (m, 5H), 2.14 (s, 3H), 2.02-1.89 (m, 1H), 1.85-1.73 (m, 3H), 1.59-1.46 (m, 1H). LCMS [M+1]$^+$ 543.1.

Example 15

Synthesis of Compound 125

5-(5-(Benzo[d]oxazol-6-yl)-8-oxo-6-thioxo-5,7-diazaspiro[3.4]octan-7-yl)-3-(trifluoromethyl)picolinonitrile Step 1: 5-(5-(4-Amino-3-hydroxyphenyl)-8-oxo-6-thioxo-5,7-diazaspiro[3.4]octan-7-yl)-3-(trifluoromethyl)picolinonitrile

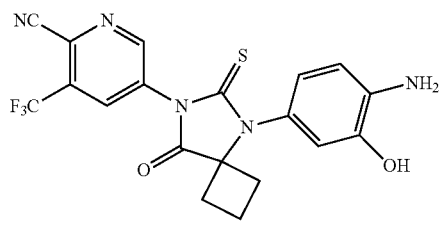 [SMILES: N#Cc1ncc(N2C(=O)C3(CCC3)N(c3ccc(N)c(O)c3)C2=S)cc1C(F)(F)F]

A mixture of 5-amino-3-(trifluoromethyl)picolinonitrile (Intermediate 1, 110 mg, 0.59 mmol), benzo[d]oxazol-6-amine (Intermediate 79, 125 mg, 0.59 mmol), and thiophosgene (0.05 mL, 0.60 mmol) in anhydrous DMA (3 mL) was stirred at 60° C. for 16 h. Methanol (3 mL) and 2M HCl (1.5 mL) were then added and the mixture was heated at 90° C. for 2 h. The reaction mixture was cooled and poured into ice/water (40 mL) and the resultant solid was filtered to afford 150 mg of 5-(5-(4-amino-3-hydroxyphenyl)-8-oxo-6-thioxo-5,7-diazaspiro[3.4]octan-7-yl)-3-(trifluoromethyl)picolinonitrile as a brown powder. LCMS [M+1]$^+$ 434.0.

Step 2: 5-(5-(Benzo[d]oxazol-6-yl)-8-oxo-6-thioxo-5,7-diazaspiro[3.4]octan-7-yl)-3-(trifluoromethyl)picolinonitrile

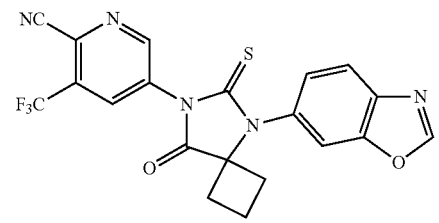 [SMILES: N#Cc1ncc(N2C(=O)C3(CCC3)N(c3ccc4ncoc4c3)C2=S)cc1C(F)(F)F]

A mixture of 5-(5-(4-amino-3-hydroxyphenyl)-8-oxo-6-thioxo-5,7-diazaspiro[3.4]octan-7-yl)-3-(trifluoromethyl)picolinonitrile (60 mg, 0.14 mmol) and triethylorthoformate (0.050 mL, 0.28 mmol) in anhydrous DMF (1 mL) was heated at 100° C., 1 h. The mixture was diluted with water, extracted with EtOAc (3×), the organics combined and washed with water (2×), brine, dried (MgSO$_4$) and concentrated. Purification by column chromatography, eluting with 30% EtOAc/hexanes provided 23 mg of 5-(5-(benzo[d]oxazol-6-yl)-8-oxo-6-thioxo-5,7-diazaspiro[3.4]octan-7-yl)-3-(trifluoromethyl)picolinonitrile as a pale yellow solid. $^1$H NMR (300 MHz, DMSO-d$_6$) δ 9.24 (d, 1H), 8.95 (s, 1H), 8.78 (d, 1H), 8.05 (d, 1H), 7.94 (d, 1H), 7.45 (dd, 1H), 2.74-2.61 (m, 2H), 2.59-2.47 (m, 2H), 2.03-1.90 (m, 1H), 1.61-1.48 (m, 1H). LCMS [M+1]$^+$ 444.0.

Example 16

Synthesis of Compound 126

5-(5-(3-Fluoro-4-(2-(1-methyl-1H-pyrazol-5-yl)ethoxy)phenyl)-8-oxo-6-thioxo-5,7-diazaspiro[3.4]octan-7-yl)-3-(trifluoromethyl)picolinonitrile

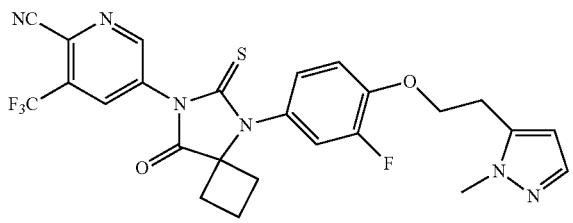 [SMILES: Cn1nccc1CCOc1ccc(N2C(=S)N(c3cnc(C#N)c(C(F)(F)F)c3)C(=O)C23CCC3)cc1F]

A mixture of 5-(5-(3-fluoro-4-hydroxyphenyl)-8-oxo-6-thioxo-5,7-diazaspiro[3.4]octan-7-yl)-3-(trifluoromethyl)picolinonitrile (Compound 1, 100 mg, 0.23 mmol), 2-(1-methyl-1H-pyrazol-5-yl)ethanol (43.5 mg, 0.34 mmol), triphenylphosphine (89 mg, 0.34 mmol), and diisopropyl azodicarboxylate (0.07 mL, 0.34 mmol) in THF (5 mL) was stirred at room temperature for 18 h. The reaction mixture was absorbed on silica gel and purified by column chromatography on silica gel eluting with EtOAc/hexanes to afford impure desired product that was repurified by reverse phase HPLC (acetonitrile/water:TFA). The fractions containing the desired compound were combined, acetonitrile was removed in vacuo, and the remaining aqueous layer was treated with a saturated solution of sodium bicarbonate. The aqueous layer was extracted with DCM (3×), the organics were combined, dried over sodium sulfate, and evaporated to dryness to afford 29 mg of 5-(5-(3-fluoro-4-(2-(1-methyl-1H-pyrazol-5-yl)ethoxy)phenyl)-8-oxo-6-thioxo-5,7-diazaspiro[3.4]octan-7-yl)-3-(trifluoromethyl) picolinonitrile as a beige solid. LCMS [M+1]$^+$ 545.5.

Example 17

Synthesis of Compound 127

5-(5-(3-Fluoro-4-(2-(pyrrolidin-1-yl)ethoxy)phenyl)-8-oxo-6-thioxo-5,7-diazaspiro[3.4]octan-7-yl)-3-(trifluoromethyl)picolinonitrile

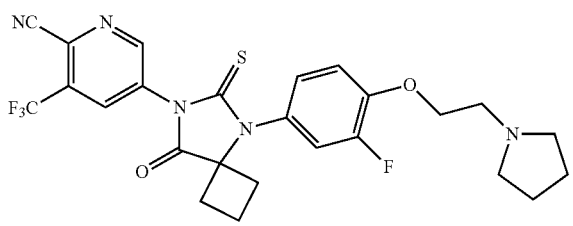 [SMILES: N#Cc1ncc(N2C(=O)C3(CCC3)N(c3ccc(OCCN4CCCC4)c(F)c3)C2=S)cc1C(F)(F)F]

A mixture of 5-(5-(3-fluoro-4-hydroxyphenyl)-8-oxo-6-thioxo-5,7-diazaspiro[3.4]octan-7-yl)-3-(trifluoromethyl)picolinonitrile (Compound 1, 100 mg, 0.23 mmol), 2-(pyrrolidin-1-yl)ethanol (35 μL, 0.30 mmol), triphenylphosphine (79 mg, 0.30 mmol), and diisopropyl azodicarboxylate (60 μL, 0.30 mmol) in THF (5 mL) was stirred at room temperature for 2 days. The reaction mixture was absorbed on silica gel and purified by column chromatography on silica gel eluting with 0 to 10% MeOH/DCM to afford impure desired product that was repurified by reverse phase HPLC (acetonitrile/water, 0.1% TFA). The fractions containing the desired compound were combined, acetonitrile was removed in vacuo, and the remaining aqueous layer was treated with a saturated solution of sodium bicarbonate. The aqueous layer was extracted with DCM (3×), the organics were combined, dried over sodium sulfate, and evaporated to dryness to afford 30 mg of 5-(5-(3-fluoro-4-(2-(pyrrolidin-1-yl)ethoxy)phenyl)-8-oxo-6-thioxo-5,7-diazaspiro[3.4]octan-7-yl)-3-(trifluoromethyl)picolinonitrile as a white solid. $^1$H NMR (300 MHz, DMSO-d$_6$) δ 9.21 (d, 1H), 8.74 (d, 1H), 7.40 (t, 1H), 7.35 (dd, 1H), 7.22 (d, 1H), 4.24 (t, 2H), 2.86 (t, 2H), 2.65-2.42 (m, 8H), 1.98-1.95 (m, 1H), 1.70 (m, 4H), 1.60-1.54 (m, 1H). LCMS [M+1]$^+$ 534.9.

Example 18

Synthesis of Compound 128

5-(5-(4-(Benzyloxy)-3-fluorophenyl)-8-oxo-6-thioxo-5,7-diazaspiro[3.4]octan-7-yl)-3-(trifluoromethyl)picolinonitrile

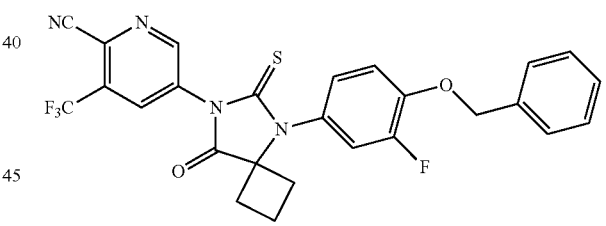

A mixture of 5-(5-(3-fluoro-4-hydroxyphenyl)-8-oxo-6-thioxo-5,7-diazaspiro[3.4]octan-7-yl)-3-(trifluoromethyl)picolinonitrile (Example 1, 100 mg, 0.23 mmol), benzyl alcohol (35 μL, 0.30 mmol) triphenylphosphine (79 mg, 0.30 mmol), and diisopropyl azodicarboxylate (60 μL, 0.30 mmol) in THF (5 mL) was stirred at room temperature for 2 days then heated to 60° C. overnight. The reaction mixture was absorbed on silica gel and purified by column chromatography on silica gel eluting with 0 to 50% EtOAc/Hexanes to afford impure desired product. The solid was triturated in MeOH, filtered, and dried to afford 36 mg of 5-(5-(4-(benzyloxy)-3-fluorophenyl)-8-oxo-6-thioxo-5,7-diazaspiro[3.4]octan-7-yl)-3-(trifluoromethyl)picolinonitrile as a white solid. $^1$H NMR (300 MHz, DMSO-d$_6$) δ 9.21 (d, 1H), 8.75 (d, 1H), 7.53-7.36 (m, 7H), 7.23 (d, 1H), 5.28 (s, 2H), 2.66-2.60 (m, 2H), 2.53-2.43 (m, 2H), 2.02-1.92 (m, 1H), 1.61-1.55 (m, 1H).

Example 19

Synthesis of Compound 129

5-(5-(4-((1-Methylpiperidin-4-yl)oxy)phenyl)-8-oxo-6-thioxo-5,7-diazaspiro[3.4]octan-7-yl)-3-(trifluoromethyl)picolinonitrile

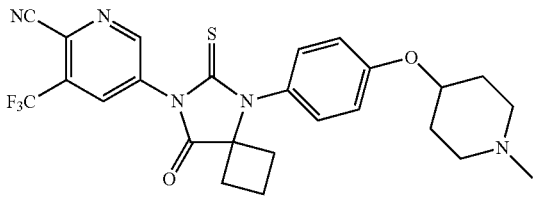 [SMILES: CN1CCC(Oc2ccc(N3C(=S)N(c4cnc(C#N)c(C(F)(F)F)c4)C(=O)C34CCC4)cc2)CC1]

To a solution of 5-(5-(4-hydroxyphenyl)-8-oxo-6-thioxo-5,7-diazaspiro[3.4]octan-7-yl)-3-(trifluoromethyl)picolinonitrile (Compound 63, 150 mg, 0.36 mmol), 1-methylpiperidin-4-ol (50 µL, 0.39 mmol), and triphenylphosphine (125 mg, 0.47 mmol) in anhydrous THF (2 mL) was added diisopropyl azodicarboxylate (0.1 mL, 0.47 mmol) and the reaction mixture was stirred at room temperature overnight. Additional 1-methylpiperidin-4-ol (50 µL, 0.39 mmol), triphenylphosphine (125 mg, 0.47 mmol) and diisopropyl azodicarboxylate (0.1 mL, 0.47 mmol) was added and the reaction was allowed to stir an additional 16 h. The mixture was partitioned between EtOAc and water and the aqueous layer was extracted with EtOAc (2×). The combined organics were washed with water and brine, then dried over magnesium sulfate and concentrated in vacuo. Purification by silica gel chromatography (0 to 80% EtOAc/hexanes, then 0 to 5% MeOH/dichloromethane) gave impure product which was further purified by preparative HPLC (40 to 75% acetonitrile/water, 0.1% TFA) to afford 45 mg of 5-(5-(4-((1-methylpiperidin-4-yl)oxy)phenyl)-8-oxo-6-thioxo-5,7-diazaspiro[3.4]octan-7-yl)-3-(trifluoromethyl)picolinonitrile as a pale yellow solid. $^1$H NMR (300 MHz, DMSO-$d_6$) δ 9.22 (d, 1H), 8.76 (d, 1H), 7.30 (d, 2H), 7.15 (d, 2H), 4.52-4.39 (m, 1H), 2.72-2.56 (m, 4H), 2.49-2.38 (m, 2H), 2.25-2.14 (m, 5H), 2.03-1.90 (m, 3H), 1.77-1.49 (m, 3H). LCMS [M+1]$^+$ 516.0.

Compounds 130 to 201 were synthesized following the procedure described in Example 16 from the appropriate phenols and alcohols (phenols and alcohols were either commercially available, synthesized in the Intermediates section, or synthesized from published procedures).

Example 20

Synthesis of Compound 202

5-(5-(4-(2-(4-Acetylpiperazin-1-yl)ethoxy)-3-fluorophenyl)-8-oxo-6-thioxo-5,7-diazaspiro[3.4]octan-7-yl)-3-(trifluoromethyl)picolinonitrile

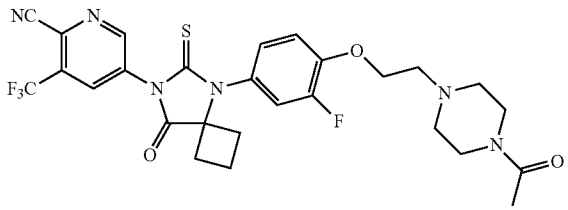 [SMILES: CC(=O)N1CCN(CCOc2ccc(N3C(=S)N(c4cnc(C#N)c(C(F)(F)F)c4)C(=O)C34CCC4)cc2F)CC1]

A mixture of 5-(5-(3-fluoro-4-(2-(piperazin-1-yl)ethoxy)phenyl)-8-oxo-6-thioxo-5,7-diazaspiro[3.4]octan-7-yl)-3-(trifluoromethyl)picolinonitrile (Compound 174, 50 mg, 0.1 mmol), acetic anhydride (13 µL, 0.14 mmol), and triethylamine (40 µL, 0.27 mmol) in DCM (2 mL) was stirred at room temperature for 2 days. The reaction mixture was absorbed on silica gel and purified by column chromatography on silica gel eluting with 0 to 10% MeOH/DCM to afford 34 mg of 5-(5-(4-(2-(4-acetylpiperazin-1-yl)ethoxy)-3-fluorophenyl)-8-oxo-6-thioxo-5,7-diazaspiro[3.4]octan-7-yl)-3-(trifluoromethyl)picolinonitrile as a white solid. $^1$H NMR (300 MHz, DMSO-$d_6$) δ 9.21 (s, 1H), 8.74 (s, 1H), 7.42 (t, 1H), 7.35 (dd, 1H), 7.22 (m, 1H), 4.28 (t, 2H), 3.42 (m, 4H), 2.80 (t, 2H), 2.65-2.59 (m, 2H), 2.54-2.44 (m, 6H), 1.98 (m, 4H), 1.57 (m, 1H). LCMS [M+1]$^+$ 591.9.

Example 21

Synthesis of Compound 203

5-(5-(3-Fluoro-4-methoxyphenyl)-8-oxo-6-thioxo-5,7-diazaspiro[3.4]octan-7-yl)-3-(trifluoromethyl)picolinonitrile

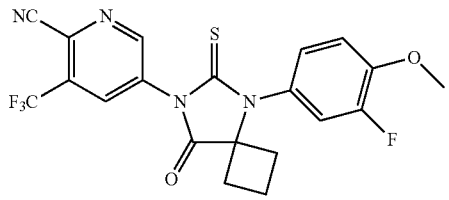 [SMILES: COc1ccc(N2C(=S)N(c3cnc(C#N)c(C(F)(F)F)c3)C(=O)C23CCC3)cc1F]

A mixture of 5-(5-(3-fluoro-4-hydroxyphenyl)-8-oxo-6-thioxo-5,7-diazaspiro[3.4]octan-7-yl)-3-(trifluoromethyl)picolinonitrile (Compound 1, 100 mg, 0.23 mmol), methyl iodide (0.14 mL, 0.23 mmol), and potassium carbonate (31 mg, 0.23 mmol) in acetone (4 mL) was stirred at room temperature for 4 h. Excess potassium carbonate was removed and the reaction mixture was absorbed on silica gel and purified by column chromatography on silica gel eluting with 0 to 30% EtOAc/hexanes to afford 74 mg of 5-(5-(3-fluoro-4-methoxyphenyl)-8-oxo-6-thioxo-5,7-diazaspiro[3.4]octan-7-yl)-3-(trifluoromethyl)picolinonitrile as a white solid. LCMS [M+1]$^+$ 451.4

Compounds 204 and 205 were synthesized following the procedure described in Example 21 from the appropriate phenols.

Example 22

Synthesis of Compound 206

5-(8-Oxo-5-(4-(pyrimidin-2-yloxy)phenyl)-6-thioxo-5,7-diazaspiro[3.4]octan-7-yl)-3-(trifluoromethyl)picolinonitrile

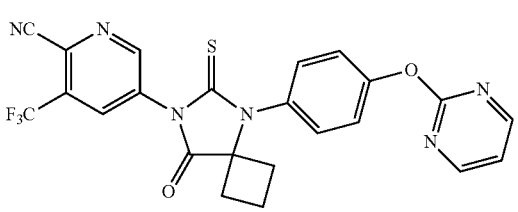 [SMILES: N#Cc1ncc(N2C(=O)C3(CCC3)N(c3ccc(Oc4ncccn4)cc3)C2=S)cc1C(F)(F)F]

A mixture of 5-(5-(4-hydroxyphenyl)-8-oxo-6-thioxo-5,7-diazaspiro[3.4]octan-7-yl)-3-(trifluoromethyl)picolinonitrile (Compound 63, 50 mg, 0.12 mmol), 2-chloropyrimidine (17 mg, 0.15 mmol), and cesium carbonate (60 mg, 0.18 mmol) in anhydrous THF (1.2 mL) was heated at reflux overnight. The reaction mixture was cooled to room temperature and water was added. The aqueous was extracted with EtOAc (3×), the organics combined and washed with brine, dried (MgSO$_4$) and concentrated. Purification by column chromatography on silica gel eluting with 0 to 60% EtOAc/hexanes provided 30 mg of 5-(8-oxo-5-(4-(pyrimidin-2-yloxy)phenyl)-6-thioxo-5,7-diazaspiro[3.4]octan-7-yl)-3-(trifluoromethyl)picolinonitrile as an off-white solid. $^1$H NMR (300 MHz, DMSO-d$_6$) δ 9.24 (d, 1H), 8.78 (d, 1H), 8.73 (d, 2H), 7.48 (dd, 4H), 7.35 (t, 1H), 2.72-2.61 (m, 2H), 2.54-2.42 (m, 2H), 2.10-1.93 (m, 1H), 1.69-1.52 (m, 1H). LCMS [M+1]$^+$ 497.8.

Example 23

Synthesis of Compound 207

5-(8-Oxo-5-(4-(pyrazin-2-yloxy)phenyl)-6-thioxo-5,7-diazaspiro[3.4]octan-7-yl)-3-(trifluoromethyl)picolinonitrile

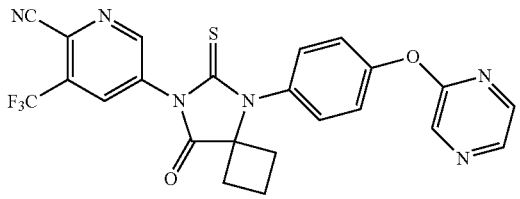 [SMILES: N#Cc1ncc(N2C(=O)C3(CCC3)N(c3ccc(Oc4cnccn4)cc3)C2=S)cc1C(F)(F)F]

A mixture of 5-(5-(4-hydroxyphenyl)-8-oxo-6-thioxo-5,7-diazaspiro[3.4]octan-7-yl)-3-(trifluoromethyl)picolinonitrile (Compound 63, 100 mg, 0.24 mmol), NaH (14 mg, 0.36 mmol, 60% dispersion in oil) and chloropyrazine (0.025 mL, 0.29 mmol) in anhydrous DMF (1.4 mL) was heated at 90° C. for 16 h. Additional chloropyrazine (0.025 mL, 0.29 mmol) was added and heating was continued for 16 h. The reaction mixture was cooled to room temperature and water was added. The aqueous was extracted with EtOAc (3×), the organics combined and washed with brine, dried (MgSO$_4$) and concentrated. Purification by column chromatography on silica gel eluting with 0 to 50% EtOAc/hexanes afforded 50 mg of impure product. Further purification by preparative HPLC (30 to 100% acetonitrile/water, 10 min) provided 10 mg of 5-(8-oxo-5-(4-(pyrazin-2-yloxy)phenyl)-6-thioxo-5,7-diazaspiro[3.4]octan-7-yl)-3-(trifluoromethyl)picolinonitrile as an off-white solid. $^1$H NMR (300 MHz, DMSO-d$_6$) δ 9.23 (d, 1H), 8.78 (d, 1H), 8.65 (d, 1H), 8.46 (d, 1H), 8.31 (dd, 1H), 7.48 (dd, 4H), 2.75-2.60 (m, 2H), 2.57-2.42 (m, 2H), 2.06-1.94 (m, 1H), 1.68-1.53 (m, 1H). LCMS [M+1]$^+$ 496.9.

Compounds 208 and 209 were synthesized following the procedure described in Example 23 from the appropriate phenols.

Example 24

Synthesis of Compound 210

3-Methyl-5-(8-oxo-5-(4-(piperidin-4-yloxy)phenyl)-6-thioxo-5,7-diazaspiro[3.4]octan-7-yl)picolinonitrile

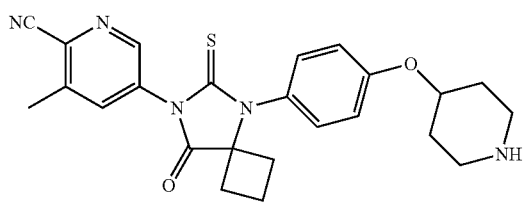 [SMILES: Cc1cc(N2C(=O)C3(CCC3)N(c3ccc(OC4CCNCC4)cc3)C2=S)cnc1C#N]

Tert-butyl 4-(4-(7-(6-cyano-5-methylpyridin-3-yl)-8-oxo-6-thioxo-5,7-diazaspiro[3.4]octan-5-yl)phenoxy)piperidine-1-carboxylate (prepared by reaction of 5-(5-(4-hydroxyphenyl)-8-oxo-6-thioxo-5,7-diazaspiro[3.4]octan-7-yl)-3-methylpicolinonitrile (Compound 77) with tert-butyl 4-hydroxypiperidine-1-carboxylate, according to Example 16, 300 mg, 0.55 mmol) was stirred in 2M HCl/methanol (1.5 mL) at room temperature overnight. The mixture was concentrated and purified by column chromatography, eluting with 10% MeOH/DCM to provide 230 mg of 3-methyl-5-(8-oxo-5-(4-(piperidin-4-yloxy)phenyl)-6-thioxo-5,7-diazaspiro[3.4]octan-7-yl)picolinonitrile as a white solid. $^1$H NMR (300 MHz, DMSO-d$_6$) δ 8.72 (d, 1H), 8.14 (d, 1H), 7.30 (d, 2H), 7.13 (d, 2H), 4.53-4.42 (m, 1H), 3.94-3.86 (m, 1H), 3.02-2.83 (m, 3H), 2.66-2.50 (m, 5H), 2.49-2.33 (m, 3H), 2.11-1.80 (m, 3H), 1.60-1.33 (m, 3H). LCMS [M+1]$^+$ 448.1.

Example 25

Synthesis of Compound 211

5-(8-Oxo-5-(4-(piperidin-4-yloxy)phenyl)-6-thioxo-5,7-diazaspiro[3.4]octan-7-yl)-3-(trifluoromethyl)picolinonitrile

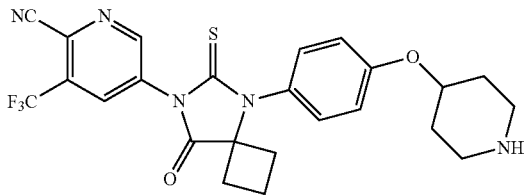 [SMILES: N#Cc1ncc(N2C(=O)C3(CCC3)N(c3ccc(OC4CCNCC4)cc3)C2=S)cc1C(F)(F)F]

The title compound was synthesized as described in Example 24 using Compound 63 as the starting material. $^1$H NMR (300 MHz, DMSO-d$_6$) δ 9.22 (d, 1H), 8.75 (d, 1H), 7.29 (d, 2H), 7.16 (d, 2H), 4.48 (m, 1H), 3.32 (s, 1H), 3.01-2.94 (dt, 2H), 2.64-2.57 (m, 4H), 2.51-2.38 (m, 2H), 1.98-1.95 (m, 3H), 1.58-1.43 (m, 3H). LCMS [M+1]$^+$ 502.2.

Example 26

Synthesis of Compound 212

5-(8-Oxo-5-(4-((1-propionylpiperidin-4-yl)oxy)phenyl)-6-thioxo-5,7-diazaspiro[3.4]octan-7-yl)-3-(trifluoromethyl)picolinonitrile

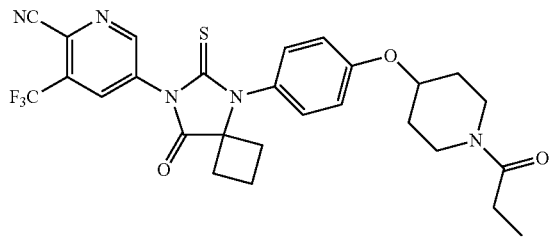 [SMILES: CCC(=O)N1CCC(Oc2ccc(N3C(=S)N(c4cnc(C#N)c(C(F)(F)F)c4)C(=O)C34CCC4)cc2)CC1]

Propionyl chloride (17 μL, 0.2 mmol) was added to a mixture of 5-(8-oxo-5-(4-(piperidin-4-yloxy)phenyl)-6-thioxo-5,7-diazaspiro[3.4]octan-7-yl)-3-(trifluoromethyl)picolinonitrile (50 mg, 0.1 mmol) and triethylamine (28 μL, 0.2 mmol) in THF (2 mL) and the resulting milky mixture was stirred at room temperature overnight. Methanol was added to quench the reaction and the mixture was absorbed on silica gel and purified by column chromatography on silica gel eluting with 50 to 100% EtOAc/hexanes to afford 21 mg of 5-(8-oxo-5-(4-((1-propionylpiperidin-4-yl)oxy)phenyl)-6-thioxo-5,7-diazaspiro[3.4]octan-7-yl)-3-(trifluoromethyl)picolinonitrile as a white solid. $^1$H NMR (300 MHz, DMSO-d$_6$) δ 9.15 (d, 1H), 8.69 (s, 1H), 7.25 (d, 2H), 7.13 (d, 2H), 4.62 (m, 1H), 3.85 (m, 1H), 3.62 (m, 1H), 3.29 (m, 1H), 3.15 (m, 1H), 2.55-2.52 (m, 2H), 2.42 (m, 2H), 2.39-2.25 (m, 2H), 1.92-1.88 (m, 3H), 1.50-1.45 (m, 3H), 0.93 (t, 3H). LCMS [M+1]$^+$ 558.1.

Compounds 213 to 219 were synthesized following the procedure described in Example 26 from the appropriate piperidines and the appropriate acid chlorides, chloroformates, alkyl bromides, or sulfonyl chlorides.

Example 27

Synthesis of Compound 220

5-(5-(4-((1-Isopropylpiperidin-4-yl)oxy)phenyl)-8-oxo-6-thioxo-5,7-diazaspiro[3.4]octan-7-yl)-3-(trifluoromethyl)picolinonitrile

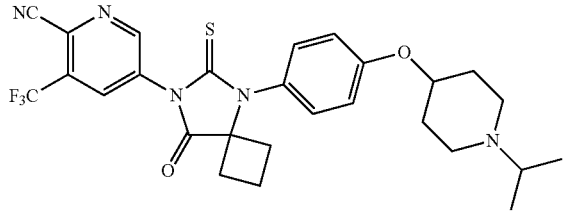 [SMILES: CC(C)N1CCC(Oc2ccc(N3C(=S)N(c4cnc(C#N)c(C(F)(F)F)c4)C(=O)C34CCC4)cc2)CC1]

To a solution of 5-(8-oxo-5-(4-(piperidin-4-yloxy)phenyl)-6-thioxo-5,7-diazaspiro[3.4]octan-7-yl)-3-(trifluoromethyl)picolinonitrile (50 mg, 0.10 mmol) in anhydrous THF (1 mL) was added 2-bromopropane (20 μL, 0.20 mmol) followed by cesium carbonate (100 mg, 0.30 mmol). The reaction mixture was heated at 70° C. overnight. DMF (1 mL) was added to improve solubility and the reaction was heated at 85° C. for 3 h. The mixture was cooled to room temperature and partitioned between water and EtOAc. The aqueous was extracted further with EtOAc (2×) and the combined organics were washed with water, then brine. The organics were dried over magnesium sulfate, filtered and concentrated. Purification by preparative HPLC provided 5 mg of 5-(5-(4-((1-isopropylpiperidin-4-yl)oxy)phenyl)-8-oxo-6-thioxo-5,7-diazaspiro[3.4]octan-7-yl)-3-(trifluoromethyl)picolinonitrile as an off-white solid. $^1$H NMR (300 MHz, DMSO-d$_6$) δ 9.04 (d, 1H), 8.30 (d, 1H), 7.13 (d, 2H), 6.99 (d, 2H), 4.37-4.26 (m, 1H), 2.81-2.33 (m, 10H), 2.25-1.74 (m, 5H), 1.00 (d, 6H). LCMS [M+1]$^+$ 544.0.

Example 28

Synthesis of Compound 221

Ethyl 2-(4-(4-(7-(6-cyano-5-(trifluoromethyl)pyridin-3-yl)-8-oxo-6-thioxo-5,7-diazaspiro[3.4]octan-5-yl)phenoxy)piperidin-1-yl)acetate

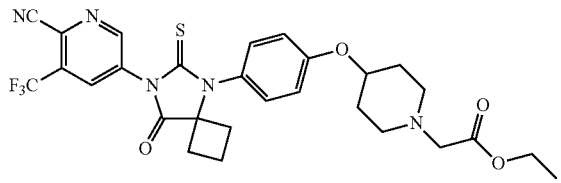 [SMILES: CCOC(=O)CN1CCC(Oc2ccc(N3C(=S)N(c4cnc(C#N)c(C(F)(F)F)c4)C(=O)C34CCC4)cc2)CC1]

The title compound was synthesized as described in Example 27 using 5-(8-oxo-5-(4-(piperidin-4-yloxy)phenyl)-6-thioxo-5,7-diazaspiro[3.4]octan-7-yl)-3-(trifluoromethyl)picolinonitrile and ethyl 2-bromoacetate as starting materials. LCMS [M+1]$^+$ 588.1.

Example 29

Synthesis of Compound 222

4-(4-(7-(6-Cyano-5-(trifluoromethyl)pyridin-3-yl)-8-oxo-6-thioxo-5,7-diazaspiro[3.4]octan-5-yl)phenoxy)piperidine-1-carboxamide

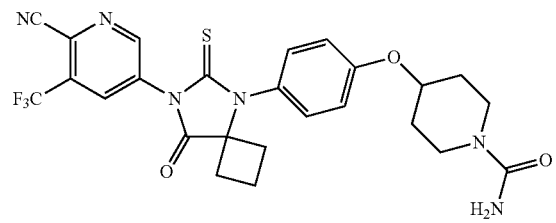 [SMILES: N#Cc1ncc(N2C(=O)C3(CCC3)N(c3ccc(OC4CCN(C(N)=O)CC4)cc3)C2=S)cc1C(F)(F)F]

A mixture of 5-(8-oxo-5-(4-(piperidin-4-yloxy)phenyl)-6-thioxo-5,7-diazaspiro[3.4]octan-7-yl)-3-(trifluoromethyl)picolinonitrile (70 mg, 0.14 mmol) and isocyanatotrimethylsilane (23 μL, 0.17 mmol) in DCM (3 mL) was stirred at room temperature overnight. Water was added and the mixture was stirred vigorously for 1 h. The aqueous layer was extracted with DCM (3×), the organics were combined, dried over sodium sulfate, and evaporated to dryness. Column chromatography on silica gel (0 to 20% MeOH/DCM) afforded 55 mg of 4-(4-(7-(6-cyano-5-(trifluoromethyl)pyridin-3-yl)-8-oxo-6-thioxo-5,7-diazaspiro[3.4]octan-5-yl)phenoxy)piperidine-1-carboxamide as a white solid. ¹H NMR (300 MHz, DMSO-d$_6$) δ 9.15 (s, 1H), 8.69 (s, 1H), 7.23 (d, 2H), 7.12 (d, 2H), 5.92 (s, 2H), 4.53 (m, 1H), 3.67-3.63 (m, 2H), 3.08-3.04 (m, 2H), 2.44 (m, 2H), 2.39 (m, 2H), 1.88 (m, 3H), 1.46 (m, 3H). LCMS [M+1]⁺ 545.2

Example 30

Synthesis of Compound 223

5-(5-(4-(2-Hydroxyethoxy)phenyl)-8-oxo-6-thioxo-5,7-diazaspiro[3.4]octan-7-yl)-3-methylpicolinonitrile

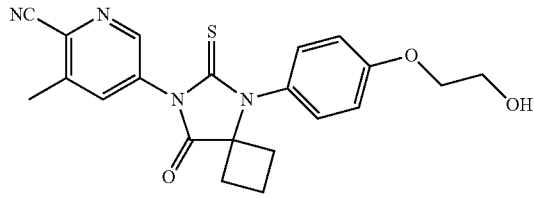 [SMILES: Cc1cc(N2C(=O)C3(CCC3)N(c3ccc(OCCO)cc3)C2=S)cnc1C#N]

Dihydrofuran-2,5-dione (604 mg, 6.87 mmol) in DMF (5 mL) was added to a mixture of 5-(5-(4-hydroxyphenyl)-8-oxo-6-thioxo-5,7-diazaspiro[3.4]octan-7-yl)-3-methylpicolinonitrile (500 mg, 1.37 mmol) and potassium carbonate (378 mg, 2.74 mmol) in DMF (10 mL) and the resulting mixture was heated to 85° C. overnight. The mixture was cooled to room temperature and partitioned between water and EtOAc. The aqueous was extracted further with EtOAc (2×) and the combined organics were washed with water, then brine. The organics were dried over sodium sulfate, filtered, and concentrated. Column chromatography on silica gel (50 to 100% EtOAc/hexanes) afforded 396 mg of 5-(5-(4-(2-hydroxyethoxyl)phenyl)-8-oxo-6-thioxo-5,7-diazaspiro[3.4]octan-7-yl)-3-methylpicolinonitrile as a white solid. ¹H NMR (300 MHz, DMSO-d$_6$) δ 8.71 (d, 1H), 8.14 (d, 1H), 7.33 (d, 2H), 7.13 (d, 2H), 4.92 (t, 1H), 4.11-4.05 (m, 2H), 3.78-3.73 (m, 2H), 2.63-2.5 (m, 5H), 2.49-2.37 (m, 2H), 2.00-1.90 (m, 1H), 1.56-1.51 (m, 1H). LCMS [M+1]⁺ 409.0.

Example 31

Synthesis of Compound 224

4-(7-(6-Cyano-5-(trifluoromethyl)pyridin-3-yl)-8-oxo-6-thioxo-5,7-diazaspiro[3.4]octan-5-yl)-2-fluorobenzoic acid

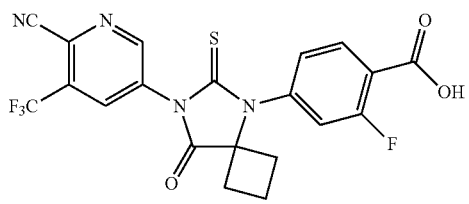 [SMILES: N#Cc1ncc(N2C(=O)C3(CCC3)N(c3ccc(C(=O)O)c(F)c3)C2=S)cc1C(F)(F)F]

A mixture of ethyl 4-(7-(6-cyano-5-(trifluoromethyl)pyridin-3-yl)-8-oxo-6-thioxo-5,7-diazaspiro[3.4]octan-5-yl)-2-fluorobenzoate (Compound 3, 1 g, 2.03 mmol) and NaOH (3M, 10 mL) in MeOH (10 mL) was stirred at room temperature for 18 h. Aqueous HCl (2M) was added to the reaction mixture until the pH=2 and the aqueous layer was extracted with DCM (5×), the organics were combined, dried over sodium sulfate, and evaporated to dryness to afford 900 mg of 4-(7-(6-cyano-5-(trifluoromethyl)pyridin-3-yl)-8-oxo-6-thioxo-5,7-diazaspiro[3.4]octan-5-yl)-2-fluorobenzoic acid as a light yellow solid. ¹H NMR (300 MHz, DMSO-d$_6$) δ 13.58 (s, 1H), 9.22 (s, 1H), 8.75 (s, 1H), 8.13 (t, 1H), 7.51 (dd, 1H), 7.43 (dd, 1H), 2.69-2.49 (m, 4H), 2.03-1.93 (m, 1H), 1.63-1.57 (m, 1H).

Compounds 225 to 228 were synthesized following the procedure described in Example 31 from the corresponding ester.

Example 32

Synthesis of Compound 229

5-(7-(6-Carbamoyl-5-(trifluoromethyl)pyridin-3-yl)-8-oxo-6-thioxo-5,7-diazaspiro[3.4]octan-5-yl)-2-fluorobenzoic acid

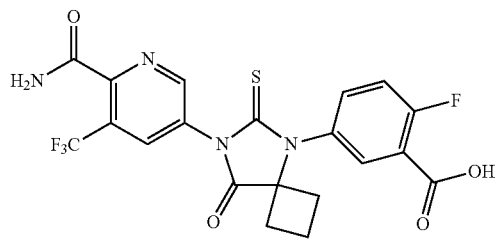 [SMILES: NC(=O)c1ncc(N2C(=O)C3(CCC3)N(c3ccc(F)c(C(=O)O)c3)C2=S)cc1C(F)(F)F]

The title compound was synthesized as a by-product in the synthesis of Compound 226. ¹H NMR (300 MHz, DMSO-d$_6$) δ 13.63 (s, 1H), 8.95 (s, 1H), 8.50 (s, 1H), 8.27 (s, 1H), 7.95 (m, 2H), 7.72 (m, 1H), 7.58 (t, 1H), 2.65 (m, 2H), 2.45 (m, 2H), 1.97 (m, 1H), 1.56 (m, 1H). LCMS [M+1]⁺ 483.4.

Example 33

Synthesis of Compound 230

4-(4-(7-(6-Cyano-5-(trifluoromethyl)pyridin-3-yl)-8-oxo-6-thioxo-5,7-diazaspiro[3.4]octan-5-yl)phenyl)-N-methylbutanamide

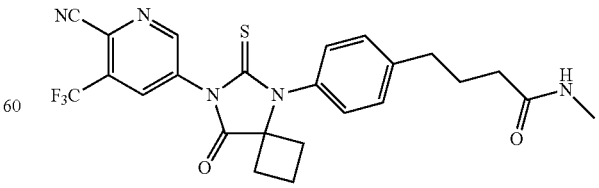

To a solution of 4-(4-(7-(6-cyano-5-(trifluoromethyl)pyridin-3-yl)-8-oxo-6-thioxo-5,7-diazaspiro[3.4]octan-5-yl)phenyl)butanoic acid (Compound 227, 85 mg, 0.17 mmol)

in DCM (2 mL) were added triethylamine (0.013 mL, 0.09 mmol) and 4-nitrophenyl chloroformate (15 mg, 0.07 mmol). The mixture was stirred at room temperature for 1 h and methylamine (0.3 mL, 2M in THF) was added. After 30 min, the mixture was diluted with water and extracted with EtOAc (2×). The organic layers were dried over magnesium sulfate and concentrated. Column chromatography on silica gel (Hexane:EtOAc=1:1) afforded 35 mg (40%) of 4-(4-(7-(6-cyano-5-(trifluoromethyl)pyridin-3-yl)-8-oxo-6-thioxo-5,7-diazaspiro[3.4]octan-5-yl)phenyl)-N-methylbutanamide as a white solid. $^1$H NMR (400 MHz, CDCl$_3$) δ 9.11 (d, 1H), 8.38 (d, 1H), 7.42 (d, 2H), 7.22 (d, 2H), 2.86-2.81 (m, 3H), 2.81-2.73 (t, 2H), 2.73-2.64 (m, 2H), 2.64-2.53 (m, 2H), 2.26 (t, 2H), 2.24-2.17 (m, 1H), 2.11-2.01 (m, 2H), 1.69 (m, 1H). LCMS [M+1]$^+$ 502.0.

Example 34

Synthesis of Compound 231

4-(7-(6-Cyano-5-(trifluoromethyl)pyridin-3-yl)-8-oxo-6-thioxo-5,7-diazaspiro[3.4]octan-5-yl)-2-fluorobenzamide

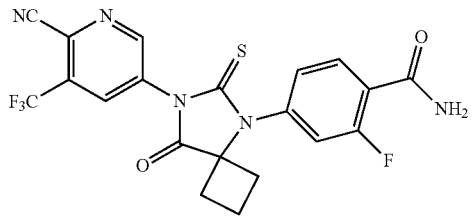 [SMILES: N#Cc1ncc(N2C(=O)C3(CCC3)N(c3ccc(C(N)=O)c(F)c3)C2=S)cc1C(F)(F)F]

To a suspension of 4-(7-(6-cyano-5-(trifluoromethyl)pyridin-3-yl)-8-oxo-6-thioxo-5,7-diazaspiro[3.4]octan-5-yl)-2-fluorobenzoic acid (Compound 224, 500 mg, 1.08 mmol) in DCM was added DMF (cat., 0.1 mL), followed by oxalyl chloride (0.14 mL, 1.61 mmol). The mixture was stirred at room temperature for 4 h then concentrated in vacuo to produce a yellow residue that was further dried on a high vacuum pump. Ammonia (0.5M in dioxane, 40 mL, 20 mmol) was directly added to the residue and the mixture was stirred at room temperature overnight. MeOH was added and the mixture was absorbed onto silica gel and purified by flash chromatography (50 to 100% EtOAc/Hexanes) to afford impure desired product that was repurified by reverse phase HPLC (acetonitrile/water:TFA). The fractions containing the desired compound were combined, acetonitrile was removed in vacuo, and the remaining aqueous layer was treated with a saturated solution of sodium bicarbonate. The aqueous layer was extracted with DCM (3×), the organics were combined, dried over sodium sulfate, and evaporated to dryness to afford 100 mg of 4-(7-(6-cyano-5-(trifluoromethyl)pyridin-3-yl)-8-oxo-6-thioxo-5,7-diazaspiro[3.4]octan-5-yl)-2-fluorobenzamide as a white solid. $^1$H NMR (300 MHz, DMSO-d$_6$) δ 9.21 (s, 1H), 8.75 (s, 1H), 7.95 (s, 1H), 7.87 (t, 1H), 7.80 (s, 1H), 7.46 (dd, 1H), 7.37 (dd, 1H), 2.69-2.62 (m, 2H), 2.55-2.47 (m, 2H), 2.00 (m, 1H), 1.58 (m, 1H).

Compounds 232 and 233 were synthesized following the procedure described in Example 34 from the appropriate carboxylic acids.

Example 35

Synthesis of Compound 234

4-(7-(6-Cyano-5-(trifluoromethyl)pyridin-3-yl)-8-oxo-6-thioxo-5,7-diazaspiro[3.4]octan-5-yl)-2-fluoro-N-(2-(pyrrolidin-1-yl)ethyl)benzamide

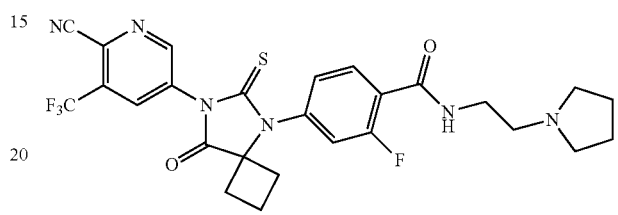

A mixture of 4-(7-(6-cyano-5-(trifluoromethyl)pyridin-3-yl)-8-oxo-6-thioxo-5,7-diazaspiro[3.4]octan-5-yl)-2-fluorobenzoic acid (Compound 224, 100 mg, 0.21 mmol), 2-(pyrrolidin-1-yl)ethanamine (32 mg, 0.28 mmol), HATU (106 mg, 0.28 mmol), and DIEA (0.1 mL, 0.63 mmol) in DCM (3 mL) and DMF (1.5 mL) was stirred at room temperature for 18 h. Brine and EtOAc were added and the aqueous layer was extracted with EtOAc (4×), the organics were combined, dried over sodium sulfate, and evaporated to dryness. The residue was purified by column chromatography on silica gel eluting with 0 to 10% MeOH/DCM to afford impure desired product that was repurified by reverse phase HPLC (acetonitrile/water:TFA). The fractions containing the desired compound were combined, acetonitrile was removed in vacuo, and the remaining aqueous layer was treated with a saturated solution of sodium bicarbonate. The aqueous layer was extracted with DCM (3×), the organics were combined, dried over sodium sulfate, and evaporated to dryness to afford 88 mg of 4-(7-(6-cyano-5-(trifluoromethyl)pyridin-3-yl)-8-oxo-6-thioxo-5,7-diazaspiro[3.4]octan-5-yl)-2-fluoro-N-(2-(pyrrolidin-1-yl)ethyl)benzamide as an off-white solid. LCMS [M+1]$^+$ 561.1.

Example 36

Synthesis of Compound 235

N-Benzyl-4-(7-(6-cyano-5-(trifluoromethyl)pyridin-3-yl)-8-oxo-6-thioxo-5,7-diazaspiro[3.4]octan-5-yl)-2-fluorobenzamide

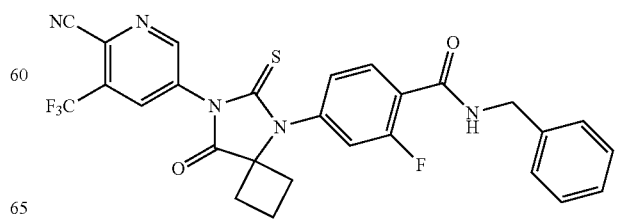

A mixture of 4-(7-(6-cyano-5-(trifluoromethyl)pyridin-3-yl)-8-oxo-6-thioxo-5,7-diazaspiro[3.4]octan-5-yl)-2-fluorobenzoic acid (Compound 224, 68 mg, 0.14 mmol), benzylamine (22 mg, 0.21 mmol), HATU (70 mg, 0.18 mmol), and DIEA (40 µL, 0.21 mmol) in DMF (3 mL) was stirred at room temperature for 3 h. The crude reaction mixture was purified by reverse phase HPLC (acetonitrile/water:TFA) to afford 51 mg of N-benzyl-4-(7-(6-cyano-5-(trifluoromethyl)pyridin-3-yl)-8-oxo-6-thioxo-5,7-diazaspiro[3.4]octan-5-yl)-2-fluorobenzamide as a white solid. $^1$H NMR (300 MHz, DMSO-$d_6$) δ 9.22 (d, 1H), 9.12 (t, 1H), 8.75 (d, 1H), 7.87 (t, 1H), 7.49 (dd, 1H), 7.40 (dd, 1H), 7.37-7.31 (m, 4H), 7.29-7.24 (m, 1H), 4.51 (d, 1H), 2.69-2.63 (m, 2H), 2.55-2.44 (m, 2H), 2.03-1.94 (m, 1H), 1.62-1.56 (m, 1H). LCMS [M+1]$^+$ 554.5.

Example 37

Synthesis of Compound 236

4-(7-(6-Cyano-5-(trifluoromethyl)pyridin-3-yl)-8-oxo-6-thioxo-5,7-diazaspiro[3.4]octan-5-yl)-2-fluoro-N-(2-(pyridin-2-yl)ethyl)benzamide

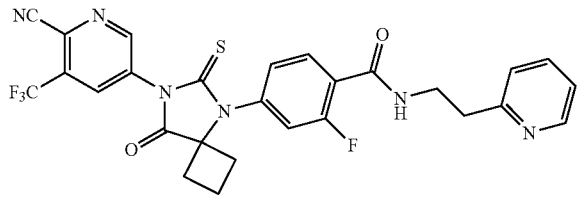

A mixture of 4-(7-(6-cyano-5-(trifluoromethyl)pyridin-3-yl)-8-oxo-6-thioxo-5,7-diazaspiro[3.4]octan-5-yl)-2-fluorobenzoic acid (Compound 224, 70 mg, 0.15 mmol), 2-(pyridin-2-yl)ethanamine (24 mg, 0.20 mmol), HATU (74 mg, 0.20 mmol), and DIEA (80 µL, 0.45 mmol) in DMF (3 mL) was stirred at room temperature overnight. The crude reaction mixture was purified by reverse phase HPLC (acetonitrile/water, 0.1% TFA). The fractions containing the desired compound were combined, acetonitrile was removed in vacuo, and the remaining aqueous layer was treated with a saturated solution of sodium bicarbonate. The aqueous layer was extracted with DCM (3×), the organics were combined, dried over sodium sulfate, and evaporated to dryness to afford 51 mg of 4-(7-(6-cyano-5-(trifluoromethyl)pyridin-3-yl)-8-oxo-6-thioxo-5,7-diazaspiro[3.4]octan-5-yl)-2-fluoro-N-(2-(pyridin-2-yl)ethyl)benzamide as a white solid. $^1$H NMR (300 MHz, DMSO-$d_6$) δ 9.22 (d, 1H), 8.75 (d, 1H), 8.66 (t, 1H), 8.52 (d, 1H), 7.82-7.70 (m, 2H), 7.47-7.22 (m, 4H), 3.65 (q, 2H), 3.01 (t, 2H), 2.68-2.62 (m, 2H), 2.54-2.43 (m, 2H), 2.03-1.93 (m, 1H), 1.60-1.57 (m, 1H). LCMS [M+1]$^+$ 569.5.

Example 38

Synthesis of Compound 237

4-(7-(6-Cyano-5-(trifluoromethyl)pyridin-3-yl)-8-oxo-6-thioxo-5,7-diazaspiro[3.4]octan-5-yl)-fluoro-N-(3-(pyrrolidin-1-yl)propyl)benzamide

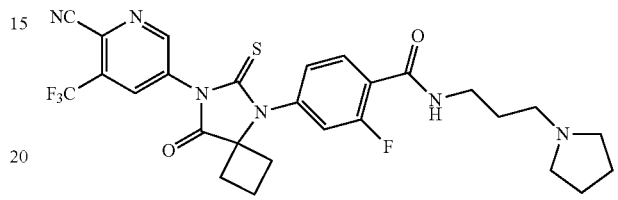

A mixture of 4-(7-(6-cyano-5-(trifluoromethyl)pyridin-3-yl)-8-oxo-6-thioxo-5,7-diazaspiro[3.4]octan-5-yl)-2-fluorobenzoic acid (Compound 224, 550 mg, 1.18 mmol), 3-(pyrrolidin-1-yl)propan-1-amine (303 mg, 2.37 mmol), HATU (673 mg, 1.77 mmol), and DIEA (0.6 mL, 3.54 mmol) in DMF (25 mL) was stirred at room temperature overnight. Brine and EtOAc were added and the aqueous layer was extracted with EtOAc (4×), the organics were combined, dried over sodium sulfate, and evaporated to dryness. The residue was purified by column chromatography on silica gel eluting with 0 to 20% MeOH/DCM to afford 4-(7-(6-cyano-5-(trifluoromethyl)pyridin-3-yl)-8-oxo-6-thioxo-5,7-diazaspiro[3.4]octan-5-yl)-2-fluoro-N-(3-(pyrrolidin-1-yl)propyl)benzamide as a pale orange solid. $^1$H NMR (300 MHz, DMSO-$d_6$) δ 9.22 (d, 1H), 8.75 (d, 1H), 8.64 (t, 1H), 7.83 (t, 1H), 7.47 (dd, 1H), 7.38 (dd, 1H), 3.35 (m, 4H), 2.65-2.54 (m, 6H), 2.53-2.43 (m, 2H), 2.03-1.93 (m, 1H), 1.74 (m, 6H), 1.64-1.53 (m, 1H). LCMS [M+1]$^+$ 575.1.

The trifluoroacetic acid salt was prepared according to the following procedure: A mixture of 4-(7-(6-cyano-5-(trifluoromethyl)pyridin-3-yl)-8-oxo-6-thioxo-5,7-diazaspiro[3.4]octan-5-yl)-2-fluorobenzoic acid (Compound 224, 70 mg, 0.15 mmol), 3-(pyrrolidin-1-yl)propan-1-amine (25 mg, 0.20 mmol), HATU (74 mg, 0.20 mmol), and DIEA (80 µL, 0.45 mmol) in DMF (3 mL) was stirred at room temperature overnight. The crude reaction mixture was purified by reverse phase HPLC (acetonitrile/water, 0.1% TFA) to afford 60 mg of 4-(7-(6-cyano-5-(trifluoromethyl)pyridin-3-yl)-8-oxo-6-thioxo-5,7-diazaspiro[3.4]octan-5-yl)-2-fluoro-N-(3-(pyrrolidin-1-yl)propyl)benzamide 2,2,2-trifluoroacetate as pale yellow solid. $^1$H NMR (300 MHz, DMSO-$d_6$) δ 9.47 (s, 1H), 9.22 (d, 1H), 8.75 (d, 1H), 8.68 (t, 1H), 7.86 (t, 1H), 7.49 (dd, 1H), 7.41 (dd, 1H), 3.56 (m, 2H), 3.40-3.34 (m, 2H), 3.23-3.16 (m, 2H), 3.07-3.96 (m, 2H), 2.70-2.64 (m, 2H), 2.54-2.43 (m, 2H), 2.08-1.85 (m, 7H), 1.60-1.55 (m, 1H). LCMS [M+1]$^+$ 575.6.

Compounds 238 to 311 were synthesized following the procedure described in Example 35 from the appropriate acids and amines (amines were either commercially available or synthesized from literature procedures).

Example 39

Synthesis of Compound 312

4-(7-(6-Cyano-5-(trifluoromethyl)pyridin-3-yl)-6,8-dioxo-5,7-diazaspiro[3.4]octan-5-yl)-2-fluoro-N-methylbenzamide

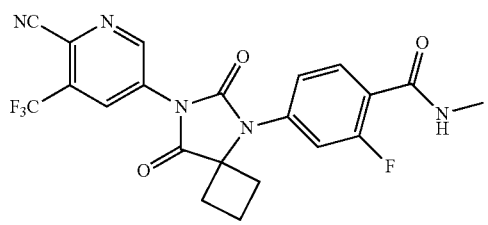 [SMILES: CNC(=O)c1ccc(N2C(=O)N(c3cnc(C#N)c(C(F)(F)F)c3)C(=O)C23CCC3)cc1F]

A mixture of 4-(7-(6-cyano-5-(trifluoromethyl)pyridin-3-yl)-8-oxo-6-thioxo-5,7-diazaspiro[3.4]octan-5-yl)-2-fluoro-N-methylbenzamide (synthesized as described for Example 1 using 5-amino-3-(trifluoromethyl) picolinonitrile (Intermediate 1) and of 4-((1-cyanocyclobutyl)amino)-2-fluoro-N-methylbenzamide (Intermediate 21) as starting materials) (90 mg, 0.19 mmol) and $H_2O_2$ (30%, 0.72 mL) in MeOH (8 mL) was stirred at room temperature for 5 days. The reaction mixture was diluted with EtOAc (10 mL) and the organic layer was washed with water, brine, and dried over magnesium sulfate. The residue obtained was purified by reverse phase HPLC (acetonitrile/water:TFA) to obtain 10 mg of 4-(7-(6-cyano-5-(trifluoromethyl)pyridin-3-yl)-6,8-dioxo-5,7-diazaspiro[3.4]octan-5-yl)-2-fluoro-N-methylbenzamide as a white solid. 1H NMR (500 MHz, CDCl$_3$) δ 9.28 (d, 1H), 8.54 (d, 1H), 8.23 (t, 1H), 7.33 (m, 1H), 7.27 (m, 1H), 6.93 (m, 1H), 3.07 (d, 3H), 2.71 (m, 2H), 2.57 (m, 2H), 2.28 (m, 1H), 1.82 (m, 1H).

Example 40

Synthesis of Compound 313

4-(7-(6-Cyano-5-(trifluoromethyl)pyridin-3-yl)-8-oxo-6-thioxo-5,7-diazaspiro[3.4]octan-5-yl)-N-(3-(3,3-difluoropyrrolidin-1-yl)propyl)-2-fluorobenzamide Step 1: 3-(4-(7-(6-Cyano-5-(trifluoromethyl)pyridin-3-yl)-8-oxo-6-thioxo-5,7-diazaspiro[3.4]octan-5-yl)-2-fluorobenzamido)propyl methanesulfonate

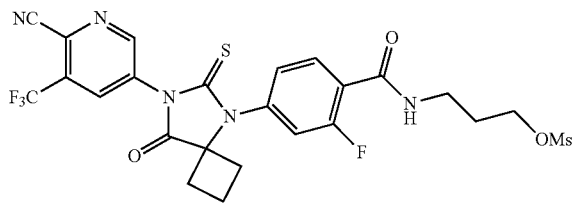 [SMILES: CS(=O)(=O)OCCCNC(=O)c1ccc(N2C(=S)N(c3cnc(C#N)c(C(F)(F)F)c3)C(=O)C23CCC3)cc1F]

A mixture of 4-(7-(6-cyano-5-(trifluoromethyl)pyridin-3-yl)-8-oxo-6-thioxo-5,7-diazaspiro[3.4]octan-5-yl)-2-fluoro-N-(3-hydroxypropyl)benzamide (Compound 306, 80 mg, 0.15 mmol) and triethylamine (22 µL, 0.16 mmol) in THF (5 mL) was cooled to 0° C. Methanesulfonyl chloride (23 µL, 0.3 mmol) was added dropwise and the mixture was stirred at room temperature overnight. Brine and EtOAc were added and the aqueous layer was extracted with EtOAc (2×), the organics were combined, dried over sodium sulfate, and evaporated to dryness to afford crude 3-(4-(7-(6-cyano-5-(trifluoromethyl)pyridin-3-yl)-8-oxo-6-thioxo-5,7-diazaspiro[3.4]octan-5-yl)-2-fluorobenzamido)propyl methanesulfonate that was used as is.

Step 2: 4-(7-(6-Cyano-5-(trifluoromethyl)pyridin-3-yl)-8-oxo-6-thioxo-5,7-diazaspiro[3.4]octan-5-yl)-N-(3-(3,3-difluoropyrrolidin-1-yl)propyl)-2-fluorobenzamide

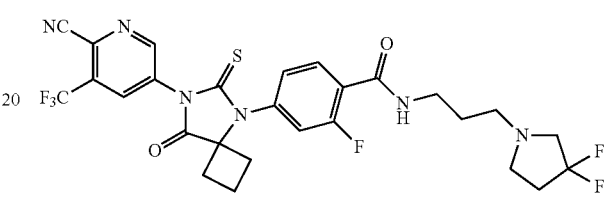

A mixture of 3-(4-(7-(6-cyano-5-(trifluoromethyl)pyridin-3-yl)-8-oxo-6-thioxo-5,7-diazaspiro[3.4]octan-5-yl)-2-fluorobenzamido)propyl methanesulfonate (45 mg, 0.075 mmol), 3,3-difluoropyrrolidine hydrochloride (54 mg, 0.37 mmol), and triethylamine (0.14 mL, 1.05 mmol) in THF (2 mL) was heated to 70° C. overnight. Brine and EtOAc were added to a cooled reaction mixture and the aqueous layer was extracted with EtOAc (2×), the organics were combined, dried over sodium sulfate, and evaporated to dryness. The residue obtained was purified by reverse phase HPLC (acetonitrile/water:TFA) to obtain 4.2 mg of 4-(7-(6-cyano-5-(trifluoromethyl)pyridin-3-yl)-8-oxo-6-thioxo-5,7-diazaspiro[3.4]octan-5-yl)-N-(3-(3,3-difluoropyrrolidin-1-yl)propyl)-2-fluorobenzamide. 1H NMR (300 MHz, DMSO-d$_6$) δ 9.15 (s, 1H), 8.68 (d, 1H), 8.51 (t, 1H), 7.72 (t, 1H), 7.39 (dd, 1H), 7.30 (dd, 1H), 3.25 (m, 4H), 2.80 (t, 2H), 2.64-2.58 (m, 4H), 2.44-2.40 (m, 2H), 2.16 (m, 2H), 1.91 (m, 1H), 1.64-1.45 (m, 3H). LCMS [M+1]$^+$ 611.1.

Assays

Example 41

AR in Cell Western Assay

LNCaP cells (8,000/well) were plated in RPMI media containing 10% Charcoal Dextran Stripped Serum into plates coated with poly-d-lysine. After 24 hours cells were treated with compound from 30 µM to 0.0003 µM. At 20 hours post compound addition the cells were fixed (30% formaldehyde in PBS) for 20'. Cells were permeabilized in PBS 0.1% Triton (50 µl/well, three times for 5' each) and blocked with LiCor blocking buffer (50 µl/well, 90'). The wells were then incubated overnight at 4° C. with the rabbit IgG androgen receptor antibody (AR-N20, Santa Cruz antibody) diluted 1:1000 in LiCor blocking buffer/0.1% Tween-20. Wells were washed with 0.1% Tween-20/PBS (50 µl/well, 5' each) and then incubated in goat anti-rabbit IRDye™ 800CW (1:1000) and DRAQ5 DNA dye (1:10, 0000 for 5 mM stock) diluted in 0.2% Tween-20/0.01% SDS/LiCor blocking buffer in the dark (90'). Cells were washed (50 μl/well, 5' each) in 0.1% Tween-20/PBS. Wash buffer was removed and plates were read using the LiCor Odyssey.

Example 42

AR Fluorescent Polarization Assay (Invitrogen)

Compounds to be tested were diluted to 2× the final desired concentration in AR Green Assay Buffer (final DMSO: 0.6%). Fluormone AL Green and the rat AR Ligand Binding Domain were diluted to 2× the final desired concentration (Fluormone: 2 nM, AR LBD: 50 nM) in AR Green Assay Buffer containing 2 mM DTT. The AR LBD/Fluormone solution was added to all the wells of a 384 well black plate (10 μl/well). The compounds were added to the AR LBD/Fluormone solution (10 μl/well). The plate was incubated for 4 hours in the dark. The fluorescence polarization of each well was measured using an excitation wavelength of 485 nm and emission wavelength of 530 nm.

Example 43

Prostate Cancer Cell Viability Assays

LNCaP, LNCaP AR, PC3, and VCaP cells were adjusted to a concentration of 30,000 cells per mL in RPMI containing 10% FBS and 20 mM HEPES. 16 microliters of the cell suspension was added to each well of a 384 well plate, and the cells were incubated overnight to allow the cells to adhere. The following day a seven point, serial semilog dilution of each compound was added to the cells in 16 μL at a final concentration ranging from 30-0.003 μM. After 5 days' compound exposure, 16 μL of CellTiter-GLo (Promega, Madison Wis.) was added to the cells the relative luminescence units (RLUs) of each well was determined. CellTiter-Glo added to 32 μL of medium without cells was used to obtain a background value. The Percent viability of each sample was determined as follows:

(RLU sample–RLU background/RLU untreated cells–RLU background)×100=% viability

Example 44

LNCaP-AR Luciferase Transcriptional Reporter Assays

LNCaP-AR-Luc were maintained in RPMI 1640 supplemented with 10% FCS (Cancer Res 2006; 66: (21). Nov. 1, 2006). Transcriptional assays were performed by seeding 100 μL of cells at a density of 25,000 cells/mL into 96-well cell culture plates in RPMI 1640 supplemented with 10% charcoal stripped serum and allowed to attach overnight. For AR agonist assays, the compounds were serially diluted and 50 μL of compound plus RPMI 1640 supplemented with charcoal stripped serum was added to the cells. For AR antagonist assays, the compounds were serially diluted and 50 μL of compound with RPMI plus R1881 supplemented with charcoal stripped serum were added to the cells. The final R1881 concentration used in the antagonist assays was 0.1 nM. Following 40 hour incubation the medium was removed and the cells were lysed in 40 μL of lysis buffer (25 mM Tris Phosphate, 2 mM CDTA, 10% Glycerol, 0.5% Triton X-100, 2 mM DTT). Firefly luciferase activity was measured immediately following the addition of 50 μL luciferase buffer (20 mM tricine, 0.1 mM EDTA, 1.07 mM $(MgCo_3)_4$ $Mg(OH)_2 \cdot 5H_2O$, 2.67 mM $MgSO_4$, 33.3 mM DTT, 270 μM Coenzyme A, 470 μM luciferin, 530 μM ATP).

Example 45

AR-VP16 DNA Binding Assays

HepG2 cells were maintained in RPMI 1640 supplemented with 10% FCS. AR-VP16 DNA binding assays were performed by seeding 100 μL of cells at a density of 250,000 cells/mL into 96-well cell culture plates in RPMI 1640 supplemented with 10% charcoal stripped serum and allowed to attach overnight. Cells were transiently transfected using Lipofectin (Life Technologies) according to the manufacturer's protocol. Triplicate transfections were performed using 33.3 ng AR-VP16 pCDNA3 (expression vector), 66.7 ng 4×ARE-Luciferase (reporter vector), 16.7 ng CMVpRL (normalization vector), and 43.3 ng pCMX (filler DNA). Transfected cells were incubated overnight then treated with ligand. For agonist assays, compounds were serially diluted and 50 μL of compound plus RPMI 1640 supplemented with charcoal stripped serum was added to the cells. For antagonist assays, the compounds were serially diluted and 50 μL of compound with RPMI supplemented with charcoal stripped serum plus methyltrienolone (R1881) were added to the cells. The final R1881 concentration used in the antagonist assays was 0.1 nM. Following 48 hour incubation the medium was removed and the cells were lysed in 40 μL of lysis buffer (25 mM Tris Phosphate, 2 mM CDTA, 10% Glycerol, 0.5% Triton X-100, 2 mM DTT). Firefly luciferase activity was measured immediately following the addition of 40 μL luciferase buffer (20 mM tricine, 0.1 mM EDTA, 1.07 mM $(MgCo_3)_4$ $Mg(OH)_2 \cdot 5H_2O$, 2.67 mM $MgSO_4$, 33.3 mM DTT, 270 μM Coenzyme A, 470 μM luciferin, 530 μM ATP). Renilla luciferase was measured following the addition of 40 μL colelenterazine buffer (1.1 M NaCl, 2.2 mM $Na_2EDTA$, 0.22 M $KxPO_4$ (pH 5.1), 0.44 mg/mL BSA, 1.3 mM $NaN_3$, 1.43 μM coelenterazine, final pH adjusted to 5.0).

Illustrative biological data for representative compounds disclosed herein is presented in the following table:

| Compound # | ARVP16 DNA Binding Assay (Agonist mode): Agonist?[1] | ARVP16 DNA Binding Assay (Antagonist mode): $IC_{50}$ <1.0 μM |
|---|---|---|
| 1 | No | Yes |
| 2 | No | No |
| 3 | No | No |
| 4 | No | Yes |
| 5 | No | Yes |
| 6 | No | Yes |
| 7 | No | Yes |
| 8 | No | No |
| 9 | No | Yes |
| 10 | No | No |
| 11 | No | Yes |
| 12 | No | Yes |
| 13 | No | Yes |
| 14 | No | No |
| 15 | No | No |
| 16 | No | Yes |
| 17 | Yes | Yes |
| 18 | Yes | Yes |
| 19 | No | No |
| 20 | No | Yes |
| 21 | No | Yes |
| 22 | No | Yes |
| 23 | No | No |
| 24 | No | No |

| Compound # | ARVP16 DNA Binding Assay (Agonist mode): Agonist?[1] | ARVP16 DNA Binding Assay (Antagonist mode): IC$_{50}$ <1.0 μM |
|---|---|---|
| 25 | No | Yes |
| 26 | Yes | Yes |
| 27 | No | Yes |
| 28 | No | Yes |
| 29 | No | Yes |
| 30 | No | Yes |
| 31 | No | Yes |
| 32 | No | Yes |
| 33 | No | Yes |
| 34 | No | No |
| 35 | No | No |
| 36 | No | Yes |
| 37 | No | Yes |
| 38 | No | No |
| 39 | Yes | Yes |
| 40 | No | Yes |
| 41 | No | Yes |
| 42 | No | Yes |
| 43 | No | Yes |
| 44 | No | Yes |
| 45 | No | Yes |
| 46 | No | Yes |
| 47 | No | Yes |
| 48 | No | Yes |
| 49 | No | Yes |
| 50 | No | Yes |
| 51 | No | Yes |
| 52 | No | Yes |
| 53 | Yes | Yes |
| 54 | No | No |
| 55 | Yes | Yes |
| 56 | No | Yes |
| 57 | No | Yes |
| 58 | Yes | Yes |
| 59 | No | Yes |
| 60 | Yes | Yes |
| 61 | No | No |
| 62 | No | No |
| 63 | No | Yes |
| 64 | No | Yes |
| 65 | Yes | Yes |
| 66 | Yes | Yes |
| 67 | Yes | Yes |
| 68 | No | No |
| 69 | No | Yes |
| 70 | No | Yes |
| 71 | No | No |
| 72 | Yes | Yes |
| 73 | Yes | Yes |
| 74 | Yes | Yes |
| 75 | Yes | Yes |
| 76 | Yes | Yes |
| 77 | No | No |
| 78 | No | No |
| 79 | No | Yes |
| 80 | No | Yes |
| 81 | No | No |
| 82 | No | Yes |
| 83 | No | No |
| 84 | Yes | Yes |
| 85 | Yes | Yes |
| 86 | No | Yes |
| 87 | No | Yes |
| 88 | No | Yes |
| 89 | No | Yes |
| 90 | No | No |
| 91 | No | No |
| 92 | No | Yes |
| 93 | No | No |
| 94 | No | Yes |
| 95 | Yes | Yes |
| 96 | No | Yes |
| 97 | Yes | Yes |
| 98 | No | Yes |
| 99 | Yes | Yes |
| 100 | No | Yes |
| 101 | No | No |
| 102 | No | No |
| 103 | No | Yes |
| 104 | No | Yes |
| 105 | No | Yes |
| 106 | No | Yes |
| 107 | No | Yes |
| 108 | Yes | Yes |
| 109 | No | Yes |
| 110 | No | Yes |
| 111 | No | No |
| 112 | No | Yes |
| 113 | No | Yes |
| 114 | No | No |
| 115 | No | Yes |
| 116 | No | Yes |
| 117 | No | No |
| 118 | No | No |
| 119 | No | Yes |
| 120 | No | No |
| 121 | No | No |
| 122 | No | No |
| 123 | No | No |
| 124 | No | Yes |
| 125 | No | Yes |
| 126 | Yes | Yes |
| 127 | No | Yes |
| 128 | No | Yes |
| 129 | No | Yes |
| 130 | No | Yes |
| 131 | No | Yes |
| 132 | No | No |
| 133 | No | Yes |
| 134 | No | Yes |
| 135 | No | Yes |
| 136 | No | Yes |
| 137 | No | Yes |
| 138 | No | No |
| 139 | No | Yes |
| 140 | No | No |
| 141 | Yes | No |
| 142 | Yes | Yes |
| 143 | Yes | Yes |
| 144 | Yes | Yes |
| 145 | Yes | Yes |
| 146 | No | Yes |
| 147 | No | Yes |
| 148 | Yes | Yes |
| 149 | No | Yes |
| 150 | Yes | Yes |
| 151 | No | No |
| 152 | No | Yes |
| 153 | No | Yes |
| 154 | No | Yes |
| 155 | No | No |
| 156 | Yes | Yes |
| 157 | Yes | Yes |
| 158 | No | No |
| 159 | No | No |
| 160 | No | No |
| 161 | No | No |
| 162 | No | No |
| 163 | No | No |
| 164 | No | No |
| 165 | No | No |
| 166 | No | No |
| 167 | No | No |
| 168 | No | Yes |
| 169 | No | Yes |
| 170 | Yes | Yes |
| 171 | No | Yes |
| 172 | No | Yes |
| 173 | No | Yes |
| 174 | No | Yes |

| Compound # | ARVP16 DNA Binding Assay (Agonist mode): Agonist?[1] | ARVP16 DNA Binding Assay (Antagonist mode): IC$_{50}$ <1.0 μM |
|---|---|---|
| 175 | No | Yes |
| 176 | No | Yes |
| 177 | No | Yes |
| 178 | No | Yes |
| 179 | Yes | Yes |
| 180 | Yes | Yes |
| 181 | Yes | Yes |
| 182 | Yes | Yes |
| 183 | No | Yes |
| 184 | Yes | Yes |
| 185 | No | Yes |
| 186 | Yes | Yes |
| 187 | No | Yes |
| 188 | No | Yes |
| 189 | No | Yes |
| 190 | No | Yes |
| 191 | No | No |
| 192 | No | No |
| 193 | No | Yes |
| 194 | No | Yes |
| 195 | No | Yes |
| 196 | No | Yes |
| 197 | No | No |
| 198 | No | Yes |
| 199 | No | Yes |
| 200 | Yes | Yes |
| 201 | No | Yes |
| 202 | Yes | Yes |
| 203 | No | Yes |
| 204 | No | Yes |
| 205 | No | Yes |
| 206 | No | Yes |
| 207 | No | Yes |
| 208 | No | Yes |
| 209 | No | Yes |
| 210 | No | No |
| 211 | No | Yes |
| 212 | Yes | Yes |
| 213 | Yes | Yes |
| 214 | Yes | Yes |
| 215 | Yes | Yes |
| 216 | No | No |
| 217 | No | Yes |
| 218 | No | Yes |
| 219 | Yes | Yes |
| 220 | No | Yes |
| 221 | No | No |
| 222 | Yes | Yes |
| 223 | No | Yes |
| 224 | No | No |
| 225 | No | Yes |
| 226 | No | No |
| 227 | No | No |
| 228 | No | No |
| 229 | No | Yes |
| 230 | No | Yes |
| 231 | No | Yes |
| 232 | No | Yes |
| 233 | No | No |
| 234 | No | No |
| 235 | No | Yes |
| 236 | No | Yes |
| 237 | No | Yes |
| 238 | No | No |
| 239 | No | No |
| 240 | No | No |
| 241 | No | No |
| 242 | No | Yes |
| 243 | No | No |
| 244 | No | Yes |
| 245 | No | No |
| 246 | No | No |
| 247 | No | No |
| 248 | No | No |
| 249 | No | Yes |
| 250 | No | No |
| 251 | No | No |
| 252 | No | Yes |
| 253 | No | No |
| 254 | No | No |
| 255 | No | Yes |
| 256 | No | Yes |
| 257 | No | Yes |
| 258 | No | Yes |
| 259 | No | Yes |
| 260 | No | Yes |
| 261 | No | Yes |
| 262 | No | Yes |
| 263 | Yes | Yes |
| 264 | No | Yes |
| 265 | No | Yes |
| 266 | No | Yes |
| 267 | No | Yes |
| 268 | No | Yes |
| 269 | No | Yes |
| 270 | No | No |
| 271 | No | No |
| 272 | No | Yes |
| 273 | No | Yes |
| 274 | No | Yes |
| 275 | No | No |
| 276 | No | No |
| 277 | No | Yes |
| 278 | No | Yes |
| 279 | No | Yes |
| 280 | No | Yes |
| 281 | No | Yes |
| 282 | No | Yes |
| 283 | No | Yes |
| 284 | No | Yes |
| 285 | No | No |
| 286 | No | Yes |
| 287 | No | Yes |
| 288 | No | Yes |
| 289 | No | Yes |
| 290 | No | Yes |
| 291 | No | Yes |
| 292 | No | No |
| 293 | No | Yes |
| 294 | No | Yes |
| 295 | No | Yes |
| 296 | No | Yes |
| 297 | No | Yes |
| 298 | No | Yes |
| 299 | No | Yes |
| 300 | No | Yes |
| 301 | No | Yes |
| 302 | No | Yes |
| 303 | No | No |
| 304 | No | Yes |
| 305 | No | Yes |
| 306 | No | Yes |
| 307 | No | Yes |
| 308 | No | Yes |
| 309 | No | Yes |
| 310 | No | No |
| 311 | No | No |
| 312 | No | No |
| 313 | No | Yes |

[1]Agonist defined as a compound whose Emax in the ARVP16 DNA Binding Assay (Agonist mode) is >20x DMSO control Example 46

GABA-Gated Cl Channel Antagonist Radioligand Binding Assay

Membrane homogenates of cerebral cortex (120 μg protein) are incubated for 120 min at 22° C. with 3 nM

[$^{35}$S]-TBPS in the absence or presence of the test compound in a buffer containing 50 mM Na$_2$HPO$_4$/KH$_2$PO$_4$ (pH 7.4) and 500 mM NaCl. Nonspecific binding is determined in the presence of 20 μM picrotoxinin. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard). The results are expressed as a percent inhibition of the control radioligand specific binding. The standard reference compound is picrotoxinin, which is tested in each experiment at several concentrations to obtain a competition curve from which its IC$_{50}$ is calculated.

In this assay, the following representative compounds disclosed herein demonstrated an inhibition of less than 65% at 10 μM in the GABA-gated Cl-Channel Binding Assay: Compound 5, Compound 13, Compound 124, Compound 168, Compound 171, Compound 208, Compound 218, Compound 237, Compound 268, Compound 291.

In Vivo Assay(s)

Example 47

Castrate Resistant Prostate Cancer Xenograft Studies

Six to Seven week old male SCID Hairless Outbred mice (SHO, Charles Rivers Laboratories) underwent bilateral orchiectomy under isoflurane anesthesia. LNCaP/AR cells were grown in RPMI at 5% CO$_2$, 37° C. Cells were spun down and re-suspended in 50% serum-free RPMI and 50% Matrigel at 1×10$^7$ cells/ml. LNCaP/AR cells were subcutaneously injected (100 μl/animal) on the right flank 3-5 days post castration. Tumor volume (length×width$^2$/2) was monitored weekly. When tumors reached an average volume of ~200 mm$^3$ animals were randomized into treatment groups. During the treatment period tumor volume was monitored bi-weekly. At the termination of study tumors were collected and stored for further analyses.

Pharmaceutical Compositions

Example 48

Parenteral Composition

To prepare a parenteral pharmaceutical composition suitable for administration by injection (subcutaneous, intravenous, and the like), 100 mg of a water-soluble salt of a compound of Formula (I), (Ia), (II), (III), (IV), (V), (VI), (VII), (VIII), (VIIIa), (IX), (IXa) or (X) is dissolved in sterile water and then mixed with 10 mL of 0.9% sterile saline. The mixture is incorporated into a dosage unit form suitable for administration by injection In another embodiment, the following ingredients are mixed to form an injectable formulation: 1.2 g of a compound of Formula (I), (Ia), (II), (III), (IV), (V), (VI), (VII), (VIII), (VIIIa), (IX), (IXa) or (X), 2.0 mL of sodium acetate buffer solution (0.4 M), HCl (1 N) or NaOH (1 M) (q.s. to suitable pH), water (distilled, sterile) (q.s. to 20 mL). All of the above ingredients, except water, are combined and stirred and if necessary, with slight heating if necessary. A sufficient quantity of water is then added.

Example 49

Oral Solution

To prepare a pharmaceutical composition for oral delivery, an aqueous 20% propylene glycol solution is prepared. To this is added a sufficient amount of compound of Formula (I), (Ia), (II), (III), (IV), (V), (VI), (VII), (VIII), (VIIIa), (IX), (IXa) or (X) to provide a 20 mg/mL solution of the compound of Formula (I), (Ia), (II), (III), (IV), (V), (VI), (VII), (VIII), (VIIIa), (IX), (IXa) or (X).

Example 50

Oral Capsule

To prepare a pharmaceutical composition for oral delivery, 100 mg of a compound of Formula (I), (Ia), (II), (III), (IV), (V), (VI), (VII), (VIII), (VIIIa), (IX), (IXa) or (X) is mixed with 750 mg of starch. The mixture is incorporated into an oral dosage unit such as a hard gelatin capsule, which is suitable for oral administration.

In another embodiment, 100 mg of a compound of Formula (I), (Ia), (II), (III), (IV), (V), (VI), (VII), (VIII), (VIIIa), (IX), (IXa) or (X) is placed into Size 4 capsule, or size 1 capsule (hypromellose or hard gelatin) and the capsule is closed.

Example 51

Oral Tablet

A tablet is prepared by mixing 48% by weigh of a compound of Formula (I), (Ia), (II), (III), (IV), (V), (VI), (VII), (VIII), (VIIIa), (IX), (IXa) or (X), 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250 mg.

Example 52

Topical Gel Composition

To prepare a pharmaceutical topical gel composition, 100 mg of a compound of Formula (I), (Ia), (II), (III), (IV), (V), (VI), (VII), (VIII), (VIIIa), (IX), (IXa) or (X) is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

The examples and embodiments described herein are for illustrative purposes only and various modifications or changes suggested to persons skilled in the art are to be included within the spirit and purview of this application and scope of the appended claims.

What is claimed is:

1. A pharmaceutical composition comprising a pharmaceutically acceptable carrier, diluent, or excipient and a compound of Formula (Ia), or a pharmaceutically acceptable salt or N-oxide thereof, said composition formulated in a dosage form suitable for delivering a therapeutically effective amount of the compound when administered in a single dosage form or in a divided dosage form multiple times over the span of one day:

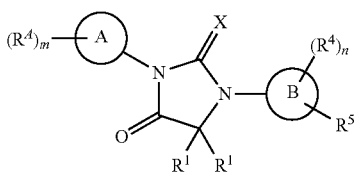

Formula (Ia)

wherein,
ring A is pyridinyl;
m is 1, 2, 3 or 4;
each $R^A$ is independently halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —N(R$^9$)$_2$, —C(=O)N(R$^9$)$_2$, C$_1$-C$_6$alkyl, C$_1$-C$_6$fluoroalkyl, C$_1$-C$_6$fluoroalkoxy, C$_1$-C$_6$alkoxy, or C$_1$-C$_6$heteroalkyl;
both $R^1$ are taken together with the carbon atom to which they are attached to form a C$_3$-C$_6$cycloalkyl;
X is S or O;
ring B is phenyl;
n is 1, or 2;
each $R^4$ is independently hydrogen, halogen, —CN, —NO$_2$, —OH, —OR$^9$, —SR$^9$, —S(=O)R$^{10}$, —S(=O)$_2$R$^{10}$, —N(R$^{11}$)S(=O)$_2$R$^{10}$, —S(=O)$_2$N(R$^9$)$_2$, —C(=O)R$^{10}$, —OC(=O)R$^{10}$, —CO$_2$R$^9$, —OCO$_2$R$^{10}$, —N(R$^9$)$_2$, —C(=O)N(R$^9$)$_2$, —OC(=O)N(R$^9$)$_2$, —NR$^{11}$C(=O)N(R$^9$)$_2$, —NR$^{11}$C(=O)R$^{10}$, —NR$^{11}$C(=O)OR$^{10}$, C$_1$-C$_6$alkyl, C$_1$-C$_6$fluoroalkyl, C$_1$-C$_6$fluoroalkoxy, or C$_1$-C$_6$alkoxy;
$R^5$ is -L$^1$-L$^2$-R$^6$; and
(i) L$^1$ is —O—, —S—, —OC(=O)—, or —OC(=O)O—; and
(ii) L$^2$ is C$_1$-C$_6$alkylene, C$_1$-C$_6$fluoroalkylene or C$_1$-C$_6$heteroalkylene;
or
$R^5$ is L$^1$-R$^7$; and L$^1$ is —O—, —S—, —OC(=O)—, or —OC(=O)O—;
$R^6$ and $R^7$ are independently optionally substituted piperidinyl;
said optional substituents including at least one of alkyl, fluoroalkyl, —CN, halo, —C(O)—O—(C$_{1-6}$ alkyl), —CH$_2$—C(O)—O—(C$_{1-6}$ alkyl), —NH$_2$, —NH(CH$_3$), —N(CH$_3$)$_2$, —OH, —CO$_2$H, —C(O)NH$_2$, —C(O)NH (alkyl), —C(O)N(alkyl)$_2$, alkoxy, fluoroalkoxy, -(alkyl) sulfonyl, -(alkylene)-OH, or —C(O)-(alkyl);
each $R^9$ is independently H, C$_1$-C$_6$alkyl, or C$_1$-C$_6$fluoroalkyl;
$R^{10}$ is C$_1$-C$_6$alkyl; and
$R^{11}$ is independently H or C$_1$-C$_4$alkyl.

2. The pharmaceutical composition of claim 1, wherein both $R^1$ are taken together with the carbon atom to which they are attached to form a cyclopropyl, cyclobutyl, cyclopentyl, or cyclohexyl;
X is S; and
each $R^A$ is independently halogen, —CN, —NO$_2$, —OH, C$_1$-C$_6$alkyl, C$_1$-C$_6$fluoroalkyl, C$_1$-C$_6$fluoroalkoxy, or C$_1$-C$_6$alkoxy; and
$R^6$ and $R^7$ are independently piperidinyl optionally substituted with at least one alkyl, —C(O)—O—(C$_{1-6}$ alkyl), —CH$_2$—C(O)—O—(C$_{1-6}$ alkyl), —NH$_2$, —NH(CH$_3$), —N(CH$_3$)$_2$, —OH, —CO$_2$H, —C(O)NH$_2$, —C(O)NH(alkyl), —C(O)N(alkyl)$_2$, -(alkyl)sulfonyl, -(alkylene)-OH, or —C(O)(C$_{1-6}$ alkyl.

3. The pharmaceutical composition of claim 2, wherein:
each $R^4$ is independently hydrogen, halogen, —CN, —NO$_2$, —OH, C$_1$-C$_4$alkyl, C$_1$-C$_4$fluoroalkyl, C$_1$-C$_4$fluoroalkoxy, or C$_1$-C$_4$alkoxy;
$R^5$ is -L$^1$-L$^2$-R$^6$; and
(i) L$^1$ is —O— or —S—; and
(ii) L$^2$ is C$_1$-C$_6$alkylene, C$_1$-C$_6$fluoroalkylene or C$_1$-C$_6$heteroalkylene;
or $R^5$ is -L$^1$-R$^7$; and L$^1$ is —O— or —S.

4. The pharmaceutical composition of claim 1, wherein the compound of Formula (Ia) has the structure of Formula (II):

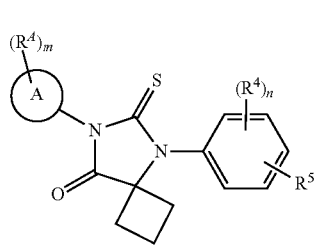

Formula (II)

wherein,

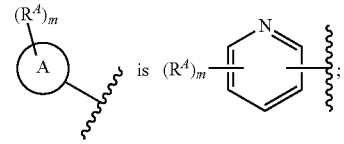

m is 2;
one $R^A$ is —CN, —NO$_2$, —S(=O)$_2$R$^{10}$, —S(=O)$_2$N(R$^9$)$_2$, —C(=O)R$^{10}$, —CO$_2$R$^9$, or —C(=O)N(R$^9$)$_2$; and the other $R^A$ is halogen, —OH, C$_1$-C$_6$alkyl, C$_1$-C$_6$fluoroalkyl, C$_1$-C$_6$fluoroalkoxy, or C$_1$-C$_6$alkoxy;
n is 1;
each $R^4$ is independently hydrogen, halogen, C$_1$-C$_6$alkyl, C$_1$-C$_6$fluoroalkyl, C$_1$-C$_6$fluoroalkoxy, or C$_1$-C$_6$alkoxy;
$R^5$ is -L$^1$-L$^2$-R$^6$; and (i) L$^1$ is —O—; and (ii) L$^2$ is C$_1$-C$_6$alkylene, C$_1$-C$_6$fluoroalkylene or C$_1$-C$_6$heteroalkylene;
or
$R^5$ is L$^1$-R$^7$; and L$^1$ is —O—;
or is a pharmaceutically acceptable salt, or N-oxide thereof.

5. The pharmaceutical composition of claim 1, wherein the compound of Formula (Ia) has the structure of Formula (VI):

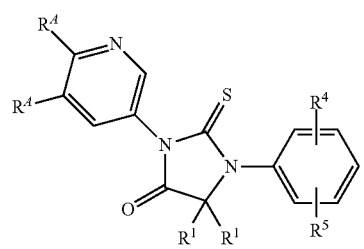

Formula (VI)

H wherein,
one $R^A$ is —CN, —NO$_2$, —S(=O)$_2$R$^{10}$, —S(=O)$_2$N(R$^9$)$_2$, —C(=O)R$^{10}$, —CO$_2$R$^9$, or —C(=O)N(R$^9$)$_2$;
and the other $R^A$ is H, halogen, —OH, C$_1$-C$_6$alkyl, C$_1$-C$_6$fluoroalkyl, C$_1$-C$_6$fluoroalkoxy, or C$_1$-C$_6$alkoxy;
both $R^1$ are taken together with the carbon atom to which they are attached to form a C$_3$-C$_6$cycloalkyl;
$R^4$ is hydrogen, halogen, C$_1$-C$_4$alkyl, C$_1$-C$_4$fluoroalkyl, C$_1$-C$_4$fluoroalkoxy, or C$_1$-C$_4$alkoxy,
$R^6$ and $R^7$ are piperidinyl optionally substituted with at least one alkyl, —C(O)—O—(C$_{1-6}$ alkyl), —CH$_2$—C(O)—O—(C$_{1-6}$ alkyl), —CO$_2$H, —C(O)NH$_2$, —C(O)NH(alkyl), —C(O)N(alkyl)$_2$, -(alkyl)sulfonyl, -(alkylene)-OH, or —C(O)—(C$_{1-6}$ alkyl);
or is a pharmaceutically acceptable salt, or N-oxide thereof.

6. A pharmaceutical composition of claim 1, wherein the compound of Formula (Ia) has a structure of Formula (VIIIa):

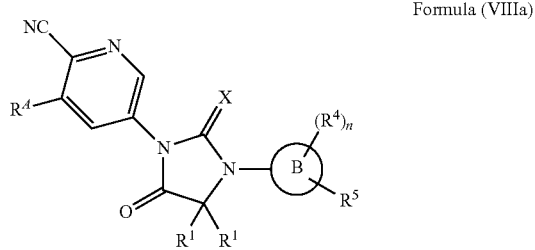

Formula (VIIIa)

wherein,
$R^A$ is C$_1$-C$_6$alkyl or C$_1$-C$_6$fluoroalkyl.

7. The pharmaceutical composition of claim 1, wherein:
X is S;
$R^4$ is hydrogen, halogen, C$_1$-C$_3$alkyl, C$_1$-C$_3$fluoroalkyl, C$_1$-C$_3$fluoroalkoxy, or C$_1$-C$_3$alkoxy; and
$R^6$ and $R^7$ are independently piperidinyl optionally substituted with at least one alkyl, —C(O)—O—(C$_{1-6}$ alkyl), —CH$_2$—C(O)—O—(C$_{1-6}$ alkyl), -(alkyl)sulfonyl, -(alkylene)-OH, —C(O)—(C$_{1-6}$ alkyl), or carbamoyl.

8. The pharmaceutical composition of claim 7, wherein the compound of Formula (VIIIa) has the structure of Formula (IXa):

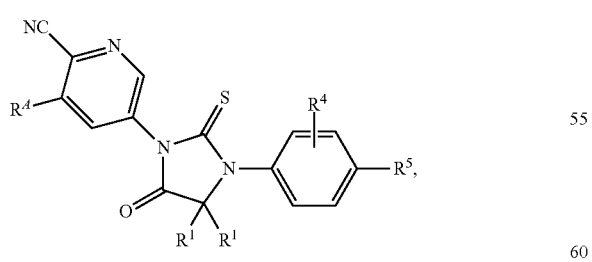

Formula (IXa)

or is a pharmaceutically acceptable salt, or N-oxide thereof.

9. The pharmaceutical composition of claim 8, wherein:
$L^2$ is C$_1$-C$_6$alkylene;
$R^6$ or $R^7$ are independently piperidinyl optionally substituted with at least one alkyl, —C(O)—O-(alkyl), —CH$_2$—C(O)—O—(C$_{1-6}$ alkyl), -(alkyl)sulfonyl, -(alkylene)-OH, —CH$_2$—C(O)—(C$_{1-6}$ alkyl), or carbamoyl.

10. The pharmaceutical composition of claim 9, wherein:
$R^A$ is —CH$_3$ or CF$_3$.

11. The pharmaceutical composition of claim 1, wherein the compound is
3-Methyl-5-(5-(4-((1-methylpiperidin-4-yl)oxy)phenyl)-8-oxo-6-thioxo-5,7-diazaspiro[3.4]octan-7-yl)picolinonitrile;
5-(5-(4-((1-Methylpiperidin-4-yl)oxy)phenyl)-8-oxo-6-thioxo-5,7-diazaspiro[3.4]octan-7-yl)-3-(trifluoromethyl)picolinonitrile;
5-(5-(3-Fluoro-4-(2-(piperidin-1-yl)ethoxy)phenyl)-8-oxo-6-thioxo-5,7-diazaspiro[3.4]octan-7-yl)-3-(trifluoromethyl)picolinonitrile;
5-(5-(2-Fluoro-4-(2-(piperidin-1-yl)ethoxy)phenyl)-8-oxo-6-thioxo-5,7-diazaspiro[3.4]octan-7-yl)-3-(trifluoromethyl)picolinonitrile;
5-(5-(2-Fluoro-4-((1-methylpiperidin-4-yl)oxy)phenyl)-8-oxo-6-thioxo-5,7-diazaspiro[3.4]octan-7-yl)-3-(trifluoromethyl)picolinonitrile;
5-(5-(3-Fluoro-4-((1-methylpiperidin-4-yl)oxy)phenyl)-8-oxo-6-thioxo-5,7-diazaspiro[3.4]octan-7-yl)-3-methylpicolinonitrile;
5-(5-(3-Fluoro-4-((1-methylpiperidin-4-yl)oxy)phenyl)-8-oxo-6-thioxo-5,7-diazaspiro[3.4]octan-7-yl)-3-(trifluoromethyl)picolinonitrile;
3-Methyl-5-(8-oxo-5-(4-(piperidin-4-yloxy)phenyl)-6-thioxo-5,7-diazaspiro[3.4]octan-7-yl)picolinonitrile;
5-(8-Oxo-5-(4-(piperidin-4-yloxy)phenyl)-6-thioxo-5,7-diazaspiro[3.4]octan-7-yl)-3-(trifluoromethyl)picolinonitrile;
5-(8-Oxo-5-(4-((1-propionylpiperidin-4-yl)oxy)phenyl)-6-thioxo-5,7-diazaspiro[3.4]octan-7-yl)-3-(trifluoromethyl)picolinonitrile;
5-(5-(4-((1-isobutyrylpiperidin-4-yl)oxy)phenyl)-8-oxo-6-thioxo-5,7-diazaspiro[3.4]octan-7-yl)-3-(trifluoromethyl)picolinonitrile;
Ethyl 4-(4-(7-(6-cyano-5-(trifluoromethyl)pyridin-3-yl)-8-oxo-6-thioxo-5,7-diazaspiro[3.4]octan-5-yl)phenoxy)piperidine-1-carboxylate;
5-(5-(4-((1-Acetylpiperidin-4-yl)oxy)phenyl)-8-oxo-6-thioxo-5,7-diazaspiro[3.4]octan-7-yl)-3-methylpicolinonitrile;
5-(5-(4-((1-Ethylpiperidin-4-yl)oxy)phenyl)-8-oxo-6-thioxo-5,7-diazaspiro[3.4]octan-7-yl)-3-methylpicolinonitrile;
5-(5-(4-((1-(2-Hydroxyethyl)piperidin-4-yl)oxy)phenyl)-8-oxo-6-thioxo-5,7-diazaspiro[3.4]octan-7-yl)-3-methylpicolinonitrile;
5-(5-(4-((1-(2-hydroxyethyl)piperidin-4-yl)oxy)phenyl)-8-oxo-6-thioxo-5,7-diazaspiro[3.4]octan-7-yl)-3-(trifluoromethyl)picolinonitrile;
5-(5-(4-((1-(Methylsulfonyl)piperidin-4-yl)oxy)phenyl)-8-oxo-6-thioxo-5,7-diazaspiro[3.4]octan-7-yl)-3-(trifluoromethyl)picolinonitrile;
5-(5-(4-((1-Isopropylpiperidin-4-yl)oxy)phenyl)-8-oxo-6-thioxo-5,7-diazaspiro[3.4]octan-7-yl)-3-(trifluoromethyl)picolinonitrile;
Ethyl 2-(4-(4-(7-(6-cyano-5-(trifluoromethyl)pyridin-3-yl)-8-oxo-6-thioxo-5,7-diazaspiro[3.4]octan-5-yl)phenoxy)piperidin-1-yl)acetate;
4-(4-(7-(6-Cyano-5-(trifluoromethyl)pyridin-3-yl)-8-oxo-6-thioxo-5,7-diazaspiro[3.4]octan-5-yl)phenoxy)piperidine-1-carboxamide; or
a pharmaceutically acceptable salt, or N-oxide thereof.

12. The pharmaceutical composition of claim 1, wherein the compound is:
- 5-(5-(4-((1-Methylpiperidin-4-yl)oxy)phenyl)-8-oxo-6-thioxo-5,7-diazaspiro[3.4]octan-7-yl)-3-(trifluoromethyl) picolinonitrile;
- 5-(5-(2-Fluoro-4-((1-methylpiperidin-4-yl)oxy)phenyl)-8-oxo-6-thioxo-5,7-diazaspiro[3.4]octan-7-yl)-3-(trifluoromethyl) picolinonitrile;
- 3-Methyl-5-(5-(4-((1-methylpiperidin-4-yl)oxy)phenyl)-8-oxo-6-thioxo-5,7-diazaspiro[3.4]octan-7-yl) picolinonitrile;
- 5-(5-(3-Fluoro-4-((1-methylpiperidin-4-yl)oxy)phenyl)-8-oxo-6-thioxo-5,7-diazaspiro[3.4]octan-7-yl)-3-methyl-picolinonitrile;
- 5-(5-(3-Fluoro-4-((1-methylpiperidin-4-yl)oxy)phenyl)-8-oxo-6-thioxo-5,7-diazaspiro[3.4]octan-7-yl)-3-(trifluoromethyl)-picolinonitrile;
- 3-Methyl-5-(8-oxo-5-(4-(piperidin-4-yloxy)phenyl)-6-thioxo-5,7-diazaspiro[3.4]octan-7-yl)picolinonitrile;
- 5-(8-Oxo-5-(4-(piperidin-4-yloxy)phenyl)-6-thioxo-5,7-diazaspiro[3.4]octan-7-yl)-3-(trifluoromethyl)picolinonitrile;

or a pharmaceutically acceptable salt or N-oxide thereof.

13. The pharmaceutical composition of claim 1, wherein the compound is 5-(5-(4-((1-Methylpiperidin-4-yl)oxy)phenyl)-8-oxo-6-thioxo-5,7-diazaspiro[3.4]octan-7-yl)-3-(trifluoromethyl)picolinonitrile, or a pharmaceutically acceptable salt or N-oxide thereof.

14. The pharmaceutical composition of claim 1, wherein the compound is 5-(5-(2-Fluoro-4-((1-methylpiperidin-4-yl)oxy)phenyl)-8-oxo-6-thioxo-5,7-diazaspiro[3.4]octan-7-yl)-3-(trifluoromethyl) picolinonitrile, or a pharmaceutically acceptable salt or N-oxide thereof.

15. The pharmaceutical composition of claim 1, wherein the compound is 3-Methyl-5-(5-(4-((1-methylpiperidin-4-yl)oxy)phenyl)-8-oxo-6-thioxo-5,7-diazaspiro[3.4]octan-7-yl) picolinonitrile, or a pharmaceutically acceptable salt or N-oxide thereof.

16. The pharmaceutical composition of claim 1, wherein the compound is 5-(5-(3-Fluoro-4-((1-methylpiperidin-4-yl)oxy)phenyl)-8-oxo-6-thioxo-5,7-diazaspiro[3.4]octan-7-yl)-3-methyl-picolinonitrile, or a pharmaceutically acceptable salt or N-oxide thereof.

17. The pharmaceutical composition of claim 1, wherein the compound is 5-(5-(3-Fluoro-4-((1-methylpiperidin-4-yl)oxy)phenyl)-8-oxo-6-thioxo-5,7-diazaspiro[3.4]octan-7-yl)-3-(trifluoromethyl)-picolinonitrile, or a pharmaceutically acceptable salt or N-oxide thereof.

18. The pharmaceutical composition of claim 1, wherein the compound is 3-Methyl-5-(8-oxo-5-(4-(piperidin-4-yloxy)phenyl)-6-thioxo-5,7-diazaspiro[3.4]octan-7-yl)picolinonitrile, or a pharmaceutically acceptable salt or N-oxide thereof.

19. The pharmaceutical composition of claim 1, wherein the compound is 5-(8-Oxo-5-(4-(piperidin-4-yloxy)phenyl)-6-thioxo-5,7-diazaspiro[3.4]octan-7-yl)-3-(trifluoromethyl) picolinonitrile, or a pharmaceutically acceptable salt or N-oxide thereof.

20. The pharmaceutical composition of claim 1, formulated in a dosage form suitable for delivering a therapeutically effective amount of the compound when administered in a single dosage form.

21. The pharmaceutical composition of claim 12, formulated in a dosage form suitable for delivering a therapeutically effective amount of the compound when administered in a single dosage form.

22. The pharmaceutical composition of claim 1, formulated in a divided dosage form suitable for delivering a therapeutically effective amount of the compound when administered multiple times over the span of one day.

23. The pharmaceutical composition of claim 12, formulated in a divided dosage form suitable for delivering a therapeutically effective amount of the compound when administered multiple times over the span of one day.

24. The pharmaceutical composition of claim 1, formulated in an oral dosage form and containing the compound in an amount in a range of from about 1 mg to about 500 mg.

25. The pharmaceutical composition of claim 12, formulated in an oral dosage form and containing the compound in an amount in a range of from about 1 mg to about 500 mg.

26. A method of treating a patient with prostate cancer comprising administering to the patient a therapeutically effective amount of a compound of Formula (Ia), or a pharmaceutically acceptable salt thereof or N-oxide thereof, wherein the therapeutically effective amount of the compound or pharmaceutically acceptable salt or N-oxide thereof is administered in a single dosage form or in a divided dosage form multiple times over the span of one day:

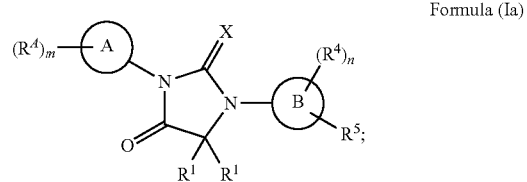

Formula (Ia)

and wherein the compound of Formula (Ia) is:
- 5-(5-(4-((1-Methylpiperidin-4-yl)oxy)phenyl)-8-oxo-6-thioxo-5,7-diazaspiro[3.4]octan-7-yl)-3-(trifluoromethyl) picolinonitrile;
- 5-(5-(2-Fluoro-4-((1-methylpiperidin-4-yl)oxy)phenyl)-8-oxo-6-thioxo-5,7-diazaspiro[3.4]octan-7-yl)-3-trifluoromethyl) picolinonitrile;
- 3-Methyl-5-(5-(4-((1-methylpiperidin-4-yl)ox)phenyl)-8-oxo-6-thioxo-5,7-diazaspiro[3.4]octan-7-yl) picolinonitrile;
- 5-(5-(3-Fluoro-4-((1-methylpiperidin-4-yl)oxy)phenyl)-8-oxo-6-thioxo-5,7-diazaspiro[3.4]octan-7-yl)-3-methyl-picolinonitrile;
- 5-(5-(3-Fluoro-4-((1-methylpiperidin-4-yl)oxy)phenyl)-8-oxo-6-thioxo-5,7-diazaspiro[3.4]octan-7-yl)-3-(trifluoromethyl)-picolinonitrile;
- 3-Methyl-S-(8-oxo-5-(4-(piperidin-4-yloxy)phenyl)-6-thioxo-5,7-diazaspiro[3.4]octan-7-yl)picolinonitrile; or
- 5-(8-Oxo-5-(4-(piperidin-4-yloxy)phenyl)-6-thioxo-5,7-diazaspiro[3.4]octan-7-yl)-3-(trifluoromethyl)picolinonitrile.

27. The method of claim 26, wherein the compound is 5-(5-(4-((1-Methylpiperidin-4-yl)oxy)phenyl)-8-oxo-6-thioxo-5,7-diazaspiro[3.4]octan-7-yl)-3-trifluoromethyl)picolinonitrile, or a pharmaceutically acceptable salt or N-oxide thereof.

28. The method of claim 26, wherein the compound is 5-(5-(2-Fluoro-4-((1-methylpiperidin-4-yl)oxy)phenyl)-8-oxo-6-thioxo-5,7-diazaspiro[3.4]octan-7-yl)-3-(trifluoromethyl) picolinonitrile, or a pharmaceutically acceptable salt or N-oxide thereof.

29. The method of claim 26, wherein the compound is 3-Methyl-5-(5-(4-((1-methylpiperidin-4-yl)oxy)phenyl)-8- oxo-6-thioxo-5,7-diazaspiro[3.4]octan-7-yl) picolinonitrile, or a pharmaceutically acceptable salt or N-oxide thereof.

30. The method of claim 26, wherein the compound is 5-(5-(3-Fluoro-4-((1-methylpiperidin-4-yl)oxy)phenyl)-8-oxo-6-thioxo-5,7-diazaspiro[3.4]octan-7-yl)-3-methyl-picolinonitrile, or a pharmaceutically acceptable salt or N-oxide thereof.

31. The method of claim 26, wherein the compound is 5-(5-(3-Fluoro-4-((1-methylpiperidin-4-yl)oxy)phenyl)-8-oxo-6-thioxo-5,7-diazaspiro[3.4]octan-7-yl)-3-(trifluoromethyl)-picolinonitrile, or a pharmaceutically acceptable salt or N-oxide thereof.

32. The method of claim 26, wherein the compound is 3-Methyl-5-(8-oxo-5-(4-(piperidin-4-yloxy)phenyl)-6-thioxo-5,7-diazaspiro[3.4]octan-7-yl)picolinonitrile, or a pharmaceutically acceptable salt or N-oxide thereof.

33. The method of claim 26, wherein the compound is 5-(8-Oxo-5-(4-(piperidin-4-yloxy)phenyl)-6-thioxo-5,7-diazaspiro[3.4]octan-7-yl)-3-(trifluoromethyl)picolinonitrile, or a pharmaceutically acceptable salt or N-oxide thereof.

34. The method of claim 26, wherein the therapeutically effective amount of the compound is administered in a single dosage form.

35. The method of claim 26, wherein the therapeutically effective amount of the compound is administered in a single dosage form.

36. The method of claim 26, wherein the therapeutically effective amount of the compound is administered in a divided dosage form multiple times over the span of one day.

37. The method of claim 26, wherein the therapeutically effective amount of the compound is administered in a divided dosage form multiple times over the span of one day.

38. The method of claim 26, wherein the compound is administered to the patient in a range from about 0.01 to about 10 mg compound per kg per body weight per day.

39. The method of claim 26, wherein the compound is administered to the patient in an amount ranging from about 1 mg per day to about 1000 mg per day.

40. The method of claim 26, wherein the compound is administered to the patient in a range from about 0.01 to about 10 mg compound per kg per body weight per day.

41. The method of claim 26, wherein the compound is administered to the patient in an amount ranging from about 1 mg per day to about 1000 mg per day.

42. The method of claim 26, wherein the prostate cancer is a hormone dependent cancer.

* * * * *